(12) United States Patent
Tracey, Jr. et al.

(10) Patent No.: US 8,017,316 B2
(45) Date of Patent: Sep. 13, 2011

(54) METHODS AND COMPOSITIONS FOR THE IDENTIFICATION OF INSECT REPELLENT COMPOUNDS

(75) Inventors: William D. Tracey, Jr., Chapel Hill, NC (US); Nancy Stearns, Durham, NC (US); Lixian Zhong, Durham, NC (US); Yifan Xu, New York, NY (US); Jason Caldwell, Durham, NC (US); Allison Weaver, Cary, NC (US); Angela Hofhine, Durham, NC (US)

(73) Assignee: Duke University, Durham, NC (US)

( * ) Notice: Subject to any disclaimer, the term of this patent is extended or adjusted under 35 U.S.C. 154(b) by 242 days.

(21) Appl. No.: 12/283,670

(22) Filed: Sep. 15, 2008

(65) Prior Publication Data
US 2009/0176229 A1   Jul. 9, 2009

Related U.S. Application Data

(60) Provisional application No. 60/993,816, filed on Sep. 14, 2007.

(51) Int. Cl.
  *C12Q 1/00*     (2006.01)
  *C12Q 1/68*     (2006.01)
  *C07K 14/435*   (2006.01)

(52) U.S. Cl. ................. 435/4; 435/6; 530/350

(58) Field of Classification Search .......... None
See application file for complete search history.

(56) References Cited

U.S. PATENT DOCUMENTS
7,018,617 B1   3/2006   Tracey et al.

OTHER PUBLICATIONS

Bessou & Perl (1969) *Journal of Neurophysiology* 32: 1025-1 043.
Dogan et al. (1999) *Medical and Veterinary Entomology* 13:97-100.
Larsson et al. (2004) *Neuron* 43:703-714.
Tracey et al. (2003) *Cell* 113:261-273.
Wang & Woolf (2005) *Neuron* 46:9-12.

*Primary Examiner* — Ruixiang Li
(74) *Attorney, Agent, or Firm* — Jenkins, Wilson, Taylor & Hunt, P.A.

(57) ABSTRACT

Methods for identifying a candidate compound with an ability to modulate cation transport through a transient receptor potential (TRP) channel in a cell are disclosed. The methods can include (a) providing a cell expressing a recombinant nucleic acid sequence encoding an transient receptor potential (TRP) channel gene product or a functional fragment or derivative thereof; (b) contacting the cell with the candidate compound; (c) comparing cation transport in the cell in the absence of the candidate compound with cation transport in the cell in the presence of the candidate compound; and (d) identifying a candidate compound through the comparing step that modulates cation transport in the cell through the transient receptor potential (TRP) channel. Also disclosed are nucleic acid and amino acid sequences for insect TRP channel gene products, antibodies that bind to the disclosed TRP channels, and recombinant host cells the include the disclosed biosequences.

8 Claims, 27 Drawing Sheets
(11 of 27 Drawing Sheet(s) Filed in Color)

Figure 12 (cont'd)

SEQUENCE LISTING

```
<160> NUMBER OF SEQ ID NOS: 34

<210> SEQ ID NO 1
<211> LENGTH: 12284
<212> TYPE: DNA
<213> ORGANISM: Artificial Sequence
<220> FEATURE:
<223> OTHER INFORMATION: Artificially constructed expression vector

<400> SEQUENCE: 1
```

```
catgatgaaa taacataagg tggtcccgtc gatagccgaa gcttaccgaa gtatacactt      60
aaattcagtg cacgtttgct tgttgagagg aaaggttgtg tgcggacgaa ttttttttg     120 aaaacattaa cccttacgtg gaataaaaaa aaatgaaata ttgcaaattt tgctgcaaag    180
ctgtgactgg agtaaaatta attcacgtgc cgaagtgtgc tattaagaga aaattgtggg    240
agcagagcct tgggtgcagc cttggtgaaa actcccaaat ttgtgatacc cactttaatg    300
attcgcagtg gaaggctgca cctgcaaaag gtcagacatt taaaaggagg cgactcaacg    360
cagatgccgt acctagtaaa gtgatagagc ctgaaccaga aaagataaaa gaaggctata    420
ccagtgggag tacacaaaca gagtaagttt gaatagtaaa aaaaatcatt tatgtaaaca    480
ataacgtgac tgtgcgttag gtcctgttca ttgtttaatg aaaataagag cttgagggaa    540
aaaattcgta ctttggagta cgaaatgcgt cgtttagagc agcagccgaa ttaattctag    600
ttccagtgaa atccaagcat tttctaaatt aaatgtattc ttattattat agttgttatt    660
tttgatatat ataaacaaca ctattatgcc caccattttt ttgagatgca tctacacaag    720
gaacaaacac tggatgtcac tttcagttca aattgtaacg ctaatcactc cgaacaggtc    780
acaaaaaatt accttaaaaa gtcataatat taaattagaa taaatatagc tgtgagggaa    840
atatatacaa atatattgga gcaaataaat tgtacataca aatatttatt actaatttct    900
attgagacga aatgaaccac tcggaaccat ttgagcgaac cgaatcgcgc ggaactaacg    960
acagtcgctc caaggtcgtc gaacaaaagg tgaatgtgtt gcggagagcg ggtgggagac   1020
agcgaaagag caactacgaa acgtggtgtg gtggaggtga attatgaaga gggcgcgcga   1080
tttgaaaagt atgtatataa aaaatatatc ccggtgtttt atgtagcgat aaacgagttt   1140
ttgatgtaag gtatgcaggt gtgtaagtct tttggttaga agacaaatcc aaagtctact   1200
tgtggggatg ttcgaagggg aaatacttgt attctatagg tcatatcttg tttttattgg   1260
cacaaatata attacattag ctttttgagg gggcaataaa cagtaaacac gatggtaata   1320
atggtaaaaa aaaaaacaag cagttatttc ggatatatgt cggctactcc ttgcgtcggg   1380
cccgaagtct tagagccaga tatgcgagca cccggaagct cacgatgaga atggccagac   1440
ccacgtagtc cagcggcaga tcggcggcgg agaagttaag cgtctccagg atgaccttgc   1500
ccgaactggg gcacgtggtg ttcgacgatg tgcagctaat ttcgcccggc tccacgtccg   1560
cccattggtt aatcagcaga ccctcgttgg cgtaacggaa ccatgagagg tacgacaacc   1620
atttgaggta tactggcacc gagcccgagt tcaagaagaa gccgccaaag agcaggaatg   1680
gtatgataac cggcggaccc acagacagcg ccatcgaggt cgaggagctg cgcaggata    1740 ttagatatcc gaaggacgtt gacacattgg ccaccagagt gaccagcgcc aggcagttga   1800
agaagtgcag cactccggcc cgcagtccga tcatcggata ggcaatcgcc gtgaagacca   1860
gtggcactgt gagaaaaagc ggtaattcgg caatcgtttt gcccagaaag tatgtgtcac   1920
agcgataaag tcgacttcgg gcctccctca taaaaactgg cagctctgag gtgaacacct   1980
aaatcgaatc gattcattag aaagttagta aattattaat atgcaaatgt attctaaaca   2040
agacttacat ttatcgtggc aaagacgttt tgaaggtca tgttggtcag gaagaggaag    2100
atggctccgt tgatattcat cacgcccact tgcgtgagtt gttggcccaa aaagatgagg   2160
ccaatcaaga tggcaaccat ctgcaaatta aaatgttact cgcatctcat taatattcat   2220
atcttcaaca tgttcgcgag ttaaatgaaa tttatttatt ttctgcaaaa ctataaacta   2280
tacatctcat tgaaaaaaac taagaagggt gtggaatcag gcaattctaa ctaaaatcta   2340
gcgaatttgt ttccaagaat tgtaagcgtt atatcatttg tttccactgg aaccactcac   2400
```

```
cgttgtctga ataagtcgca cttttacgag gagtggttcc ttgagcaccg acagccagga    2460
tcgccacagg accgcccgga actgcatgaa ccaggtggcc ttgtaggtgt acccattctc    2520
cggctgctcc agtggcttct ccaaattttt ggtggccaac aactgctcca tatcccgggc    2580
tactttgcta atagcaaaat tgtcgcatat cttggcgatc cgatcacggg actcgatctc    2640
ccgtccgggc acaacggcca acacctgtac gtaaaagtcc gccggattgt agttggtagg    2700
acactgggca cccacgctgg ataggagttg agatgtaatg taatgctaga tacccttaat    2760
aaacacatcg aactcactag gaaaagaagt cgacggcttc gctgggagtg cccaagaaag    2820
ctaccctgcc ctcggccatc agaaggatct tgtcaaagag ctcaaacagc tcggaagacg    2880
gctgatgaat ggtcaggatg acggtcttgc ccttctgcga cagcttcttc agcacctgga    2940
cgacgctgtg ggcggtaaat gagtccagtc cggaggtggg ctcatcgcag atcagaagcg    3000
gcggatcggt tagtgcctcg gaggcgaatg ccagacgctt cctttctccg ccggacagac    3060 cttt cacc ct gccgggcaca ccgatgatcg tgtgctgaca tttgctgagc gaaagctcct    3120
ggatcacctg atccacgcgg gccactcgct gccgataggt cagatgtcgt ggcatccgca    3180
ccatggcctg gaaaatcagg tgttccctgg ccgttaggga gccgataaag aggtcatcct    3240
gctggacata ggcgcacctg gcctgcatct ccttggcgtc cacaggttgg ccattgagca    3300
gtcgcatccc ggatggcgat acttgatgcc cctgcggcga tcgaaaggca agggcattca    3360
gcagggtcgt ctttccggca ccggaactgc ccatcacggc caaaagttcg cccggatagg    3420
ccacgccgca aactgagttt caaattggta attggaccct ttattaagat ttcacacaga    3480
tcagccgact gcgaatagaa actcaccgtt cttgagcaaa tgtttcctgg gcgccggtat    3540
gtgtcgctcg ttgcagaata gtccgcgtgt ccggttgacc agctgccgcc atccggagcc    3600
cggctgattg accgccccaa agatgtccat attgtgccag cataggtgga ggttctcggc    3660
tagttggccg ctccctgaac cggagtcctc cggcggactg ggtggcagga gcgtgccgta    3720 gttttttggcc tgcccgaagc cctggttaat gcagctctgc gaagccgctc cgctgtcacc    3780
ctgcaatgat agggg atctc aaatatcaac tacaagcgtt atgctcatct aaccccgaac    3840
aaaacgaagt atcctacgaa gtaggtttat acttttattt attttttgtg catctaggat    3900
cagcttaaaa tatctggttg ttatattttt tgtaaaaaag aatgtagtcg aaaatgaatg    3960
cctttagatg tcttgatcat gatatgatct taaaaattgt cttatatagc gagcacagct    4020
accagaataa tctgtttcgt gtcactattt gtttgtgcga ttgcggtttg ggattttttgt    4080 gggtcgcagt tctcacgccg cagacaattt gatgttgcaa tcgcagttcc tatagatcaa    4140
gtgaacttaa gatgtatgca catgtactac tcacattgtt cagatgctcg gcagatgggt    4200
gtttgctgcc tccgcgaatt aatagctcct gatcctcttg gcccattgcc gggattttc    4260 acactttccc ctgcttaccc acccaaaacc aatcaccacc caatcactc aaaaaacaaa    4320 caaaaataag aagcgagagg agttttggca cagcactttg tgtttaattg atggcgtaaa    4380
ccgcttggag cttcgtcacg aaaccgctga caaagtgcaa ctgaaggcgg acattgacgc    4440
taggtaacgc tacaaacggt ggcgaaagag atagcggacg cagcggcgaa agagacgcg    4500 atatttctgt ggacagagaa ggaggcaaac agcgctgact ttgagtggaa tgtcattttg    4560
agtgagaggt aatcgaaaga acctggtact tcaaataccc ttgatcgaa gtaaatttaa    4620 aactgatcag ataagttcaa tgatgtccag tgcagtaaaa aataaaaaaa aaatatgttt    4680
ttttaaatct acattctcca aaaagggtt ttattaactt acatacatac taaggccttc    4740
tagtggatcc gatccagaca tgataagata cattgatgag tttggacaaa ccacaactag    4800
```

```
aatgcagtga aaaaaatgct ttatttgtga aatttgtgat gctattgctt tatttgtaac      4860
cattataagc tgcaataaac aagttaacaa caacaattgc attcatttta tgtttcaggt      4920
tcagggggag gtgtgggagg ttttttaaag caagtaaaac ctctacaaat gtggtatggc      4980
tgattatgat ctctagtcaa ggcactatac atcaaatatt ccttattaac ccctttacaa      5040
attaaaaagc taaaggtaca caattttga gcatagttat taatagcaga cactctatgc       5100
ctgtgtggag taagaaaaaa cagtatgtta tgattataac tgttatgcct acttataaag      5160
gttacagaat attttccat aattttcttg tatagcagtg cagcttttc ctttgtggtg        5220 taaatagcaa agcaagcaag agttctatta ctaaacacag catgactcaa aaaacttagc      5280
aattctgaag gaaagtcctt ggggtcttct acctttctct tctttttgg aggagtagaa       5340 tgttgagagt cagcagtagc ctcatcatca ctagatggca tttcttctga gcaaaacagg     5400
ttttcctcat taaaggcatt ccaccactgc tcccattcat cagttccata ggttggaatc      5460
taaaatacac aaacaattag aatcagtagt ttaacacatt atacacttaa aaatttata      5520 tttaccttag agctttaaat ctctgtaggt agtttgtcca attatgtcac accacagaag      5580
taaggttcct tcacaaagat cctctagagg taccgagctc ggatccacta gtaacggccg      5640
ccagtgtgct ggaattcgcc cttaacattt gaaattaaat atttactcgg gtacaaatag      5700
tacagtaatg atattcgttt atacaatatt tactgtctat ataaccatta tatactactt      5760
acttactgac aattattaag ggttttgttc aatttcatta ctcgtatgtt aataaaaaca      5820
atttccgact aactcggctc tttaaactga atgttaaatg caaatcgttc taaaaggttg      5880
attagtctca taaatactaa agctaccaaa atacattctc catcacttcc ggtcctggac      5940
cagctgtatt aattgctcca gcttgtactc gatcagcttc agtcgactgt cgttgatctg      6000
ttcctgtttc cgcctctgct ccgccgcgtt cttctgatcg attacctcga gggcccgttt      6060
gaccacccgg ccgctcatct gggagcactt tccggtgagc agggaacagc agcagggcag      6120
aagtctaagc ggtggatcca acagcttctt ctggggcact gcagcactca ggggcaattg      6180
ctgaaagcta gccttcttaa gggtcctcat ttcgaaggga tcgctcattg gaataagcac      6240 tttgttttcca tcgttcggca gcacggaaat ctgacgcaga cttaagtagt tcgggtagat     6300
gttcatcaaa cgttggcaga tgctgcggaa gagatggttg cccaacaaaa acccagcgcg      6360
tccgtggcca gtgagaacct gctcgtaccg actaaggacg ttggttctgc aaatggctcc     6420
gttcagttcc gcctgagcct taataaccta gataatgaat aacgccggaa atgggattag      6480
cgaagggaaa taatacgaat ggcgatagac ctacttgggt gtcgctcact gcaagaccgt     6540
tcaaaaggtt gaacagcact atcgtcataa agatcacgaa gagcaggaaa atcaggtagg      6600
tgtagatgct ggtaaactgg atgcttccgg cgtcaaactc gcctgtcagc atcacaatgg      6660
tcttgatcac ggcctcgata ggcttggtaa atgtgttgaa gccctgttcc tcgtccttcc      6720
cctccttctt ccccagaggt ggacatggcg tagcgctttt agactggtct tcctccactg      6780
acttgccgaa gaggatatag aaacacaggc tgaaggtgag cacgaagatc gagtagaggg      6840
taaagctctt taagaagctg tttgacacct ctcgcagcat cagcatgtgc gtcgaaattg     6900
agagcactgg cagggagccc actagtaaac aaaactccat ggagacgagt aggatggtaa     6960
atacggctaa gacgcgctgc gtctccttgt cgaagctgga ttccatgcag gtaaagatag      7020
atagtgtaat aagagccacc tccataatat tcgttataga ccaaaagtac cgaactggag      7080
acattatcca ctgatgcac  tcccgtaata taaggtagct gattcccagc caggaaagca      7140
atccgaaaaa tgcagtaaga gccctttgat cgctttcgtg gaacttgagg agcgtgtagg      7200
```

```
taattatgga ggcggtaaaa agcgagtata tcaggaagtt caggtagaat atcacggaaa   7260
gtcggtgcca cttgaggaat agaaagctcg agatcagcgg gtgctggagc aggtggcgca   7320
tctccttcga ctcggcgatg aatgcgatcg gggccatttc gtcttgcagc tggttgagtc   7380
cggagtctct ctcctggcgc attaggttct tataatcgat gatgatctca aagttctggt   7440
caccaggcct ctctccgttt gtggtgatac acgagtcgaa gtgctcttcg agaacctcgg   7500
gtggcatgtc cttgatgggt agtgtgccaa atgcgctctt agaaccaatg taggcaccgt   7560
tcttcaggag ttttttgcatc gcactcgtgt tgcggtactt aacagcgaag aacagaggca   7620
ccaggcgtcc ggaatcagct tcgttgatgt ctacgcgatc gctgttaatg agcaattcaa   7680
agcagcgctg gtgctggag ccatcatacg gtggctcatc cagacggccg attactgcat   7740
ttagtagctt ggagtctgga gtaagtcgca ggtttggctc cttaagcagt cgctccaacg   7800
cctgccagtt accgtatatc acggccgtct ctacgagatt ggcctcgttg gccctgcctg   7860
gtctcgagtt gatatccatg ccagtggaca aaatgacatc gaaggctcgc tgcctgcccc   7920
tcttgatgct ctcctgcagc agtccgaagt attcctcctg gtgggcattt agttggttat   7980
ccgctccgcc tttgagattc tgcaagtact cagcgaactg ctgctcaaac agtgtttcgt   8040
ccccgtcccg tagagtcctt tgaagagttt ggatgtcaat ctccggcccg gtatgacgct   8100
cttccggcag cttaagctcc ggaaattgcg cctgcagcag tctgcgcacc tccccgttt   8160
ggtaactatc gatatccagc tccggatggt ccagaaagag ctgaatcagt tccttcttcc   8220
cagccttcac cttgctcttt ctcagcacat ggtgcaaggg tgtgaactcg ccctggtcta   8280
cgatattcgg cgaggcgccg tagtccagca agagttgcat gcaggagtac acgtctgggg   8340
cattttcatc cgtgagattc ttggcaagtg agttaagtgg agtaagctgc ccatattttc   8400
tatcaacctg gactttgttt ccggggcggt acttaaggag agccgccagg tttcctggat   8460
ccctagagtc agccgcatag ctgattgcgg ccttgtccag cttcttgttg atctgtgaag   8520
atgaactgtg gttagatggt gtccgacctc tactccttgt tgctctactc acgtagttca   8580
cctggctgcc gtggtcgatg caggcttcaa tgaagtcacg acaacctggt gttgagagtg   8640
ccttctcgta gatactggta tggcggtcgt cttgtagatc ggccagggca ccgctgtcca   8700
gggcagcaac gaactgtcgg atgtcctgct tggccaaagc tccagctagc tgggcctgcg   8760
gatcaatgaa gccgcagttg ttaaagtcca ttggtttggt ctgcaaagaa agagcagcca   8820
cggaaagggc gaattctgca gatatccatc acactggcgg ccgcagatct gttaacgaat   8880
tcccaattcc ctattcagag ttctcttctt gtattcaata attacttctt ggcagatttc   8940
agtagttgca gttgatttac ttggttgctg gttacttttta attgattcac tttaacttgc   9000
actttactgc agattgttta gcttgttcag ctgcgcttgt ttatttgctt agctttcgct   9060
tagcgacgtg ttcactttgc ttgtttgaat tgaattgtcg ctccgtagac gaagcgcctc   9120
tatttatact ccggcgctcg ctagagtctc cgctcggagg acagtactcc gctcggagga   9180
cagtactccg ctcggaggac agtactccgc tcggaggaca gtactccgct cggaggacag   9240
tactccgacc tgcaggcatg caagcttgga tccgagctca tgcagaagct tgcgtactc   9300
gcaaattatt aaaaataaaa ctttaaaaat aatttcgtct aattaatatt atgagttaat   9360
tcaaaccca cggacatgct aagggttaat caacaatcat atcgctgtct cactcagact   9420
caatacgaca ctcagaatac tattcctttc actcgcactt attgcaagca tacgttaagt   9480
ggatgtctct tgccgacggg accacctttat gttatttcat catggtctgg ccattctcat   9540
cgtgagcttc cgggtgctcg catatctggc tctaagactt cgggcccgac gcaaggagta   9600
```

```
gccgacatat atccgaaata actgcttgtt tttttttta ccattattac catcgtgttt    9660
actgtttatt gccccctcaa aaagctaatg taattatatt tgtgccaata aaacaagat    9720
atgacctata gaatacaagt atttcccctt cgaacatccc cacaagtaga ctttggattt   9780
gtcttctaac caaaagactt acacacctgc ataccttaca tcaaaaactc gtttatcgct   9840
acataaaaca ccgggatata ttttttatat acatacttt caaatcgcgc gccctcttca    9900
taattcacct ccaccacacc acgtttcgta gttgctcttt cgctgtctcc cacccgctct   9960
ccgcaacaca ttcaccttt gttcgacgac cttggagcga ctgtcgttag ttccgcgcga   10020
ttcggtgcgg tatttcacac cgcatatggt gcactctcag tacaatctgc tctgatgccg  10080
catagttaag ccagcccga cacccgccaa cacccgctga cgcgccctga cgggcttgtc   10140
tgctcccggc atccgcttac agacaagctg tgaccgtctc cgggagctgc atgtgtcaga  10200
ggttttcacc gtcatcaccg aaacgcgcga gacgaaaggg cctcgtgata cgcctatttt  10260
tataggttaa tgtcatgata ataatggttt cttagacgtc aggtggcact tttcggggaa  10320
atgtgcgcgg aacccctatt tgtttatttt tctaaataca ttcaaatatg tatccgctca  10380
tgagacaata accctgataa atgcttcaat aatattgaaa aaggaagagt atgagtattc  10440
aacatttccg tgtcgccctt attcccttt ttgcggcatt ttgccttcct gtttttgctc   10500
acccagaaac gctggtgaaa gtaaaagatg ctgaagatca gttgggtgca cgagtgggtt  10560
acatcgaact ggatctcaac agcggtaaga tccttgagag ttttcgcccc gaagaacgtt  10620
ttccaatgat gagcactttt aaagttctgc tatgtggcgc ggtattatcc cgtgttgacg  10680
ccgggcaaga gcaactcggt cgccgcatac actattctca gaatgacttg gttgagtact  10740
caccagtcac agaaaagcat cttacggatg gcatgacagt aagagaatta tgcagtgctg  10800
ccataaccat gagtgataac actgcggcca acttacttct gacaacgatc ggaggaccga  10860
aggagctaac cgcttttttg cacaacatgg gggatcatgt aactcgcctt gatcgttggg  10920
aaccggagct gaatgaagcc ataccaaacg acgagcgtga ccacgatg cctgtagcaa    10980
tggcaacaac gttgcgcaaa ctattaactg gcgaactact tactctagct tcccggcaac  11040
aattaataga ctggatggag gcggataaag ttgcaggacc acttctgcgc tcggcccttc  11100
cggctggctg gtttattgct gataaatctg gagccggtga gcgtgggtct cgcggtatca  11160
ttgcagcact ggggccagat ggtaagccct cccgtatcgt agttatctac acgacgggga  11220
gtcaggcaac tatggatgaa cgaaatagac agatcgctga gataggtgcc tcactgatta  11280
agcattggta actgtcagac caagtttact catatatact ttagattgat ttaaaacttc  11340
atttttaatt taaaaggatc taggtgaaga tcctttttga taatctcatg accaaaatcc  11400
cttaacgtga gttttcgttc cactgagcgt cagaccccgt agaaaagatc aaaggatctt  11460
cttgagatcc ttttttttctg cgcgtaatct gctgcttgca acaaaaaaa ccaccgctac   11520
cagcggtggt ttgtttgccg gatcaagagc taccaactct ttttccgaag gtaactggct  11580
tcagcagagc gcagatacca atactgtcc ttctagtgta gccgtagtta ggccaccact   11640
tcaagaactc tgtagcaccg cctacatacc tcgctctgct aatcctgtta ccagtggctg  11700
ctgccagtgg cgataagtcg tgtcttaccg ggttggactc aagacgatag ttaccggata  11760
aggcgcagcg gtcgggctga acggggggtt cgtgcacaca gcccagcttg gagcgaacga  11820
cctacaccga actgagatac ctacagcgtg agcattgaga aagcgccacg cttcccgaag  11880
ggagaaaggc ggacaggtat ccggtaagcg gcagggtcgg aacaggagag cgcacgaggg  11940
agcttccagg gggaaacgcc tggtatcttt atagtcctgt cgggtttcgc cacctctgac  12000
```

```
ttgagcgtcg attttttgtga tgctcgtcag gggggcggag cctatggaaa aacgccttct    12060
tcttgaactc gggctcggtg ccagtatacc tcaaatggtt gtcgtacctc tcatggttcc    12120
gttacgccaa cgagggtctg ctgattaacc aatgggcgga cgtggagccg ggcgaaatta    12180
gctgcacatc gtcgaacacc acgtgcccca gttcgggcaa ggtcatcctg agacgctta    12240 acttctccgc cgccgatctg ccgctggact acgtgggtct ggcc                      12284
```

```
<210> SEQ ID NO 2
<211> LENGTH: 8493
<212> TYPE: DNA
<213> ORGANISM: Artificial Sequence
<220> FEATURE:
<223> OTHER INFORMATION: Artificially constructed expression vector

<400> SEQUENCE: 2
```

```
gcgcccaata cgcaaaccgc ctctccccgc gcgttggccg attcattaat gcaggcaact      60
cgtgaaaggt aggcggatca gcggccgcag catgcaattc tatattctaa aaacacaaat     120
gatacttcta aaaaaaaatc atgaatggca tcaactctga atcaaatctt tgcagatgca     180
cctacttctc atttccactg tcacatcatt tttccagatc tcgctgcctg ttatgtggcc     240
cacaaaccaa gacacgtttt atggccatta agctggctg atcgtcgcca aacaccaaat      300
acataatgaa tatgtacaca ttcgagaaag aagcgatcaa agaagcgtct tcgggcggag     360
taggagaatg cggaggagaa ggagaacgag ctgatctagt atctctccac aatccaatgc     420
caactgacca actggccata ttcggagcaa tttgaagcca atttccatcg cctggcgatc     480
gctccattct tggctatatg ttttttcaccg ttacccgggg ccattttcaa agactcgtcg     540
gcaagataag attgtgtcac tcgctgtctc tcttcatttg tcgaagaatg ctgaggaatt     600
tcgcgatgac gtcggcgagt attttgaaga tgagaataa tttgtattta tacgaaaatc     660
agttagtgga atttttctaca aaacatgtt atctatagat aattttgttg caaaatatgt     720
tgactatgac aaagattgta tgtatatacc tttaatgtat tctcattttc ttatgtattt     780
ataatggcaa tgatgatact gatgatattt taagatgatg ccagaccaaa aggcttgaat     840
ttctgcgtct tttgccgaac gcagtgcatg tgcaattgtt gttttttgga atattcaatt     900
ttcggactgt ccgctttgat ttcagttttct tggcttattc aaaaagcaaa gtaaagccaa     960
aaaagcgaga tggcaatacc aaatgcggca aaacggtagt ggaaggaaag gggtgcgggg    1020
cagcggaagg aagggtgggg cggggcgtgg cggggtctgt ggctgggcgc gacgtcaccg    1080
acgttggagc cactccttg accatgtgtg cgtgtgtgta ttattcgtgt ctcgccactc    1140
gccggttgtt tttttctttt tatgctgcgc tctctctagc gccatctcgc ttacgcatgc    1200
tcaacgcacc gcatgttgcc gtttcctttt atgcgtcatt ttggctcgaa ataggcaatt    1260
atttaaacaa agattagtca acgaaaacgc taaaataaat aagtctacaa tatggttact    1320
tattgccatg tgtgtgcagc caacgatagc aacaaaagca acaacacagg tggctttccc    1380
tctttcactt tttgtttgca agccgcgtgc gagcaagacg gcacgaccgg caaacgcaat    1440
tacgctgaca aagagcagac gaagttttgg cgaaaaacat caaggcgcct gatacgaatg    1500
catttgcaat aacaattgcg atatttaata ttgtttatga agctgtttga cttcaaaaca    1560
cacaaaaaaa aaaataaaac aaattatttg aaagagaatt aggaatcgga cgcttatcgt    1620
tagggtaaca acaagaaatg cttactgagt cacagcctct ggaaaactgc cgcaagccag    1680
agagagagag aaaaagaggg agagcagctt agaccgcatg tgcttgtgtg tgaggcgtct    1740
ctctcttcgt ctctgttgcg caaacgcata gactgcactg agaaaatcga ttacctattt    1800
```

```
tttatgaatg aatatttgca ctattactat tcaaaactat taagatagca atcacattca   1860
atagccaaat actataccac ctgagcgatg caacgaaatg atcaatttga gcaaaaatgc   1920
tgcatattta ggacggcatc attatagaaa tgcttcttgc tgtgtacttt tctctcgtct   1980
ggcagctgtt tcgccgttat tgttaaaacc ggcttaagtt aggtgtgttt tctacgacta   2040
gtgaatgccc tactagaaga tgtgtgttgc acaaaatgtc cctggaataa ccaatttgaa   2100
gtgcagatag cagtaaacgt aagctaatat gaatattatt taactgtaat gttttaatat   2160
cgctggacat tactaataaa cccactataa acacatgtac atatgtatgt tttggcatac   2220
aatgagtagt tggggaaaaa atgtgtaaaa gcaccgtgac catcacagca taaagataac   2280
cagctgaagt atcgaatatg agtaaccccc aaattgaatc acatgccgca actgatagga   2340
cccatggaag tacactcttc atggcgatat acaagacaca cacaagcacg aacacccagt   2400
tgcggaggaa attctccgta aatgaaaacc caatcggcga acaattcata cccatatatg   2460
gtaaaagttt tgaacgcgac ttgagagcgg agagcattgc ggctgataag gttttagcgc   2520
taagcgggct ttataaaacg ggctgcggga ccagttttca tatcactacc gtttgagttc   2580
ttgtgctgtg tggatactcc tcccgacaca aagccgctcc atcagccagc agtcgtctaa   2640
tccagagacc ccggatccag atatcgaggc ctgtctagag aagcttgttc gaatctcgag   2700
tgcgcgcttc cggaggtata cacctaggcg gtaccactgc agtgaattcg gagctctacc   2760
ggtatacaag tttgtacaaa aaagcaggct ccgcggccgc ccccttcacc atggacttta   2820
acaactgcgg cttcattgat ccgcaggccc agctagctgg agctttggcc aagcaggaca   2880
tccgacagtt cgttgctgcc ctggacagcg gtgccctggc cgatctacaa gacgaccgcc   2940
ataccagtat ctacgagaag gcactctcaa caccaggttg tcgtgacttc attgaagcct   3000
gcatcgacca cggcagccag gtgaactacg tgagtagagc aacaaggagt agaggtcgga   3060
caccatctaa ccacagttca tcttcacaga tcaacaagaa gctggacaag gccgcaatca   3120
gctatgcggc tgactctagg gatccaggaa acctggcggc tctccttaag taccgccccg   3180
gaaacaaagt ccaggttgat agaaaatatg ggcagcttac tccacttaac tcacttgcca   3240
agaatctcac ggatgaaaat gccccagacg tgtactcctg catgcaactc ttgctggact   3300
acggcgcctc gccgaatatc gtagaccagg gcgagttcac acccttgcac catgtgctga   3360
gaaagagcaa ggtgaaggct gggaagaagg aactgattca gctctttctg gaccatccgg   3420
agctggatat cgatagttac cgaaacgggg aggtgcgcag actgctgcag gcgcaatttc   3480
cggagcttaa gctgccggaa gagcgtcata ccgggccgga gattgacatc caaactcttc   3540
aaaggactct acgggacggg gacgaaacac tgtttgagca gcagttcgct gagtacttgc   3600
agaatctcaa aggcggagcg gataaccaac taaatgccca ccaggaggaa tacttcggac   3660
tgctgcagga gagcatcaag aggggcaggc agcgagcctt cgatgtcatt ttgtccactg   3720
gcatggatat caactcgaga ccaggcaggg ccaacgaggc caatctcgta gagacggccg   3780
tgatatacgg taactggcag gcgttggagc gactgcttaa ggagccaaac ctgcgactta   3840
ctccagactc caagctacta aatgcagtaa tcggccgtct ggatgagcca ccgtatgatg   3900
gctccagcca ccagcgctgc tttgaattgc tcattaacag cgatcgcgta gacatcaacg   3960
aagctgattc cggacgcctg gtgcctctgt tcttcgctgt taagtaccgc aacacgagtg   4020
cgatgcaaaa actcctgaag aacggtgcct acattggttc taagagcgca tttggcacac   4080
tacccatcaa ggacatgcca cccgaggttc tcgaagagca cttcgactcg tgtatcacca   4140
caaacggaga gaggcctggt gaccagaact ttgagatcat catcgattat aagaacctaa   4200
```

```
tgcgccagga gagagactcc ggactcaacc agctgcaaga cgaaatggcc ccgatcgcat   4260
tcatcgccga gtcgaaggag atgcgccacc tgctccagca cccgctgatc tcgagctttc   4320
tattcctcaa gtggcaccga ctttccgtga tattctacct gaacttcctg atatactcgc   4380
tttttaccgc ctccataatt acctacacgc tcctcaagtt ccacgaaagc gatcaagggg   4440
ctcttactgc attttcgga ttgctttcct ggctgggaat cagctacctt atattacggg   4500
agtgcatcca gtggataatg tctccagttc ggtacttttg gtctataacg aatattatgg   4560
aggtggctct tattacacta tctatcttta cctgcatgga atccagcttc gacaaggaga   4620
cgcagcgcgt cttagccgta tttaccatcc tactcgtctc catggagttt tgtttactag   4680
tgggctccct gccagtgctc tcaatttcga cgcacatgct gatgctgcga gaggtgtcaa   4740
acagcttctt aaagagcttt accctctact cgatcttcgt gctcaccttc agcctgtgtt   4800
tctatatcct cttcggcaag tcagtggagg aagaccagtc taaaagcgct acgccatgtc   4860
cacctctggg gaagaaggag gggaaggacg aggaacaggg cttcaacaca tttaccaagc   4920
ctatcgaggc cgtgatcaag accattgtga tgctgacagg cgagtttgac gccggaagca   4980
tccagtttac cagcatctac acctacctga ttttcctgct cttcgtgatc tttatgacga   5040
tagtgctgtt caaccttttg aacggtcttg cagtgagcga cacccaagta ggtctatcgc   5100
cattcgtatt atttcccttc gctaatccca tttccggcgt tattcattat ctaggttatt   5160
aaggctcagg cggaactgaa cggagccatt tgcagaacca acgtccttag tcggtacgag   5220
caggttctca ctggccacgg acgcgctggg ttttttgttgg gcaaccatct cttccgcagc   5280
atctgccaac gtttgatgaa catctacccg aactacttaa gtctgcgtca gatttccgtg   5340
ctgccgaacg atggaaacaa agtgcttatt ccaatgagcg atcccttcga aatgaggacc   5400
cttaagaagg ctagctttca gcaattgccc ctgagtgctg cagtgcccca gaagaagctg   5460
ttggatccac cgcttagact tctgccctgc tgctgttccc tgctcaccgg aaagtgctcc   5520
cagatgagcg gccgggtggt caaacgggcc ctcgaggtaa tcgatcagaa gaacgcggcg   5580
gagcagaggc ggaaacagga acagatcaac gacagtcgac tgaagctgat cgagtacaag   5640
ctggagcaat aatacagct ggtccaggac cggaagtgat ggagaatgaa gggtgggcgc   5700
gccgacccag ctttcttgta caaagtggtg acgtaagcta gcaggatctt tgtgaaggaa   5760
ccttacttct gtggtgtgac ataattggac aaactaccta cagagattta aagctctaag   5820
gtaaatataa aatttttaag tgtataatgt gttaaactac tgattctaat tgtttgtgta   5880
ttttagattc caacctatgg aactgatgaa tgggagcagt ggtggaatgc ctttaatgag   5940
gaaaacctgt tttgctcaga gaaatgcca tctagtgatg atgaggctac tgctgactct   6000
caacattcta ctcctccaaa aagaagaga aaggtagaag acccccaagga ctttccttca   6060 gaattgctaa gttttttgag tcatgctgtg tttagtaata gaactcttgc ttgctttgct   6120
atttacacca caaaggaaaa agctgcactg ctatacaaga aaattatgga aaaatattct   6180 gtaacccttta taagtaggca taacagttat aatcataaca tactgttttt tcttactcca   6240
cacaggcata gagtgtctgc tattaataac tatgctcaaa aattgtgtac ctttagcttt   6300
ttaatttgta aaggggttaa taaggaatat ttgatgtata gtgccttgac tagagatcat   6360
aatcagccat accacatttg tagaggtttt acttgcttta aaaaacctcc cacacctccc   6420
cctgaacctg aaacataaaa tgaatgcaat tgttgttgtt aacttgttta ttgcagctta   6480
taatggttac aaataaagca atagcatcac aaatttcaca aataaagcat ttttttcact   6540
gcattctagt tgtggttgt ccaaactcat caatgtatct tatcatgtct ggatcccgtt   6600
```

-continued

```
taaactacgc gtaattcaaa cagggttctg gcgtcgttct cgtactgttt tccccaggcc      6660
agtgctttag cgttattgaa aaggaagag tatgagtatt caacatttcc gtgtcgccct       6720
tattcccttt tttgcggcat tttgccttcc tgttttgct cacccagaaa cgctggtgaa       6780
agtaaaagat gctgaagatc agttgggtgc acgagtgggt tacatcgaac tggatctcaa     6840
cagcggtaag atccttgaga gttttcgccc cgaagaacgt tttccaatga tgagcacttt     6900
taaagttctg ctatgtggcg cggtattatc ccgtattgac gccgggcaag agcaactcgg     6960
tcgccgcata cactattctc agaatgactt ggttgagtac tcaccagtca cagaaaagca     7020
tcttacggat ggcatgacag taagagaatt atgcagtgct gccataacca tgagtgataa     7080
cactgcggcc aacttacttc tgacaacgat cggaggaccg aaggagctaa ccgcttttt      7140
gcacaacatg gggatcatg taactcgcct tgatcgttgg gaaccggagc tgaatgaagc      7200
cataccaaac gacgagcgtg acaccacgat gcctgtagca atggcaacaa cgttgcgcaa    7260
actattaact ggcgaactac ttactctagc ttcccggcaa caattaatag actggatgga    7320
ggcggataaa gttgcaggac cacttctgcg ctcggccctt ccggctggct ggtttattgc     7380
tgataaatct ggagccggtg agcgtgggtc tcgcggtatc attgcagcac tggggccaga    7440
tggtaagccc tcccgtatcg tagttatcta cacgacgggg agtcaggcaa ctatggatga    7500
acgaaataga cagatcgctg ataggtgc ctcactgatt aagcattggt aactgtcaga     7560
ccaagtttac tcatatatac tttagattga tttaaaactt cattttaat ttaaaaggat      7620
ctaggtgaag atcctttttg ataatctcat gaccaaatc ccttaacgtg agttttcgtt     7680
ccactgagcg tcagaccccg tagaaaagat caaggatct tcttgagatc cttttttct       7740
gcgcgtaatc tgctgcttgc aaacaaaaaa accaccgcta ccagcggtgg tttgtttgcc    7800
ggatcaagag ctaccaactc ttttccgaa ggtaactggc ttcagcagag cgcagatacc     7860
aaatactgtc cttctagtgt agccgtagtt aggccaccac ttcaagaact ctgtagcacc    7920
gcctacatac ctcgctctgc taatcctgtt accagtggct gctgccagtg gcgataagtc    7980
gtgtcttacc gggttggact caagacgata gttaccggat aaggcgcagc ggtcgggctg    8040
aacgggggt tcgtgcacac agcccagctt ggagcgaacg acctacaccg aactgagata     8100
cctacagcgt gagctatgag aaagcgccac gcttcccgaa gggagaaagg cggacaggta    8160
tccggtaagc ggcagggtcg gaacaggaga gcgcacgagg gagcttccag ggggaaacgc     8220
ctggtatctt tatagtcctg tcgggtttcg ccacctctga cttgagcgtc gatttttgtg     8280
atgctcgtca gggggggcgga gcctatgaa aaacgccagc aacgcggcct ttttacggtt     8340
cctggccttt tgctggcctt ttgctcacat gttctttcct gcgttatccc ctgattctgt    8400
ggataaccgt attaccgcct tgagtgagc tgataccgct cgccgcagcc gaacgaccga     8460
gcgcagcgag tcagtgagcg aggaagcgga aga                                 8493
```

<210> SEQ ID NO 3
<211> LENGTH: 8845
<212> TYPE: DNA
<213> ORGANISM: Artificial Sequence
<220> FEATURE:
<223> OTHER INFORMATION: Artificially constructed expression vector with epitope tags

<400> SEQUENCE: 3

```
gcgcccaata cgcaaaccgc ctctccccgc gcgttggccg attcattaat gcaggcaact      60
cgtgaaaggt aggcggatca gcggccgcag catgcaattc tatattctaa aaacacaaat    120
```

```
gatacttcta aaaaaaaatc atgaatggca tcaactctga atcaaatctt tgcagatgca      180
cctacttctc atttccactg tcacatcatt tttccgatc tcgctgcctg ttatgtggcc      240
cacaaaccaa gacacgtttt atggccatta aagctggctg atcgtcgcca acaccaaat      300 acataatgaa tatgtacaca ttcgagaaag aagcgatcaa agaagcgtct tcgggcggag      360
taggagaatg cggaggagaa ggagaacgag ctgatctagt atctctccac aatccaatgc      420
caactgacca actggccata ttcggagcaa tttgaagcca atttccatcg cctggcgatc      480
gctccattct tggctatatg ttttcaccg ttacccgggg ccattttcaa agactcgtcg      540
gcaagataag attgtgtcac tcgctgtctc tcttcatttg tcgaagaatg ctgaggaatt      600
tcgcgatgac gtcggcgagt attttgaaga atgagaataa tttgtattta tacgaaaatc      660
agttagtgga atttctaca aaaacatgtt atctatagat aattttgttg caaaatatgt      720
tgactatgac aaagattgta tgtatatacc tttaatgtat tctcattttc ttatgtattt      780
ataatggcaa tgatgatact gatgatattt taagatgatg ccagaccaaa aggcttgaat      840
ttctgcgtct tttgccgaac gcagtgcatg tgcaattgtt gttttttgga atattcaatt      900 tcggactgt ccgctttgat ttcagttct tggcttattc aaaaagcaaa gtaaagccaa      960
aaaagcgaga tggcaatacc aaatgcggca aaacggtagt ggaaggaaag gggtgcgggg     1020
cagcggaagg aagggtgggg cggggcgtgg cggggtctgt ggctgggcgc gacgtcaccg     1080
acgttggagc cactcctttg accatgtgtg cgtgtgtgta ttattcgtgt ctcgccactc     1140
gccggttgtt tttttctttt tatgctgcgc tctctctagc gccatctcgc ttacgcatgc     1200
tcaacgcacc gcatgttgcc gtttcctttt atgcgtcatt ttggctcgaa ataggcaatt     1260
atttaaacaa agattagtca acgaaaacgc taaaataaat aagtctacaa tatggttact     1320
tattgccatg tgtgtgcagc caacgatagc aacaaaagca acaacacagg tggctttccc     1380
tctttcactt tttgtttgca agccgcgtgc gagcaagacg gcacgaccgg caaacgcaat     1440
tacgctgaca aagagcagac gaagttttgg cgaaaaacat caaggcgcct gatacgaatg     1500
catttgcaat aacaattgcg atatttaata ttgtttatga agctgtttga cttcaaaaca     1560
cacaaaaaaa aaaataaaac aaattatttg aaagagaatt aggaatcgga cgcttatcgt     1620
tagggtaaca acaagaaatg cttactgagt cacagcctct ggaaaactgc cgcaagccag     1680
agagagagag aaaaagaggg agagcagctt agaccgcatg tgcttgtgtg tgaggcgtct     1740
ctctcttcgt ctctgttgcg caaacgcata gactgcactg agaaaatcga ttacctattt     1800
tttatgaatg aatatttgca ctattactat tcaaaactat taagatagca atcacattca     1860
atagccaaat actataccac ctgagcgatg caacgaaatg atcaatttga gcaaaaatgc     1920
tgcatattta ggacggcatc attatagaaa tgcttcttgc tgtgtacttt tctctcgtct     1980
ggcagctgtt tcgccgttat tgttaaaacc ggcttaagtt aggtgtgttt tctacgacta     2040
gtgaatgccc tactagaaga tgtgtgttgc acaaaatgtc cctggaataa ccaatttgaa     2100
gtgcagatag cagtaaacgt aagctaatat gaatattatt taactgtaat gttttaatat     2160
cgctggacat tactaataaa cccactataa acacatgtac atatgtatgt tttggcatac     2220
aatgagtagt tgggaaaaa atgtgtaaaa gcaccgtgac catcacagca taaagataac     2280
cagctgaagt atcgaatatg agtaacccc aaattgaatc acatgccgca actgatagga     2340
cccatggaag tacactcttc atggcgatat acaagacaca cacaagcacg aacacccagt     2400
tgcggaggaa attctccgta aatgaaaacc caatcggcga acaattcata cccatatatg     2460
gtaaaagttt tgaacgcgac ttgagagcgg agagcattgc ggctgataag gttttagcgc     2520
```

```
taagcgggct ttataaaacg ggctgcggga ccagttttca tatcactacc gtttgagttc    2580
ttgtgctgtg tggatactcc tcccgacaca aagccgctcc atcagccagc agtcgtctaa    2640
tccagagacc ccggatccag atatcgaggc ctgtctagag aagcttgttc gaatctcgag    2700
tgcgcgcttc cggaggtata cacctaggcg gtaccactgc agtgaattcg gagctccgcc    2760
accatggact acaaagacca tgacggtgat tataaagatc atgacatcga ttacaaggat    2820
gacgatgaca agcaccggtt gagctccgcc accatggagc aaaagctcat ttctgaagag    2880
gacttgaatg aaatggagca aaagctcatt tctgaagagg acttgaatga aatggagcaa    2940
aagctcattt ctgaagagga cttgaatgaa atggagcaaa agctcatttc tgaagaggac    3000
ttgaatgaaa tggagcaaaa gctcatttct gaagaggact gaatgaaat ggagagcttg    3060 ggcgacctca ccatggagca aaagctcatt tctgaagagg acttgaatca ccggtataca    3120
agtttgtaca aaaaagcagg ctccgcggcc gcccccttca ccatggactt taacaactgc    3180
ggcttcattg atccgcaggc ccagctagct ggagctttgg ccaagcagga catccgacag    3240
ttcgttgctg ccctggacag cggtgccctg ccgatctac aagacgaccg ccataccagt    3300
atctacgaga aggcactctc aacaccaggt tgtcgtgact tcattgaagc ctgcatcgac    3360
cacggcagcc aggtgaacta cgtgagtaga gcaacaagga gtagaggtcg acaccatct    3420 aaccacagtt catcttcaca gatcaacaag aagctggaca aggccgcaat cagctatgcg    3480
gctgactcta gggatccagg aaacctggcg gctctcctta agtaccgccc cggaaacaaa    3540
gtccaggttg atagaaaata tgggcagctt actccactta actcacttgc caagaatctc    3600
acggatgaaa atgccccaga cgtgtactcc tgcatgcaac tcttgctgga ctacggcgcc    3660
tcgccgaata tcgtagacca gggcgagttc acacccttgc accatgtgct gagaaagagc    3720
aaggtgaagg ctgggaagaa ggaactgatt cagctctttc tggaccatcc ggagctggat    3780
atcgatagtt accgaaacgg ggaggtgcgc agactgctgc aggcgcaatt tccggagctt    3840
aagctgccgg aagagcgtca taccgggccg gagattgaca tccaaactct tcaaaggact    3900
ctacgggacg gggacgaaac actgtttgag cagcagttcg ctgagtactt gcagaatctc    3960
aaaggcggag cggataacca actaaatgcc caccaggagg aatacttcgg actgctgcag    4020
gagagcatca gaggggcag gcagcgagcc ttcgatgtca ttttgtccac tggcatggat    4080
atcaactcga gaccaggcag ggccaacgag gccaatctcg tagagacggc cgtgatatac    4140
ggtaactggc aggcgttgga gcgactgctt aaggagccaa acctgcgact tactccagac    4200
tccaagctac taaatgcagt aatcggccgt ctggatgagc caccgtatga tggctccagc    4260
caccagcgct gctttgaatt gctcattaac agcgatcgcg tagacatcaa cgaagctgat    4320
tccgacgccc tggtgcctct gttcttcgct gttaagtacc gcaacacgag tgcgatgcaa    4380
aaactcctga agaacggtgc ctacattggt tctaagagcg catttggcac actacccatc    4440
aaggacatgc cacccgaggt tctcgaagag cacttcgact cgtgtatcac cacaaacgga    4500
gagaggcctg gtgaccagaa ctttgagatc atcatcgatt ataagaacct aatgcgccag    4560
gagagagact ccggactcaa ccagctgcaa gacgaaatgg ccccgatcgc attcatcgcc    4620
gagtcgaagg agatgcgcca cctgctccag cacccgctga tctcgagctt tctattcctc    4680
aagtggcacc gactttccgt gatattctac ctgaacttcc tgatatactc gcttttacc    4740 gcctccataa ttacctacac gctcctcaag ttccacgaaa gcgatcaaag ggctcttact    4800
gcattttccg gattgctttc ctggctggga atcagctacc ttatattacg ggagtgcatc    4860
cagtggataa tgtctccagt tcggtacttt tggtctataa cgaatattat ggaggtggct    4920
```

```
cttattacac tatctatctt tacctgcatg gaatccagct tcgacaagga gacgcagcgc    4980
gtcttagccg tatttaccat cctactcgtc tccatggagt tttgtttact agtgggctcc    5040
ctgccagtgc tctcaatttc gacgcacatg ctgatgctgc gagaggtgtc aaacagcttc    5100
ttaaagagct ttaccctcta ctcgatcttc gtgctcacct tcagcctgtg tttctatatc    5160
ctcttcggca agtcagtgga ggaagaccag tctaaaagcg ctacgccatg tccacctctg    5220
gggaagaagg aggggaagga cgaggaacag ggcttcaaca catttaccaa gcctatcgag    5280
gccgtgatca agaccattgt gatgctgaca ggcgagtttg acgccggaag catccagttt    5340
accagcatct acacctacct gattttcctg ctcttcgtga tctttatgac gatagtgctg    5400
ttcaaccttt tgaacggtct tgcagtgagc gacacccaag taggtctatc gccattcgta    5460
ttatttccct tcgctaatcc catttccggc gttattcatt atctaggtta ttaaggctca    5520
ggcggaactg aacggagcca tttgcagaac caacgtcctt agtcggtacg agcaggttct    5580
cactggccac ggacgcgctg ggttttttgtt gggcaaccat ctcttccgca gcatctgcca    5640
acgtttgatg aacatctacc cgaactactt aagtctgcgt cagatttccg tgctgccgaa    5700
cgatggaaac aaagtgctta ttccaatgag cgatcccttc gaaatgagga cccttaagaa    5760
ggctagcttt cagcaattgc ccctgagtgc tgcagtgccc cagaagaagc tgttggatcc    5820
accgcttaga cttctgccct gctgctgttc cctgctcacc ggaaagtgct cccagatgag    5880
cggccgggtg gtcaaacggg ccctcgaggt aatcgatcag aagaacgcgg cggagcagag    5940
gcggaaacag gaacagatca cgacagtcg actgaagctg atcgagtaca agctggagca    6000
attaatacag ctggtccagg accggaagtg atggagaatg aagggtgggc gcgccgaccc    6060
agctttcttg tacaaagtgg tgacgtaagc tagcaggatc tttgtgaagg aaccttactt    6120
ctgtggtgtg acataattgg acaaactacc tacagagatt taaagctcta aggtaaatat    6180
aaaattttta agtgtataat gtgttaaact actgattcta attgtttgtg tattttagat    6240
tccaacctat ggaactgatg aatgggagca gtggtggaat gcctttaatg aggaaaacct    6300
gttttgctca gaagaaatgc catctagtga tgatgaggct actgctgact ctcaacattc    6360
tactcctcca aaaaagaaga gaaaggtaga agaccccaag gactttcctt cagaattgct    6420
aagttttttg agtcatgctg tgtttagtaa tagaactctt gcttgctttg ctatttacac    6480
cacaaaggaa aaagctgcac tgctatacaa gaaaattatg gaaaaatatt ctgtaacctt    6540
tataagtagg cataacagtt ataatcataa catactgttt tttcttactc cacacaggca    6600
tagagtgtct gctattaata actatgctca aaaattgtgt acctttagct ttttaatttg    6660
taaaggggtt aataaggaat atttgatgta tagtgccttg actagagatc ataatcagcc    6720
ataccacatt tgtagaggtt ttacttgctt taaaaaacct cccacacctc ccctgaacc     6780 tgaaacataa aatgaatgca attgttgttg ttaacttgtt tattgcagct tataatggtt    6840
acaaataaag caatagcatc acaaatttca caaataaagc atttttttca ctgcattcta    6900
gttgtggttt gtccaaactc atcaatgtat cttatcatgt ctggatcccg tttaaactac    6960
gcgtaattca aacagggttc tggcgtcgtt ctcgtactgt tttccccagg ccagtgcttt    7020
agcgttattg aaaaggaag agtatgagta ttcaacattt ccgtgtcgcc cttattccct    7080 ttttttgcggc attttgcctt cctgtttttg ctcacccaga aacgctggtg aaagtaaaag    7140
atgctgaaga tcagttgggt gcacgagtgg gttacatcga actggatctc aacagcggta    7200
agatccttga gagtttcgc cccgaagaac gttttccaat gatgagcact tttaaagttc    7260
tgctatgtgg cgcggtatta tcccgtattg acgccgggca agagcaactc ggtcgccgca    7320
```

```
                                                      -continued tacactattc tcagaatgac ttggttgagt actcaccagt cacagaaaag catcttacgg      7380
atggcatgac agtaagagaa ttatgcagtg ctgccataac catgagtgat aacactgcgg      7440
ccaacttact tctgacaacg atcggaggac cgaaggagct aaccgctttt ttgcacaaca      7500
tgggggatca tgtaactcgc cttgatcgtt gggaaccgga gctgaatgaa gccataccaa      7560
acgacgagcg tgacaccacg atgcctgtag caatggcaac aacgttgcgc aaactattaa      7620
ctggcgaact acttactcta gcttcccggc aacaattaat agactggatg gaggcggata      7680
aagttgcagg accacttctg cgctcggccc ttccggctgg ctggtttatt gctgataaat      7740
ctggagccgg tgagcgtggg tctcgcggta tcattgcagc actggggcca gatggtaagc      7800
cctcccgtat cgtagttatc tacacgacgg ggagtcaggc aactatggat gaacgaaata      7860
gacagatcgc tgagataggt gcctcactga ttaagcattg gtaactgtca gaccaagttt      7920
actcatatat actttagatt gatttaaaac ttcatttta atttaaaagg atctaggtga       7980
agatcctttt tgataatctc atgaccaaaa tcccttaacg tgagttttcg ttccactgag      8040
cgtcagaccc cgtagaaaag atcaaggat cttcttgaga tccttttttt ctgcgcgtaa       8100
tctgctgctt gcaaacaaaa aaaccaccgc taccagcggt ggtttgtttg ccggatcaag      8160
agctaccaac tcttttccg aaggtaactg gcttcagcag agcgcagata ccaaatactg       8220
tccttctagt gtagccgtag ttaggccacc acttcaagaa ctctgtagca ccgcctacat      8280
acctcgctct gctaatcctg ttaccagtgg ctgctgccag tggcgataag tcgtgtctta      8340
ccgggttgga ctcaagacga tagttaccgg ataaggcgca gcggtcgggc tgaacggggg      8400
gttcgtgcac acagcccagc ttggagcgaa cgacctacac cgaactgaga tacctacagc      8460
gtgagctatg agaaagcgcc acgcttcccg aagggagaaa ggcggacagg tatccggtaa      8520
gcggcagggt cggaacagga gagcgcacga gggagcttcc agggggaaac gcctggtatc      8580
tttatagtcc tgtcgggttt cgccacctct gacttgagcg tcgatttttg tgatgctcgt      8640 cagggggggcg gagcctatgg aaaaacgcca gcaacgcggc ctttttacgg ttcctggcct      8700
tttgctggcc ttttgctcac atgttctttc ctgcgttatc ccctgattct gtggataacc      8760
gtattaccgc ctttgagtga gctgataccg ctcgccgcag ccgaacgacc gagcgcagcg      8820
agtcagtgag cgaggaagcg gaaga                                           8845

<210> SEQ ID NO 4
<211> LENGTH: 2984
<212> TYPE: DNA
<213> ORGANISM: Aedes aegypti
<220> FEATURE:
<221> NAME/KEY: CDS
<222> LOCATION: (1)..(2334)

<400> SEQUENCE: 4 atg agt acc gta aac aac gtt cag ctt ttg tgc atc gct gat cca cag         48
Met Ser Thr Val Asn Asn Val Gln Leu Leu Cys Ile Ala Asp Pro Gln
1               5                   10                  15 cgt gca ctg gcg gcc agt ctg gcc gag gga aac ata aaa cac ttt cag         96
Arg Ala Leu Ala Ala Ser Leu Ala Glu Gly Asn Ile Lys His Phe Gln
            20                  25                  30 tac gct ttg agc tgt ggc gcc gat ccg aat gtg cgg gac gaa cgc acg        144
Tyr Ala Leu Ser Cys Gly Ala Asp Pro Asn Val Arg Asp Glu Arg Thr
        35                  40                  45 ggt ttt acg gta ttc gaa cta gct tgc cag aga agc ggt agc gcc gag        192
Gly Phe Thr Val Phe Glu Leu Ala Cys Gln Arg Ser Gly Ser Ala Glu
    50                  55                  60 ttt att cag gaa agc ctc gac aac ggc gcg gat gag caa gcg caa cat        240
```

```
Phe Ile Gln Glu Ser Leu Asp Asn Gly Ala Asp Glu Gln Ala Gln His
 65                  70                  75                  80 gcg agt ggc cag tat ccc atc cac ttt gcc gta tca tca cta gat ccg        288
Ala Ser Gly Gln Tyr Pro Ile His Phe Ala Val Ser Ser Leu Asp Pro
                 85                  90                  95 aac aac gtt cga gcc ctg ttg aaa cat tcc gcc aaa act gtc gat gtg        336
Asn Asn Val Arg Ala Leu Leu Lys His Ser Ala Lys Thr Val Asp Val
            100                 105                 110 ctt tat caa aat cga acg cct ctg cat ctg atc ttc gag gtg atc gac        384
Leu Tyr Gln Asn Arg Thr Pro Leu His Leu Ile Phe Glu Val Ile Asp
        115                 120                 125 aaa agc aat tgg agc gac gcc ttc gaa tgt gtt aaa gtt ctg ctg aag        432
Lys Ser Asn Trp Ser Asp Ala Phe Glu Cys Val Lys Val Leu Leu Lys
    130                 135                 140 aac ggt gcg gac atc aat att ccc aat ggg gat aac cga aca ccc cta        480
Asn Gly Ala Asp Ile Asn Ile Pro Asn Gly Asp Asn Arg Thr Pro Leu
145                 150                 155                 160 ggt gtg ttt gta aag aac tgt aaa acg tgg aaa gcc aat tca gag tac        528
Gly Val Phe Val Lys Asn Cys Lys Thr Trp Lys Ala Asn Ser Glu Tyr
                165                 170                 175 tgg cgg aaa gac ata ctt gag tac tgc ctg aat cag acc aac gtg gac        576
Trp Arg Lys Asp Ile Leu Glu Tyr Cys Leu Asn Gln Thr Asn Val Asp
            180                 185                 190 gtc gac acc ttc agg aag ggg gag ttg agg aag aag atc ggg gac ttc        624
Val Asp Thr Phe Arg Lys Gly Glu Leu Arg Lys Lys Ile Gly Asp Phe
        195                 200                 205 ttc ccg ggc acc aag ata cca tcg tac gtc atg gag acg aat ttg aac        672
Phe Pro Gly Thr Lys Ile Pro Ser Tyr Val Met Glu Thr Asn Leu Asn
    210                 215                 220 gtg cta ata tct ctg ctg aag tcg cac aag gag gca aag ttc gac gtc        720
Val Leu Ile Ser Leu Leu Lys Ser His Lys Glu Ala Lys Phe Asp Val
225                 230                 235                 240 gcg tac agg cag tac aag gaa aag act caa cag gac tcg tca gca tgg        768
Ala Tyr Arg Gln Tyr Lys Glu Lys Thr Gln Gln Asp Ser Ser Ala Trp
                245                 250                 255 aag aaa gat aaa aca caa ctg gtg caa gct gcc gtc cat tct ggg tcc        816
Lys Lys Asp Lys Thr Gln Leu Val Gln Ala Ala Val His Ser Gly Ser
            260                 265                 270 cta gcg tcg gta aag aag ttg tgt gaa gac gat tat gct ttc gac gcc        864
Leu Ala Ser Val Lys Lys Leu Cys Glu Asp Asp Tyr Ala Phe Asp Ala
        275                 280                 285 gat tcg gga ctt gca gat ctc cta gcc aga tgt tgt agt tat gga aac        912
Asp Ser Gly Leu Ala Asp Leu Leu Ala Arg Cys Cys Ser Tyr Gly Asn
    290                 295                 300 cat gat att cta gag tat ttg ctg agc cta gtt ggc cac acg gag aag        960
His Asp Ile Leu Glu Tyr Leu Leu Ser Leu Val Gly His Thr Glu Lys
305                 310                 315                 320 gat ctc aaa cag atc aac gca cat ccg ctg ctg tcg ctg gtc atc aaa       1008
Asp Leu Lys Gln Ile Asn Ala His Pro Leu Leu Ser Leu Val Ile Lys
                325                 330                 335 gag att aac acc ctc aaa aat aag gac aaa tgt ccg ttt ttc aaa tgc       1056
Glu Ile Asn Thr Leu Lys Asn Lys Asp Lys Cys Pro Phe Phe Lys Cys
            340                 345                 350 ctc aaa tgt ttg cta gcc gat ggc cgc atc gaa atc gac aaa aca gac       1104
Leu Lys Cys Leu Leu Ala Asp Gly Arg Ile Glu Ile Asp Lys Thr Asp
        355                 360                 365 gac aaa gac ttc agc gcg ctc cac tat gca gtg aag tac aag gta gac       1152
Asp Lys Asp Phe Ser Ala Leu His Tyr Ala Val Lys Tyr Lys Val Asp
    370                 375                 380 gat gca gta gat ttg ctg ctg aaa agt tcc gcc tac att ggc aag cag       1200
```

```
            Asp Ala Val Asp Leu Leu Leu Lys Ser Ser Ala Tyr Ile Gly Lys Gln
            385                 390                 395                 400 aac atg ttc aag gag ctg ccc att tgt gaa atg agt cca gaa acg ctg          1248
Asn Met Phe Lys Glu Leu Pro Ile Cys Glu Met Ser Pro Glu Thr Leu
                405                 410                 415 gaa agc tac ctt gac tcg tgc ctc aca gcc aac gac aag cga ccg gga          1296
Glu Ser Tyr Leu Asp Ser Cys Leu Thr Ala Asn Asp Lys Arg Pro Gly
            420                 425                 430 gac gat gat tat gaa atc aat atc gat tac tcc tgt ttg gtt cca ccg          1344
Asp Asp Asp Tyr Glu Ile Asn Ile Asp Tyr Ser Cys Leu Val Pro Pro
            435                 440                 445 gaa tac aaa tct aat tac acc ggt gat aga aca gtg gcg gtc agc aat          1392
Glu Tyr Lys Ser Asn Tyr Thr Gly Asp Arg Thr Val Ala Val Ser Asn
    450                 455                 460 ttt gcc gac gaa atg ctg ccg att gtg tac atg tcc aaa tcg tca gat          1440
Phe Ala Asp Glu Met Leu Pro Ile Val Tyr Met Ser Lys Ser Ser Asp
465                 470                 475                 480 ctg aaa cat cta ttg aag cat cca gtg att tcc agt ttt gtg ttg ata          1488
Leu Lys His Leu Leu Lys His Pro Val Ile Ser Ser Phe Val Leu Ile
                485                 490                 495 aaa tgg tta aga ctt agc tta tac ttt tac att aac ttc gta ata tgc          1536
Lys Trp Leu Arg Leu Ser Leu Tyr Phe Tyr Ile Asn Phe Val Ile Cys
            500                 505                 510 aca tgc ttc ttc ctg tgt ttc acg tgg tac gtg gtg gga tgt tac gga          1584
Thr Cys Phe Phe Leu Cys Phe Thr Trp Tyr Val Val Gly Cys Tyr Gly
            515                 520                 525 cag gat aac gtc gat cag ttc ctg aaa gaa tct ctg aga atg ctg tcg          1632
Gln Asp Asn Val Asp Gln Phe Leu Lys Glu Ser Leu Arg Met Leu Ser
            530                 535                 540 ttg ttg ggt gcg aca tat atg gcg ctg aga gaa ctc ggt cag atg atg          1680
Leu Leu Gly Ala Thr Tyr Met Ala Leu Arg Glu Leu Gly Gln Met Met
545                 550                 555                 560 ctt cac gca aag atg tat ttc aaa tcg ttg gaa aac tgg atg gag ctg          1728
Leu His Ala Lys Met Tyr Phe Lys Ser Leu Glu Asn Trp Met Glu Leu
                565                 570                 575 gta ttg atc gtg gca tca ttc acg gtt ctc gtc aag gaa ttc caa cac          1776
Val Leu Ile Val Ala Ser Phe Thr Val Leu Val Lys Glu Phe Gln His
            580                 585                 590 gag atc cgg caa gtc att tca gca gtg gta att ttg ctg tca gcc ttc          1824
Glu Ile Arg Gln Val Ile Ser Ala Val Val Ile Leu Leu Ser Ala Phe
            595                 600                 605 gaa ttt acc ctg ctg gtt gga tcg ctt cca gtg ctc tct ata tcc acg          1872
Glu Phe Thr Leu Leu Val Gly Ser Leu Pro Val Leu Ser Ile Ser Thr
            610                 615                 620 cac atg gtg atg ctc aaa acg gtg tcg aaa aat ttc ctc aag agt ttg          1920
His Met Val Met Leu Lys Thr Val Ser Lys Asn Phe Leu Lys Ser Leu
625                 630                 635                 640 ata ctg tac tcc att gtt ctg gtt tcc ttt gca ttt tgc ttc tac aca          1968
Ile Leu Tyr Ser Ile Val Leu Val Ser Phe Ala Phe Cys Phe Tyr Thr
                645                 650                 655 ttg ttc aac gtg gga agc gcg aaa agt aat gcg gct ggg gca gac ggc          2016
Leu Phe Asn Val Gly Ser Ala Lys Ser Asn Ala Ala Gly Ala Asp Gly
            660                 665                 670 gat gcc gat gga aat gag gac aag ttc aac aaa ttc gcc gac atc aga          2064
Asp Ala Asp Gly Asn Glu Asp Lys Phe Asn Lys Phe Ala Asp Ile Arg
            675                 680                 685 acg tca ctg ctc aaa acg gtt gta atg tta aca gga gaa ttc gaa gct          2112
Thr Ser Leu Leu Lys Thr Val Val Met Leu Thr Gly Glu Phe Glu Ala
    690                 695                 700 gcc aac ata caa ttt gac gcc aac agt acg agc tat ctc att ttc gtc          2160
```

```
Ala Asn Ile Gln Phe Asp Ala Asn Ser Thr Ser Tyr Leu Ile Phe Val
705                 710                 715                 720
ctg ttc ata ttc ttc gtg gcc atc gtg atc ttc aat ctg atg aac ggt      2208
Leu Phe Ile Phe Phe Val Ala Ile Val Ile Phe Asn Leu Met Asn Gly
                725                 730                 735
ctg gct gtt agc gac act gcg gca atc aaa gct gag gca gaa ttg ata      2256
Leu Ala Val Ser Asp Thr Ala Ala Ile Lys Ala Glu Ala Glu Leu Ile
            740                 745                 750
gga ctg tcg caa aaa gtt gaa gtc att tcc aag tac gag aac gca ctg      2304
Gly Leu Ser Gln Lys Val Glu Val Ile Ser Lys Tyr Glu Asn Ala Leu
        755                 760                 765
aaa atg acc gga atc aac ggt ttt ctg tga gtaaccgaca tacaccgaca       2354
Lys Met Thr Gly Ile Asn Gly Phe Leu
    770                 775
agcgtcttat ctctaatcat ccctttgccc atttctagca cccaatccat attcaagctg   2414
tttccgtcga cattcctgca gctgttcccg gagtacctac cgatgcacta cgtcatagtg   2474
acgcccaacc agtcgaatag cattttcata ccgcgaccgt tccacaacgg tgacgcgaca   2534
tcccgaatcg acgtcgaaag tcacatcgag ctccttccgc tgaacaaaca tccggaggag   2594
aagatccgcc tgacgatcgg atgctgcgtg ctgccctcgt tctcccggat ggatgggaaa   2654
atcatgaagt acgccaagga gattttgcat tcgcgcaaca ggaagagcca gacagtggat   2714
aggatacaac ccttggaggc acgattgagc aagattgaac gggacctcga gcggattcta   2774
caatatctga gccactctca aactgtgaac taatctgtgt tttgtcgtgc tttgtagaat   2834
taagaaaata gtttatttat ctgttgacaa gatttcatgg tttaatcgcg cattttaaaa   2894
cagttccagt aatacattta tttaattgat attgtctgat tttactaata gaatttgtta   2954
cgattttaat aaaataataa tttacacaat                                   2984

<210> SEQ ID NO 5
<211> LENGTH: 777
<212> TYPE: PRT
<213> ORGANISM: Aedes aegypti

<400> SEQUENCE: 5

Met Ser Thr Val Asn Asn Val Gln Leu Leu Cys Ile Ala Asp Pro Gln
1               5                   10                  15

Arg Ala Leu Ala Ala Ser Leu Ala Glu Gly Asn Ile Lys His Phe Gln
            20                  25                  30

Tyr Ala Leu Ser Cys Gly Ala Asp Pro Asn Val Arg Asp Glu Arg Thr
        35                  40                  45

Gly Phe Thr Val Phe Glu Leu Ala Cys Gln Arg Ser Gly Ser Ala Glu
    50                  55                  60

Phe Ile Gln Glu Ser Leu Asp Asn Gly Ala Asp Glu Gln Ala Gln His
65                  70                  75                  80

Ala Ser Gly Gln Tyr Pro Ile His Phe Ala Val Ser Ser Leu Asp Pro
                85                  90                  95

Asn Asn Val Arg Ala Leu Leu Lys His Ser Ala Lys Thr Val Asp Val
            100                 105                 110

Leu Tyr Gln Asn Arg Thr Pro Leu His Leu Ile Phe Glu Val Ile Asp
        115                 120                 125

Lys Ser Asn Trp Ser Asp Ala Phe Glu Cys Val Lys Val Leu Leu Lys
    130                 135                 140

Asn Gly Ala Asp Ile Asn Ile Pro Asn Gly Asp Asn Arg Thr Pro Leu
145                 150                 155                 160

Gly Val Phe Val Lys Asn Cys Lys Thr Trp Lys Ala Asn Ser Glu Tyr
```

```
                            165                 170                 175
Trp Arg Lys Asp Ile Leu Glu Tyr Cys Leu Asn Gln Thr Asn Val Asp
            180                 185                 190

Val Asp Thr Phe Arg Lys Gly Glu Leu Arg Lys Lys Ile Gly Asp Phe
        195                 200                 205

Phe Pro Gly Thr Lys Ile Pro Ser Tyr Val Met Glu Thr Asn Leu Asn
    210                 215                 220

Val Leu Ile Ser Leu Leu Lys Ser His Lys Glu Ala Lys Phe Asp Val
225                 230                 235                 240

Ala Tyr Arg Gln Tyr Lys Glu Lys Thr Gln Gln Asp Ser Ser Ala Trp
                245                 250                 255

Lys Lys Asp Lys Thr Gln Leu Val Gln Ala Ala Val His Ser Gly Ser
            260                 265                 270

Leu Ala Ser Val Lys Lys Leu Cys Glu Asp Asp Tyr Ala Phe Asp Ala
        275                 280                 285

Asp Ser Gly Leu Ala Asp Leu Leu Ala Arg Cys Cys Ser Tyr Gly Asn
    290                 295                 300

His Asp Ile Leu Glu Tyr Leu Leu Ser Leu Val Gly His Thr Glu Lys
305                 310                 315                 320

Asp Leu Lys Gln Ile Asn Ala His Pro Leu Leu Ser Leu Val Ile Lys
                325                 330                 335

Glu Ile Asn Thr Leu Lys Asn Lys Asp Lys Cys Pro Phe Phe Lys Cys
            340                 345                 350

Leu Lys Cys Leu Leu Ala Asp Gly Arg Ile Glu Ile Asp Lys Thr Asp
        355                 360                 365

Asp Lys Asp Phe Ser Ala Leu His Tyr Ala Val Lys Tyr Lys Val Asp
    370                 375                 380

Asp Ala Val Asp Leu Leu Lys Ser Ser Ala Tyr Ile Gly Lys Gln
385                 390                 395                 400

Asn Met Phe Lys Glu Leu Pro Ile Cys Glu Met Ser Pro Glu Thr Leu
                405                 410                 415

Glu Ser Tyr Leu Asp Ser Cys Leu Thr Ala Asn Asp Lys Arg Pro Gly
            420                 425                 430

Asp Asp Asp Tyr Glu Ile Asn Ile Asp Tyr Ser Cys Leu Val Pro Pro
        435                 440                 445

Glu Tyr Lys Ser Asn Tyr Thr Gly Asp Arg Thr Val Ala Val Ser Asn
    450                 455                 460

Phe Ala Asp Glu Met Leu Pro Ile Val Tyr Met Ser Lys Ser Ser Asp
465                 470                 475                 480

Leu Lys His Leu Leu Lys His Pro Val Ile Ser Ser Phe Val Leu Ile
                485                 490                 495

Lys Trp Leu Arg Leu Ser Leu Tyr Phe Tyr Ile Asn Phe Val Ile Cys
            500                 505                 510

Thr Cys Phe Phe Leu Cys Phe Thr Trp Tyr Val Val Gly Cys Tyr Gly
        515                 520                 525

Gln Asp Asn Val Asp Gln Phe Leu Lys Glu Ser Leu Arg Met Leu Ser
    530                 535                 540

Leu Leu Gly Ala Thr Tyr Met Ala Leu Arg Glu Leu Gly Gln Met Met
545                 550                 555                 560

Leu His Ala Lys Met Tyr Phe Lys Ser Leu Glu Asn Trp Met Glu Leu
                565                 570                 575

Val Leu Ile Val Ala Ser Phe Thr Val Leu Val Lys Glu Phe Gln His
            580                 585                 590
```

-continued

```
Glu Ile Arg Gln Val Ile Ser Ala Val Val Ile Leu Leu Ser Ala Phe
            595                 600                 605
Glu Phe Thr Leu Leu Val Gly Ser Leu Pro Val Leu Ser Ile Ser Thr
610                 615                 620
His Met Val Met Leu Lys Thr Val Ser Lys Asn Phe Leu Lys Ser Leu
625                 630                 635                 640
Ile Leu Tyr Ser Ile Val Leu Val Ser Phe Ala Phe Cys Phe Tyr Thr
                645                 650                 655
Leu Phe Asn Val Gly Ser Ala Lys Ser Asn Ala Ala Gly Ala Asp Gly
            660                 665                 670
Asp Ala Asp Gly Asn Glu Asp Lys Phe Asn Lys Phe Ala Asp Ile Arg
    675                 680                 685
Thr Ser Leu Leu Lys Thr Val Val Met Leu Thr Gly Glu Phe Glu Ala
690                 695                 700
Ala Asn Ile Gln Phe Asp Ala Asn Ser Thr Ser Tyr Leu Ile Phe Val
705                 710                 715                 720
Leu Phe Ile Phe Phe Val Ala Ile Val Ile Phe Asn Leu Met Asn Gly
                725                 730                 735
Leu Ala Val Ser Asp Thr Ala Ala Ile Lys Ala Glu Ala Glu Leu Ile
            740                 745                 750
Gly Leu Ser Gln Lys Val Glu Val Ile Ser Lys Tyr Glu Asn Ala Leu
    755                 760                 765
Lys Met Thr Gly Ile Asn Gly Phe Leu
770                 775
```

<210> SEQ ID NO 6
<211> LENGTH: 50448
<212> TYPE: DNA
<213> ORGANISM: Anopheles gambiae

<400> SEQUENCE: 6

```
catcggcgca atcgggtcgt tccgcgttgt tgcttatagt ccaactggac tggtccatat      60
cgtttccatc ttgttgcgtc gctcgtacaa ggacaattta gcgacaaaat gcttttttccg    120
tatgaaaatt cacgtctacg gtcctgcgtg gctacggtcg gtacgttgtt cccttgccgg    180
cttcatagga aatgtatcaa acgctctccc cgtttttctct atacctaata ttttttctcc    240
gcaaattgaa catgctttgg caatatcaat tgaaatggat aatatacatt ttgtaccgtc    300
tatttatagt gaagtgcgca aacgcttccc gaaggttatc aagttggtaa gtagctttga    360
tcgggtttaa ctattccttt gtcactctgt gcttaattat tcggtgccca ttatcgttag    420
gatgatatcg ttctgccgcc cccaatcagc ttcgacgtgc cggaagacga tacgaagctg    480
ccggaggcga aggcctcgtt cctatgcgac acgtccggtg ccgatctggt gcggcaattt    540
ttggaacaat actttaccat ctacgattcc gataataggc aaccgctgct ggaagcctat    600
cacgagcacg ccatgttttc gctgacggtt aacacaacct accaaagcaa tcagcaaaag    660
tgagtacatc ttccactgtt ccgtgcgttg tctgtgcttt gtgatacatt ttagactata    720
aatccaccct tttttttgtt gttgtcaaat gcttaggttg ggtgcgtaca tatccggaag    780
tcgcaacatt aagcacaaga cagacctgga ctcccgctgt cggtttctga agcagggacg    840
tctgcaggtc gtatcgcatc tgtcctcact gccaccaacc aagcacgatc tgacatcgtt    900
tgccgtagat ctaaccctgt tcacggtaag taagacttgc ggtattagct cccccatcat    960
tcaaagcatt taacatttcg tttccaactg ttcgaatgtt cacttcacag ccgcacatgc   1020
tgcaactaac cgtcacgggc gtgtttaagg agcgcaaggg cagcggcaat atggagcaga   1080
```

```
tacgatcgtt tcagcgtacg ctcgtgatcg taccgtcgaa cggtggtttc tgcatacgca    1140
acgaaatgat gcacgtgaac acggtgacgc gggcacagga aaacaaagcg ttcaagggggg   1200 cagaaaacgg catgccgcag cagcaagcgg caccatcggc cgcccccacc gtaccggccg    1260
tggtcggtgt ggccgcgact gttccgctgg tgccggacga caacaccaag ctgcagatga    1320
tacaggcgct gtcggcgcag accaacatga cgccgaatg gagcaaacgc tgcctggagg     1380
aaacgaactg ggactatccg cgtgccgagt ttgcgttcgc cgagctacac aaacagaacc    1440
ggataccgcc ggaagcgttc agaacgaatt aaaccatttt tgtaggcgga atgtagtgga    1500
aagtaattca tcaatcataa gttagtttgt tttaagggtt agcagacgtt agcggacaaa    1560
tttggtcggt tattacaata ggttttaggt tttctcgtac agatcatgcg ttgtactttt    1620
cccgttgatt tttttcttc ctcacacaca cacacgcaac ccaaagtagt gcgcccccggc   1680 aagcaaatat gcgttgagtt aaggaagaaa aaaacacac aaaaacaaca tattacccgc     1740
actttgctcg ggccggaaaa cgcactacaa ggtcgctcgt ttgctacaca tattttcgtt    1800
acccaaagcg caatatctca cggaacatgg ttcgcgtaag atattgcact tcggagcaaa    1860
ggacaaagct agttttgttt tgtctctcaa caaccgaacg tgacgagcaa atgttggaaa    1920
acagattgtt tgtatgaatt atgctgaaaa aaaaacattc accttaccag ccagtcacgg    1980
tgataggaac gttttactc tctacgttcc aacgtaatat gtccggaaca ttgcaatcat     2040
gtcgcaacga gtttgctttt cggtttctcc tatactaaga tgtacagaaa gttgattaaa    2100
gattcacaat ttccacatat tttttaatgc tagccagcaa tttattctca tcacatcacg    2160
gtgtgtagtg cgtgtgttac ggagagcgta gctttgttag ttgtagaccg gttgcgtcat    2220
gattaccagc taggacctga acaccgccac agacgaccca ggtcaagtca aggttgagct    2280
ttgaatttgc gtctgttctg acatttttca ttcgactgga aagcaaactg tgttaatgtt    2340
tatataatat gcctaacaaa attgaacctg agcttttgag gaattttatt tttatctttt    2400
tttgcgtgta ttcaagcaat tcgttagcgg aaatagtata tgaattttaa ctacggcaca    2460
cactacattg tacagcttat ttagaacgaa catgaatgag ggtgaatatg aaaaaaagta    2520
atataaataa tacatggtaa ttctagtaat gacagaagca aatgctgatg cggattttt     2580 tttcattgtt ttattgaaag aaattattta agtttgtagg tgtatttgtg ccattttcag    2640
tatgaatact gctttaacaa cttgtagtta agtttgcaac aattgttttt gttttttttt    2700
tttttacttt tagttttacg aaattctata acaacattag caatgttacc aatttgatta    2760
agttacattt gttctttttt tgtttctata acagttacca ttattcatga ggcattctac    2820
tggtgttttt ttgagcttta gcttttgact tcatgcgttt atggtttctt ttaatgaatt    2880
tgaatccgca atttaaagat caagtgagat gaattgtttc ctcagttttc aaccattttt    2940 ctttttttc ttccttgcct tttctagcct aatatttgag ggataccat acaccagact      3000 atctttttat gtaatctaat gtctctggga taatccaaaa gttattaccc gtgtataacg    3060
acccccttaa tttgatgttg acattttcg acctaaagta taagacacta aatattgttt     3120
taattatttg cctctttacc tgcgatcata cctgtcgaat aggagaaacc ggttgaaaga    3180
atctactcaa tacgtctttt atgtaattct atttatttca taattatacc cgtgtagaaa    3240 tgttttcaa ttattcgtaa aaacataaca ttcaaacaca tgcacatcag cctttttctt     3300
tggtttactg gctcaatttt tcatcggtat agacagacag cgaacaaatc acttgcaaga    3360
tttacgtatt tacataatgc atatttaaca tatctacttt caactaatct tatttcactc    3420
aatcattttg taaagcaatt gtgtctttcc atagcaaaat cctctattta agtgaagatt    3480
```

```
taaaggcaat gatcggaagg acatgcacca tcgatccact aaacttgttg cgttacacag    3540
ttgccgttac atggtagcgt tacaaaagtt atcttgcgtg ttacaaacat caacgcgcgt    3600
tactgctttg taatgaataa ttaaaaaaac agtgagcaaa tatctttact ttaaaattcc    3660
taccaacgaa aacaaaacca atctcatcag gcacattctg agagcctcgt aagcctcgtc    3720
agggagttaa acggtaggac aacaaggggc acattttgt  cgactactgt aactgaaatt    3780
acattggttg aggcaaagca agtgataaat ggacgattgt gaagccaccg taacctaaca    3840
atgataagcg atcgcaaata aaagcgagag caggagcgca atcaatcaat tgtcgtcccg    3900
gtaaaagggc gtagcctaac gggatttcaa tgcttaatta aacgcccaat ggcggaagga    3960
ataagataat ggcaacgagg ggcagttcat aaaaaaatca atttagtatg attggtacga    4020
aaaaaaaata tccttggaac ttaaaccaca gcttcattgt cgtttaaggc agcgtttaca    4080
ttaaagccag aagaggctat ataaataac  caagtaatgg tcgattatta aatggatatt    4140
caagaagatt tcagtttcat gtaaaaaaaa cacacgtaat gatggcagta cacgtatact    4200
aaatccacta attatttagt gttgctattt ggtttatgtg ataaagagag ctcttacaag    4260
ctgcaagctg caattgtaga atggaagacg cttcaagagg atacatatta aacacaaaca    4320
attgcattaa aaataatcac ttaatgcatt acactaattt taccaattt  ccacaaaaac    4380 gtaccagtta aaataacgta caccaaaaga aagttttcc  ctctccttgt tttaagaaca    4440
caacgaccaa aaagtcctcc ctcaatgcat gcaggattgc ctaccggtag cgcaattga     4500 agctgaactc tcttgaacgg ctgagtacaa aatctgctct tcccaaaaat gtgccttctg    4560
tcggaagaaa tagccacaca cgcacacacc agaacgatat tatatgcttc tatctaccag    4620
cttaccctct ggcaaagggt tggtcagttg ccggtagcag aaatgatatc agtcaatgtg    4680
cgacccggtg ttagaacaca cacgctaggg tccgaaagtg aaccgacccg cgccttccaa    4740
atcaattgcg aacgtgctgt agagcgcacc tgtgctatct gttgaacaag tcgtaccgag    4800
agccaacgtt tgacgctgtg aaacaatagt gtgttgtagg ttgtgtccac aagtagcagc    4860
tacttgcaaa agggtgccat cgaattagtt gaattgtgtt ttagtgcaac cgtacagacc    4920
gtgcggtggt tcgccgattg ttcactggtg tcgcagacaa acgatccgat ccaatcaaca    4980
tgaccgagcg acgctggtca ggcagtgtac agctagtaag gaatgattat ccaccgcttt    5040
ccatccagtg tacgccacgt gtacttatcc ctgcccgtgt cgatttagaa agctgagcgg    5100
agtttgctgg agaacaactt gaaccagttc atcaaggcgc tggcgaatga agccgacgtt    5160
aatgggaaga tgagtaaatt tccgtattca aagtattcgc tgtttgagat ggcttgcaaa    5220
acaccgggaa gagccaaatt tattgcggcc tgcctgcaac gtggtgcctt tgtggcgcag    5280
gtaagctaca gttgtcgtat tgattcgtac cgtaagctgt accacctgct gttcaggagt    5340
cagcaagcgt tagagtagtc aaagaagaat gctgggaatt agtattatgt tatactgtct    5400
atcgcaagct ttcattaaat agtgaaaacc aaaacttctg cgtttatgta actaatctag    5460
aaattagcct gcgccataac ggaaacctgc tgaaaaccca atgaaggcgt ggttgtgacc    5520
aaacttacac attagcaagt ttctgtaccg gttgctctat tcgattaaga ttaatcaaca    5580
tgaatttggt ggtttagata actataatga gattacggta gcagcagggg cattgccatt    5640
ttatactaca cgtttatcgc ccgtagctta cagataagat accttgagac acattagttt    5700
ttgtatgtgt ttatttcaaa tgtatcgcta gcagctagat caagaagggt tgattgattt    5760
acttaatctc aaaaagtaat acagcaaaaa tgtcttgagg ctagaccacc tctaaactgt    5820
gctgatggaa ctcttctccc atgcgtgatt attatcatca taccttcggt taggctttac    5880
```

```
agactaccca gaaatgaaac gttttatcta gccattaaag tagtggtttg aagagagcgg    5940
attgatgcgt cagtgttcct tgatcgtcta tagcaagcgg catcatcgga gtgacacatc    6000
tcctgttttg ataagaggag catggttttc ctttaaatgt tcataatttg aagtccctcc    6060
attaaagtac ctcaaatatt atattgtgaa aatggcagca attttcgttg aatatacgcg    6120
tgcacttagc atttagttca tttcacggcc ctgtttggag cacatcttgg acaaattgtt    6180
aaacggtcgc gcatgcagtt tagcatatca tgaacattat cagcaggcca ttaacgacgt    6240
tatcggtaca gtaacacaca ctcaggcact aatccaagac actgcttttg agcaatggcc    6300
acaatagcca caagtaaaac gttggaatgt gtccttctga tactcaacga accaacattg    6360
cataattgag tcaacatcgc agcaatgtat gcaagttgtt ccgtgataga gtgatttgca    6420
gtagaaaaat aataatcgcc aacttcttct tcttcttctt tggcgcaaca actgttgtcg    6480
gtcaaggcct gcctgtacca cttttgtggg gttggctttc agtgacttat gtattggatt    6540
acccatccat agcaggatag tcacagtcct atgtatggcg gcacgctccg tttggagctg    6600
gaacccatga cgggcatgtt gttaagtcgt acgagttgac cactgtacca cgagaccggc    6660
tttatcgcca acacttttcc aaaaataatc tgcagaacca gtacgacaag taggtcggaa    6720
tgtcttgatc gtagataatt gcttagtgca ctaagggtcg gacaaaatta tacattacgc    6780
tttttaaaat acatactttc ctcctagaaa aatccctata ccaacgagta tcccatccac    6840
ctggccgcgc tatccttcga ctgcgcaaat cttttccgaac tgctcagcgc cccgcgcatt    6900
caggtggacc aaaagtacga agatcgcaca gcgctgtacc tgttgttcga acagatcgac    6960
agcaacaatt ggaagcatgt gtttgagtgt gttaaattgc tgctaaaata cgacgccaac    7020
ataaacgcaa ccgataagta cagtgtgtca ccgatagctc tgctagtaac agctttatac    7080
gacgattgga gaaaggaaat tcttgaatac tgtttgcaga actacagcgt gaacgtagac    7140
taccggggac agcaggcgag aaaagcgatc ctgaagaact tccctggcac gaacattccc    7200
atctacgaca tggaaaaggc taccgtggat gtgttgcgga caaactgaa cgtcgagacg    7260
gaggacgagt tcttgcggc atacgagaag tactgtcagc aaaacaatgg tcacgtgccg    7320
cccgaagaag aacgcgccga gctgctatcc gtagccgtgt atcgagcgaa gctgaccgcc    7380
gctcagaagc tcgttgaagg gcagatagta gagggcaagt ttaccggcaa tccaaaacta    7440
cttttcgggcc tgctggccaa atgttgtaat cgggggaacg agcagatgct cgaatggttg    7500
ctgcaaatca taccggacga tgaggtagcg ctagtcaaca aggatcctct gctctcgctg    7560
ctcgtcaaga agatcgacgt gtacaaggac aagaaggaga gttcctatat ccgtagcatg    7620
cgcatcttgc tgaacgatcc acgtctagat atcgacaaga tcgatgtgaa aaaatgtacg    7680
gcgatgcatt acgccgtcaa gtacaagaac gattacgccc aagagctgct gctggacgag    7740
ggagcgtaca tctggggcga aaatatattc ggcgatctgc cgatcagcga gatggactcg    7800
tccctgctgg agaagcatct ggactcgtgc gtcaccaaca acgattgcaa gccgggcgac    7860
gaggactacg aagtgaggat cagctttgcc aactttatac cgccagccct caatccaaat    7920
tccgaggacg agatgcgacc gatcgtacgc atcgcacagt cacccaattc gaagcatctc    7980
ctctggcatc ccgtcatatc gagcatcttg ttgctgaagt ggatgaaagt gatccacctt    8040
ctctacctaa atctggtaat ctgtaccgtg tgtttcgttt cgtttgcgac atatatcgtg    8100
ttttgctatg cgcgggaaga taccattctc aaacaattgc tgtattgcct gtcagtgttg    8160
ggatgtgtgt atttgatcgt ccgtgaagcg tcccagttaa gactaagccc cgccacttat    8220
ctgttatcaa tggagaattt gatggagata ttgctaatcg gtgggtatgt tgcggtgctg    8280
```

```
gcgcacgagt cagccgatga gacatggtca atggtgctgg ttggagtgct tctgctgcta    8340
ggggtggagc ttacgctgca atttggcatg ctcccggtga actccattgc caccaatatg    8400
gtcatgctga agacggttac gaaaaacttt ctcatctttt tgagcttgta ctcgatcata    8460
ttggcgtcgt ttacgttaag cttttacaca gtgtttaaga tgaaggatat tgctcagctg    8520
cacgagacga acggacccga acaagcgaca ggccataacc aggacattga agatgagcat    8580
cttttccaca attttggtga gattcagctg gcgctgataa aaactacagt aatgttcact    8640
ggtaagtaca cagtcgaatt atgaacgtaa atggtcaaat atatcaaatt tcgaatatca    8700
atcgaattcg gtaatagtcc cattcagcaa gacatctcga cctaatgttt ctgtgtacat    8760
ctttagggga gtttgatgcg gcagacttac catataaatc atcctggccc atgtatgtgc    8820
tgtttccagt gtttgtgttc tctgtaacga ttgtcataaa caacctgatc aatggtctgg    8880
ccgtcagcga cacaacggtt cgtaatgact tgctgtcggg gacggaactc atttctaata    8940
acttcgcata tcaattacag accattcggg cagaatccga attagtaggc attacagaga    9000
tggtatccat tatccgtcgc tacgaaaagg cacaggaagc actcgagttc atccattcaa    9060
cgtaagtcgt ttttagacag ttgtttcttg ttcgttttgg tagatcattc tggatgtggt    9120
ggagtaatcg gtaacattgt acacgtttga ttaattatta gtaaaccaac gtattagatt    9180
aattgttgcc tgttggttga acttataatt ttttgactga actcaaattt taactgaaaa    9240
tttatcattt cctctcccct ctagattggg caaaataaag ttcctgaatc tgggatggct    9300
gtttcctaat atgaatcttt tttgcaacga gaaaccgctg catcaaattg tgctgaagcc    9360
tagcgatcaa agcctatcca caatccggca ggatcaacaa atcatcgtaa cggttgaaaa    9420
tggtggaatg cgaaagaaac gtacgagcag cacgaataat acggctgcaa atagttcgga    9480
aatgagaaat ggccaagaag aaattcaact tgtcactacg aatgaaacta tttccaacat    9540
ggagaatggt caagagcgaa ttagatttac tagcaaaaat tgtcagcttc agacgcataa    9600
aacctatcag gtaaagagtt tactgtacaa gccttttaag ggaatgctga gcaagatagt    9660
tacgaaatcg atcgagatgt tgaactcccg ccaagtgcac ggtgattcac aggcgcatcg    9720
cctatcacgc gtggaacaga acatgacaaa tatgatgcag gaactaaagg agttgaagga    9780
attggtacgg ggcattggga aaggacgacg tggagatgat aagaaaagct agaatgtagc    9840
tccttagttt tgtgagaacg gcctggccgt gttatcaatt atagttacat tcaaaaacat    9900
aaacctcacc tgacgggtaa ataaaacaat accttggtta caattctgca caaatacttg    9960
caaggattta aatattgatt acctaaaaca atatcagaag ttaggaaacg ttggcatcta    10020
tctgtcaagc atgttgcata ctattaggcg catacgcatc atgattttag atcaaatctt    10080
tcctgtcggt tcgaagaaga gtttctcaca aattaaaaaa tttgtattgt tttgtgagta    10140
agacacgaac ggcaatcgat acaatcgata tgaagcatct agtttaaacc gaaatgtgac    10200
acgtcccgca aagaaaagtt atatgtgatt caataaataa atataatcga atcacagatt    10260
cgatgccatg ccaatgccat tggcaaaata ccaatcgcag aaattaatta aagctgactc    10320
atgaaagaat acagcacccc tctgccatca gtatggtcga agtaaatcaa gctgcaagag    10380
gatccagcaa cctccgggcg caacacgcgg aatgataaca taaacattcc atggcgaaag    10440
aattcgtacc atatgaaaga tatcatccgg cgtgaaagca tacaggggtt tcaagtcgtt    10500
tttcaaaatg cgctgcatat tttgtcgctc acgaaattta ctttgattag tctagtacgt    10560
acttgagctg gttcaatgtt aatttatcc cgtccaagtt taatttgac agccctatcg       10620 aggtgtaggt ttgcctatct tttctactac ctatctctaa taaatctttt gacacattgt    10680
```

-continued

| | | | | | |
|---|---|---|---|---|---|
| atgcacaaaa | acggaaagaa | taagaagaag | cttcaaaatg | ataggtcatt | tgactcataa | 10740 |
| ctcgtttaat | gcactgcgta | atttgcattt | gaaaatgcac | accaattttg | attgtctacg | 10800 |
| tttccgttgg | cttgaatttg | gcagatagcg | ccaggtaccg | tggtagaaca | aacgtagaca | 10860 |
| attttggagt | gcaattttca | aatgctaatt | actcagtgaa | taaaaagagt | tatgggtaaa | 10920 |
| ataacccatc | attttacaga | atattttaa | acaatatata | cgttaaattt | cataaatata | 10980 |
| acgctaaaac | gcattaaagc | attggtttca | atttcaatta | gcaaaactct | gcgtaaggct | 11040 |
| gctgaaaaac | accttcatcg | ttttaaaaat | catattgtgc | ctttgaaact | agcaacggtg | 11100 |
| agctgaaata | acaatatttg | acagctaaac | taatcttgag | ctactgaaat | tgttttgcag | 11160 |
| actttcgatt | ctgacttata | aaaccctata | tattctttcc | gttttcgaaa | aacgaatagt | 11220 |
| acaattgctc | atatttcagt | tagccgatcg | cttcatcgtc | aactttctca | agattctca | 11280 |
| gagattctca | aaccgatttt | gtgccgaatc | gacaatcgtt | gagaacgtag | atttctcaaa | 11340 |
| ggcactttag | tgcttgagaa | aaagagcgtt | aagaaacccc | atggcccgc | ggtctatgag | 11400 |
| ctgttcccta | cattcgttcg | attattcact | ctgtgatcgt | gctgcgagaa | gcaactttct | 11460 |
| ttcagtgccc | ccgcgcttaa | ttgtatctaa | gttctgtttg | atttttgggt | ttctgttcgt | 11520 |
| tcataaagat | tcccaactcg | tactgtgtgg | tgcgttgtga | gaattttatg | aataagtatt | 11580 |
| gtgttaacaa | ctacaatagt | gaatccttcc | agaagcgatc | ctctgacaat | agcataaagt | 11640 |
| ttcgaagcga | gaaaatcatc | cgaaaaaaac | aaaaagcaaa | gtgcgtctgt | agtttgacga | 11700 |
| tcgtttcaaa | gtagtggtga | tagtagcgta | tggaagactc | ataaaattga | ctggaccgtg | 11760 |
| tccacatatg | gaacgtcgtg | aaacgaatga | agtgtcgccg | tccaaaaacg | gaagtcattc | 11820 |
| cggtgtcgtg | cttgaactgg | tgtcatttat | cgacgggcag | tgttggctat | tgtagcatac | 11880 |
| attcgactac | ctaccacgct | accacgcaat | tcttcatcta | aaccccacca | gtatgcaggt | 11940 |
| attaccgtca | gcattgtcag | caaaatgcga | tgcggcgctt | gctgcaagct | tcgatgcgaa | 12000 |
| cgacctgtca | aagttcaacc | gagcgctttg | caacggggca | aacgtgaatc | tacgcgatcg | 12060 |
| tgactcgcgg | tacacggtgt | tcgaattagc | atgcaaaact | cccggcaaga | agcagttcat | 12120 |
| ccgagcctgt | ctaaatcatg | gagcggtact | gtcgaggtg | cgtatggcgt | ggggttttg | 12180 |
| tctttctttc | ttttgttttt | ttttgctttg | tttgacatga | agtgatttta | attttacgac | 12240 |
| tgctaaatgc | tcggaggtga | taggcctatc | cttcctcatg | agttcttgca | ggtcccacag | 12300 |
| gcgttttggt | atagcacgat | ggcaaaatct | gtgggactcg | gatgaactcg | gaaagttttt | 12360 |
| atatacagtc | actccttgtg | taagcttgaa | gccttggttc | cataacaccc | ctggcgatct | 12420 |
| tgcgttcatt | tgaatgatgg | ctagacttag | gtctaatcat | ttcgcattgg | gtgcacatct | 12480 |
| ccagcgtgta | ggactggtcg | actccaaggt | atgtggctgc | gggcttggat | tccacgacat | 12540 |
| tgatcatcta | ttgtggtcct | gcgtggaata | cgagtctgct | cgacctgctt | tgctggacgc | 12600 |
| ggtcgaaaga | ctaggaaaat | gtactgatat | tccgattcgg | gatatattag | cggcatcgga | 12660 |
| gtgggaattc | ctgaaggcca | tattcgaatt | ctgtaggaga | aacggcttaa | ctgtgtgact | 12720 |
| ttcttcttct | tcttctttgg | ctcaacaacc | gatgtcggtc | aaggcctgcc | tgtacccact | 12780 |
| tgtgggcttg | gctttcagtg | actaattgat | tccccccat | agcaggatag | tcagtcctac | 12840 |
| gtatggcggc | gcggtctata | tggggattga | acccatgacg | ggcatgttgt | taagtcattc | 12900 |
| gagttgacga | ctgtactacg | agaccggcta | actgtgtgac | tttacttaag | caaaatatat | 12960 |
| gtgaaccaac | caacattatt | ggcaacagca | attttgcatc | ctatttgatt | tcctcttgtt | 13020 |
| tgtccatgtg | ttacatgttg | tacatcgctt | gtatgtttgt | gatggatgaa | tgtatgcatg | 13080 |

```
aatgtaagaa tgaataagtg caatgtgtat ggctgagtaa tcggcattga cggcagacag   13140
aagatctttg cttgaacgat gttcttgcaa agatttaact ggataactgg ataactgaaa   13200
caatacagac ccccgccatg tcactcggac cactgatgga aaggactaca acgatacaga   13260
ccctcgcaat gtgatttggg ccaccaaact ggactacact cggaccactt cggatggata   13320
gatttaacga aatgcctcga ttccaaacga tatagacccc cgcaatgcaa tttggaatat   13380
tgaactgaaa tagacaacct cgaaatccga atgatgtaga ccttcgccac gcttatagga   13440
ccaaaaatca tggactgaat tgttcaaaac caaaccgtcc gagtacaccc ggaataaggg   13500
caccttggct cagagaagga aatgtcaata tggattgtag cgccatgaac tacctttgta   13560
ttttctactc ttaagcaata cggccttttt ggaccgttac tcctgaataa aaaaaaaatg   13620
ctcgaaggtg caatatgggg atgcttttcc agcacgcact ggaagagatc gtttgtgacc   13680
ggccctcaaa aagattttg ggtggggccg ctgggttggt cattcgcact ttgaaacatt   13740
ggctcagcgt ttggagcagc gcttagagta aacaatacta tcgaaaacgc tagccgccgt   13800
ttcggaacag ctgcaaacat ttgcctcatt ttcttccaag gaatgactca ttttcttcca   13860
aggaaaaaca aaaagttatt tgtaggtggc aattattatt tgataaacac tcgacttgca   13920
tgagccagtg atcaagcgca tgtcagaccg ttaaaagtag ctctgaaggg catttgacgg   13980
atagaaacat gtccggatgt atccatgata ttttttaacaa atattaaaca tattctgccc   14040
gacgaagata ataatcttag aaacattaaa aagttccgac attctctgat gtacatgtgg   14100
atttgtaatt ataactagaa attcttctat ttctatcttc ctagtcgatt gagaggctcc   14160
gtagattggt agtccatagt atgcagtatg tataaggccg cggggcaatg gggattctca   14220
acactcattt tctcaaacac tcatgaatac ttttgagaaa tcctcgttct cagcgattgt   14280
tgaatcggaa caaaatcgat tttgagaatc tttgagaatc tttgagaaag ttgacgatgc   14340
agcgatcggc taactgaaat atgagcaatt gtgctatttg tttttcggta atcactttgg   14400
aaaatttgaa tacattttgt ttataattgt taacacatgt ttataattga aaaaaaaata   14460
aaaacaaatg cgatcaaaaa tatgttttct atttaaagca ccaaataaag catgagtggc   14520
aatatcagtt tctcaatgtg agaaaaagtg acgacggcca cgggctcgcg tctgagaaca   14580
agatttgggt gcttgcgaaa cttaaatgtg tgtttgagaa tgatttctct gcttgagaaa   14640
gccccatggc cccgcgtcct aacagttgac agagcactag gtgctagggc ccctgaagga   14700
tggacgatgg ggccccgaga cttgcgaaac atatgcacct ctctccccccc atcgctcgac   14760 aaacattttg gtaggacctg ggcccaatgg ccatcactcc atgagcaaca atggtcgaca   14820
ttgcaaaata tacttatttta tgagacaatt tccaatagag ggtaatataa acaagggacg   14880
gtgaggcaaa cgtatcttta ataatgagaa aatccaaaac atatgaaaaa gatttattga   14940
atttctttgt gaaatgtttc tccccaaggc ctacaaccac atacatcaat ctagaagcaa   15000
agcgcattgg ttgtgatttt attttgagcg cagccaggat tagaatcaat gattcaaaac   15060
gctgtcttat gaataggacg atgacaaatc atttacaaca atagcatggc ttgtgtggta   15120
tataataaaa agtgtcatct aggcatagtt tcttcagcaa aagttttatt gatagcaacg   15180
atacagtgca atcaaaatat ggttgaataa caaacgccat tatttcaatt cggaatgaat   15240
agacctatgc atgtgtggtt gtatgtttct tgcacagttt attattttg tgcttagaac   15300 gtttcacctc tcgctcgtag tttcatatct gttttgtggt agtagagact cgtctaaagc   15360
ggctttgaat tcctgttgga caatattgtc ccttagggag tccatgttga gccgaggctg   15420
cgtgttttct ccgcccccat tgacgcgggt gcgggcgatt ctacaactta tcgacgagtc   15480
```

```
ctgggccatc aaaccccgag gaagatgcaa acgctctgga cgtgtttgag cgacgcatct   15540
tccggaccat ctttggcggt gtgttcgagc atggaagtaa gaggtactgt tagatgaaag   15600
aatgcagcca gctgctcgcg cgctctctct gcagtaagcc gctcttactg cagttgacga   15660
gccgtgagcg ccggagagcg atcggtcggg atggatcgtt ctactgctgc gcgaagagca   15720
cagatactaa gcataggggc tgcgcggcat atacttcgtt gtaataaagc atccgtttta   15780
agttaggaaa atacaatatt tatgtgagtg tacttgtcca cctctcacca tatcacatac   15840
ggacataaaa agtacaaatc gaatattgaa aatttgtttc attatttata aaaaatcgaa   15900
aagctctatt ttttgctatt gttggctcga gcaacagaat tttatgaact cgaaaaagtc   15960
cgcaaaacag tttttttta acactttatt ctgatttaaa acggaggggt taaaaaaata   16020
ctctttcctc cgggacttta atacgcgaga aaagggcgct tcttcagccg tcgttcctta   16080
agtacccttt cgctggttcc cattcggcgc tacggttgct gcccttttccc ttcgatggtt   16140 cttcggttaa tcttcgtgtt aacttttgtg ttcgggtttg ctgatatgac gcgaacacaa   16200
ttaatacaat taaaacatat atattaacaa ataaaataat atatcacgac acacgtctgc   16260
tcgcaaccaa gctcgaatga agagagaccg atctgtccat ctcccaagcc ctgcacggct   16320
ctccgaattt caatcctaat caaatcgctc tcattacaca attcacctc attagccgcc   16380 ttcctagcat catggtccga caccggtcat gagccagggg agtacaactc gcagccaaaa   16440
cataactgtt gcaaatatgg ctgagtcata ttgaaatatt tcgccctacg atcgtggcat   16500
cgataccatc ctctcttcga agtcagagct gggagttatc tgctcaaact agcatcacga   16560
tgaacgtacc gttgatgctt gtcaacagca taagcgggtt gcggtagctt tgttgcttgg   16620
gtttccatcc ccagcaactg gtagggctta tttacaaaac aaatccttta gggcagtgtt   16680
tccatagata cgcatgcaaa tagacgcacg ttaaccgtac gcttgttttc ttcggcagaa   16740
aaaccccgaa accaacgagt atcccatcca cctggccgcg ctatccttcg acagtgaaaa   16800
tctttccgaa ttgctcagcg ccccgcgcat tcaggtggat caaaagtacg aagatcgcac   16860
agcgctgtac ctattgttcg aacagatcga cagcgacaat tggaaacatg tgtttgagtg   16920
tgttaagttg ctgctagagt acgacgccaa cataaacaca accgatgaga acagcgtatc   16980
accgatagct ctgctagtaa cagctggata cgacgaatgg agaaaggaaa ttcttgaata   17040
ctgtttgcag aactacagcg tgaacgtaga ctaccgggga cagcaggcga gaaaagcgat   17100
cgtgaagaac ttccctggca cggacattcc catctacgac atggaaaagg ttaccgtgga   17160
tgtgttgcga aacaaactga acgtcgagac ggaggacaga tttcttgcgg catacgaaaa   17220
atactgtcag caaaacaatg gtcacgtgcc gctcgaagag gatcgcgccg aactgctacc   17280
attgaccgtg catcgagcga agctgaccgt tgctcggaag ctcgttgaaa ggcagctagt   17340
agagggcaag tttaccggta atccaaaact actttccggt cttctggcta agtgttgtaa   17400
tcgagggaac gtgcagatgc tcgaatggtt gctgcaaatc ataccggatg atgaggtagc   17460
gctagtcaat gaagatccgt tgctctcgct gctcgtgaag caaatcgacg tgtacacgga   17520
caagagctcc tacatccgca tcatgcgcat cttgctgaac gatccgcgcc tagatatcga   17580
caagatcgat gggaagaaat gtacggcgat gcattacgcc gtcaagtacc agatcgatca   17640
cgcccaagag ctgctgctgg acgagggagc gtacatctgg ggcgaaaata tattcggcga   17700
tctgccgatc agcgagatgg actcgtccct gctggagaag catctggact cgtgcgtcac   17760
gaacaacgat cgcaagccgg gcgacgagga ctacgaagtg aggatcagct ttgccaactt   17820
tataccgcca gccctcaatc caaattccga ggacgagatg cgaccgatcg tacgcatcgc   17880
```

```
acagtcaccc aattctaagc atctcctctg gcatcccgtc atatcgagca tcttgttgct   17940
taagtggatg aaagtgatcc accttctcta cctaaatttg gtaatttgta gcgtgtgttt   18000
cgtttcgttt gcgatataca tcgtgttttg ctttgcgcgg aagatacca ttctcaaaca    18060
attgctgtat tgcctgtcag tgttgggatg tgtgtatttg atcgtccgtg aagcgtccca   18120
gttaagacta agccccgcca cttatctgtt atcaatggag aatttgatgg agatattgct   18180
aatcggtggg tatgttgcgg tgctggcgca cgagtcagcc gatgagacat ggtcaatggt   18240
gctggttgga gtgcttctgc tgctaggggt ggagcttacg ctgcaatttg gcatgctccc   18300
ggtgaactcc attgccacca atatggtcat gctgaagacg gttacgaaaa actttctcat   18360
ctttttgagc ttgtactcga tcatattggc gtcgtttacg ttaagctttt acacagtgtt   18420
taagatgaag gatattgctc agctgcgcaa aaaaaacgga ctcgaacaag cggcagtcca   18480
taaccaggac attgaagatg agcatctttt ccacaatttt ggtgagattc agctggcgct   18540
gataaaaact acagtaatgt tcactggtaa gtacacggtc gaattatgaa cgtaaatagt   18600
caaatatatc aaatttcgaa tgtaaatcga attcggtaat agtcccattc agcaagacat   18660
ctcgacctaa tgtttctgtg taaatcttta ggggagttta atgcggcaga cttaccatat   18720
aaatcatcct ggcccatgta tgtgctgttt ccagtatttg tgttcttcgt gaccattgtc   18780
ataaacaacc tgatcaatgg tctggccgtc agcgacacaa cggttcgtaa tggcttgcag   18840
tcggggacgg aactcatttc taataacttc gcatatcaat tacagaccat tcgggcagaa   18900
tccgaattag taggcattac ggagatggta tccattatct gccggtatga aaaggcacag   18960
aaaggatttg agttcatcca ttcaacgtaa gtcgttttg acagttgttt cttgttcatt    19020
ctggttgtat tgaagtaatc ggtaacattg tacacgcttg attagttatt aacaaacaaa   19080
cgtattagat taattgttgc atgctggctg aacttcaaat ttatcatttc ccctccctac   19140
agattgggca aaattaagtt cctgaatctg ggatggctgt ttcctaattt gaaactttt    19200
tgcaacgaga aaccgctgca tcaaattgtg ctgaagccta gcgatcaaag cctatccaca   19260
atccggcagg atcaacaaat catcgtaacg gttgaaaatg gtggaatgcg aaagaaacgt   19320
acgagcagca cgaataatac ggctgcaaat agttcggaaa tgagaaatgg ccaagaagaa   19380
attcaacttg tcactacgaa tgaaactatt ccaacatgg agaatggtca agagcgaatt    19440
agatttacta gcaaaaattg tcagcttcag acgcataaaa cctatcaggt aaagagttta   19500
ctgtacaagc ctttaaggg aatgctgagc aagatagtta cgaaatcgat cgagatgttg    19560
aactcccgcc aagtgcacgg tgaatcacag gcgcatcgcc tatcacgcgt ggaacagaac   19620
atgacaaata tgatgcagga actaaggag ttgaaggaat tggtacgggg cattgggaaa    19680
ggacgacgtg gagatgataa gaaagctag aatgtagctc cttagtttcg tgagaacggc    19740
ctggccgtgt tatcaattat agttacattc aaaaacataa acctcacctg acgggtaaat   19800
aaaacaatac cttggttaca attctgcaca aatacttgca aggatttaaa tattgattag   19860
ctaaaacgat atcagaagtt aggatacgtt agcatctatc tgtcaagcac gttgcatact   19920
gttaggcgca aacgcatcat gattttagat caaatctttc ctgtcggttc gaagaagagc   19980
ttctcgcaaa ttaaaatttt gtattgtttt ataagtaaga cacgaacggc aatcgataca   20040
atcgatatga agcatctagt ttaaaccgac atgggacacg tcccgcaaag aatagttata   20100
tgtgattcaa taaataaata taatcgaatc acagaacagt gttatttgca aactaccaat   20160
cgcagaaatt aattaaagct gactcataaa agaatacagc gcctctctgc catcagtatg   20220
gtcgctgtaa atcaagcaac aagtggagcc agcatcctcc gggcgcaaca cgcggaatga   20280
```

```
tgacataaac attccgtgcc gaaagaactc ataccaagtg aaagatatca tccggcacga   20340
tagcataacc gcatgaatgg ggaaacatat gagggaaaca gacaaaaaaa tggaggaaaa   20400
taataaaaga aagacgaaac aaagcaaatg tgtgcgtggg tcaatcgcga ccattctgtc   20460
gtggtgttgg ttttatctcg cggttgacat gtcggctgaa agtcatgacg cagcatccaa   20520
tgcgtcgaaa ccggacaaac ggctttttc ctcccggttg aatgtatggt cgcgatcagt   20580
caatgtcgaa gagaagagat gggtcctacc cacaatgcac aacaaatgtg tagtatgtat   20640
caatagcgac tttaacgcca acccttcctg ctcagtcatt cctcagctat tccaagctat   20700
tggaccgcta atcgatggag tttagttggt gtcgccacgg gtcccccata tcgaagcgaa   20760
aaccccttat gcacaaacac atatgaggta tagcgggtta agtttcaaag tgctcctcat   20820
atggtccccg attggcgtgg ttagctggtt cgctgcattc gttcgtttat tcgctctgtg   20880
gccgtgcggc gagcagcaac tggatgtcca tgccccgcg cttaattaaa tcagagtggg    20940
gttttttggg tttctgttcg ttcataaagt ttcccaacgc ggactgtgta gtgctttgta   21000
cggtttttat gtacaagtat tgtggtaaca actaaaaaag ggaatccttc cagaagcgat   21060
cctctgacaa gagcataaag tttcgaagcg aaaaaatcat ccgaaaaaaa aacaaaaagc   21120
aaagtgcgtc tgtagtttga cgatcgtttc aaagtagtgg tgatagttgc gtatggaaga   21180
ctcataaaat tgactggacc gtgtccacat atggaacgtc gtgaaacggt tcctttccct   21240
tcacgctgcc acctcagtct cttgctgctc tcgtggtact acacacactg aatgtgtcgc   21300
cgtccaacaa cggaagtcgt tccggtgtcg tgcttgaact ggtgtcattt atcgacgggc   21360
agtggtggct attgtagcat acattcgaca acctaccacg ctaccacgca attcttcatc   21420
gccctgtgta catcgacagc acaacatgag ctctcaaaag tttatgcatc taagcctcac   21480
cagcccgcag gtactgcagt cagcattgtc agcaaaatgc gatgcaactg caacacgtta   21540
ctctacacgt tcaattccca atttagctg gcgcttgctg caagcttcga tgcgaacgac    21600
ctgtcggagt tcaaccgatc gcttcgcaac ggggcaaacg tgaatctacg cgatcgtgac   21660
tcgcggtaca cggtgttcga attagcatgc aaaactcccg gcaagaagca gttcatccga   21720
gcctgtctga atcatggagc ggtactgtca gaggtacgta tggcgtaggt tttttgtctt   21780 tctttcttt ttttgtttt ttgtttgaca tgaagtgact ttaatttac gactactaaa     21840 tgctcgaagg tgcgatatgc tgatgctttt ccagcacgta ctggaagaga tcgtttgtga   21900
ccggacctca aagagatttt tgggtggggc cgctgggttg gtcattcgca ctttgaaaca   21960
ttggctcagc gtttggagca gcgcccgag caaacagtac tatcgaaaac gctagccgcc    22020
gttccggaac agctgcaaac atttgctcaa agctgtcccg gagtagtatc caatgtttgt   22080
gcgatcggag tgtgggcggg cagcagcgtt attagtttag acggcggaaa tgcgcttgcc   22140
agctggaatt gtctacatat acggtacggt ggttggtaca tgtgccgttg attgtggagg   22200
gacagatata ttgaaactca tcttgatatg gtgctccagt aagggaagca acgaaaacag   22260
cacttgcgtt tgaactagca gctttgcatg tgcagcttta tagttaaaat atgaattcga   22320
tctaaactag ccactaaatt gagaaggaaa tgagtcattc caaggaaaaa taataattg    22380 taggcggaaa ttattatttg gtaaacattc gacgtcgatg agccagtgat caagtgcatg   22440
tcagaccgtt aaaagtagct atgaagggca tttgacagat agaaacatgt ctggatgcgt   22500
ccatcaaatt tttaacaaat tttgaacatg ttctgcccgg cgaagataat aatcttagaa   22560
acaataataa gtccaacatt ctctgatgta catgtggatt tgtaattata actagaaatt   22620
cttctatttg gcgtaacgtc ctacgcggac atgccgtccc ctgtacagaa tagaatctaa   22680
```

```
tttgaaattt ctgatgacgg gttttcctgt tttttcctaa tagattatat accaatgata   22740
acgaaatcta taacgtttaa agtgttattt ggaaacaatt gttggatatt ggattgaatg   22800
cccaaatggt ttgatagtgt ctcataatgt ataccaacta ggcgatcgcc tggggcttcg   22860
tcgattgagg agccccgtag attgatagtc catagtatgc agtatgtatg tatattgaca   22920
gagcactagg tgctagggcc cctaaaggat ggacggtggg gccccgagac ttgcgaaaca   22980
tatgcacccc tctcccctc gctcgacaat cattttggta ggacctgggc ccaatggcca   23040
tcactccatg agcaacaatg gtcgacattg ccaaatatac tgatttatgg gattatttcc   23100
aatacagggc aatataaact agagacggtg aggcaagcct atctttaata atgaggaaat   23160
ccaaaaaaat acgaaaaaga tttattgaat tactttgtga aatgtttctc cccaaggcct   23220
tcaaccacat acatcaatct agaagcatag cgcattggtt gtgattttat tttgagcaca   23280
gccaggatta gaatcaattt ttcgaaacgc tgccttatga ataggacgat gacaaatcat   23340
ttacaacaat aacatgcatt gtgtggtata tagtaaaaag tatcatctaa gcatagcttc   23400
ttcagcataa gttttatcga tagcaacgat taaacgcaat caaaatatgg ttgaataaca   23460
aacgccatta tttcaattcg gaacgaatag acctatgcgc gtgcgcatgt gtgtgtgtaa   23520
tgggtttgcc cttcagcttt tgactctttt ttttacataa atcattttaa actcacttgt   23580
ttaaaagatc gacggttaag ttgatcaaca gtcacgtctg aggtgctgaa cacgatcaag   23640
aaaaagacca gagcgacaaa aaataaatta ttcgtgagaa agctatttgt tctatgtcat   23700
cgtctggcag ttgctattcg ttataaaaat caaggaaaac aacccaagcg ccacagatta   23760
agcttaaacg actggaaaat ttaatatcca tagaaaaaaa tgaaagctcc acagcttcat   23820
tggtttgatc aatagatggc gtattaaaac tgattattat attgctatcc ttttcttgca   23880
atgtgtttcg gcaagtttca tcttatcatg acctatatag ccttctaact ttccgtgcaa   23940
aaatctatat aaatggtcgt gtggtcagat gcgtgggtat caacaccaac gaccattact   24000
caaatctcac ttgcttcagt gctgatggtt cccattggag tttagtattt aaacaattgt   24060
atcgccgttc tagttctagc gatgcataac ttcaatgcat aaccatacaa cagtacagag   24120
gaaatgagaa agctctcctc caagcgatga agctcaacta gttggggtat cccaccaaga   24180
gagagccaca ccagcttttt cgctattttt agaatgcatg agtcgtttac cgtctgctaa   24240
acgaagtctt tctatattcc gtttaggtag agaacttaag tcgtttagaa gccgtttagt   24300
ggtcgtttag tggatttgtg gcacttccca agtgacattt gctcgaaatt gttttaccat   24360
atctgctcga ttagtactcg atacgcctga aattgtggat ttgtatgtga tcaagtgtgt   24420
tgaaagcgcc aagatttggt gtgatcgtaa attagacgtt cctctatcaa tggatgatgc   24480
cgtcgagctc attttcatt catagctatg gttttttgat gaaaacaaa agctaatttt   24540 atgtgacgtt attctataaa aatggttatt atttaagtat aaaatgggta catgaccaac   24600
tataacgata ggaaacatcg tttccgagcg aatctagaag aaagttacga aaagccgca   24660 tcacatttga tttaaaagga cttttctaa attcccttaa actagtgcag tttaagggaa   24720
gtttaaggat ccagtttaag gaaatttgct cgaattcccg attaatcgtg ctataaaatg   24780
tcagttgggt tgggaagtgc tttgttgttg ttttttcgtag aatatcattt taataattta   24840
catagtataa atgaataaca aagcatattt ttttcctaat cgaagcgtac aaaagttttt   24900
caaaacattt caatacactc atgtatgtaa tatctaggag ataaagcata taatttaaat   24960
ttattcaaca aattcaacat gatttaacaa gaatacaaac aagaacttac aataagaaaa   25020
acattaaaat cttttatttc tcccattcc ataaaaacat aaatcacttc gtttgtaacg   25080
```

-continued

```
gaaatcattt ttgaaaatgt gcctctcgca cgaataacac tcaaaacgcg atgcgtaacg   25140
cacgaataag cgggttgcgg tagctttgtt gcttgggtct ccatcctcca agcaactggt   25200
agggcttatt tacaaaacaa acccctttagg gcagtgtttc catagatacg catgcataca   25260
gacgcacgct aacgatacgc ttgttttctt cggcagaaaa accccgaaac cagtgagtat   25320
cccatccacc tggccgcgct atccttcgac agtgaaaatc tttccgaatt gctcagcgcc   25380
ccgcgcattc aggtggacca aaagtacgaa gatcgcacag cgctgtacct gttgttcgaa   25440
cagatcgaca gcgacaattg gaagcatgtg tttgagtgtg ttaagttgct gctaaagtac   25500
gacgccaaca taaacgcgac cgatgagaac agtgtgtcac cgatagctct gctagtaaca   25560
gctggatacg acgattggag aaaggaaatt cttgaatact gtttgcagaa ctacagcgtg   25620
aacgtagact accggcgaca gcaggcgaga aaagcgatcg tgaagaactt ccccggtacg   25680
gacattccca tctacgacat ggaaaaggtt accgtggatg tgttgcggaa caaactgtcc   25740
gccgaacgg aggacgagtt tcttgcggct tacgagaagt actgtcagca aaacaatagt   25800
cacgtgccgc gagaagaaga tcgcgctgag ctgctatccg tggccgtgta tcgagcgaag   25860
ctgaccgctg cccagaagct cgttgacggg cagatagtag agggcaagtt taccggtaag   25920
ccggaattgt tttccggcct gctggccaag tgttgtaatc gggggaatgt gcagatgctc   25980
gaatggttgc tgaaaatcat accggacgat gcggggcgc tgattaacga ggatccgctg   26040
ctctcgctgc tcgtgaagca gatcgacgtg tacaaggaca agaacaagtg tccctacttc   26100
cgcagcatgg gcatcttgct gaacgatccg cgcctggagg tggacaaaat cgatgcgaaa   26160
aaatgtacgg cgatgcacta cgccgtcaag tacaagatcc atcacgccca ggagctgctg   26220
ctggccaagg gagcgtacat cgggggcgag aacatgttcg gcgacctgcc gatcagcgag   26280
atggactcgt tcctgctgga gaagcatctg gactcgtgcg tcacgaacaa cgatcgcaag   26340
ccgggcgacg aggactacga agtgaggatc agctttgcca actttatacc gccgccccac   26400
aagcccaact acgccaagcc ggaacaggtg ccgtttaacg ggctgccgta cgaggacgag   26460
atgcgcccga tcgtacgcat ggcccagtcg tccagcacca aacggctgct gcggcatccc   26520
gtcatatcga gcatcctgct gctcaagtgg ctgaagctga tctgcttttt ctacatcaat   26580
ctggtgatct gcacgatatt cttcgtgtcc ttcacggcgt acgttgtgtt ttgctacggc   26640
caggaagatg caccgttcaa gctgttcttc tacttcctct cgttcgccgg ctggatatat   26700
ttggtcgcac gcgagctgat ccagtttctg ctgaacatgc gcgtgtacgt gcggtcgatc   26760
gagaacggga tggaggtgct gctcatcctg gcctcgggcg cggtgctgat gcgcgagttt   26820
ggcgacgaaa cgcggcgtgt cgcgtccgcc tgcgtgattc tgctgtcggc gctagagttt   26880
acgctgctcg tcggcacgct gcccgtccta tcgatctcga cccacatggt gatgctgaag   26940
acggtgtcga agaactttct caagtgtctg gtgctgtact cgatcatttt gctcgcattt   27000
gcgttcagct tctacacgct gttccggggcg aacggtggta acggcgaggc gggcgaagcg   27060
accacagaca agacagctgc cggtcaggac ggcgatggtg atgacgatca gttcaaccag   27120
ttcggggagg ttccgcttgc gttgatgaaa acagcgtgtaa tgttgaccgg tgagtaagcg   27180
ggcgtgggaa aaacggggga atacccactt ggggtgatta ttttttgcacc cttttgcata   27240
ccattagtaa agcgccattg tagcaggtgt acatatggga acgcatatgt ttaatcgata   27300
cagctacgcg gtcaacgctc actcgacatg ttataaatag cgcttttttgt tgcggcaaat   27360
ttttctaatg tgtgaattac actttcaggg gaattcgaag cggcgaacat aaaatttcaa   27420
cagtcaagct tgagctactt cgtgttcgcg ctgtttctgt tctttgtttc gatcgtgctg   27480
```

```
ttcaacctga tgaacggtct ggccgtgagc gacacgacgg taggtggctt gtttgcgcta    27540
cacagcccgt gtagatgacg tctttttat attcttcttt acactattac acagaccatc     27600
aaagcggaat ctgaaatcat cggcattacg cagaaagtgt tcctcatcaa caagtacgaa    27660
aatgcactga aaacatcgaa gcccattcgc tgcatgtaag tagcaacgtt tgccggtgcc    27720
tgttttccca atgatgactc atctgctaaa cgattaccat tgcccttttcc gtttcgcagc   27780 accgagcgaa tggcgtggct gttcccgtcc aacagtttgc agctgttctc gaacaatcaa    27840
ccgctgaagt acattgcggt caagccaaac cagtcgaacg ccatcatggt atcgtcgctc    27900
gtgccccggt acgcgcagga cgtcgagatg ggtgagttgg tggtgcagga caaaaagctg    27960
gaagtcgaag gattgctgga gcgcaacacc aagtacggta ccgaatgctg catcatgccc    28020
tgcctcaaca acatggatgg gaagatagtg aagtatgcgc tggagatttt gcactcccgc    28080
cacgagcacg tcggctcgac cgagtaccgg atgtcgcgca tggagcagaa catcgagcgg    28140
atggcgcagg agcagatcga gatgaaaaag ttgctgcaaa cgctcgctac ctcgttgcat    28200
gctaaggcgt agtcgttctg tattgcgcac aggatggaag ttgggattaa tttatgtttt    28260 tgttttttaat gctttaactg gactcatatg catttggtgt gcattttgtg aacggcatta    28320
cttcacttgc acccttacct cacgcagcta ttattgacat ttaactttgt tagtctatt     28380 taacaagcac tgaatatgct tatcattgtt acctttttaa agcggaaaca agcaacgttc     28440
ctgttcgtct taaattgcgc atgaatgcta gactgaatca aaccgatcag tcaatataac    28500
catcacaatg attctatctg aatcattacg ccttaacgat acctgcaagg atttatgaaa    28560
tgttatacct ttttacacct ttgaatctct acagtggtcg ttgcgcctga aacgattgca    28620
cttatttaca ctcatttcca ctgtttgtat aggactgttg gcattgcatt gttagcgaat    28680
tgcgttggtt gtattaatgt aatttaagc cccacaataa accattcaag tgtaacaatc    28740
ataactattg aatatattta atttacaaat acttgctcct cgctcgaacg tttagctcga    28800
aggtgtaaag cctaaccttt cccgaattga atttccttcg atttattca aagtttaatt    28860 gaaaagactc acattttgt tggaagctat cagtattatt tcatttcaca tttattcac    28920 taaaagtgat gtaaatatat cactcatgta aggaaacacg tttatggtga tcatctatca    28980
gtttgttgga agaaaaaga ttgtttaaat aaaaatttaa ataaaaaagt ctcttctgtt    29040
tcttgttgaa catatcacaa caattgagct atttgaactt gttatattaa tatcattgta    29100
atgttttgtt gtattttta tgtttatttc catgttaaat gtttataaag atctatacat    29160
ttaaaatctc agcttatttg tcattattgt gatgcagaat agtaaaaata catttgttaa    29220
acaatttgtt aaactatcaa tttaaatatt taaaataatt tttattaaca caaaaaggaa    29280
gttgagacca aacacaacag caaattgaat gataatacaa acatatttga aacgttaaaa    29340
aatacacacc ctttcaaaaa ggctctttag aatatgcaaa tgaaataaaa aaggagaaaa    29400
tatgaatgaa atattttgta acattttcgc aaacagtttg tccaccgggt gcacccacgt    29460
tgcgcgatcg cgcacaattt cgaattaagg gtagtgcgaa gcgtaacaag cgatggtggg    29520
gtgtgattcc agcaagatca ccggcgcgtg agtgattcgc cccttcctcg gtagttgttg    29580 gtggggggg ggggtgagc aaacacaaaa cacaaaaaaa agaaaccag cacaccaacc      29640 agtcactcag agagcgggag agtgcttggc cggtttcgca cagcctgcac agtcgcggct    29700
agtttcttcg gtctcgagtc atcggattcg atgcacgtgc ttccgtaaac gcgcccctcg    29760
ggtcgttcgg tgcgaattgc ggctgggcag caaacccttta cggtgtatgt gcggttccag    29820
tacttacgta cgcagcatct atcagccagt gggggaaggg agcacgcatc gcatagagtg    29880
```

```
tgtttgttgt gcgaatgctc taagctggcc aggggaaaaa gtaaggaaag aataagcgtg    29940
taaatttagt gtgaaattca agctttgcgg atattgttag tgacagtgtg tgtgtgtgtg    30000
tgtgtgctac attgtgtgtt tatggagttg caccaaagga agatgaaacg tggccgcaga    30060
tcgcttttac agtgtagtga cgaaggctaa accgtttgtt gatgagataa agcgggggaa    30120
aatacgcgat ccttagtgca gtgcagtgcg gtgtagcata agcattgatt ttctcgtcgg    30180
tgaattaagc ctaccgtgcc gtgtccaatc caatcaaccg atcgagtgag caaagtgtag    30240
atacagaaac catagtgccg tttctagtgg atcgttccct ttgcggggtt tttgtgctag    30300
caggcgcacg tgaataccag atcactcata ttattcagtt agtgcaggtg gtttactgtg    30360
tatgcaaagt gacacggcgc agcaaacttg cgtgtttaca tcagcctggg tcggaagggg    30420
atcgcgtact gcatcagaaa ggctgcattc ttcaaggtaa gacaatgcgc tacaaaaaaa    30480
gctaagtaca tagggcagat atacagacat gtgttgcgct gttgctttaa atattatttg    30540
aaattttcac acttaccttc gattcttagt accatagcat acactacttt tcatgcttta    30600
aaatagcaca aggaagagac aatccttatt gaatcattgt tcttatcaat gatgctcttt    30660
aaaagcgtat tgttattgtt caacaaccca cccagctccg tttcttcctt ttgccttctt    30720
gcaaccttcg ttgacccttta cctcgcatcg tttgcgaata tgctgctgga tgctaacccg    30780
ggccttcttc tactccccta cccaatcccc cttcccccccc acccattgat tatcttgcgc    30840
tgcacctttg cggttccaat ctcacctcgc gcggcgtgtg ccgttctcgc gcaaccgaat    30900
gtgttggttt tttcaccatt cgttttttgga gcaccattcg atgcacgacc acagtgtcac    30960
agccgggtgg tggagtggtc tccccaccgc cccggacgct gcgaccgcct cccagcccca    31020
tcgaatgcgt taatcatatt cgagcgacag gctccgtaaa aggacatacg cacacgacac    31080
gacggtacac ggcggctgcc ctgctgcaca gataccttgct gatcaatgtc accggttttg    31140
gaacgtcaca gcgaccactc cactttcagc cgccttcccc atttctactt gttgctcact    31200
tgtttgcacc cttccacgcg ggctcggaac accccgatat cggatttcag cttgtttggt    31260
tttggagtcg tgagtcgttg gttccccgt tggtaccggt ggtggagtga tccgtgcacc    31320
gttttgcgcc ccaaaagtgt cggcaacatt ctgcaagccg cacggggggaa agaaggcagt    31380 ttagcaggga aggccctgtt gcggcaggta gacgacgaga aagagacttt aattacttcc    31440
acttcgcgtt agccaattgg ccgtgctgta gttgttgttg ttgttgtctc ctccaaaccc    31500
ctctctgtag cacgggcgaa cgaaaccaac ctccaagatc gattgggccg gatttatgtg    31560
ggaactcttg gttgtgtgtg gtttgccact caacaggaaa cgaagaaggt gagaagagtg    31620
aaagagcaat agtgcgatgg gctgttgctg gatgaaggag gggagcagag gtggggccgc    31680
ccgagcggta gcaggagatc ctccgagagg catatccttg aacgggcagc atcgacgctc    31740
acgctccaca ttggcagcgg cgtgcaggct gctgcgagcg tggcgcagtc gtggcgcgtg    31800
aggcgaaagg ttgccgtgat cgtccatcac ggcggtggcg atggtgaatt tcagctccga    31860
cactctgcac aaacctgcga agctgttttt cagttttcca gttgagtcga agtcaaataa    31920
ttgccgctta ctgagaggat ttaattttga agtgtttttt ttttttttcaa aagataaatc    31980 gaactatttta ttttgttttg cttaaaagat tggtaatgtt aacttttttga tactttttgta    32040 aactttttaga ttaattattc aagaaaaaat cgttaatttt gcaaatatgt ttatatttttt    32100 tttcctaggc cttggacttg gagtgttttt aaagaattat atgactaaaa tttgctctgt    32160
aactaaattc taaacatgat agacttttaa tgttgcttct gcaacgtgtt ttttttaatca    32220 tatttagtct cttatttttat aaagtcttat ttaaaatcct acctgatgtt tctgcactac    32280
```

```
atatgtttga aagttaatta attctttaag gttaaattta atgttgataa gtgttttatt    32340
ttagtttata agcatttaat tgttgaattg tgcagtttag ttttttcaaaa caatttgaaa    32400
aagttagaaa aaagttcttg ctacgtcgga gttttaaatt tgttgtttat gaaaactttc    32460
caatgagaag aacgctcaaa aacgcgtcac tcttattgga tgttgcatgc aatgtttctc    32520
tagccagctc aacattgtaa atttcatttc caataagaaa atagggaata gggatattca    32580
acattgtcaa aagtatgtcg agcgtatacc ggagcaacca atgacagatc attctagttt    32640
ccattttat tgttgaaatg tattttacgg ggtttgattt gttcgcttac gatgttgagc    32700
tggccaaaga aaccctgtaa gttcattcgt agcaaggact gaagtcccaa gtagcaagga    32760
atgactgtcg ggctgcgtgg tactaaatga agtctcgaaa gcctgtatgt ccgcgtaaga    32820
cgttacgcca aatagaagaa ggtctttggg caagtcttat gttgccttac atctagggta    32880
gatttaaaag catctcaaaa tcaaaagtat agcaagaata caccaacgtg cattctttgc    32940
gccggaaatt caaaagggga tcgaacttct ccttgctttt acagggattg gtttggctag    33000
ttaggccggt taggccggta gtctctagtc agtttaagta gcatttgttt taataaattt    33060
atacaaagca gtgctgccta atgacaaaag ctgcgtcaac aaggtatgga aaagctatt    33120
ttgctgtgtg atgcatttct tcttcttcta tttggcgtaa cgtcctacgc ggacatgccc    33180
ggcgtgtaca gactttcgag actttattca ttacccgta gccggatagt caatccttgc    33240
tacgggggga cgggtccttt ctagacttga gcccatgacg ggcatgtttt tgagtcgttc    33300
gagttgacga ctgtaccacg ggaccgctct ccgtgtgatg catttagtac acactattaa    33360
ctgaacaata ttctatgtaa agcaacatgt gtgtctttat cggatcagtt tacataatga    33420
atacacacga ttgcaacaaa ataacaatta gctaaccctt ctctttcgta gtgcagccac    33480
acatcgagca atgccacact taatcctccc cggctaattg tatgctatcg tttgccattg    33540
gaaaagagga acagtcaaga agaagaacac attttcatcg caatcaatcg ccatcaaagg    33600
tctcgtttgt cgtcggccag caccccctcc gccagctggg tgcatcttcc tgtgccgcaa    33660
acctgatgca catgctgcta ccaggccgct aatttgcgaa acgcttcaca ccccgcagcc    33720
gttgatcgtt tgacagcggg gttctgattt tattttttac ttttttgttc gctgcttctt    33780
cccattccta ctgcccgctt tgtggcgggg tgtaatgtac ctggtctggc ttttttgttg    33840
ctgctgctgc tgctcattac tgtcaagttc acacgtgacg cgctgcgacg ttcgacgtgt    33900
cggtgtcgga cgggtatacc accctatacc agaccgcaaa accgctccac tgctgctcga    33960
ttgtgctggg tggccacagt agccccactt cggcgtgctt cgaacggttt gggttgacgt    34020
ggtggtggtg gtggtggtgg tcgggcgct gttggcacgt acagattgac gtacagcgtt    34080
gcccgcaccg gtctcgccgc tcgcccaccc ggcccattta cgagcaggtg gtgtcgcata    34140
ataaatcgcc aattgatatg ttaatgtggg gtacacgtca aacacatcgg catccacaat    34200
gccacacgcc cgtgtcgtga cgtgttgtga gcggttcgtt tcgtgcggcc cggttgcaga    34260
cagtagttgc tgcaagatgt ctttaaattg gctgcactta aacagagccg cactgtgttt    34320
tgggatcgtg tctggccgca gctgccaagc aaacactgct ggtggtattt tgtcacatcg    34380
cgatcagctt gaagcggtcg ttgctagatt gagcagtgcc gtgtggccta tattattcca    34440
tttgctgctg ctgttggtgc cccaatggtg cccgagtaaa gtgagatgag cgcccgggtg    34500
gaacgcggac tcgccctaat ctcgttgctg gatgagaatt ggatgaacga tcacatcggt    34560
cactggactg tgacccccgcc gccagtttgt atgtatgtgt gtgtgtgatc aacgacacca    34620
agccaacctg caatcgccca cactacccat cccacccagt acccacagcc gcgactacac    34680
```

```
ggattaacga ataaattaca attaggcgta aagatcgcgc acaatagata aattacgacc    34740
gcgggaggga cggattgcgt tcgcttcata ttggtcgaac cactatagca cgatgctaac    34800
gatgccgcga atgccgtcac agggtttcct ttttttttta acttttttagc ataacgacca   34860
agagtggctc gcatcgttga cgccgcgtat cgttctcgtg tgcttttttt ttttgctttc    34920
acggcaacag tagcaacaag ccgacatttt aagagcaatc gcgccaagtg cctgcctgct    34980
gcttcccccc ttttatcgcc cgggacggtt tcggaagctg gttagcggta agtaaaagtg    35040
acattgtcgc tacccgggca ggctccaaag atggagccga aaaggggcaa aacatgaccg    35100
gtttgttttg tattttgttt ttgtgtccca atcacatcga tgctagctgc tctttcatgc    35160
gctgccgcac gtcggtgcac tggatgcaaa gggatacaca ccaatcgatt accgattcgt    35220
gccgatgcat ttgcatgctt tcgatcggta caatgggcac cgcgcatgtg cggctaagtg    35280
tgtgtgtgtg aacatgccgg aacatgcgat cggcattgac ccattttttgg aatggggaag   35340
agcaccatcg ggtacaagaa ggctcgcaat cattggtgcc gtgggtttca tcttaatgcc    35400
gatgggttgc accgtgaggc ttaagggtgt acacatgtaa ggttgttgcg atacaagggt    35460
ttgggatgtt ataattcatt gggaatggca ttttcctga gcatcatcat gagggctcac     35520
gcaatgtatg cggatgttgt catgttccag ttattgttct tggcaaaaga attatattgt    35580
gaattaacat ggcttataaa atactgaata gttcgatgat attttatatta ttgaagcaat   35640
cctttgcttg caaataaaac aattacttct gaggcgttaa atcatacaag gcacaaaatt    35700
tatgcagatt ataaattaaa gttaatttta ttaggttcat tatcaaactc tttaggagtg    35760
tattgtttat catcaaaatt ctctcggttt tggtattagt tcataatact gtcagacgcg    35820
taggactgcc cgattagttc gtttggccat tatacaatta cgagcgatta aaattgcagg    35880
gagtggggaa tagggagaat ctattggacg atgttttat attgtatgtg attcgatgag    35940
ttggatcatt tgaaaagtaa aaaaatagta tacattatca atttacatcc attccagaaa    36000
aaaaaactgt cttcgtttgt gaacgctgta ttttggtctt cacagtctgg ttttttgggtt   36060
atggttttgc agaagttcct tagcgcttct cagttcattg tttatctttt ccggttttac    36120
gaaaccgtac acctagacca tcagatactc gaaaaactcg aagaagttga cttatcttca    36180
gcacgattag ataaattgaa taacagtatg tcttcaggtt tccggaagac ttcatgtttg    36240
agtattattg tctataaata agttgaataa aggataaaca aatcgtatcc tcggagcact    36300
tcttgcagta tttccactca tctttgaaag ggtatagtat ttcgaagtaa tggatgtagt    36360
ctatgaaatc aaaagtcatc agttatgtca tataatctca aagttaaacc tcagattcat    36420
tcaagaggca caacccgctc cgaatctgtt ttcatctgtt cgttgtgtag caaggcttat    36480
gcttatagga ataaactcta cattttaggg attgaaaaga tgcttattga aataaaataa   36540
caatttacat gcaattggca ccagttacta atgcacaaag catagcgcac ggttcaagaa    36600
gaatcaaagc gcaaatgaag tgatcttgtg ccacatacga gcgatgattt gtacaggttg    36660
cgtacgcatt agcctccaat gccacgccga tggaggggc caattggggg attcgcaatt    36720
tggcgtaacg gcagcgccat ttgcgaccac caccaaaaaa tgaattccgc caaaaaggtg    36780
aacaaacaaa tcgataccga tacaggcccc atctgtcgat cgtcgacgtg atcgaacagc    36840
acaatacaac agattaccat caacaacatg tgggaataaa caacaacaca cacacaaaac    36900
agacacacaa acatctccac tacacccatg atcgtttggt acttcacagt ctcgttcgcg    36960
ccaatgtgcc agcgctgtgc tttgggtagg ccaataaaat tgaatttaaa acaccaatat    37020
gcattccgtt tggtgcgcta caagcaggtg gcaggtgaat ggtctgggta atgggattgc    37080
```

```
cgagaccaac cagccagtca gccagccagc cagccaggct cggttgcgcg tgcctttgcc   37140
cgagcggctt gatgttcaat ttccttgccc ttcccgcaat gttacgcttt cgaggggacc   37200
ctcggtggtg ggtccattga attcgaacgt tccaccgatc gatcgatttg gtcgtaaata   37260
ttttggcgac aacgaaacgg tccgggtcag gtgaaccggg ggtttgccga gaatgaacga   37320
agaataaaca acgcgtttca caatcacctc tgtccgattg tgtttcccca cccttcagat   37380
cacgacaggc gacggcttaa gacgcaacca gtaacatctg tatttcttcc aaatgtgtgt   37440
gtgtggataa ttgaatctta aatcatataa acaataggga tttacgattc gattcgattg   37500
taccacatgg cgatttcgtt gcagtgcgct ggcatgaaaa gggaaaggca ctgtatggct   37560
tttagtgagg aatgtatcat tccacgccac agatttggac agcatatcgt cactaaactg   37620
tgatggtttt atttttggtg tttcggtgtt gccaatttgg acacgagcaa ttttttcattt   37680 ttttatgctc catgatgcgt cggaggagat cgatacttat gatacgcgta acagttgcgg   37740
ttttaatcgt atggttacga tctccatcat tgcacatgtg ctgcacaatt aaatagttaa   37800
aagtaactgg ataaactgat gtctttattt gtcttttat cttaccaggc tgctaataaa   37860
gtgtacaact ttaatatatt ttttttaact aaatttcaac aagagcacag cgaaagacac   37920
tgaaatagaa gcaacaaacg cacctaatgg ttcaatatct agtcatcaaa atgttttggc   37980
gtcattgccc actaatgcat ggtttgcatt acaaatctcc acagccgtgg gctgtgcaca   38040
accgttcaca ctccctctct ccctttctaa ctctctgttc tccactcgac ttagtcatgt   38100
tagattctcc ttgccgtgcc tacgcttgcc ccctgcagcc gcctagtctc ggtggtggca   38160
aaacattgac ctacatattg ggggtgcaca tgatcggtgt gtgcctttt gccagaacaa   38220 aactcacccc acggcatgag caggcaccgg gctaaccggg tggtggtgat gctgtgagtg   38280
tagttacgtt atgtttgccg tgtccctccc ccggtaaacg tccagcacga gcggttcgaa   38340
tgcgaaatgg gggtccgctg tgtcggtgcg ccgatctgtc tctgcgcgaa ctgtgcgtaa   38400
agctccagcg agcgatggga gccgtctggg aactcaatct ctgagtgctt gggagagtgg   38460
ggcgacacaa acaaaaaaaa tgctgccata aaatttctct tctccagcac agctgtcttt   38520
ggagctaacg ttttttctgtg tgtgagtgtg tccgcgaatg tagcagcaca acactggaac   38580
ggagcagtat ccacatgttt tgtgcgagcg tatagtatta tgctgctgcc tatgcttgcc   38640
tccgtcgctt ccgaacgcca gggccgttaa cccgacccgg ctatcggata accgttagat   38700
ccgattcggt cggaagagaa gaaaagcgta tcgcgagaat gggtttttgg attttagaga   38760
cggaaataat gctgagtgga ttaatgtagg gctgtggtta tattttagaa atggcttgaa   38820 atagttttg tgtaccaaaa ttggtggaat atgcgaaagt acttccataa tgcatcgttt   38880
ttaacattat ttaaaaaaaa acatataaaa aacaatatat tgaatggtgt atgcatttga   38940
actgaacttc gcacgtcgag ctgtgttgca aagctggaca gatgcactta acaaaaacaa   39000
caacatttat aacaataatt acttcaggaa catgtaggtt ttttgtatat ttaaatgcgc   39060
caaataaaaa aaacaaaaca aaaagcggg ataatgttgc caaaatgcac aggattcgtg   39120
tatcaaactt tgaacaatac atattgtaaa ataacgtaaa gttagttgct aagcagtcga   39180
ggcaatgctt taataaaaat catgatgata ccttagctat acggcgaacc gagcatcctg   39240
atggtggcga aggctggtag gatatgatgg caggggcata ttatgaggat gctggactta   39300
tgccccacca agaaggtatt caagagcgat ccatagttgc tcgaacacac cgccaaagat   39360
agtccggagg atgcgtcgct caaacaagcc cagagcgttt gcatccttcg ctcggatggt   39420
ccaggactcg tgtccataaa ggaccaccgg gcgaatcaat gtgtggtata tctcatattt   39480
```

```
ataagaggcg aaagaactcc gttggagcca aagcctctct aaactattcc aacaacaaca   39540
tatctcatat ttcgtgcgga ctcgaagtct tcttgatctc agaagtcgat gaagcccgta   39600
gtattcacga tttccctgca caatgcgtct ccggatatcg ctgctgctgt cgttttccaa   39660
agtaacaacc gtctcaaaat agcagaactc ctttactacc tcgcgattgt cgccgtcaac   39720
caatacaccg cttcctagat ggtctgagtc tccggcaagc aggtactccg tcttcgtcgc   39780
attgattctc aatccaatta ttgctgcttc gagcttttat cgggtgttgt gagttttta   39840 tcgggtttat tcgctgttgt cctgctgatg atgtggatgt catcagcgaa tccaagaaat   39900
aggagagatc ggtagaggat cgcacaacgg atgtcgttgt ctagccccgt acttcgagct   39960
tcaaaacggg tgacatctga agctatgagg tataaaatat ttacaacata gtgtacaggt   40020
ttgaccacat cacataaggg cttaattgat gttctgaacg gcttgaaaaa agctattttc   40080
ttcttctttg gcacaacgac ctttgtcggt caaggcctga cgactactca accactaatg   40140
tgtctttact tacagtgacc tattgattac ccacagtagg cacactggtt atacgtattg   40200
agacacgttc ggggcttgaa cccatgacga gcacgttgtt aagaaatgcg aattgacgac   40260
tgcaccacga aggatgtgat acgtactagg ataaataaca ttattgagtt tcatttattg   40320
cttttacaat gtttagtgtt attttaccaa cattagtatt atcatcacta cgcgtgtgtt   40380
gaccccaggt gtacttccag tacttaacaa caaaacatga ttgttttaga aggaatattc   40440
atggtgagga cttccttaac ttttaaacct tttatcaaaa tattttgctt ttacatcaca   40500
gaaaatcaca aataagggggt ttattttgtc tgagtaattg gctagtggcg tccttttaac   40560
atttaccgaa ttgttgtgta tttattcaat ttgattgccg tccgagattc caggcgctgc   40620
tgccacagct cttgacgtac gatcgatttg tcaataaaac atctttaatg agttctattt   40680
catgtgttgt gtctgttttt ttttctttct tctcccttc acagaacccc ttccggcaaa   40740
cccttatcaa cggcgacaat cggcaaggac aaggagttat taatgtcaca ccgcccccta   40800
gcccccgccc gccattgagt aatcccgctg acaatgagca gagcgtgcag ggcgctgcgt   40860
acacacctcg gctaaggcaa ttcggtgtcc caagccaagt gactaaagtt cagcggaacg   40920
cgggcttacg gcacaaggtg acaagtggtt cgctgctaac ggcaaggatg agtccctcgt   40980
tcgtcatcag ccagataagc gcttggaagc agcagcaaca acaacaacaa caacaccccc   41040
gcaagtccta atgccggcga tggcccacag gtgcaccaca cccgccgcca catcttcacc   41100
accaagcgca cccagctcat cgccgtcacc gtttgccgcc cagcgggaag ggccagcgtt   41160
gccgaacggg gccgaacacg taccaaagcc tgccaagggt cgccggtgg gagcggaggt   41220 aggaacggtc cggcctgcgg tgggtacggt ggttggcggc ctaattggaa agtttgagtg   41280 cagcaggag tgcgcgcccg ctgacgtcaa agtgacagca acagtggtc gagcgggcga   41340 tagcgcgctt atcgccgata gggacagtcc catcacgaac gggcgagcgg cccgcccgc   41400 gtacgacgga caagtgcgca ccgctcggta ccgggcgagc gtgacgggta gcgagcggcc   41460
cgataagccg gtgatgggcg cccgcggtgc cacggggaac gctgggcggc tgtgtgcggg   41520
cgacacgctg aacgcggaga tgagcgccgc ctgtgtgcgt agggcgggcg ggcggcagcg   41580
caagacggtc gtctacagcc ggctgtgcct ggacgatgcg ctgctgctgg aggctggagg   41640
caatggtgcc gacgggtccg ggcggctgga cggctgggcc accgccagg cggaagtgat   41700 ccgctttccc tgcgtggagc gactgatcga actgtacgca aacatcatcc gccagaagga   41760
ggctgaagtg caaagattta tgagcagtat tgtaaggagc ggccgataaaa gtcgattaga   41820 taagggtgtg cgtcggtggc aggggggaagc ggatgggccg cacggcagca aacgacagcg   41880
```

```
acaaggtgac atcgagcgca agacactggc agcgctacct gcgtcagtgt cgctcgaatc   41940
actgtcgcaa gcgaagacgc ccgagcccga ccgcaccagt acgataccgt ccggcgacga   42000
cgcggcacgt gtcagccgca ccagcaccag cccggcccag tcagacgaag gttggcgcag   42060
cgacgacgag gaacgggagc gcgcagccca ccaggacccg gcgatgaaga accgcgacaa   42120
ggtgacgcgc tcggccagct ccgattcggc cctcgggctg gacgacgagc tgagcgcgca   42180
ggagcagcag caggcgatcg caaccgtcgg caaggtgcgg cggctcacgc tcggcgtgtc   42240
cgacataccg ctgcgggcgg ccctgctgcc cgtgccggaa ccggccaccc tgcccagcct   42300
caccctcacc gaccagcact gcccgaccgt ggtgcgcagc aagatgatac tggaggcgca   42360
gctgatcgag ctgccgctgg caggcggcga gctaccggcg aacagcaac cggggcagca   42420 gcagctcggc tgcccgccga gcacgtccgt gtcgcggcgc gagtccgccc aaagctacat   42480
cagtgacgcg gggaccgagg gcgtccggta cgtccgcacg ccgtccgtgg tcgtgtcgga   42540
ctactcggac gacacgatgt gcggcatcac gctggaggag atcgagtact ccggcgcgca   42600
ccggttgcgg cgcggctcgg ccgactgcga gtcggacatc agtgcggcct cgtcctgcag   42660
caatctgaac tactgcggct cgtccatcag cgcgctggac gggtgcgagt accagtgcgg   42720
gctgcgcacg cccgagcgca aggtgtccga ctgctcgacc tgctccaccg tcagctgcga   42780
cgaggacgag ggctactcgc gggtggtgcg cgcgaagctc gccacgctca gctgtctgcc   42840
cgcggccgac acggtcgcgg aggagacgga gctgccccg gcggtgcccg catcgcccgc   42900
caagccggtg gccccggttg cagcaatcgc cgagccgggc gagacgggag cggacgttcg   42960
cgtgtgcagc aaaaagaagg ttagttccgt tggcaacagc tgtggataga gaggggagg   43020 ggggagggga gggggtatta cctctgcctc gtaggattaa gttagttaag ctatgtttat   43080
tccagacaca cacaacagcg ggttgtttgt atattttgta agcagcttta acgcaataaa   43140
ctcaaaacta gtattacaat ggtacaatgg tagcggagtt aaggtacgaa tgcaatcggt   43200
gcaacatttt gcgcatacac taccaaacac attatgcagt ttttttttc ttcagccaaa   43260 caaatcgggc caaccaacat cccaacaaac cgtcccacac agccacacag ctaatgatta   43320
tgcgcggggg ttttttttt gtattcatca atcgttcctt ccagtccccg tccgcggcgg   43380
agtctgtgta cggggagagg gggggtgga ggggtttcgt cttcttctta ttgtttttat   43440
gtgtccgaag ctacctaatc agtaaatcga ccgccattga cgtcacggtg cggggtgtaa   43500
acagtgcccg taccggtaat ggagatcggc tgtgggccgt tccagctccg ggcgagggtt   43560
ttggaatatt tgtgtcaatt aaaccgcgcc gtttaggcaa tcggggccaa ctgggaatc   43620 atggagatgg acaggcgaca gggtagctaa gcacgtgtcg gcacgggcag aagcgtacga   43680
tttagaagtg taacgaagat tcttagcacc aactgatgga ccaaacagat cggtaacagc   43740
tccatcttgg aggtagtttg tggcgtccaa tatctattgt cagcactgtc aaatcaatgt   43800
gtgtttgcac cactaccacc gtttgcacag tgttgtcgta ccgataatgg ttgctggcag   43860
cagtcacgaa gaaacatcat gtagtgtcat aatatttgga caggcggtcc acgagcgacg   43920
gaacaagtag cagcacccgc gtgaggcgac ggtcccctaga acggcctgtt ccgttttgg    43980 tgtatttatt ccggcactaa tgccccgcc gtgttcttca atagcaaaaa ggtagaatga    44040
gccgtaaaag catgtgtatg tgtgtgagca tcgcgctata atgttgcaac gaaagtgaga    44100
agctcgtaca gcggggggctc atgagcttgg tgagcagcgt ccgctaccga gcagcgcggt   44160
gattcgcggt tccaaacgat ttacttcttc ggggcggcct ccgcttcacc gtctgatccg    44220
tctctccttg agcgctgatt ccgtgcgcgg tggcggaatg acgtcaatgg tgtggccgct   44280
```

```
acatgctgcg ccgcaaagtt tcgagctgca cagcacattg ttgagtttgg cccatcaagt    44340
ggcatttgat tggagcttgt acggggggggg agatgggagc gagccgccag tgggacttat   44400
ggcctttatc gcaagcgtaa caacttaatg accgatgcga gaaggaagca cacacaaacg    44460
aaaaaaaaag caccagagag ttgtaacggg tgatgacggg atcagccaac tgtaatgtgg    44520
gcacggcttg cacactggat cggggtgtcg agtacatcaa gagctgttcg ttgaggagta    44580
tggattgatg agtaatcggt accgaacggt aatacaaaaa aaaacgattt gaagagttta    44640
gtccacggcc ggcttaagcc accatggaca cctcttatgc tgtgatcggg actgggcaga    44700
gtcattatgc tggcagtagc tgtgtgtgtg ttccgctttt cttggccaga agtgtaataa    44760
acctaatcca cggcgagaaa catagcaccc gaccagaatg tttgcaaaca caggccgtta    44820
tcgcgttaaa aatagagagc gttgtcatgg gatggtaaac gattcagtca caaatggcaa    44880
ccgtgggaca catttacatt gttccgtgtt gcgataagcc ccagcacaat ttcagccgta    44940
gcagccatga ggcccatgcc tatcttattg ctcccacagg cccggattga cagcaagacg    45000
gggttttcgt ctactagcac tggtttgccc aaaaaaagaa acgcgttatc aaccgatacg    45060
gttcccgtt gtatcgccaa cgatttcgtt atttgttttc gggtttgtat tgggtgcgtt     45120
tgtgtactaa ttctttatgc gctgtggttg gcaagatagc tcataattga agcaaaacaa    45180
aacaactctt aaagtaaaag aacacaacca tcactggtgg tgatgaaatg aagtaagtaa    45240
taaatgagta aataataaat aaatcactta aagcaacaaa aatcgaagga gtcaacagtc    45300
gcaagtcaat aactttgtta tactaaacgt ttcccaatca cctttttgtg caaatctttg    45360
aaaacgaaaa ccgatcatga aggggcaacg atcaaatacc aaacaaacaa acaaacaaac    45420
actgcaaacc gaaaaacgga ggcatgtaaa gtgagagggc gatgttaacc tgattatatc    45480
cgccaagtag ccaaaatgcg aatgaagagg agaaagcgaa ttagcaatga cgcaagcaac    45540
aagcagcggc gcactggaaa aggattggaa aagattatag aattagattg aactaacaga    45600
aaatgtattt catcagctgt aaattgacca gcgttgacgt cagtatcgtc ggtcggttac    45660
ggacgatggg tttaggccgt tttgtgcatt tataagtgca atcacacttc aaacgagtgt    45720
ttatacgcta ccatcataag aaagtttcat tgaaaaggaa atatcgtaca acaatcgttg    45780
tagcggctag tgtggtgcta tatgtattta catatctttt gctgattttg catacaatgt    45840
taatggtttt aaattaagta aataaaatca gttaaaaatg aggtgtaaaa ataccaaaaa    45900
aactgatttt gggaatttat tgaaatgaaa caccatttgt gtgtgtgctc gttttttgtca   45960
agccctgtac gcctcacaaa gcttttcacg ctttcgaatt gcatacttt aggggcttta     46020
aagctcgcgg ctttggcgag ccatgcaata tattttactg agcagaatac atcatatcaa    46080
agagtaaatc aacatttgaa atagttattt tgaggctata gagatattaa atagtaaaga    46140
gcaaaatgtt tacctgttca aatattcctg aggtgttccc tgagtggtat cttctgtcga    46200
gccgtaagcg tgctttaatc aatactacca ttgcatatct gtagagtata ttgcttcgac    46260
aggtgtcaga tcattcgcca cagaatggtg aaaaataaat gtttgttgat taatgtcata    46320
aattatggag catacgattt aaattttgta tttctgtatt aataagaaaa ccattgattt    46380
attaattatt tcgtaccaat gtcgaaaaat gcaatacatt caaaataaca tcaatgctaa    46440
attgtaacat tcacttttct tctttctcca ccctttttc caggttagta tagctaatat     46500
gagctgaatg tgcgtgtacc gggcaaatcg agggttcgta gctacacgcc ttttgtccgt    46560
ggaagtcttt tgttcccgac agatagctga atcatgaacg attggcgtga accgttttca    46620
ttcattgcaa gtgaaccgta agtaactgag agtaaggtgc tgttgtgctg tacaagcgaa    46680
```

```
acattccggc aaccgataca gccttgacat atgtgtgtgt gtgtgtttgc tgagtcccgt    46740
ttcgaaacgt ggaaaggtta aaagcaattg aaaaatatgt agattacttg tgtttcggtt    46800
gcaccacatc gcagtcggtt gttacacatc gctcgaacag ttttgaattt tgtaaaaaaa    46860
ataataataa aataaaaata taatccgccc aagtgaggct ggataactct ggagatccgg    46920
ccaaactgaa acactcccgc gctggtagcg ttaccatacc ggtcacagaa acaaatgagg    46980
atcagccaag gcaaatacag ccacattttt ttttccttcg cccaggacta tggcaagaaa    47040
atgataaatc gattatgtct gactcagtct gacgggctgt gcgtttgcct tgtctagcaa    47100
atatttgact ttcttttgct gcctgccttt tgcttagctt gcaaactctc aatcattcat    47160
taatatgggt caaaacaggg acactaaggc ggtactgaaa agcacgttat aagcgttaca    47220
gatcacggga cggtgatggt aagcgacagc acaacatcgt ttgatttgtt tttttttgtt    47280
ttgaaaatga tctggatgaa acaaatgaaa agggaggggg tggggggggg gggggtgagg    47340
tggaaagata acaaaacggg cgtcgatgt tagtgcgaca tgtatagcac gggtaaaatt     47400
agctacccga aacgattaat ctttccttct aatggcaacg ccataaatga ctgcgaacat    47460
taatgagatt gattaatcaa attagatgaa ctaaattaca cgtttcaggg ggttttactg    47520
ggacaatgct tcttcccaac ttaatggttg tcttgtgtca agatgatttt gcactttagg    47580
cgtcagatat aaggactata attgatgata atgatgttat taaaaataa ataacgaaaa      47640 caaagcaaac catgttaaaa acattgtctg ctgttgttgt ggaacaaggg agaagatatt    47700
tgctgaagat tgttagagca cgtgtgaata taacccacta taaagcactt acctgatgat    47760
tagtttaaac gattcgagta gttgtgtcct ttaacgcaac ttgtgagaaa actttaaatg    47820
ttacataaaa ctctccgaga tctattacag atagctttt gtgtgtgcat gattttacaa     47880
gatctataat tatttaaaca aaactcttga agcactcctt cacctcctaa tctaacaaca    47940
accttctgca agcaagatgg agcaagagag aaaacaagcc caagatgcac attcaaacgt    48000
atgagagcgt agtaaatatc gcattgtatc ctgccatacc accacgcaag gcatacacag    48060
aaccgaagcg aaatagagaa agggagagca acgttgcgcg ttgatacggg ggtaaacaat    48120 ccgcttttcaa gagcggcgag agaaaacatc gtgcccgaat cgtgaaaaat tcgtttccat    48180
tctgcgggat gctgtggcac aaacctggtc gccacgagct tcacagtcgc aaagtcatcg    48240
cccgtgcatc cagtcgcgcg tttcgctcgc ggtcggtgaa ttgatgtgag tgtgcgcgtc    48300
acgttcatga tagtccggct ggttaagcgg actaagtcgt ggttttaag gtaatggaac      48360 aacaagctcg acgatgatca ccatcgtagt gtacgtgttg atttggtgtg gctgtgtttg    48420
tgtgtgtgtg tggtctatgg tgttagacgt gcataatttg tgtatcagac gatcattagc    48480
ctgcttgatg agctgctgct gctgctcaag agaaaaacaa caaatcacaa aagtgacaca    48540
aacaaaaagg agtgctgcga tgcttcggta ttgttgtttt ccgtctggcg tggcctgctg    48600
catccaccag catggatgct ctctcggctc tccacctgcc accgctgatt attaagagcg    48660
actcgaaacc ctaccgaccg ccatgcttcc cggtgccacc gtcaaatcaa cgcaaaagct    48720
gcaactgccc tgacgtaacg gagggacaaa ttgaaataga tttagtgatt agccgaccga    48780
cagccgcatg tgtgccggct gtgtgcaccg acgattgctt cgtggggtct tcttcagcg     48840 cacccgcccg tgaagggttt attttttctt cttctctgca ttgctgcgat actgcgggcg    48900
aaagaagttg aaaaggttgt gggcaaaaac cgacgggatc acgggaggtg caaaagtggc    48960
tcgcgaatcc ttcgtttgag gctcaggctt tctttttcct ttcctttcct actcgtaatc    49020
ggcctccctg cgcattcgtt agcgtcttta tttcgaacct gtcgatcgtg tgagtgtgta    49080
```

-continued

```
tcgatcgtaa taatcaattt acatttatga aatatatcaa ccagttttg cctttgattg    49140 attttgatcc aggtgcgagc gggtcgcgct catgtacaca cacacgcgcg agcccttcca    49200
cgcttcacgt ttgtcctgct cgaccccccc tccctcaaaa gctcgccctc tatctctctc    49260
gctcggtgta tctcgcgcga tcgtagtggt ggtgcaggag atctcgtcga tctgttcagc    49320
aaaactgacg cgccgaaggt gccaatggag gaatgtatgc agcagtgctg cagggacctg    49380
gtagggacag tcggctggca acgcctaata cggaacggaa cgtatcgaat gctacaaatt    49440
gtttacatgc cagatggatg gctgcagtag aagaggtgca cggggagaga caaacggatg    49500
aaagagaaaa gaaaagcgac tagttgcagt tgccgtgtga tttgtaccta caggtacgcg    49560
agatggtacg acagttttg ctaaacaaat tcatatggtc cacgcgaacc tggtgcaagc    49620
ccgagtgtgc tagaatagtt gctgacaggg taagaggatc taatttgcgt ccaattagct    49680
acctcacaca atcttaaatg ggatggaagg tctttgggct atgttttgtt agcatcttta    49740
atgtgcttta aagcatgaaa tatgaacatc tcgtgatttt gtgcttaatc ttcttgctta    49800
acctaatgtg cacaaacaaa cacactacca ttcgtttaca aacagatcac attgaaaccg    49860
aagcaggcac acaacaaaat acaattaaat cttttgcaa aaggtaacga cagcttacga    49920
cgcagaaggg aacgtgttgt tgtgttgcta ccttgtccta ggttgtacca caaaaaaga    49980 agcgaaacaa atgaactatt tttctgctct ttctcacctc ccaaaagccg atcacactac    50040
tgtttagctt ttgttgttga gccctgctgt cagagctagc gcgtgaaccg cgtgtagcgc    50100
cttggcggca cactaattta ccataacaaa agtgttccta acaatcgttc gagtgcgtca    50160
ctcgcacctc tcgaactaat gttggagaag ctgctagaat aatgatgaca ggctgagtat    50220
acaggggggt ctaaggtaga gccgtacggt agtgatcgga accattaaac actattgtaa    50280
acattagtag acaatttagt acattcataa ttggatgcaa aatgggcttt acaatttaaa    50340
attctaaacg attaccatca acttcctcca taaaaaatgc ttacagatag gtatcagtga    50400
aacgaaggta tcgtaacctt tgccgtccac actgtttacg cacccaga                50448
```

<210> SEQ ID NO 7
<211> LENGTH: 2983
<212> TYPE: DNA
<213> ORGANISM: Anopheles gambiae
<220> FEATURE:
<221> NAME/KEY: CDS
<222> LOCATION: (236)..(2371)

<400> SEQUENCE: 7

```
ccacgcgtcc gcccacgcgt ccgtgctgct aaagtacgac gccaacataa acgcgaccga     60
tgagaacagt gtgtcaccga tagctctgct agtaacagct ggatacgacg attggagaaa    120
ggaaattctt gaatactgtt tgcagaacta cagcgtgaac gtagactacc ggcgacagca    180
ggcgagaaaa gcgatcgtga agaacttccc cggtacggac attcccatct acgac atg    238
                                                                Met
                                                                  1 gaa aag gtt acc gtg gat gtg ttg cgg aac aaa ctg tcc gcc gga acg    286
Glu Lys Val Thr Val Asp Val Leu Arg Asn Lys Leu Ser Ala Gly Thr
          5                   10                  15 gag gac gag ttt ctt gcg gct tac gag aag tac tgg cag caa aac aat    334
Glu Asp Glu Phe Leu Ala Ala Tyr Glu Lys Tyr Trp Gln Gln Asn Asn
     20                  25                  30 agt cac gtg ccg cga gaa gaa gat cgc gct gag ctg cta tcc gtg gcc    382
Ser His Val Pro Arg Glu Glu Asp Arg Ala Glu Leu Leu Ser Val Ala
 35                  40                  45 gtg tat cga gcg aag ctg acc gct gcc cag aag ctc gtt gac ggg cag    430
Val Tyr Arg Ala Lys Leu Thr Ala Ala Gln Lys Leu Val Asp Gly Gln
 50                  55                  60
```

-continued

| | | | | | | | | | | | | | | | | |
|---|---|---|---|---|---|---|---|---|---|---|---|---|---|---|---|---|
| Val | Tyr | Arg | Ala | Lys | Leu | Thr | Ala | Ala | Gln | Lys | Leu | Val | Asp | Gly | Gln | |
| 50 | | | | 55 | | | | | 60 | | | | | 65 | | |

| ata | gta | gag | ggc | aag | ttt | acc | ggt | aag | ccg | gaa | ttg | ttt | tcc | ggc | ctg | 478 |
|---|---|---|---|---|---|---|---|---|---|---|---|---|---|---|---|---|
| Ile | Val | Glu | Gly | Lys | Phe | Thr | Gly | Lys | Pro | Glu | Leu | Phe | Ser | Gly | Leu | |
| | | | 70 | | | | | 75 | | | | | 80 | | | |

| ctg | gcc | aag | tgt | tgt | aat | cgg | ggg | aat | gtg | cag | atg | ctc | gaa | tgg | ttg | 526 |
|---|---|---|---|---|---|---|---|---|---|---|---|---|---|---|---|---|
| Leu | Ala | Lys | Cys | Cys | Asn | Arg | Gly | Asn | Val | Gln | Met | Leu | Glu | Trp | Leu | |
| | | | | 85 | | | | | 90 | | | | | 95 | | |

| ctg | aaa | atc | ata | ccg | gac | gat | gcg | ggg | gcg | ctg | att | aac | gag | gat | ccg | 574 |
|---|---|---|---|---|---|---|---|---|---|---|---|---|---|---|---|---|
| Leu | Lys | Ile | Ile | Pro | Asp | Asp | Ala | Gly | Ala | Leu | Ile | Asn | Glu | Asp | Pro | |
| | | | 100 | | | | | 105 | | | | | 110 | | | |

| ctg | ctc | tcg | ctg | ctc | gtg | aag | cag | atc | gac | gtg | tac | aag | gac | aag | aac | 622 |
|---|---|---|---|---|---|---|---|---|---|---|---|---|---|---|---|---|
| Leu | Leu | Ser | Leu | Leu | Val | Lys | Gln | Ile | Asp | Val | Tyr | Lys | Asp | Lys | Asn | |
| | 115 | | | | 120 | | | | | 125 | | | | | | |

| aag | tgt | ccc | tac | ttc | cgc | agc | atg | ggc | atc | ttg | ctg | aac | gat | ccg | cgc | 670 |
|---|---|---|---|---|---|---|---|---|---|---|---|---|---|---|---|---|
| Lys | Cys | Pro | Tyr | Phe | Arg | Ser | Met | Gly | Ile | Leu | Leu | Asn | Asp | Pro | Arg | |
| 130 | | | | | 135 | | | | | 140 | | | | | 145 | |

| ctg | gag | gtg | gac | aaa | atc | gat | gcg | aaa | aaa | tgt | acg | gcg | atg | cac | tac | 718 |
|---|---|---|---|---|---|---|---|---|---|---|---|---|---|---|---|---|
| Leu | Glu | Val | Asp | Lys | Ile | Asp | Ala | Lys | Lys | Cys | Thr | Ala | Met | His | Tyr | |
| | | | | 150 | | | | | 155 | | | | | 160 | | |

| gcc | gtc | aag | tac | aag | atc | gat | cac | gcc | cag | gag | ctg | ctg | ctg | gcc | aag | 766 |
|---|---|---|---|---|---|---|---|---|---|---|---|---|---|---|---|---|
| Ala | Val | Lys | Tyr | Lys | Ile | Asp | His | Ala | Gln | Glu | Leu | Leu | Leu | Ala | Lys | |
| | | 165 | | | | | 170 | | | | | 175 | | | | |

| gga | gcg | tac | atc | ggg | ggc | gag | aac | atg | ttc | ggc | gac | ctg | ccg | atc | agc | 814 |
|---|---|---|---|---|---|---|---|---|---|---|---|---|---|---|---|---|
| Gly | Ala | Tyr | Ile | Gly | Gly | Glu | Asn | Met | Phe | Gly | Asp | Leu | Pro | Ile | Ser | |
| | | | 180 | | | | | 185 | | | | | 190 | | | |

| gag | atg | gac | tcg | ttc | ctg | ctg | gag | aag | cat | ctg | gac | tcg | tgc | gtc | acg | 862 |
|---|---|---|---|---|---|---|---|---|---|---|---|---|---|---|---|---|
| Glu | Met | Asp | Ser | Phe | Leu | Leu | Glu | Lys | His | Leu | Asp | Ser | Cys | Val | Thr | |
| | 195 | | | | | 200 | | | | | 205 | | | | | |

| aac | aac | gat | cgc | aag | ccg | ggc | gac | gag | gac | tac | gaa | gtg | agg | atc | agc | 910 |
|---|---|---|---|---|---|---|---|---|---|---|---|---|---|---|---|---|
| Asn | Asn | Asp | Arg | Lys | Pro | Gly | Asp | Glu | Asp | Tyr | Glu | Val | Arg | Ile | Ser | |
| 210 | | | | | 215 | | | | | 220 | | | | | 225 | |

| ttt | gcc | aac | ttt | ata | ccg | ccg | gcc | cac | aag | ccc | aac | tac | gcc | aag | ccg | 958 |
|---|---|---|---|---|---|---|---|---|---|---|---|---|---|---|---|---|
| Phe | Ala | Asn | Phe | Ile | Pro | Pro | Ala | His | Lys | Pro | Asn | Tyr | Ala | Lys | Pro | |
| | | | | 230 | | | | | 235 | | | | | 240 | | |

| gaa | cag | gtg | ccg | ttt | aac | ggg | ctg | ccg | tac | gag | gac | gag | atg | cgc | ccg | 1006 |
|---|---|---|---|---|---|---|---|---|---|---|---|---|---|---|---|---|
| Glu | Gln | Val | Pro | Phe | Asn | Gly | Leu | Pro | Tyr | Glu | Asp | Glu | Met | Arg | Pro | |
| | | | 245 | | | | | 250 | | | | | 255 | | | |

| atc | gta | cgc | atg | gcc | cag | tcg | tcc | agc | acc | aaa | cgg | ctg | ctg | cgg | cat | 1054 |
|---|---|---|---|---|---|---|---|---|---|---|---|---|---|---|---|---|
| Ile | Val | Arg | Met | Ala | Gln | Ser | Ser | Ser | Thr | Lys | Arg | Leu | Leu | Arg | His | |
| | | 260 | | | | | 265 | | | | | 270 | | | | |

| ccc | gtc | ata | tcg | agc | atc | ctg | ctc | aag | tgg | ctg | aag | ctg | atc | tgc | | 1102 |
|---|---|---|---|---|---|---|---|---|---|---|---|---|---|---|---|---|
| Pro | Val | Ile | Ser | Ser | Ile | Leu | Leu | Lys | Trp | Leu | Lys | Leu | Ile | Cys | | |
| 275 | | | | | 280 | | | | | 285 | | | | | | |

| ttt | ttc | tac | atc | aat | ctg | gtg | atc | tgc | acg | ata | ttc | ttc | gtg | tcc | ttc | 1150 |
|---|---|---|---|---|---|---|---|---|---|---|---|---|---|---|---|---|
| Phe | Phe | Tyr | Ile | Asn | Leu | Val | Ile | Cys | Thr | Ile | Phe | Phe | Val | Ser | Phe | |
| 290 | | | | | 295 | | | | | 300 | | | | | 305 | |

| acg | gcg | tac | gtt | gtg | ttt | tgc | tac | ggc | cag | gaa | gat | gca | ccg | ttc | aag | 1198 |
|---|---|---|---|---|---|---|---|---|---|---|---|---|---|---|---|---|
| Thr | Ala | Tyr | Val | Val | Phe | Cys | Tyr | Gly | Gln | Glu | Asp | Ala | Pro | Phe | Lys | |
| | | | 310 | | | | | 315 | | | | | 320 | | | |

| ctg | ttc | ttc | tac | ttc | ctc | tcg | ttc | gcc | ggc | tgg | ata | tat | ttg | gtc | gca | 1246 |
|---|---|---|---|---|---|---|---|---|---|---|---|---|---|---|---|---|
| Leu | Phe | Phe | Tyr | Phe | Leu | Ser | Phe | Ala | Gly | Trp | Ile | Tyr | Leu | Val | Ala | |
| | | 325 | | | | | 330 | | | | | 335 | | | | |

| cgc | gag | ctg | atc | cag | ttt | ctg | ctg | aac | atg | cgc | gtg | tac | gtg | cgg | tcg | 1294 |
|---|---|---|---|---|---|---|---|---|---|---|---|---|---|---|---|---|
| Arg | Glu | Leu | Ile | Gln | Phe | Leu | Leu | Asn | Met | Arg | Val | Tyr | Val | Arg | Ser | |
| | 340 | | | | | 345 | | | | | 350 | | | | | |

| atc | gag | aac | ggg | atg | gag | gtg | ctg | ctc | atc | ctg | gcc | tcg | ggc | gcg | gtg | 1342 |
|---|---|---|---|---|---|---|---|---|---|---|---|---|---|---|---|---|
| Ile | Glu | Asn | Gly | Met | Glu | Val | Leu | Leu | Ile | Leu | Ala | Ser | Gly | Ala | Val | |
| 355 | | | | | 360 | | | | | 365 | | | | | | |

| ctg | atg | cgc | gag | ttt | ggc | gac | gaa | acg | cgg | cgt | gtc | gcg | tcc | gcc | tgc | 1390 |

-continued

```
              Leu Met Arg Glu Phe Gly Asp Glu Thr Arg Arg Val Ala Ser Ala Cys
                  370                 375                 380                 385 gtg att ctc ctg tcg gcg cta gag ttt acg ctg ctc gtc ggc acg ctg         1438
Val Ile Leu Leu Ser Ala Leu Glu Phe Thr Leu Leu Val Gly Thr Leu
                    390                 395                 400 ccc gtc cta tcg atc tcg acc cac atg gtg atg ctg aag acg gtg tcg         1486
Pro Val Leu Ser Ile Ser Thr His Met Val Met Leu Lys Thr Val Ser
                    405                 410                 415 aag aac ttt ctc aag tgt ctg gtg ctg tac tcg atc att ttg ctc gca         1534
Lys Asn Phe Leu Lys Cys Leu Val Leu Tyr Ser Ile Ile Leu Leu Ala
                    420                 425                 430 ttt gcg ttc agc ttc tac acg ctg ttc cgg gcg aac ggt ggt aac ggc         1582
Phe Ala Phe Ser Phe Tyr Thr Leu Phe Arg Ala Asn Gly Gly Asn Gly
                    435                 440                 445 gag gcg ggc gaa gcg acc aca gac aag aca gct gcc ggt cag gac ggc         1630
Glu Ala Gly Glu Ala Thr Thr Asp Lys Thr Ala Ala Gly Gln Asp Gly
450                 455                 460                 465 gat ggt gat gac gat cag ttc aac cag ttc ggg gag gtt ccg ctt gcg         1678
Asp Gly Asp Asp Asp Gln Phe Asn Gln Phe Gly Glu Val Pro Leu Ala
                    470                 475                 480 ttg atg aaa aca gcg gta atg ttg acc ggg gaa ttc gaa gcg gcg aac         1726
Leu Met Lys Thr Ala Val Met Leu Thr Gly Glu Phe Glu Ala Ala Asn
                    485                 490                 495 ata aaa ttt caa cag tca agc ttg agc tac ttc gtg ttc gcg ctg ttt         1774
Ile Lys Phe Gln Gln Ser Ser Leu Ser Tyr Phe Val Phe Ala Leu Phe
                    500                 505                 510 ctg ttc ttt gtt tcg atc gtg ctg ttc aac ctg atg aac ggt ctg gcc         1822
Leu Phe Phe Val Ser Ile Val Leu Phe Asn Leu Met Asn Gly Leu Ala
515                 520                 525 gtg agc gac acg acg acc atc aaa gcg gaa tct gaa atc atc ggc att         1870
Val Ser Asp Thr Thr Thr Ile Lys Ala Glu Ser Glu Ile Ile Gly Ile
530                 535                 540                 545 acg cag aaa gtg ttc ctc atc aac aag tac gaa aat gca ctg aaa aca         1918
Thr Gln Lys Val Phe Leu Ile Asn Lys Tyr Glu Asn Ala Leu Lys Thr
                    550                 555                 560 tcg aag ccc att cgc tgc atc acc gag cga atg gcg tgg ctg ttc ccg         1966
Ser Lys Pro Ile Arg Cys Ile Thr Glu Arg Met Ala Trp Leu Phe Pro
                    565                 570                 575 tcc aac agt ttg cag ctg ttc tcg aac aat caa ccg ctg aag tac att         2014
Ser Asn Ser Leu Gln Leu Phe Ser Asn Asn Gln Pro Leu Lys Tyr Ile
                    580                 585                 590 gcg gtc aag cca aac cag tcg aac gcc atc atg gta tcg tcg ctc gtg         2062
Ala Val Lys Pro Asn Gln Ser Asn Ala Ile Met Val Ser Ser Leu Val
                    595                 600                 605 ccc cgg tac gcg cag gac gtc gag atg ggt gag ttg gtg gtg cag gac         2110
Pro Arg Tyr Ala Gln Asp Val Glu Met Gly Glu Leu Val Val Gln Asp
610                 615                 620                 625 aaa aag ctg gaa gtc gaa gga ttg ctg gag cgc aac acc aag tac ggt         2158
Lys Lys Leu Glu Val Glu Gly Leu Leu Glu Arg Asn Thr Lys Tyr Gly
                    630                 635                 640 acc gaa tgc tgc atc atg ccc tgc ctc aac aac atg gat ggg aag ata         2206
Thr Glu Cys Cys Ile Met Pro Cys Leu Asn Asn Met Asp Gly Lys Ile
                    645                 650                 655 gtg aag tat gcg ctg gag att ttg cac tcc cgc cac gag cac gtc ggc         2254
Val Lys Tyr Ala Leu Glu Ile Leu His Ser Arg His Glu His Val Gly
                    660                 665                 670 tcg acc gag tac cgg atg tcg cgc atg gag cag aac atc gag cgg atg         2302
Ser Thr Glu Tyr Arg Met Ser Arg Met Glu Gln Asn Ile Glu Arg Met
                    675                 680                 685 gcg cag gag cag atc gag atg aaa aag ttg ctg caa acg ctc gtc acc         2350
```

```
Ala Gln Glu Gln Ile Glu Met Lys Lys Leu Leu Gln Thr Leu Val Thr
690                 695                 700                 705 tcg ttg caa gct aag gcg tag tcgttctgta ttgcgcacag gatgggagtt            2401
Ser Leu Gln Ala Lys Ala
                710 gggattaatt tatggttttg tttttaaatg ctttaactga ctcaaatgca tttggtttgc       2461 attttgtgaa cggcattact ccacttgcac ccttacctca cgcagctatt attgacattg       2521 aagtttgtaa gtctatttta actagcactc agtttgctta tcattgttac cttttaaag        2581 cggaaacaag caacgttcct gttcgtctta aatcgcgcat gaatgctaga ctgaatcaaa       2641 ccgatcagtc aatataacca tcacaatgat tctatctgaa tcattacgcc ttaacgatac       2701 ctgcaaggat ttatgaaatg ttatacccttt ttacacccttt gaatctctac agtggtcgtt    2761 acacatgaaa cgattgcact tatttacact catttccact gtttgtatat gactgttggc      2821 attgcattgt tagcgaaacg ttggttgtat taatgtaatt ttaagtccca caataaataa      2881 ttcaagtgta acaatcataa ctattgaata tatttaattt acaataaaa aaaaaaaaaa       2941 aaaaaaaaaa aaaaaaaaaa aaaaaaaaaa aaaaaaaaaa ag                         2983

<210> SEQ ID NO 8
<211> LENGTH: 711
<212> TYPE: PRT
<213> ORGANISM: Anopheles gambiae

<400> SEQUENCE: 8

Met Glu Lys Val Thr Val Asp Val Leu Arg Asn Lys Leu Ser Ala Gly
1               5                   10                  15

Thr Glu Asp Glu Phe Leu Ala Ala Tyr Glu Lys Tyr Trp Gln Gln Asn
                20                  25                  30

Asn Ser His Val Pro Arg Glu Glu Asp Arg Ala Glu Leu Leu Ser Val
            35                  40                  45

Ala Val Tyr Arg Ala Lys Leu Thr Ala Ala Gln Lys Leu Val Asp Gly
        50                  55                  60

Gln Ile Val Glu Gly Lys Phe Thr Gly Lys Pro Glu Leu Phe Ser Gly
65                  70                  75                  80

Leu Leu Ala Lys Cys Cys Asn Arg Gly Asn Val Gln Met Leu Glu Trp
                85                  90                  95

Leu Leu Lys Ile Ile Pro Asp Asp Ala Gly Ala Leu Ile Asn Glu Asp
                100                 105                 110

Pro Leu Leu Ser Leu Leu Val Lys Gln Ile Asp Val Tyr Lys Asp Lys
            115                 120                 125

Asn Lys Cys Pro Tyr Phe Arg Ser Met Gly Ile Leu Leu Asn Asp Pro
        130                 135                 140

Arg Leu Glu Val Asp Lys Ile Asp Ala Lys Lys Cys Thr Ala Met His
145                 150                 155                 160

Tyr Ala Val Lys Tyr Lys Ile Asp His Ala Gln Glu Leu Leu Leu Ala
                165                 170                 175

Lys Gly Ala Tyr Ile Gly Gly Glu Asn Met Phe Gly Asp Leu Pro Ile
            180                 185                 190

Ser Glu Met Asp Ser Phe Leu Leu Glu Lys His Leu Asp Ser Cys Val
        195                 200                 205

Thr Asn Asn Asp Arg Lys Pro Gly Asp Glu Asp Tyr Glu Val Arg Ile
    210                 215                 220

Ser Phe Ala Asn Phe Ile Pro Pro Ala His Lys Pro Asn Tyr Ala Lys
225                 230                 235                 240
```

-continued

```
Pro Glu Gln Val Pro Phe Asn Gly Leu Pro Tyr Glu Asp Glu Met Arg
            245                 250                 255

Pro Ile Val Arg Met Ala Gln Ser Ser Thr Lys Arg Leu Leu Arg
        260                 265                 270

His Pro Val Ile Ser Ser Ile Leu Leu Lys Trp Leu Lys Leu Ile
        275                 280                 285

Cys Phe Phe Tyr Ile Asn Leu Val Ile Cys Thr Ile Phe Phe Val Ser
        290                 295                 300

Phe Thr Ala Tyr Val Val Phe Cys Tyr Gly Gln Glu Asp Ala Pro Phe
305                 310                 315                 320

Lys Leu Phe Phe Tyr Phe Leu Ser Phe Ala Gly Trp Ile Tyr Leu Val
                325                 330                 335

Ala Arg Glu Leu Ile Gln Phe Leu Leu Asn Met Arg Val Tyr Val Arg
                340                 345                 350

Ser Ile Glu Asn Gly Met Glu Val Leu Leu Ile Leu Ala Ser Gly Ala
            355                 360                 365

Val Leu Met Arg Glu Phe Gly Asp Glu Thr Arg Arg Val Ala Ser Ala
        370                 375                 380

Cys Val Ile Leu Leu Ser Ala Leu Glu Phe Thr Leu Leu Val Gly Thr
385                 390                 395                 400

Leu Pro Val Leu Ser Ile Ser Thr His Met Val Met Leu Lys Thr Val
                405                 410                 415

Ser Lys Asn Phe Leu Lys Cys Leu Val Leu Tyr Ser Ile Ile Leu Leu
            420                 425                 430

Ala Phe Ala Phe Ser Phe Tyr Thr Leu Phe Arg Ala Asn Gly Gly Asn
        435                 440                 445

Gly Glu Ala Gly Glu Ala Thr Thr Asp Lys Thr Ala Ala Gly Gln Asp
450                 455                 460

Gly Asp Gly Asp Asp Asp Gln Phe Asn Gln Phe Gly Glu Val Pro Leu
465                 470                 475                 480

Ala Leu Met Lys Thr Ala Val Met Leu Thr Gly Glu Phe Glu Ala Ala
                485                 490                 495

Asn Ile Lys Phe Gln Gln Ser Ser Leu Ser Tyr Phe Val Phe Ala Leu
            500                 505                 510

Phe Leu Phe Phe Val Ser Ile Val Leu Phe Asn Leu Met Asn Gly Leu
        515                 520                 525

Ala Val Ser Asp Thr Thr Thr Ile Lys Ala Glu Ser Glu Ile Ile Gly
        530                 535                 540

Ile Thr Gln Lys Val Phe Leu Ile Asn Lys Tyr Glu Asn Ala Leu Lys
545                 550                 555                 560

Thr Ser Lys Pro Ile Arg Cys Ile Thr Glu Arg Met Ala Trp Leu Phe
                565                 570                 575

Pro Ser Asn Ser Leu Gln Leu Phe Ser Asn Asn Gln Pro Leu Lys Tyr
            580                 585                 590

Ile Ala Val Lys Pro Asn Gln Ser Asn Ala Ile Met Val Ser Ser Leu
        595                 600                 605

Val Pro Arg Tyr Ala Gln Asp Val Glu Met Gly Glu Leu Val Val Gln
        610                 615                 620

Asp Lys Lys Leu Glu Val Glu Gly Leu Leu Glu Arg Asn Thr Lys Tyr
625                 630                 635                 640

Gly Thr Glu Cys Cys Ile Met Pro Cys Leu Asn Asn Met Asp Gly Lys
                645                 650                 655

Ile Val Lys Tyr Ala Leu Glu Ile Leu His Ser Arg His Glu His Val
            660                 665                 670
```

| | | |
|---|---|---|
| Gly Ser Thr Glu Tyr Arg Met Ser Arg Met Glu Gln Asn Ile Glu Arg | | |
| 675 680 685 | | |
| Met Ala Gln Glu Gln Ile Glu Met Lys Lys Leu Leu Gln Thr Leu Val | | |
| 690 695 700 | | |
| Thr Ser Leu Gln Ala Lys Ala | | |
| 705 710 | | |

<210> SEQ ID NO 9
<211> LENGTH: 2151
<212> TYPE: DNA
<213> ORGANISM: Anopheles gambiae
<220> FEATURE:
<221> NAME/KEY: CDS
<222> LOCATION: (1)..(2151)

<400> SEQUENCE: 9

| | | |
|---|---|---|
| gca cag aag gat tat acg caa ttc atc caa gcg ctc gaa aat ggt gca | | 48 |
| Ala Gln Lys Asp Tyr Thr Gln Phe Ile Gln Ala Leu Glu Asn Gly Ala | | |
| 1 5 10 15 | | |
| gac gtg aat ggg cga atg cgc aac tca aac tat tcg att ttt gag ctg | | 96 |
| Asp Val Asn Gly Arg Met Arg Asn Ser Asn Tyr Ser Ile Phe Glu Leu | | |
| 20 25 30 | | |
| gct tgt aaa act ccg gga agt gcc aaa tat att gcg gcg tgt ctt aag | | 144 |
| Ala Cys Lys Thr Pro Gly Ser Ala Lys Tyr Ile Ala Ala Cys Leu Lys | | |
| 35 40 45 | | |
| cgt ggt gcc ctt gcg aca gag gaa aac ctt gaa act aag cta tgc cct | | 192 |
| Arg Gly Ala Leu Ala Thr Glu Glu Asn Leu Glu Thr Lys Leu Cys Pro | | |
| 50 55 60 | | |
| atc cat cta gct gcg caa tcc cac gat tgc gaa aat ctt tcc gag ctg | | 240 |
| Ile His Leu Ala Ala Gln Ser His Asp Cys Glu Asn Leu Ser Glu Leu | | |
| 65 70 75 80 | | |
| ctc aat gct tca ggc att cta gtg gat cag atg tac gag gat caa acc | | 288 |
| Leu Asn Ala Ser Gly Ile Leu Val Asp Gln Met Tyr Glu Asp Gln Thr | | |
| 85 90 95 | | |
| gct ttg cag atg ctg ttt aag gaa att gac ggt gaa aat cat acg aaa | | 336 |
| Ala Leu Gln Met Leu Phe Lys Glu Ile Asp Gly Glu Asn His Thr Lys | | |
| 100 105 110 | | |
| gtg ttc gaa tgc att aaa ctg ttg ttg aag cat cag gcc aac atc aac | | 384 |
| Val Phe Glu Cys Ile Lys Leu Leu Leu Lys His Gln Ala Asn Ile Asn | | |
| 115 120 125 | | |
| gtg acc gat tcg gag agt gtc tca cca ata gcg tta ctc tta ata ccc | | 432 |
| Val Thr Asp Ser Glu Ser Val Ser Pro Ile Ala Leu Leu Leu Ile Pro | | |
| 130 135 140 | | |
| ggc aaa gac gct tgg cgg aaa gtc ata cta gat tac tgt ttg aca agc | | 480 |
| Gly Lys Asp Ala Trp Arg Lys Val Ile Leu Asp Tyr Cys Leu Thr Ser | | |
| 145 150 155 160 | | |
| tac aac gtg tac gtc gac ttt cgt gat gga cag gca aga aaa gcg atc | | 528 |
| Tyr Asn Val Tyr Val Asp Phe Arg Asp Gly Gln Ala Arg Lys Ala Ile | | |
| 165 170 175 | | |
| gaa caa cac ttt ccc ggc acg gtc att cca ccg ata gct gca tcg agc | | 576 |
| Glu Gln His Phe Pro Gly Thr Val Ile Pro Pro Ile Ala Ala Ser Ser | | |
| 180 185 190 | | |
| gtt atg ctg gat gtg ttg agg gat aaa tta atg gcc gcc cct gag gaa | | 624 |
| Val Met Leu Asp Val Leu Arg Asp Lys Leu Met Ala Ala Pro Glu Glu | | |
| 195 200 205 | | |
| gac ttt att gtg gct tat gag cgc tac tgt gaa caa aac cat ggg ccc | | 672 |
| Asp Phe Ile Val Ala Tyr Glu Arg Tyr Cys Glu Gln Asn His Gly Pro | | |
| 210 215 220 | | |
| atg gtt gat gag aaa aag tgt gcc gaa ttg ctg tcg atc gct ttg tat | | 720 |
| Met Val Asp Glu Lys Lys Cys Ala Glu Leu Leu Ser Ile Ala Leu Tyr | | |
| 225 230 235 240 | | |

| | | |
|---|---|---|
| cga gaa agg cag aaa gcg gcc gaa aag ctc cta gaa aag caa ata gtt<br>Arg Glu Arg Gln Lys Ala Ala Glu Lys Leu Leu Glu Lys Gln Ile Val<br>    245                 250                 255 | 768 | |
| gct agg aag ttt gtt ggc aat ctt tca ctc ctt tcc ggc atg ctg gcc<br>Ala Arg Lys Phe Val Gly Asn Leu Ser Leu Leu Ser Gly Met Leu Ala<br>260                 265                 270 | 816 | |
| aag tgt tgc aat cga ggc aat att aca atg ctt gaa tgg ttg ctc aac<br>Lys Cys Cys Asn Arg Gly Asn Ile Thr Met Leu Glu Trp Leu Leu Asn<br>        275                 280                 285 | 864 | |
| atc atc cca aac gat gcg gta cga cac gta aac gaa gat ccg ctc cta<br>Ile Ile Pro Asn Asp Ala Val Arg His Val Asn Glu Asp Pro Leu Leu<br>    290                 295                 300 | 912 | |
| tcc ctg ctc gtg aag caa atc ggc cgg gag cat aaa tcg tgc aag gac<br>Ser Leu Leu Val Lys Gln Ile Gly Arg Glu His Lys Ser Cys Lys Asp<br>305                 310                 315                 320 | 960 | |
| aaa ggc aac tgt tca ttc ttt cgc agt atg gtg att ttg ctg aac gat<br>Lys Gly Asn Cys Ser Phe Phe Arg Ser Met Val Ile Leu Leu Asn Asp<br>                325                 330                 335 | 1008 | |
| ccg cgc att gac gtg gac aag gtc gat cga ctg aaa tgt agc gcg ttg<br>Pro Arg Ile Asp Val Asp Lys Val Asp Arg Leu Lys Cys Ser Ala Leu<br>            340                 345                 350 | 1056 | |
| cat tat gcc gcc aag tac aag atc gat cac gcg cag gag ctg ctg att<br>His Tyr Ala Ala Lys Tyr Lys Ile Asp His Ala Gln Glu Leu Leu Ile<br>        355                 360                 365 | 1104 | |
| ggc cgc ggt gcc tac atc ggg ggt gaa gat ctg aac ggc aat ttg ctg<br>Gly Arg Gly Ala Tyr Ile Gly Gly Glu Asp Leu Asn Gly Asn Leu Leu<br>370                 375                 380 | 1152 | |
| atg cgc gag atg cag aaa cat ctt gac tcg ttc gtg acg agc aac gac<br>Met Arg Glu Met Gln Lys His Leu Asp Ser Phe Val Thr Ser Asn Asp<br>385                 390                 395                 400 | 1200 | |
| cgc tgg ccg ggt gac gaa gac ttc gag gtg cgc att aac tgt gcc aac<br>Arg Trp Pro Gly Asp Glu Asp Phe Glu Val Arg Ile Asn Cys Ala Asn<br>                405                 410                 415 | 1248 | |
| ttt ata ccg ccg aca cag aag ctg aac gga aaa cga atg ctc ctc tac<br>Phe Ile Pro Pro Thr Gln Lys Leu Asn Gly Lys Arg Met Leu Leu Tyr<br>            420                 425                 430 | 1296 | |
| gac gag gac gag atg cgg ccg atc gaa cgg ttg gca aac tgc tca aaa<br>Asp Glu Asp Glu Met Arg Pro Ile Glu Arg Leu Ala Asn Cys Ser Lys<br>        435                 440                 445 | 1344 | |
| atc acg gcc caa ctg ctg tgg cat ccg gcg att gcg agc att ttg atg<br>Ile Thr Ala Gln Leu Leu Trp His Pro Ala Ile Ala Ser Ile Leu Met<br>450                 455                 460 | 1392 | |
| ctc aag tgg atg cgg ttg att tcg ttc ctg tac atc aat tta ctg ttc<br>Leu Lys Trp Met Arg Leu Ile Ser Phe Leu Tyr Ile Asn Leu Leu Phe<br>465                 470                 475                 480 | 1440 | |
| gcc tgc atg ttt gcc gta tcg ttt tca atc tac att gtg ttc tac tat<br>Ala Cys Met Phe Ala Val Ser Phe Ser Ile Tyr Ile Val Phe Tyr Tyr<br>                485                 490                 495 | 1488 | |
| gca cag gaa tca acg aaa ctc aaa ctg tgc ctt tac ttg ctt tca ctt<br>Ala Gln Glu Ser Thr Lys Leu Lys Leu Cys Leu Tyr Leu Leu Ser Leu<br>            500                 505                 510 | 1536 | |
| ttc gga tgg att tat ttg acc gca agg gag cta gta cag ttc ttc ata<br>Phe Gly Trp Ile Tyr Leu Thr Ala Arg Glu Leu Val Gln Phe Phe Ile<br>        515                 520                 525 | 1584 | |
| aac acc cgc gtt tac gtc gac tcg atg gag aac gtt atg gag ctg gtg<br>Asn Thr Arg Val Tyr Val Asp Ser Met Glu Asn Val Met Glu Leu Val<br>530                 535                 540 | 1632 | |
| ctt atc gtt gga tca gcc acg gta ctg ttc ttc aaa gag tct acc aat<br>Leu Ile Val Gly Ser Ala Thr Val Leu Phe Phe Lys Glu Ser Thr Asn<br>545                 550                 555                 560 | 1680 | |

```
gag tca tgg tct atc gtg ctg gtc ggt gtg ctg ctg ctg ctt ggc atc    1728
Glu Ser Trp Ser Ile Val Leu Val Gly Val Leu Leu Leu Leu Gly Ile
            565                 570                 575 gag cta acg ctg caa att gga gca ata ccg gtg aac tcc atc tac acc    1776
Glu Leu Thr Leu Gln Ile Gly Ala Ile Pro Val Asn Ser Ile Tyr Thr
            580                 585                 590 aac atg gtc atg ctg aag acg gtt acg aaa aac ttt gtc cag tgt ttg    1824
Asn Met Val Met Leu Lys Thr Val Thr Lys Asn Phe Val Gln Cys Leu
            595                 600                 605 ggc ttc tac tcg atc ata ctg ctg tcg ttt acg ttt agc ttt tac aca    1872
Gly Phe Tyr Ser Ile Ile Leu Leu Ser Phe Thr Phe Ser Phe Tyr Thr
            610                 615                 620 ctg ttt agg ctg agg gaa ggt acg cca ctg ccc ggg gcg gtt gag aac    1920
Leu Phe Arg Leu Arg Glu Gly Thr Pro Leu Pro Gly Ala Val Glu Asn
625                 630                 635                 640 gag aac tcc acc aag gcg gat gaa gtg cat cac ttc aat agt ttt cat    1968
Glu Asn Ser Thr Lys Ala Asp Glu Val His His Phe Asn Ser Phe His
            645                 650                 655 gag gtg cca ctt gca ctg tta aaa act gcc gta atg ttt act ggt gag    2016
Glu Val Pro Leu Ala Leu Leu Lys Thr Ala Val Met Phe Thr Gly Glu
            660                 665                 670 ttt gaa gcg gca gac att agg ttc aac ata tcg tgg ccc atg tac ttg    2064
Phe Glu Ala Ala Asp Ile Arg Phe Asn Ile Ser Trp Pro Met Tyr Leu
            675                 680                 685 ctg ttt cca ctg ttc gta ttc ttt gtc acg atc gtc ata aac aat ctg    2112
Leu Phe Pro Leu Phe Val Phe Phe Val Thr Ile Val Ile Asn Asn Leu
            690                 695                 700 atg aat ggt ctg gcg gtc agc aat acc tcg gta cgt aag                2151
Met Asn Gly Leu Ala Val Ser Asn Thr Ser Val Arg Lys
705                 710                 715

<210> SEQ ID NO 10
<211> LENGTH: 717
<212> TYPE: PRT
<213> ORGANISM: Anopheles gambiae

<400> SEQUENCE: 10

Ala Gln Lys Asp Tyr Thr Gln Phe Ile Gln Ala Leu Glu Asn Gly Ala
1               5                   10                  15

Asp Val Asn Gly Arg Met Arg Asn Ser Asn Tyr Ser Ile Phe Glu Leu
            20                  25                  30

Ala Cys Lys Thr Pro Gly Ser Ala Lys Tyr Ile Ala Ala Cys Leu Lys
        35                  40                  45

Arg Gly Ala Leu Ala Thr Glu Glu Asn Leu Glu Thr Lys Leu Cys Pro
    50                  55                  60

Ile His Leu Ala Ala Gln Ser His Asp Cys Glu Asn Leu Ser Glu Leu
65                  70                  75                  80

Leu Asn Ala Ser Gly Ile Leu Val Asp Gln Met Tyr Glu Asp Gln Thr
                85                  90                  95

Ala Leu Gln Met Leu Phe Lys Glu Ile Asp Gly Glu Asn His Thr Lys
            100                 105                 110

Val Phe Glu Cys Ile Lys Leu Leu Lys His Gln Ala Asn Ile Asn
        115                 120                 125

Val Thr Asp Ser Glu Ser Val Ser Pro Ile Ala Leu Leu Leu Ile Pro
    130                 135                 140

Gly Lys Asp Ala Trp Arg Lys Val Ile Leu Asp Tyr Cys Leu Thr Ser
145                 150                 155                 160

Tyr Asn Val Tyr Val Asp Phe Arg Asp Gly Gln Ala Arg Lys Ala Ile
```

```
                    165                 170                 175
Glu Gln His Phe Pro Gly Thr Val Ile Pro Ile Ala Ala Ser Ser
                180                 185                 190
Val Met Leu Asp Val Leu Arg Asp Lys Leu Met Ala Ala Pro Glu Glu
                195                 200                 205
Asp Phe Ile Val Ala Tyr Glu Arg Tyr Cys Glu Gln Asn His Gly Pro
                210                 215                 220
Met Val Asp Glu Lys Lys Cys Ala Glu Leu Leu Ser Ile Ala Leu Tyr
225                 230                 235                 240
Arg Glu Arg Gln Lys Ala Ala Glu Lys Leu Leu Glu Lys Gln Ile Val
                245                 250                 255
Ala Arg Lys Phe Val Gly Asn Leu Ser Leu Leu Ser Gly Met Leu Ala
                260                 265                 270
Lys Cys Cys Asn Arg Gly Asn Ile Thr Met Leu Glu Trp Leu Leu Asn
                275                 280                 285
Ile Ile Pro Asn Asp Ala Val Arg His Val Asn Glu Asp Pro Leu Leu
                290                 295                 300
Ser Leu Leu Val Lys Gln Ile Gly Arg Glu His Lys Ser Cys Lys Asp
305                 310                 315                 320
Lys Gly Asn Cys Ser Phe Phe Arg Ser Met Val Ile Leu Leu Asn Asp
                325                 330                 335
Pro Arg Ile Asp Val Asp Lys Val Asp Arg Leu Lys Cys Ser Ala Leu
                340                 345                 350
His Tyr Ala Ala Lys Tyr Lys Ile Asp His Ala Gln Glu Leu Leu Ile
                355                 360                 365
Gly Arg Gly Ala Tyr Ile Gly Gly Glu Asp Leu Asn Gly Asn Leu Leu
                370                 375                 380
Met Arg Glu Met Gln Lys His Leu Asp Ser Phe Val Thr Ser Asn Asp
385                 390                 395                 400
Arg Trp Pro Gly Asp Glu Asp Phe Glu Val Arg Ile Asn Cys Ala Asn
                405                 410                 415
Phe Ile Pro Pro Thr Gln Lys Leu Asn Gly Lys Arg Met Leu Leu Tyr
                420                 425                 430
Asp Glu Asp Glu Met Arg Pro Ile Glu Arg Leu Ala Asn Cys Ser Lys
                435                 440                 445
Ile Thr Ala Gln Leu Leu Trp His Pro Ala Ile Ala Ser Ile Leu Met
                450                 455                 460
Leu Lys Trp Met Arg Leu Ile Ser Phe Leu Tyr Ile Asn Leu Leu Phe
465                 470                 475                 480
Ala Cys Met Phe Ala Val Ser Phe Ser Ile Tyr Ile Val Phe Tyr Tyr
                485                 490                 495
Ala Gln Glu Ser Thr Lys Leu Lys Leu Cys Leu Tyr Leu Leu Ser Leu
                500                 505                 510
Phe Gly Trp Ile Tyr Leu Thr Ala Arg Glu Leu Val Gln Phe Phe Ile
                515                 520                 525
Asn Thr Arg Val Tyr Val Asp Ser Met Glu Asn Val Met Glu Leu Val
                530                 535                 540
Leu Ile Val Gly Ser Ala Thr Val Leu Phe Phe Lys Glu Ser Thr Asn
545                 550                 555                 560
Glu Ser Trp Ser Ile Val Leu Val Gly Val Leu Leu Leu Gly Ile
                565                 570                 575
Glu Leu Thr Leu Gln Ile Gly Ala Ile Pro Val Asn Ser Ile Tyr Thr
                580                 585                 590
```

```
Asn Met Val Met Leu Lys Thr Val Thr Lys Asn Phe Val Gln Cys Leu
            595                 600                 605
Gly Phe Tyr Ser Ile Ile Leu Ser Phe Thr Phe Ser Phe Tyr Thr
    610                 615                 620
Leu Phe Arg Leu Arg Glu Gly Thr Pro Leu Pro Gly Ala Val Glu Asn
625                 630                 635                 640
Glu Asn Ser Thr Lys Ala Asp Glu Val His His Phe Asn Ser Phe His
                645                 650                 655
Glu Val Pro Leu Ala Leu Leu Lys Thr Ala Val Met Phe Thr Gly Glu
            660                 665                 670
Phe Glu Ala Ala Asp Ile Arg Phe Asn Ile Ser Trp Pro Met Tyr Leu
    675                 680                 685
Leu Phe Pro Leu Phe Val Phe Val Thr Ile Val Ile Asn Asn Leu
690                 695                 700
Met Asn Gly Leu Ala Val Ser Asn Thr Ser Val Arg Lys
705                 710                 715

<210> SEQ ID NO 11
<211> LENGTH: 2193
<212> TYPE: DNA
<213> ORGANISM: Apis mellifera
<220> FEATURE:
<221> NAME/KEY: CDS
<222> LOCATION: (67)..(2193)

<400> SEQUENCE: 11
ctgtatgaca agttcagtac gctaagggat ttacatttac tttgcatcat cgttttagac      60 tcgaat atg gat ctt gag gat gaa acc ttg caa atg cat ctt ttg cac       108
       Met Asp Leu Glu Asp Glu Thr Leu Gln Met His Leu Leu His
       1               5                   10 gat tac act aca aat tct ata aaa tct caa acg ata tat aaa ctg ctc       156
Asp Tyr Thr Thr Asn Ser Ile Lys Ser Gln Thr Ile Tyr Lys Leu Leu
15                  20                  25                  30 tta gat tat tta cga aca aaa aat ttt aga cat ttc aaa tgt ctt gtt       204
Leu Asp Tyr Leu Arg Thr Lys Asn Phe Arg His Phe Lys Cys Leu Val
                35                  40                  45 gag caa aat ttg aag aag caa cca cct atc att aat ata aac tac gct       252
Glu Gln Asn Leu Lys Lys Gln Pro Pro Ile Ile Asn Ile Asn Tyr Ala
            50                  55                  60 tat ccg aat caa tcg aat gaa act ttc ttg gac atc gct tgc aag aat       300
Tyr Pro Asn Gln Ser Asn Glu Thr Phe Leu Asp Ile Ala Cys Lys Asn
        65                  70                  75 ggc ctt tca gag ttc gta aaa ttt cta ttg gaa aaa ggg gcg aag gtg       348
Gly Leu Ser Glu Phe Val Lys Phe Leu Leu Glu Lys Gly Ala Lys Val
    80                  85                  90 aac agg atc aac gaa gtc cat aat cgt gga cca att cac ttt gct acc       396
Asn Arg Ile Asn Glu Val His Asn Arg Gly Pro Ile His Phe Ala Thr
95                  100                 105                 110 gaa aat ggc cat gcg gat gtc ctt agt ata tta ttg gat gaa ccc acg       444
Glu Asn Gly His Ala Asp Val Leu Ser Ile Leu Leu Asp Glu Pro Thr
                115                 120                 125 ata aat cca aat ctg gag gtt gta caa caa aca gct ttg cac ata gct       492
Ile Asn Pro Asn Leu Glu Val Val Gln Gln Thr Ala Leu His Ile Ala
            130                 135                 140 gtg aag aag aat gat ttg aaa tgt gct tcg ttg ctt cta gag aaa gga       540
Val Lys Lys Asn Asp Leu Lys Cys Ala Ser Leu Leu Leu Glu Lys Gly
        145                 150                 155 gct agt cct aat att ccc aat aac aaa ggt tta aca gct tta cat ata       588
Ala Ser Pro Asn Ile Pro Asn Asn Lys Gly Leu Thr Ala Leu His Ile
    160                 165                 170
```

-continued

| | |
|---|---|
| gca gcc atg aag gat tac aga aat atg gtg aac cta att ttg gaa aaa<br>Ala Ala Met Lys Asp Tyr Arg Asn Met Val Asn Leu Ile Leu Glu Lys<br>175                    180                    185                    190 | 636 |
| act aaa cac gct ttg aat tta gac act tac aaa gat tac aac gat caa<br>Thr Lys His Ala Leu Asn Leu Asp Thr Tyr Lys Asp Tyr Asn Asp Gln<br>                    195                    200                    205 | 684 |
| act gct agg caa ata tta gaa aaa aaa ata ccg aat att tca ttg cct<br>Thr Ala Arg Gln Ile Leu Glu Lys Lys Ile Pro Asn Ile Ser Leu Pro<br>          210                    215                    220 | 732 |
| cct atc gag aaa caa aat gta aat att cat gat ttg aag tat tat tta<br>Pro Ile Glu Lys Gln Asn Val Asn Ile His Asp Leu Lys Tyr Tyr Leu<br>          225                    230                    235 | 780 |
| aat gcc aac gat gag atg aat ttc tta aga tgt tta aaa atc gtt caa<br>Asn Ala Asn Asp Glu Met Asn Phe Leu Arg Cys Leu Lys Ile Val Gln<br>240                    245                    250 | 828 |
| aat gat atg tta aac aat gat ata gag aca ttg atc gaa atg gcc gtt<br>Asn Asp Met Leu Asn Asn Asp Ile Glu Thr Leu Ile Glu Met Ala Val<br>255                    260                    265                    270 | 876 |
| caa aaa aat ttc aaa gaa gca atc att ctt ttg tta gaa aga aca aaa<br>Gln Lys Asn Phe Lys Glu Ala Ile Ile Leu Leu Leu Glu Arg Thr Lys<br>                    275                    280                    285 | 924 |
| gaa att aaa tgc aac tta gaa aag gct gcg aat tta gca att caa cga<br>Glu Ile Lys Cys Asn Leu Glu Lys Ala Ala Asn Leu Ala Ile Gln Arg<br>          290                    295                    300 | 972 |
| ggt tca cca cat atc ctt cga cag ata ttg gaa act gat att gaa gtt<br>Gly Ser Pro His Ile Leu Arg Gln Ile Leu Glu Thr Asp Ile Glu Val<br>          305                    310                    315 | 1020 |
| aaa agc gat ttg tta tta aat gct tgc ata gaa ctc aat ata cca cat<br>Lys Ser Asp Leu Leu Leu Asn Ala Cys Ile Glu Leu Asn Ile Pro His<br>320                    325                    330 | 1068 |
| aaa gga gga tcg caa gat atg agt gat cgt ttg gaa tgt ttt aat tta<br>Lys Gly Gly Ser Gln Asp Met Ser Asp Arg Leu Glu Cys Phe Asn Leu<br>335                    340                    345                    350 | 1116 |
| atc ttg gaa aga gaa gat gtg gat gtt cga tgc ata gat ggc aaa gga<br>Ile Leu Glu Arg Glu Asp Val Asp Val Arg Cys Ile Asp Gly Lys Gly<br>                    355                    360                    365 | 1164 |
| aat act cca ctt cac tat gca gca aaa gct gat tgt cgc gag gcg gtg<br>Asn Thr Pro Leu His Tyr Ala Ala Lys Ala Asp Cys Arg Glu Ala Val<br>          370                    375                    380 | 1212 |
| aca tta ttg ctc gaa aaa gga agc tat atc ggt cac atg aac aat ttc<br>Thr Leu Leu Leu Glu Lys Gly Ser Tyr Ile Gly His Met Asn Asn Phe<br>          385                    390                    395 | 1260 |
| ggc att cca cca gtt gcc gat att tct ata tct act tta tct caa tat<br>Gly Ile Pro Pro Val Ala Asp Ile Ser Ile Ser Thr Leu Ser Gln Tyr<br>400                    405                    410 | 1308 |
| ttt gac gac tgc ata gta gct aga aaa gag cga acg aac gaa tat aca<br>Phe Asp Asp Cys Ile Val Ala Arg Lys Glu Arg Thr Asn Glu Tyr Thr<br>415                    420                    425                    430 | 1356 |
| att gaa ttt gat tac aaa tca tta ttc gca ttt aga gaa att ctt caa<br>Ile Glu Phe Asp Tyr Lys Ser Leu Phe Ala Phe Arg Glu Ile Leu Gln<br>                    435                    440                    445 | 1404 |
| tta ctc tct tcg cca tgt cac tat atg tta tgt ttg gaa aac tgg atc<br>Leu Leu Ser Ser Pro Cys His Tyr Met Leu Cys Leu Glu Asn Trp Ile<br>          450                    455                    460 | 1452 |
| gaa atg acg tta ata ata ctt gga ttt tct att tta aat ggc gct act<br>Glu Met Thr Leu Ile Ile Leu Gly Phe Ser Ile Leu Asn Gly Ala Thr<br>          465                    470                    475 | 1500 |
| aca caa gtc gca gcc gtt aca ata tta tta tcc gcc tgg gaa tta gta<br>Thr Gln Val Ala Ala Val Thr Ile Leu Leu Ser Ala Trp Glu Leu Val<br>480                      485                    490 | 1548 |

```
att ttg att ggc aag cat cct cga atg tcc act gct ttt gca ctg gct      1596
Ile Leu Ile Gly Lys His Pro Arg Met Ser Thr Ala Phe Ala Leu Ala
495                 500                 505                 510 ttc ttc att ctc ttt aaa gat ggc ggt aat gaa aat ttt cca gat cct      1644
Phe Phe Ile Leu Phe Lys Asp Gly Gly Asn Glu Asn Phe Pro Asp Pro
            515                 520                 525 ggg cac tcg tta ttc aag act att atc atg ctc act gga gaa ttc gac      1692
Gly His Ser Leu Phe Lys Thr Ile Ile Met Leu Thr Gly Glu Phe Asp
        530                 535                 540 gct aat gac att ccc ttt gtt tcg cat cct att ctt agt cat ttt gtt      1740
Ala Asn Asp Ile Pro Phe Val Ser His Pro Ile Leu Ser His Phe Val
    545                 550                 555 ttt att ctc ttt gtt ttc ctt atc gca ata gtg ttg ttt aat tta cta      1788
Phe Ile Leu Phe Val Phe Leu Ile Ala Ile Val Leu Phe Asn Leu Leu
560                 565                 570 aat ggt tta gca gtc agc gac act gtg aat att ctt gaa aag gca gaa      1836
Asn Gly Leu Ala Val Ser Asp Thr Val Asn Ile Leu Glu Lys Ala Glu
575                 580                 585                 590 ttg gta gga tta att tcc aga ata cga att ctt gct tac att gaa aat      1884
Leu Val Gly Leu Ile Ser Arg Ile Arg Ile Leu Ala Tyr Ile Glu Asn
            595                 600                 605 gtg att att caa gca cct ttt aca cat gga tca tat tgt tta att tgt      1932
Val Ile Ile Gln Ala Pro Phe Thr His Gly Ser Tyr Cys Leu Ile Cys
        610                 615                 620 agc aat ctt ttg tct ggc tgg aga tgt aat cca tta gca ttt ctt att      1980
Ser Asn Leu Leu Ser Gly Trp Arg Cys Asn Pro Leu Ala Phe Leu Ile
    625                 630                 635 cag aaa att ctc ctt ttt ccg aac tat tta aat agt ggt aaa ctg aat      2028
Gln Lys Ile Leu Leu Phe Pro Asn Tyr Leu Asn Ser Gly Lys Leu Asn
640                 645                 650 gtg ata tcg tac gac agc ttg gaa act tat gaa aat att att aaa cag      2076
Val Ile Ser Tyr Asp Ser Leu Glu Thr Tyr Glu Asn Ile Ile Lys Gln
655                 660                 665                 670 gct aaa aat att ttg atg aaa aaa ggt caa gaa tcg gat aat gaa aaa      2124
Ala Lys Asn Ile Leu Met Lys Lys Gly Gln Glu Ser Asp Asn Glu Lys
            675                 680                 685 ata ttt agt aaa tta gaa aaa ttg gaa aaa aga ttc atg aca atg gaa      2172
Ile Phe Ser Lys Leu Glu Lys Leu Glu Lys Arg Phe Met Thr Met Glu
        690                 695                 700 ttt tgt tac aac tgt gat tga                                          2193
Phe Cys Tyr Asn Cys Asp
        705
```

<210> SEQ ID NO 12
<211> LENGTH: 708
<212> TYPE: PRT
<213> ORGANISM: Apis mellifera

<400> SEQUENCE: 12

```
Met Asp Leu Glu Asp Glu Thr Leu Gln Met His Leu Leu His Asp Tyr
1               5                   10                  15

Thr Thr Asn Ser Ile Lys Ser Gln Thr Ile Tyr Lys Leu Leu Leu Asp
            20                  25                  30

Tyr Leu Arg Thr Lys Asn Phe Arg His Phe Lys Cys Leu Val Glu Gln
        35                  40                  45

Asn Leu Lys Lys Gln Pro Pro Ile Ile Asn Ile Asn Tyr Ala Tyr Pro
    50                  55                  60

Asn Gln Ser Asn Glu Thr Phe Leu Asp Ile Ala Cys Lys Asn Gly Leu
65                  70                  75                  80
```

-continued

```
Ser Glu Phe Val Lys Phe Leu Leu Glu Lys Gly Ala Lys Val Asn Arg
             85                  90                  95
Ile Asn Glu Val His Asn Arg Gly Pro Ile His Phe Ala Thr Glu Asn
            100                 105                 110
Gly His Ala Asp Val Leu Ser Ile Leu Leu Asp Glu Pro Thr Ile Asn
            115                 120                 125
Pro Asn Leu Glu Val Val Gln Gln Thr Ala Leu His Ile Ala Val Lys
        130                 135                 140
Lys Asn Asp Leu Lys Cys Ala Ser Leu Leu Leu Lys Gly Ala Ser
145                 150                 155                 160
Pro Asn Ile Pro Asn Asn Lys Gly Leu Thr Ala Leu His Ile Ala Ala
            165                 170                 175
Met Lys Asp Tyr Arg Asn Met Val Asn Leu Ile Leu Glu Lys Thr Lys
            180                 185                 190
His Ala Leu Asn Leu Asp Thr Tyr Lys Asp Tyr Asn Asp Gln Thr Ala
            195                 200                 205
Arg Gln Ile Leu Glu Lys Lys Ile Pro Asn Ile Ser Leu Pro Pro Ile
        210                 215                 220
Glu Lys Gln Asn Val Asn Ile His Asp Leu Lys Tyr Tyr Leu Asn Ala
225                 230                 235                 240
Asn Asp Glu Met Asn Phe Leu Arg Cys Leu Lys Ile Val Gln Asn Asp
            245                 250                 255
Met Leu Asn Asn Asp Ile Glu Thr Leu Ile Glu Met Ala Val Gln Lys
            260                 265                 270
Asn Phe Lys Glu Ala Ile Ile Leu Leu Leu Glu Arg Thr Lys Glu Ile
            275                 280                 285
Lys Cys Asn Leu Glu Lys Ala Ala Asn Leu Ala Ile Gln Arg Gly Ser
        290                 295                 300
Pro His Ile Leu Arg Gln Ile Leu Glu Thr Asp Ile Glu Val Lys Ser
305                 310                 315                 320
Asp Leu Leu Leu Asn Ala Cys Ile Glu Leu Asn Ile Pro His Lys Gly
            325                 330                 335
Gly Ser Gln Asp Met Ser Asp Arg Leu Glu Cys Phe Asn Leu Ile Leu
            340                 345                 350
Glu Arg Glu Asp Val Asp Val Arg Cys Ile Asp Gly Lys Gly Asn Thr
            355                 360                 365
Pro Leu His Tyr Ala Ala Lys Ala Asp Cys Arg Glu Ala Val Thr Leu
        370                 375                 380
Leu Leu Glu Lys Gly Ser Tyr Ile Gly His Met Asn Asn Phe Gly Ile
385                 390                 395                 400
Pro Pro Val Ala Asp Ile Ser Ile Ser Thr Leu Ser Gln Tyr Phe Asp
            405                 410                 415
Asp Cys Ile Val Ala Arg Lys Glu Arg Thr Asn Glu Tyr Thr Ile Glu
            420                 425                 430
Phe Asp Tyr Lys Ser Leu Phe Ala Phe Arg Glu Ile Leu Gln Leu Leu
            435                 440                 445
Ser Ser Pro Cys His Tyr Met Leu Cys Leu Glu Asn Trp Ile Glu Met
        450                 455                 460
Thr Leu Ile Ile Leu Gly Phe Ser Ile Leu Asn Gly Ala Thr Thr Gln
465                 470                 475                 480
Val Ala Ala Val Thr Ile Leu Leu Ser Ala Trp Glu Leu Val Ile Leu
            485                 490                 495
Ile Gly Lys His Pro Arg Met Ser Thr Ala Phe Ala Leu Ala Phe Phe
            500                 505                 510
```

```
Ile Leu Phe Lys Asp Gly Gly Asn Glu Asn Phe Pro Asp Pro Gly His
        515                 520                 525
Ser Leu Phe Lys Thr Ile Ile Met Leu Thr Gly Glu Phe Asp Ala Asn
        530                 535                 540
Asp Ile Pro Phe Val Ser His Pro Ile Leu Ser His Phe Val Phe Ile
545                 550                 555                 560
Leu Phe Val Phe Leu Ile Ala Ile Val Leu Phe Asn Leu Leu Asn Gly
                565                 570                 575
Leu Ala Val Ser Asp Thr Val Asn Ile Leu Glu Lys Ala Glu Leu Val
            580                 585                 590
Gly Leu Ile Ser Arg Ile Arg Ile Leu Ala Tyr Ile Glu Asn Val Ile
        595                 600                 605
Ile Gln Ala Pro Phe Thr His Gly Ser Tyr Cys Leu Ile Cys Ser Asn
        610                 615                 620
Leu Leu Ser Gly Trp Arg Cys Asn Pro Leu Ala Phe Leu Ile Gln Lys
625                 630                 635                 640
Ile Leu Leu Phe Pro Asn Tyr Leu Asn Ser Gly Lys Leu Asn Val Ile
                645                 650                 655
Ser Tyr Asp Ser Leu Glu Thr Tyr Glu Asn Ile Ile Lys Gln Ala Lys
            660                 665                 670
Asn Ile Leu Met Lys Lys Gly Gln Glu Ser Asp Asn Glu Lys Ile Phe
        675                 680                 685
Ser Lys Leu Glu Lys Leu Glu Lys Arg Phe Met Thr Met Glu Phe Cys
        690                 695                 700
Tyr Asn Cys Asp
705
```

<210> SEQ ID NO 13
<211> LENGTH: 11699
<212> TYPE: DNA
<213> ORGANISM: Artificial Sequence
<220> FEATURE:
<223> OTHER INFORMATION: Artificially constructed expression vector

<400> SEQUENCE: 13

```
ggccagaccc acgtagtcca gcggcagatc ggcggcggag aagttaagcg tctccaggat      60
gaccttgccc gaactggggc acgtggtgtt cgacgatgtg cagctaattt cgcccggctc     120
cacgtccgcc cattggttaa tcagcagacc ctcgttggcg taacggaacc atgagaggta     180
cgacaaccat ttgaggtata ctggcaccga gcccgagttc aagaagaagg cgttttttcca    240
taggctccgc cccctgacg agcatcacaa aaatcgacgc tcaagtcaga ggtggcgaaa      300
cccgacagga ctataaagat accaggcgtt tcccctgga agctccctcg tgcgctctcc      360
tgttccgacc ctgccgctta ccggatacct gtccgccttt ctcccttcgg gaagcgtggc     420
gctttctcaa tgctcacgct gtaggtatct cagttcggtg taggtcgttc gctccaagct     480
gggctgtgtg cacgaacccc ccgttcagcc cgaccgctgc gccttatccg gtaactatcg     540
tcttgagtcc aacccggtaa gacacgactt atcgccactg gcagcagcca ctggtaacag     600
gattagcaga gcgaggtatg taggcggtgc tacagagttc ttgaagtggt ggcctaacta     660
cggctacact agaaggacag tatttggtat ctgcgctctg ctgaagccag ttaccttcgg     720
aaaaagagtt ggtagctctt gatccggcaa acaaaccacc gctggtagcg gtggtttttt     780
tgtttgcaag cagcagatta cgcgcagaaa aaaaggatct caagaagatc ctttgatctt     840
ttctacgggg tctgacgctc agtggaacga aaactcacgt taagggattt tggtcatgag     900
```

```
attatcaaaa aggatcttca cctagatcct tttaaattaa aaatgaagtt ttaaatcaat    960
ctaaagtata tatgagtaaa cttggtctga cagttaccaa tgcttaatca gtgaggcacc   1020
tatctcagcg atctgtctat ttcgttcatc catagttgcc tgactccccg tcgtgtagat   1080
aactacgata cgggagggct taccatctgg ccccagtgct gcaatgatac cgcgagaccc   1140
acgctcaccg gctccagatt tatcagcaat aaaccagcca gccggaaggg ccgagcgcag   1200
aagtggtcct gcaactttat ccgcctccat ccagtctatt aattgttgcc gggaagctag   1260
agtaagtagt tcgccagtta atagtttgcg caacgttgtt gccattgcta caggcatcgt   1320
ggtgtcacgc tcgtcgtttg gtatggcttc attcagctcc ggttcccaac gatcaaggcg   1380
agttacatga tcccccatgt tgtgcaaaaa agcggttagc tccttcggtc ctccgatcgt   1440
tgtcagaagt aagttggccg cagtgttatc actcatggtt atggcagcac tgcataattc   1500
tcttactgtc atgccatccg taagatgctt ttctgtgact ggtgagtact caaccaagtc   1560
attctgagaa tagtgtatgc ggcgaccgag ttgctcttgc ccggcgtcaa cacgggataa   1620
taccgcgcca catagcagaa ctttaaaagt gctcatcatt ggaaaacgtt cttcggggcg   1680
aaaactctca aggatcttac cgctgttgag atccagttcg atgtaaccca ctcgtgcacc   1740
caactgatct tcagcatctt ttactttcac cagcgtttct gggtgagcaa aaacaggaag   1800
gcaaaatgcc gcaaaaaagg gaataagggc gacacggaaa tgttgaatac tcatactctt   1860
cctttttcaa tattattgaa gcatttatca gggttattgt ctcatgagcg gatacatatt   1920
tgaatgtatt tagaaaaata aacaaatagg ggttccgcgc acatttcccc gaaaagtgcc   1980
acctgacgtc taagaaacca ttattatcat gacattaacc tataaaaata ggcgtatcac   2040
gaggcccttt cgtctcgcgc gtttcggtga tgacggtgaa aacctctgac acatgcagct   2100
cccggagacg gtcacagctt gtctgtaagc ggatgccggg agcagacaag cccgtcaggg   2160
cgcgtcagcg ggtgttggcg ggtgtcgggg ctggcttaac tatgcggcat cagagcagat   2220
tgtactgaga gtgcaccata tgcggtgtga aataccgcac cgaatcgcgc ggaactaacg   2280
acagtcgctc caaggtcgtc gaacaaaagg tgaatgtgtt gcggagagcg ggtgggagac   2340
agcgaaagag caactacgaa acgtggtgtg gtggaggtga attatgaaga gggcgcgcga   2400
tttgaaaagt atgtatataa aaaatatatc ccggtgtttt atgtagcgat aaacgagttt   2460
ttgatgtaag gtatgcaggt gtgtaagtct tttggttaga agacaaatcc aaagtctact   2520
tgtggggatg ttcgaagggg aaatacttgt attctatagg tcatatcttg ttttttattgg  2580
cacaaatata attacattag ctttttgagg gggcaataaa cagtaaacac gatggtaata   2640
atggtaaaaa aaaaaacaag cagttatttc ggatatatgt cggctactcc ttgcgtcggg   2700
cccgaagtct tagagccaga tatgcgagca cccggaagct cacgatgaga atggccagac   2760
catgatgaaa taacataagg tggtcccgtc ggcaagagac atccacttaa cgtatgcttg   2820
caataagtgc gagtgaaagg aatagtattc tgagtgtcgt attgagtctg agtgagacag   2880
cgatatgatt gttgattaac ccttagcatg tccgtggggt ttgaattaac tcataatatt   2940
aattagacga aattattttt aaagttttat ttttaataat ttgcgagtac gcaaagcttc   3000
tgcatgagct cggatccaag cttgcatgcc tgcaggtcgg agtactgtcc tccgagcgga   3060
gtactgtcct ccgagcggag tactgtcctc cgagcggagt actgtcctcc gagcggagta   3120
ctgtcctccg agcggagact ctagcgagcg ccggagtata aatagaggcg cttcgtctac   3180
ggagcgacaa ttcaattcaa acaagcaaag tgaacacgtc gctaagcgaa agctaagcaa   3240
ataaacaagc gcagctgaac aagctaaaca atctgcagta aagtgcaagt taaagtgaat   3300
```

```
caattaaaag taaccagcaa ccaagtaaat caactgcaac tactgaaatc tgccaagaag   3360
taattattga atacaagaag agaactctga atagggaatt gggaattatc gaggcctgtc   3420
tagagaagct tgttcgaatc tcgagtgcgc gcttccggag gtatacacct aggcggtacc   3480
actgcagtga attcggagct ccgccaccat ggactacaaa gaccatgacg gtgattataa   3540
agatcatgac atcgattaca aggatgacga tgacaagcac cggttgagct ccgccaccat   3600
ggagcaaaag ctcatttctg aagaggactt gaatgaaatg gagcaaaagc tcatttctga   3660
agaggacttg aatgaaatgg agcaaaagct catttctgaa gaggacttga atgaaatgga   3720
gcaaaagctc atttctgaag aggacttgaa tgaaatggag caaaagctca tttctgaaga   3780
ggacttgaat gaaatggaga gcttgggcga cctcaccatg gagcaaaagc tcatttctga   3840
agaggacttg aatcaccggt atacaagttt gtacaaaaaa gcaggctccg cggccgcccc   3900
cttcaccatg gaaaaggtta ccgtggatgt gttgcggaac aaactgtccg ccggaacgga   3960
ggacgagttt cttgcggctt acgagaagta ctggcagcaa acaatagtc acgtgccgcg    4020 agaagaagat cgcgctgagc tgctatccgt ggccgtgtat cgagcgaagc tgaccgctgc   4080
ccagaagctc gttgacgggc agatagtaga gggcaagttt accggtaagc cggaattgtt   4140
ttccggcctg ctggccaagt gttgtaatcg ggggaatgtg cagatgctcg aatggttgct   4200
gaaaatcata ccggacgatg cggggggcgct gattaacgag gatccgctgc tctcgctgct   4260
cgtgaagcag atcgacgtgt acaaggacaa gaacaagtgt ccctacttcc gcagcatggg   4320
catcttgctg aacgatccgc gcctggaggt ggacaaaatc gatgcgaaaa aatgtacggc   4380
gatgcactac gccgtcaagt acaagatcga tcacgcccag gagctgctgc tggccaaggg   4440
agcgtacatc gggggcgaga acatgttcgg cgacctgccg atcagcgaga tggactcgtt   4500
cctgctggag aagcatctgg actcgtgcgt cacgaacaac gatcgcaagc cgggcgacga   4560
ggactacgaa gtgaggatca gctttgccaa ctttatccg ccggcccaca gcccaactca    4620
cgccaagccg gaacaggtgc cgtttaacgg gctgccgtac gaggacgaga tgcgcccgat   4680
cgtacgcatg gcccagtcgt ccagcaccaa acggctgctg cggcatcccg tcatatcgag   4740
catcctgctg ctcaagtggc tgaagctgat ctgcttttc tacatcaatc tggtgatctg    4800
cacgatattc ttcgtgtcct tcacggcgta cgttgtgttt tgctacggcc aggaagatgc   4860
accgttcaag ctgttcttct acttcctctc gttcgccggc tggatatatt tggtcgcacg   4920
cgagctgatc cagtttctgc tgaacatgcg cgtgtacgtg cggtcgatcg agaacgggat   4980
ggaggtgctc ctcatcctgg cctcgggcgc ggtgctgatg cgcgagtttg gcgacgaaac   5040
gcggcgtgtc gcgtccgcct gcgtgattct gctgtcggcg ctagagttta cgctgctcgt   5100
cggcacgctc ccgtcctat cgatctcgac ccacatggta tgctgaaga cggtgtcgaa       5160 gaactttctc aagtgtctgg tgctgtactc gatcattttg ctcgcatttg cgttcagctt   5220
ctacacgctg ttccgggcga acggtggtaa cggcgaggcg ggcgaagcga ccacagacaa   5280
gacagctgcc ggtcaggacg gcgatggtga tgacgatcag ttcaaccagt tcggggaggt   5340
tccgcttgcg ttgatgaaaa cagcggtaat gttgaccggg gaattcgaag cggcgaacat   5400
aaaatttcaa cagtcaagct tgagctactt cgtgttcgcg ctgtttctgt tctttgtttc   5460
gatcgtgctg ttcaacctga tgaacggtct ggccgtgagc gacacgacga ccatcaaagc   5520
ggaatctgaa atcatcggca ttacgcagaa agtgttcctc atcaacaagt acgaaaatgc   5580
actgaaaaca tcgaagccca ttcgctgcat caccgagcga atggcgtggc tgttcccgtc   5640
caacagtttg cagctgttct cgaacaatca accgctgaag tacattgcgg tcaagccaaa   5700
```

```
ccagtcgaac gccatcatgg tatcgtcgct cgtgccccgg tacgcgcagg acgtcgagat    5760
gggtgagttg gtggtgcagg acaaaaagct ggaagtcgaa ggattgctgg agcgcaacac    5820
caagtacggt accgaatgct gcatcatgcc ctgcctcaac aacatggatg gaagatagt     5880 gaagtatgcg ctggagattt tgcactcccg ccacgagcac gtcggctcga ccgagtaccg    5940
gatgtcgcgc atggagcaga acatcgagcg gatggcgcag gagcagatcg agatgaaaaa    6000
gttgctgcaa acgctcgtca cctcgttgca agctaaggcg tagaagggtg ggcgcgccga    6060
cccagctttc ttgtacaaag tggtgacgta agctagagga tctttgtgaa ggaaccttac    6120
ttctgtggtg tgacataatt ggacaaacta cctacagaga tttaaagctc taaggtaaat    6180
ataaaatttt taagtgtata atgtgttaaa ctactgattc taattgtttg tgtattttag    6240
attccaacct atggaactga tgaatgggag cagtggtgga atgcctttaa tgaggaaaac    6300 ctgtttttgct cagaagaaat gccatctagt gatgatgagg ctactgctga ctctcaacat    6360
tctactcctc caaaaaagaa gagaaaggta gaagacccca aggactttcc ttcagaattg    6420
ctaagttttt tgagtcatgc tgtgtttagt aatagaactc ttgcttgctt tgctatttac    6480
accacaaagg aaaagctgc actgctatac aagaaaatta tggaaaaata ttctgtaacc    6540
tttataagta ggcataacag ttataatcat aacatactgt ttttcttac tccacacagg     6600 catagagtgt ctgctattaa taactatgct caaaaattgt gtacctttag ctttttaatt    6660
tgtaaagggg ttaataagga atatttgatg tatagtgcct tgactagaga tcataatcag    6720
ccataccaca tttgtagagg ttttacttgc tttaaaaaac ctcccacacc tccccctgaa    6780
cctgaaacat aaaatgaatg caattgttgt tgttaacttg tttattgcag cttataatgg    6840
ttacaaataa agcaatagca tcacaaattt cacaaataaa gcatttttt cactgcattc     6900 tagttgtggt ttgtccaaac tcatcaatgt atcttatcat gtctggatcg gatccactag    6960
aaggccttag tatgtatgta agttaataaa accctttttt ggagaatgta gatttaaaaa    7020
aacatatttt ttttttattt tttactgcac tggacatcat tgaacttatc tgatcagttt    7080
taaatttact tcgatccaag ggtatttgaa gtaccaggtt ctttcgatta cctctcactc    7140
aaaatgacat tccactcaaa gtcagcgctg tttgcctcct tctctgtcca cagaaatatc    7200
gccgtctctt tcgccgctgc gtccgctatc tctttcgcca ccgtttgtag cgttacctag    7260
cgtcaatgtc cgccttcagt tgcactttgt cagcggtttc gtgacgaagc tccaagcggt    7320
ttacgccatc aattaaacac aaagtgctgt gccaaaactc ctctcgcttc ttattttttgt   7380 ttgttttttg agtgattggg gtggtgattg gttttgggtg ggtaagcagg gaaagtgtg     7440 aaaaatcccg gcaatgggcc aagaggatca ggagctatta attcgcggag gcagcaaaca    7500
cccatctgcc gagcatctga acaatgtgag tagtacatgt gcatacatct taagttcact    7560
tgatctatag gaactgcgat tgcaacatca aattgtctgc ggcgtgagaa ctgcgaccca    7620
caaaatcccc aaaccgcaat cgcacaaaca aatagtgaca cgaaacagat tattctggta    7680
gctgtgctcg ctatataaga caatttttaa gatcatatca tgatcaagac atctaaaggc    7740
attcattttc gactacattc tttttttacaa aaaatataac aaccagatat tttaagctga    7800
tcctagatgc acaaaaaata aataaaagta taaacctact tcgtaggata cttcgttttg    7860
ttcggggtta gatgagcata acgcttgtag ttgatatttg agatccccta tcattgcagg    7920
gtgacagcgg agcggcttcg cagagctgca ttaaccaggg cttcgggcag gccaaaaact    7980
acggcacgct cctgccaccc agtccgccgg aggactccgg ttcagggagc ggccaactag    8040
ccgagaacct cacctatgcc tggcacaata tggacatctt tggggcggtc aatcagccgg    8100
```

```
gctccggatg cggcagctg gtcaaccgga cacgcggact attctgcaac gagcgacaca    8160
taccggcgcc caggaaacat ttgctcaaga acggtgagtt tctattcgca gtcggctgat    8220
ctgtgtgaaa tcttaataaa gggtccaatt accaatttga aactcagttt gcggcgtggc    8280
ctatccgggc gaacttttgg ccgtgatggg cagttccggt gccggaaaga cgaccctgct    8340
gaatgccctt gcctttcgat cgccgcaggg catccaagta tcgccatccg ggatgcgact    8400
gctcaatggc caacctgtgg acgccaagga gatgcaggcc aggtgcgcct atgtccagca    8460
ggatgacctc tttatcggct ccctaacggc cagggaacac ctgatttttcc aggccatggt    8520 gcggatgcca cgacatctga cctatcggca gcgagtggcc cgcgtggatc aggtgatcca    8580
ggagctttcg ctcagcaaat gtcagcacac gatcatcggt gtgcccggca gggtgaaagg    8640
tctgtccggc ggagaaagga agcgtctggc attcgcctcc gaggcactaa ccgatccgcc    8700
gcttctgatc tgcgatgagc ccacctccgg actggactca tttaccgccc acagcgtcgt    8760
ccaggtgctg aagaagctgt cgcagaaggg caagaccgtc atcctgacca ttcatcagcc    8820
gtcttccgag ctgtttgagc tctttgacaa gatccttctg atggccgagg cagggtagc    8880 tttcttgggc actcccagcg aagccgtcga cttcttttcc tagtgagttc gatgtgttta    8940
ttaagggtat ctagcattac attacatctc aactcctatc cagcgtgggt gcccagtgtc    9000
ctaccaacta caatccggcg gacttttacg tacaggtgtt ggccgttgtg cccggacggg    9060
agatcgagtc ccgtgatcgg atcgccaaga tatgcgacaa ttttgctatt agcaaagtag    9120
cccgggatat ggagcagttg ttggccacca aaaatttgga gaagccactg gagcagccgg    9180
agaatgggta cacctacaag gccacctggt tcatgcagtt ccgggcggtc ctgtggcgat    9240
cctggctgtc ggtgctcaag gaaccactcc tcgtaaaagt gcgacttatt cagacaacgg    9300
tgagtggttc cagtggaaac aaatgatata acgcttacaa ttcttggaaa caaattcgct    9360
agattttagt tagaattgcc tgattccaca cccttcttag ttttttttcaa tgagatgtat    9420 agtttatagt tttgcagaaa ataaataaat ttcatttaac tcgcgaacat gttgaagata    9480
tgaatattaa tgagatgcga gtaacatttt aatttgcaga tggttgccat cttgattggc    9540
ctcatctttt tgggccaaca actcacgcaa gtgggcgtga tgaatatcaa cggagccatc    9600
ttcctcttcc tgaccaacat gacctttcaa aacgtctttg ccacgataaa tgtaagtctt    9660
gtttagaata catttgcata ttaataattt actaactttc taatgaatcg attcgattta    9720
ggtgttcacc tcagagctgc cagttttttat gagggaggcc cgaagtcgac tttatcgctg    9780
tgacacatac tttctgggca aaacgattgc cgaattaccc cttttttctca cagtgccact    9840 ggtcttcacg gcgattgcct atccgatgat cggactgcgg gccggagtgc tgcacttctt    9900
caactgcctg gcgctggtca ctctggtggc caatgtgtca acgtccttcg gatatctaat    9960
atcctgcgcc agctcctcga cctcgatggc gctgtctgtg gtccgccgg ttatcatacc    10020 attcctgctc tttggcggct tcttcttgaa ctcgggctcg gtgccagtat acctcaaatg    10080
gttgtcgtac ctctcatggt tccgttacgc caacgagggt ctgctgatta ccaatgggc    10140 ggacgtggag ccgggcgaaa ttagctgcac atcgtcgaac accacgtgcc ccagttcggg    10200
caaggtcatc ctggagacgc ttaacttctc cgccgccgat ctgccgctgg actacgtggg    10260 tctgccatt ctcatcgtga gcttccgggt gctcgcatat ctggctctaa gacttcgggc    10320
ccgacgcaag gagtagccga catatatccg aaataactgc ttgttttttt ttttaccatt    10380
attaccatcg tgtttactgt ttattgcccc ctcaaaaagc taatgtaatt atatttgtgc    10440
caataaaaac aagatatgac ctatagaata caagtatttc cccttcgaac atccccacaa    10500
```

-continued

```
gtagactttg gatttgtctt ctaaccaaaa gacttacaca cctgcatacc ttacatcaaa   10560
aactcgttta tcgctacata aaacaccggg atatatttt tatatacata cttttcaaat    10620
cgcgcgccct cttcataatt cacctccacc acaccacgtt tcgtagttgc tctttcgctg   10680
tctcccaccc gctctccgca acacattcac cttttgttcg acgaccttgg agcgactgtc   10740
gttagttccg cgcgattcgg ttcgctcaaa tggttccgag tggttcattt cgtctcaata   10800
gaaattagta ataaatattt gtatgtcaa tttatttgct ccaatatatt tgtatatatt    10860
tccctcacag ctatatttat tctaatttaa tattatgact ttttaaggta attttttgtg   10920
acctgttcgg agtgattagc gttacaattt gaactgaaag tgacatccag tgtttgttcc   10980
ttgtgtagat gcatctcaaa aaaatggtgg gcataatagt gttgtttata tatatcaaaa   11040
ataacaacta taataataag aatacattta atttagaaaa tgcttggatt tcactggaac   11100
tagaattaat tcggctgctg ctctaaacga cgcatttcgt actccaaagt acgaattttt   11160
tccctcaagc tcttatttc attaaacaat gaacaggacc taacgcacag tcacgttatt   11220
gtttacataa atgattttt ttactattca aacttactct gtttgtgtac tcccactggt   11280
atagccttct tttatcttt ctggttcagg ctctatcact ttactaggta cggcatctgc    11340
gttgagtcgc ctccttttaa atgtctgacc ttttgcaggt gcagccttcc actgcgaatc   11400
attaaagtgg gtatcacaaa tttgggagtt ttccaccaagg ctgcacccaa ggctctgctc   11460
ccacaatttt ctcttaatag cacacttcgg cacgtgaatt aatttactc cagtcacagc    11520 tttgcagcaa aatttgcaat atttcatttt tttttattcc acgtaagggt taatgttttc   11580 aaaaaaaat tcgtccgcac acaacctttc ctctcaacaa gcaaacgtgc actgaattta    11640
agtgtatact tcggtaagct tcggctatcg acgggaccac cttatgttat ttcatcatg    11699
```

```
<210> SEQ ID NO 14
<211> LENGTH: 4080
<212> TYPE: DNA
<213> ORGANISM: Culex quinquefasciatus
<220> FEATURE:
<221> NAME/KEY: CDS
<222> LOCATION: (1)..(4080)

<400> SEQUENCE: 14 atg cat cca acg gtg gac att aag cag tgg aag ctc gat aaa gcc aaa         48
Met His Pro Thr Val Asp Ile Lys Gln Trp Lys Leu Asp Lys Ala Lys
1               5                   10                  15 att gag aaa caa ctc ata gag ggt tta aaa gac gct ctg ttg gag cga         96
Ile Glu Lys Gln Leu Ile Glu Gly Leu Lys Asp Ala Leu Leu Glu Arg
            20                  25                  30 gat gta gag agc ttc aaa gat cag ctt gac cgg aat ctt ccc gag ttg        144
Asp Val Glu Ser Phe Lys Asp Gln Leu Asp Arg Asn Leu Pro Glu Leu
        35                  40                  45 gat cga ctg tac cag gag cag tcc aac tcg gat gat gat ggt gcg ttc        192
Asp Arg Leu Tyr Gln Glu Gln Ser Asn Ser Asp Asp Asp Gly Ala Phe
    50                  55                  60 aaa aac aag aaa ctt aga agg ttt ttc ggt gaa gtg atc tgc cct cga        240
Lys Asn Lys Lys Leu Arg Arg Phe Phe Gly Glu Val Ile Cys Pro Arg
65                  70                  75                  80 gat gac cac gtc cag ttt gtg gca cca ttt ctg gac aaa att ccc atc        288
Asp Asp His Val Gln Phe Val Ala Pro Phe Leu Asp Lys Ile Pro Ile
                85                  90                  95 gtc aac gaa ccg gtg cag cag ctg cgg aat caa cac cca ctt cac ata        336
Val Asn Glu Pro Val Gln Gln Leu Arg Asn Gln His Pro Leu His Ile
            100                 105                 110 gcc att cag gcg aaa gca ttt tcg gtg gtg gag acc ttg ctg acg atc        384
```

|     |     |     |     |     |     |     |     |     |     |     |     |     |     |      |
|-----|-----|-----|-----|-----|-----|-----|-----|-----|-----|-----|-----|-----|-----|------|
| Ala | Ile | Gln | Ala | Lys | Ala | Phe | Ser | Val | Val | Glu | Thr | Leu | Leu | Thr Ile |
|     | 115 |     |     |     | 120 |     |     |     |     | 125 |     |     |     |      |

```
gac ggc atc aac gtc aac gct cag ctc aag aac caa act ccg ctg atg      432
Asp Gly Ile Asn Val Asn Ala Gln Leu Lys Asn Gln Thr Pro Leu Met
    130             135                 140 ttg ctc atc aaa atg att act ccg gag aat ttt gaa gca gtg ctg caa      480
Leu Leu Ile Lys Met Ile Thr Pro Glu Asn Phe Glu Ala Val Leu Gln
145             150                 155                 160 acc att cgt ctt ctg gcg tcc aag ggt gcc gac ata aac gtt ggt gac      528
Thr Ile Arg Leu Leu Ala Ser Lys Gly Ala Asp Ile Asn Val Gly Asp
            165                 170                 175 tac cga gct cat ccg ctg tcg gtg gtg tgc cag ctg acg acg atc ggt      576
Tyr Arg Ala His Pro Leu Ser Val Val Cys Gln Leu Thr Thr Ile Gly
        180                 185                 190 gtg tcg gag aag cgc cgg ctg ctg gag tta tgc aag gag aac ttc aag      624
Val Ser Glu Lys Arg Arg Leu Leu Glu Leu Cys Lys Glu Asn Phe Lys
    195                 200                 205 tgt gac gtg gac agt gtg ttc aac gga cag gct cgt cgg gat atc gaa      672
Cys Asp Val Asp Ser Val Phe Asn Gly Gln Ala Arg Arg Asp Ile Glu
210                 215                 220 gcg ctg ttt ggt gat ttg tgt ttt ggg cga caa cag tcc gaa ctg tca      720
Ala Leu Phe Gly Asp Leu Cys Phe Gly Arg Gln Gln Ser Glu Leu Ser
225             230                 235                 240 acg gcc agc ctc aag tct ctg ctg ctg aag gga aag gag gag gag ttt      768
Thr Ala Ser Leu Lys Ser Leu Leu Leu Lys Gly Lys Glu Glu Glu Phe
            245                 250                 255 gtg aag gga ttc tat gaa ctg tac gag aat ttg gtc cgg gaa aag aag      816
Val Lys Gly Phe Tyr Glu Leu Tyr Glu Asn Leu Val Arg Glu Lys Lys
        260                 265                 270 gag agg gat ttg tac gag ctg ctg gct cag gcg gca gtg aaa aat agg      864
Glu Arg Asp Leu Tyr Glu Leu Leu Ala Gln Ala Ala Val Lys Asn Arg
    275                 280                 285 agt ctt tgt gtg gag aga atg ttc agt aaa tgt aag cat gag cga gtt      912
Ser Leu Cys Val Glu Arg Met Phe Ser Lys Cys Lys His Glu Arg Val
290                 295                 300 ttt gaa acg gtt gaa gca aag aag aaa ctc agc gag gtg ctg aaa gtt      960
Phe Glu Thr Val Glu Ala Lys Lys Lys Leu Ser Glu Val Leu Lys Val
305             310                 315                 320 gtt tgc tgt aaa ggg ttc gta aag gtt ttg aag ttg ttt ctt aag ttt     1008
Val Cys Cys Lys Gly Phe Val Lys Val Leu Lys Leu Phe Leu Lys Phe
            325                 330                 335 atc tcc gac tcc aaa gtt ttc aac gaa tca gca ctg gcg ttg atc tgc     1056
Ile Ser Asp Ser Lys Val Phe Asn Glu Ser Ala Leu Ala Leu Ile Cys
        340                 345                 350 gtc agg aga ttg cag aag aga cgg gtt cca gaa atg gtc gag tgt tta     1104
Val Arg Arg Leu Gln Lys Arg Arg Val Pro Glu Met Val Glu Cys Leu
    355                 360                 365 gac gta cta ctg caa aac agt aga att aat gtg gac aat gct gat cac     1152
Asp Val Leu Leu Gln Asn Ser Arg Ile Asn Val Asp Asn Ala Asp His
370                 375                 380 ctc ggg atg aca gcg cta cat ttt gcc gtc caa cat gac atg gac gaa     1200
Leu Gly Met Thr Ala Leu His Phe Ala Val Gln His Asp Met Asp Glu
385             390                 395                 400 gaa gcg tta caa atc atg acg aaa gga aaa ccg tac ctc gga cag cta     1248
Glu Ala Leu Gln Ile Met Thr Lys Gly Lys Pro Tyr Leu Gly Gln Leu
            405                 410                 415 aat cgt ttc aac aag tca ccg cta cac ttg atg agt gct acg gtt ctg     1296
Asn Arg Phe Asn Lys Ser Pro Leu His Leu Met Ser Ala Thr Val Leu
        420                 425                 430 caa aga tac ctg gat tgg tgc att tcg gtg gaa gga gtt cgt tcg gat    1344
```

-continued

| | | |
|---|---|---|
| Gln Arg Tyr Leu Asp Trp Cys Ile Ser Val Glu Gly Val Arg Ser Asp<br>435                    440                    445 | | |
| gac ctt gga gag aat atc cac atc aac ttg gcg gga ttt gta cct caa<br>Asp Leu Gly Glu Asn Ile His Ile Asn Leu Ala Gly Phe Val Pro Gln<br>450                    455                    460 | 1392 | |
| acg aga aca aat cga gct gaa gtt aca tac act agc act cct act gaa<br>Thr Arg Thr Asn Arg Ala Glu Val Thr Tyr Thr Ser Thr Pro Thr Glu<br>465                    470                    475                    480 | 1440 | |
| gaa acg gtc gag aat ggt att tca aaa agt aca ttt atg aat aac gct<br>Glu Thr Val Glu Asn Gly Ile Ser Lys Ser Thr Phe Met Asn Asn Ala<br>485                    490                    495 | 1488 | |
| ggt cag ctg ttc aaa gca ttt atg aag gaa cct aaa cga tca gat ctg<br>Gly Gln Leu Phe Lys Ala Phe Met Lys Glu Pro Lys Arg Ser Asp Leu<br>500                    505                    510 | 1536 | |
| cta cca gaa tgt tca gtg tta caa aga aat tcg aaa gag atc gat cca<br>Leu Pro Glu Cys Ser Val Leu Gln Arg Asn Ser Lys Glu Ile Asp Pro<br>515                    520                    525 | 1584 | |
| ttc ggg tat att gcg gac tcc aag gag ctg aga cca ctg cta aag cat<br>Phe Gly Tyr Ile Ala Asp Ser Lys Glu Leu Arg Pro Leu Leu Lys His<br>530                    535                    540 | 1632 | |
| cca gtg atc atg agc atc ctg ctc gtc aag tgg ttc cag atc cag agg<br>Pro Val Ile Met Ser Ile Leu Leu Val Lys Trp Phe Gln Ile Gln Arg<br>545                    550                    555                    560 | 1680 | |
| att ctt tac ctt aaa tta ggc aaa agt gtg ctt ctc gca gtg ctg ttc<br>Ile Leu Tyr Leu Lys Leu Gly Lys Ser Val Leu Leu Ala Val Leu Phe<br>565                    570                    575 | 1728 | |
| acg ctg tat gcc ata act gac aca acg aag aac acg act ttg agt tgg<br>Thr Leu Tyr Ala Ile Thr Asp Thr Thr Lys Asn Thr Thr Leu Ser Trp<br>580                    585                    590 | 1776 | |
| ata ctt tgg acc tgc tgc ttc ttt cta gtg gct acc ttt gca atc gtt<br>Ile Leu Trp Thr Cys Cys Phe Phe Leu Val Ala Thr Phe Ala Ile Val<br>595                    600                    605 | 1824 | |
| ttc gtt gtc gtc atc ttt aaa tcc agc aac tac tgc aca gcg caa cgg<br>Phe Val Val Val Ile Phe Lys Ser Ser Asn Tyr Cys Thr Ala Gln Arg<br>610                    615                    620 | 1872 | |
| tct tcc ttc aaa gca caa ttc aac tac acg gag ctg ata ata ttt cca<br>Ser Ser Phe Lys Ala Gln Phe Asn Tyr Thr Glu Leu Ile Ile Phe Pro<br>625                    630                    635                    640 | 1920 | |
| cta gcg acc gtg agc tta ttt aat cac agc act acc ctt ctc gcc atc<br>Leu Ala Thr Val Ser Leu Phe Asn His Ser Thr Thr Leu Leu Ala Ile<br>645                    650                    655 | 1968 | |
| ata atc gtc ctc gcc ggg atc aac atc gta act cac atg ggc tcg ctg<br>Ile Ile Val Leu Ala Gly Ile Asn Ile Val Thr His Met Gly Ser Leu<br>660                    665                    670 | 2016 | |
| cct tcg tcc tca ctc tcg aca agc atc gtc atg ctg gag act gtc agc<br>Pro Ser Ser Ser Leu Ser Thr Ser Ile Val Met Leu Glu Thr Val Ser<br>675                    680                    685 | 2064 | |
| aga aac ttc ctc aaa agt ctc cta atc tac gtg atc ata ctg ctt gca<br>Arg Asn Phe Leu Lys Ser Leu Leu Ile Tyr Val Ile Ile Leu Leu Ala<br>690                    695                    700 | 2112 | |
| ttt gga ttt ggc ttc ttc gtg ctg tat tct gac aac aat gtg cag gaa<br>Phe Gly Phe Gly Phe Phe Val Leu Tyr Ser Asp Asn Asn Val Gln Glu<br>705                    710                    715                    720 | 2160 | |
| gac agc ggc ttc agc tcg ttc aaa acg ctg gaa agc tcc atc att aag<br>Asp Ser Gly Phe Ser Ser Phe Lys Thr Leu Glu Ser Ser Ile Ile Lys<br>725                    730                    735 | 2208 | |
| gcg ctg gtt atg cta act ggt gag ctc gat gcc tcg tca atc gag ttc<br>Ala Leu Val Met Leu Thr Gly Glu Leu Asp Ala Ser Ser Ile Glu Phe<br>740                    745                    750 | 2256 | |
| aaa tca aac cgt gcc agc tac atc ttg ttt ttg ggc ttc ata ttt ttg | 2304 | |

```
                Lys Ser Asn Arg Ala Ser Tyr Ile Leu Phe Leu Gly Phe Ile Phe Leu
                    755                 760                 765 gtg acg ctg gtg att gca aac tta atc aac gga atc gcc gtc agt gat         2352
Val Thr Leu Val Ile Ala Asn Leu Ile Asn Gly Ile Ala Val Ser Asp
770                 775                 780 atc tcg gta atc cgt caa gag gcc gaa gtg att gcc ctt gct aaa aaa         2400
Ile Ser Val Ile Arg Gln Glu Ala Glu Val Ile Ala Leu Ala Lys Lys
785                 790                 795                 800 gtc aaa act ttg gcc cac tac gaa gaa gtg aac aac aga ttc aac ttc         2448
Val Lys Thr Leu Ala His Tyr Glu Glu Val Asn Asn Arg Phe Asn Phe
                805                 810                 815 aac gag aaa tcc ttc ttc agc tac tac gag ccc cag ctg atc gtt ctg         2496
Asn Glu Lys Ser Phe Phe Ser Tyr Tyr Glu Pro Gln Leu Ile Val Leu
            820                 825                 830 ccc cgt gaa aac aac aaa atc cta gcg aaa ccc aag cgc acc ccc gaa         2544
Pro Arg Glu Asn Asn Lys Ile Leu Ala Lys Pro Lys Arg Thr Pro Glu
        835                 840                 845 cca aaa gac aaa gcg ttc cac acg tgg cca ctg ccg cga acc gtt cgc         2592
Pro Lys Asp Lys Ala Phe His Thr Trp Pro Leu Pro Arg Thr Val Arg
850                 855                 860 aaa atg ttc cac ctg gac aac cgg tgc cac tgc ctg gac gag gac att         2640
Lys Met Phe His Leu Asp Asn Arg Cys His Cys Leu Asp Glu Asp Ile
865                 870                 875                 880 gtc gcc gcc att cgg gac att ctg gac gct cga acc agt ggg cac gcg         2688
Val Ala Ala Ile Arg Asp Ile Leu Asp Ala Arg Thr Ser Gly His Ala
                885                 890                 895 ggc cag ctg gag ctg aac ctc aag tcg tac gac gag cgg ctg ttg cgt         2736
Gly Gln Leu Glu Leu Asn Leu Lys Ser Tyr Asp Glu Arg Leu Leu Arg
            900                 905                 910 ctc gag gaa aag atc gac ctg ctg ctg cgt atg tcc gcg ggg gaa            2784
Leu Glu Glu Lys Ile Asp Leu Leu Leu Arg Met Ser Ala Gly Glu
        915                 920                 925 aag cca ccg gaa agt gct gcc ggc cat caa agg tgg aag aag gcc gcg         2832
Lys Pro Pro Glu Ser Ala Ala Gly His Gln Arg Trp Lys Lys Ala Ala
930                 935                 940 acc gca atg atc gga cag tac agg ctg agg aat ctg ccg cga cgt ggt         2880
Thr Ala Met Ile Gly Gln Tyr Arg Leu Arg Asn Leu Pro Arg Arg Gly
945                 950                 955                 960 gat acc ctc ata aaa aca tta aag gaa cac atc ctc gcc aaa aac atc         2928
Asp Thr Leu Ile Lys Thr Leu Lys Glu His Ile Leu Ala Lys Asn Ile
                965                 970                 975 gaa caa ttt caa gca acc ctc aca caa gga gtg tca gac cta aac caa         2976
Glu Gln Phe Gln Ala Thr Leu Thr Gln Gly Val Ser Asp Leu Asn Gln
            980                 985                 990 ctg tac gcc cga tta ccg ttc gaa  aag aac aca ctc gcc  ccg gaa gac       3024
Leu Tyr Ala Arg Leu Pro Phe Glu  Lys Asn Thr Leu Ala  Pro Glu Asp
        995                 1000                1005 tct ttc cgg aac aag tgc cta  cga cag ttc ttc ggc  gac ttg tgc           3069
Ser Phe Arg Asn Lys Cys Leu  Arg Gln Phe Phe Gly  Asp Leu Cys
1010                1015                1020 tcc acc gag gga agt tcc cag  ttc atc acg atc ttc  atc tcg att           3114
Ser Thr Glu Gly Ser Ser Gln  Phe Ile Thr Ile Phe  Ile Ser Ile
    1025                1030                1035 ctc ccg ctg gaa aac gaa cca  att cag cag tcc aag  aac caa tac           3159
Leu Pro Leu Glu Asn Glu Pro  Ile Gln Gln Ser Lys  Asn Gln Tyr
    1040                1045                1050 cca atc cac atc gct ctg aat  gcg aaa gca ttc gcc  aat gcc gaa           3204
Pro Ile His Ile Ala Leu Asn  Ala Lys Ala Phe Ala  Asn Ala Glu
    1055                1060                1065 acg cta  ctg cag ctg ccc acg  gtc aac gtg gac gcc  atg tgg cag          3249
```

```
Thr Leu Leu Gln Leu Pro Thr Val Asn Val Asp Ala Met Trp Gln
    1070            1075                1080 aag caa acc ccg ctg atg atg ctg ttc aag atg gcc acc ggc gtc    3294
Lys Gln Thr Pro Leu Met Met Leu Phe Lys Met Ala Thr Gly Val
        1085            1090            1095 acc ttt gga gcg gtc aag caa ctg atc atg ctg ttg gga gag aaa    3339
Thr Phe Gly Ala Val Lys Gln Leu Ile Met Leu Leu Gly Glu Lys
    1100            1105            1110 ggt gcc gat atc aac ctg ggc gac tac cgg gca cat ccg ttg tcc    3384
Gly Ala Asp Ile Asn Leu Gly Asp Tyr Arg Ala His Pro Leu Ser
    1115            1120            1125 gta ctt tgt aac tct acc agc tta gat ctg gat cag aag cgt gac    3429
Val Leu Cys Asn Ser Thr Ser Leu Asp Leu Asp Gln Lys Arg Asp
    1130            1135            1140 ttg gta gag tat tgc cgg caa cat ttc gtc tgc gac ttg gat agc    3474
Leu Val Glu Tyr Cys Arg Gln His Phe Val Cys Asp Leu Asp Ser
    1145            1150            1155 acg ttt gaa ggg caa gcc aga aag gac gtt gag gca acg ttt acc    3519
Thr Phe Glu Gly Gln Ala Arg Lys Asp Val Glu Ala Thr Phe Thr
    1160            1165            1170 gat ttg aag ttt gat caa cgg cga tcg gag att acc gct gca acg    3564
Asp Leu Lys Phe Asp Gln Arg Arg Ser Glu Ile Thr Ala Ala Thr
    1175            1180            1185 atg gag tcc ttt ctg ttg gaa gga aag agt caa gag ttt gtc aac    3609
Met Glu Ser Phe Leu Leu Glu Gly Lys Ser Gln Glu Phe Val Asn
    1190            1195            1200 gaa ttt gac gag ttc atc gtc aaa tcg ccg gaa ccc agc aag gtt    3654
Glu Phe Asp Glu Phe Ile Val Lys Ser Pro Glu Pro Ser Lys Val
    1205            1210            1215 tac gaa ctg tta cag aaa gca gtc att cgg aat cgg ata aga tgc    3699
Tyr Glu Leu Leu Gln Lys Ala Val Ile Arg Asn Arg Ile Arg Cys
    1220            1225            1230 att caa aag att tta ata gcc gta gag caa aat ccc aaa gat ttg    3744
Ile Gln Lys Ile Leu Ile Ala Val Glu Gln Asn Pro Lys Asp Leu
    1235            1240            1245 gat cca cta ccc tac aaa gaa ata ata tcc aag acg atc aag ctt    3789
Asp Pro Leu Pro Tyr Lys Glu Ile Ile Ser Lys Thr Ile Lys Leu
    1250            1255            1260 gtc tgt gcc aaa ggg cag ccg gaa atc cta aaa ctg ttc ttg aaa    3834
Val Cys Ala Lys Gly Gln Pro Glu Ile Leu Lys Leu Phe Leu Lys
    1265            1270            1275 cat ata gaa cct gcg gaa atc ttc aac gag cga ccg ctg gga ctc    3879
His Ile Glu Pro Ala Glu Ile Phe Asn Glu Arg Pro Leu Gly Leu
    1280            1285            1290 gtc tgc gtt aga aat cta gcc aaa aag atc acc aat gag ctt tgt    3924
Val Cys Val Arg Asn Leu Ala Lys Lys Ile Thr Asn Glu Leu Cys
    1295            1300            1305 gaa tgt ttg gag cta ctg ctg gaa gat tcc cgg ata gcg ttt gat    3969
Glu Cys Leu Glu Leu Leu Leu Glu Asp Ser Arg Ile Ala Phe Asp
    1310            1315            1320 aaa aca gat cac gaa aac aag gga gca ctc gag tat gcc att gag    4014
Lys Thr Asp His Glu Asn Lys Gly Ala Leu Glu Tyr Ala Ile Glu
    1325            1330            1335 cac aat ttg gga ctt gtg gta cgg cga atg atg ggc gtt gac aag    4059
His Asn Leu Gly Leu Val Val Arg Arg Met Met Gly Val Asp Lys
    1340            1345            1350 cat ata cgg atg ccg gaa taa                                    4080
His Ile Arg Met Pro Glu
    1355
```

```
<210> SEQ ID NO 15
<211> LENGTH: 1359
<212> TYPE: PRT
<213> ORGANISM: Culex quinquefasciatus

<400> SEQUENCE: 15

Met His Pro Thr Val Asp Ile Lys Gln Trp Lys Leu Asp Lys Ala Lys
1               5                   10                  15

Ile Glu Lys Gln Leu Ile Glu Gly Leu Lys Asp Ala Leu Leu Glu Arg
            20                  25                  30

Asp Val Glu Ser Phe Lys Asp Gln Leu Asp Arg Asn Leu Pro Glu Leu
        35                  40                  45

Asp Arg Leu Tyr Gln Glu Gln Ser Asn Ser Asp Asp Gly Ala Phe
    50                  55                  60

Lys Asn Lys Lys Leu Arg Arg Phe Phe Gly Glu Val Ile Cys Pro Arg
65                  70                  75                  80

Asp Asp His Val Gln Phe Val Ala Pro Phe Leu Asp Lys Ile Pro Ile
                85                  90                  95

Val Asn Glu Pro Val Gln Gln Leu Arg Asn Gln His Pro Leu His Ile
            100                 105                 110

Ala Ile Gln Ala Lys Ala Phe Ser Val Val Glu Thr Leu Leu Thr Ile
        115                 120                 125

Asp Gly Ile Asn Val Asn Ala Gln Leu Lys Asn Gln Thr Pro Leu Met
    130                 135                 140

Leu Leu Ile Lys Met Ile Thr Pro Glu Asn Phe Glu Ala Val Leu Gln
145                 150                 155                 160

Thr Ile Arg Leu Leu Ala Ser Lys Gly Ala Asp Ile Asn Val Gly Asp
                165                 170                 175

Tyr Arg Ala His Pro Leu Ser Val Val Cys Gln Leu Thr Thr Ile Gly
            180                 185                 190

Val Ser Glu Lys Arg Arg Leu Leu Glu Leu Cys Lys Glu Asn Phe Lys
        195                 200                 205

Cys Asp Val Asp Ser Val Phe Asn Gly Gln Ala Arg Arg Asp Ile Glu
    210                 215                 220

Ala Leu Phe Gly Asp Leu Cys Phe Gly Arg Gln Gln Ser Glu Leu Ser
225                 230                 235                 240

Thr Ala Ser Leu Lys Ser Leu Leu Leu Lys Gly Lys Glu Glu Phe
                245                 250                 255

Val Lys Gly Phe Tyr Glu Leu Tyr Glu Asn Leu Val Arg Glu Lys Lys
            260                 265                 270

Glu Arg Asp Leu Tyr Glu Leu Leu Ala Gln Ala Ala Val Lys Asn Arg
        275                 280                 285

Ser Leu Cys Val Glu Arg Met Phe Ser Lys Cys Lys His Glu Arg Val
    290                 295                 300

Phe Glu Thr Val Glu Ala Lys Lys Leu Ser Glu Val Leu Lys Val
305                 310                 315                 320

Val Cys Cys Lys Gly Phe Val Lys Val Leu Lys Leu Phe Lys Phe
                325                 330                 335

Ile Ser Asp Ser Lys Val Phe Asn Glu Ser Ala Leu Ala Leu Ile Cys
            340                 345                 350

Val Arg Arg Leu Gln Lys Arg Arg Val Pro Glu Met Val Glu Cys Leu
        355                 360                 365

Asp Val Leu Leu Gln Asn Ser Arg Ile Asn Val Asp Asn Ala Asp His
    370                 375                 380

Leu Gly Met Thr Ala Leu His Phe Ala Val Gln His Asp Met Asp Glu
```

```
            385                 390                 395                 400
Glu Ala Leu Gln Ile Met Thr Lys Gly Lys Pro Tyr Leu Gly Gln Leu
                405                 410                 415

Asn Arg Phe Asn Lys Ser Pro Leu His Leu Met Ser Ala Thr Val Leu
                420                 425                 430

Gln Arg Tyr Leu Asp Trp Cys Ile Ser Val Glu Gly Val Arg Ser Asp
                435                 440                 445

Asp Leu Gly Glu Asn Ile His Ile Asn Leu Ala Gly Phe Val Pro Gln
                450                 455                 460

Thr Arg Thr Asn Arg Ala Glu Val Thr Tyr Thr Ser Thr Pro Thr Glu
465                 470                 475                 480

Glu Thr Val Glu Asn Gly Ile Ser Lys Ser Thr Phe Met Asn Asn Ala
                485                 490                 495

Gly Gln Leu Phe Lys Ala Phe Met Lys Glu Pro Lys Arg Ser Asp Leu
                500                 505                 510

Leu Pro Glu Cys Ser Val Leu Gln Arg Asn Ser Lys Glu Ile Asp Pro
                515                 520                 525

Phe Gly Tyr Ile Ala Asp Ser Lys Glu Leu Arg Pro Leu Leu Lys His
                530                 535                 540

Pro Val Ile Met Ser Ile Leu Leu Val Lys Trp Phe Gln Ile Gln Arg
545                 550                 555                 560

Ile Leu Tyr Leu Lys Leu Gly Lys Ser Val Leu Leu Ala Val Leu Phe
                565                 570                 575

Thr Leu Tyr Ala Ile Thr Asp Thr Thr Lys Asn Thr Thr Leu Ser Trp
                580                 585                 590

Ile Leu Trp Thr Cys Cys Phe Phe Leu Val Ala Thr Phe Ala Ile Val
                595                 600                 605

Phe Val Val Ile Phe Lys Ser Ser Asn Tyr Cys Thr Ala Gln Arg
610                 615                 620

Ser Ser Phe Lys Ala Gln Phe Asn Tyr Thr Glu Leu Ile Ile Phe Pro
625                 630                 635                 640

Leu Ala Thr Val Ser Leu Phe Asn His Ser Thr Thr Leu Leu Ala Ile
                645                 650                 655

Ile Ile Val Leu Ala Gly Ile Asn Ile Val Thr His Met Gly Ser Leu
                660                 665                 670

Pro Ser Ser Ser Leu Ser Thr Ser Ile Val Met Leu Glu Thr Val Ser
                675                 680                 685

Arg Asn Phe Leu Lys Ser Leu Leu Ile Tyr Val Ile Leu Leu Ala
                690                 695                 700

Phe Gly Phe Gly Phe Phe Val Leu Tyr Ser Asp Asn Val Gln Glu
705                 710                 715                 720

Asp Ser Gly Phe Ser Ser Phe Lys Thr Leu Glu Ser Ser Ile Ile Lys
                725                 730                 735

Ala Leu Val Met Leu Thr Gly Glu Leu Asp Ala Ser Ser Ile Glu Phe
                740                 745                 750

Lys Ser Asn Arg Ala Ser Tyr Ile Leu Phe Leu Gly Phe Ile Phe Leu
                755                 760                 765

Val Thr Leu Val Ile Ala Asn Leu Ile Asn Gly Ile Ala Val Ser Asp
                770                 775                 780

Ile Ser Val Ile Arg Gln Glu Ala Glu Val Ile Ala Leu Ala Lys Lys
785                 790                 795                 800

Val Lys Thr Leu Ala His Tyr Glu Glu Val Asn Asn Arg Phe Asn Phe
                805                 810                 815
```

```
Asn Glu Lys Ser Phe Phe Ser Tyr Tyr Glu Pro Gln Leu Ile Val Leu
            820                 825                 830

Pro Arg Glu Asn Asn Lys Ile Leu Ala Lys Pro Lys Arg Thr Pro Glu
            835                 840                 845

Pro Lys Asp Lys Ala Phe His Thr Trp Pro Leu Pro Arg Thr Val Arg
850                     855                 860

Lys Met Phe His Leu Asp Asn Arg Cys His Cys Leu Asp Glu Asp Ile
865                     870                 875                 880

Val Ala Ala Ile Arg Asp Ile Leu Asp Ala Arg Thr Ser Gly His Ala
                885                 890                 895

Gly Gln Leu Glu Leu Asn Leu Lys Ser Tyr Asp Glu Arg Leu Leu Arg
            900                 905                 910

Leu Glu Glu Lys Ile Asp Leu Leu Leu Arg Met Ser Ala Gly Glu
            915                 920                 925

Lys Pro Pro Glu Ser Ala Ala Gly His Gln Arg Trp Lys Lys Ala Ala
            930                 935                 940

Thr Ala Met Ile Gly Gln Tyr Arg Leu Arg Asn Leu Pro Arg Arg Gly
945                     950                 955                 960

Asp Thr Leu Ile Lys Thr Leu Lys Glu His Ile Leu Ala Lys Asn Ile
                965                 970                 975

Glu Gln Phe Gln Ala Thr Leu Thr Gln Gly Val Ser Asp Leu Asn Gln
            980                 985                 990

Leu Tyr Ala Arg Leu Pro Phe Glu  Lys Asn Thr Leu Ala  Pro Glu Asp
            995                 1000                1005

Ser Phe Arg Asn Lys Cys Leu  Arg Gln Phe Gly  Asp Leu Cys
    1010                1015                1020

Ser Thr Glu Gly Ser Ser Gln  Phe Ile Thr Ile Phe  Ile Ser Ile
    1025                1030                1035

Leu Pro Leu Glu Asn Glu Pro  Ile Gln Gln Ser Lys  Asn Gln Tyr
    1040                1045                1050

Pro Ile His Ile Ala Leu Asn  Ala Lys Ala Phe Ala  Asn Ala Glu
    1055                1060                1065

Thr Leu Leu Gln Leu Pro Thr  Val Asn Val Asp Ala  Met Trp Gln
    1070                1075                1080

Lys Gln Thr Pro Leu Met Met  Leu Phe Lys Met Ala  Thr Gly Val
    1085                1090                1095

Thr Phe Gly Ala Val Lys Gln  Leu Ile Met Leu Leu  Gly Glu Lys
    1100                1105                1110

Gly Ala Asp Ile Asn Leu Gly  Asp Tyr Arg Ala His  Pro Leu Ser
    1115                1120                1125

Val Leu Cys Asn Ser Thr Ser  Leu Asp Leu Asp Gln  Lys Arg Asp
    1130                1135                1140

Leu Val Glu Tyr Cys Arg Gln  His Phe Val Cys Asp  Leu Asp Ser
    1145                1150                1155

Thr Phe Glu Gly Gln Ala Arg  Lys Asp Val Glu Ala  Thr Phe Thr
    1160                1165                1170

Asp Leu Lys Phe Asp Gln Arg  Arg Ser Glu Ile Thr  Ala Ala Thr
    1175                1180                1185

Met Glu Ser Phe Leu Leu Glu  Gly Lys Ser Gln Glu  Phe Val Asn
    1190                1195                1200

Glu Phe Asp Glu Phe Ile Val  Lys Ser Pro Glu Pro  Ser Lys Val
    1205                1210                1215

Tyr Glu Leu Leu Gln Lys Ala  Val Ile Arg Asn Arg  Ile Arg Cys
    1220                1225                1230
```

-continued

```
Ile Gln Lys Ile Leu Ile Ala Val Glu Gln Asn Pro Lys Asp Leu
    1235                1240                1245

Asp Pro Leu Pro Tyr Lys Glu Ile Ile Ser Lys Thr Ile Lys Leu
    1250                1255                1260

Val Cys Ala Lys Gly Gln Pro Glu Ile Leu Lys Leu Phe Leu Lys
    1265                1270                1275

His Ile Glu Pro Ala Glu Ile Phe Asn Glu Arg Pro Leu Gly Leu
    1280                1285                1290

Val Cys Val Arg Asn Leu Ala Lys Lys Ile Thr Asn Glu Leu Cys
    1295                1300                1305

Glu Cys Leu Glu Leu Leu Leu Glu Asp Ser Arg Ile Ala Phe Asp
    1310                1315                1320

Lys Thr Asp His Glu Asn Lys Gly Ala Leu Glu Tyr Ala Ile Glu
    1325                1330                1335

His Asn Leu Gly Leu Val Val Arg Arg Met Met Gly Val Asp Lys
    1340                1345                1350

His Ile Arg Met Pro Glu
    1355
```

<210> SEQ ID NO 16
<211> LENGTH: 2448
<212> TYPE: DNA
<213> ORGANISM: Tribolium castaneum
<220> FEATURE:
<221> NAME/KEY: CDS
<222> LOCATION: (1)..(2448)

<400> SEQUENCE: 16

```
atg act cct aaa aat tcg gaa acc gaa ttc tct aaa ata gaa ctt gag      48
Met Thr Pro Lys Asn Ser Glu Thr Glu Phe Ser Lys Ile Glu Leu Glu
1               5                   10                  15 gaa ttt gac gaa cca cca aat gtt tcc aaa cta gcc gaa gat ctt tta     96
Glu Phe Asp Glu Pro Pro Asn Val Ser Lys Leu Ala Glu Asp Leu Leu
            20                  25                  30 atc gca gtc caa aaa aac gcc att ccc gaa att aaa cac cta gtt tcg    144
Ile Ala Val Gln Lys Asn Ala Ile Pro Glu Ile Lys His Leu Val Ser
        35                  40                  45 caa aat cgg agt atc cta tca tac gaa tac cca ttt tac gag cac caa    192
Gln Asn Arg Ser Ile Leu Ser Tyr Glu Tyr Pro Phe Tyr Glu His Gln
    50                  55                  60 acc atc cta cta ctg gcc tgt aac gac tca cac aac atg tgc tca gtg    240
Thr Ile Leu Leu Leu Ala Cys Asn Asp Ser His Asn Met Cys Ser Val
65                  70                  75                  80 aca cgc gaa gtc atc gaa act tta atc gaa ctc gga gcg aat tgt aac    288
Thr Arg Glu Val Ile Glu Thr Leu Ile Glu Leu Gly Ala Asn Cys Asn
                85                  90                  95 gaa ccc agc aga aac gac cac tgg gaa ccc ctc cat tac acc gcc ctt    336
Glu Pro Ser Arg Asn Asp His Trp Glu Pro Leu His Tyr Thr Ala Leu
            100                 105                 110 aac gcc aac aaa acc aaa atg caa aca att ctc cca cac agc caa atc    384
Asn Ala Asn Lys Thr Lys Met Gln Thr Ile Leu Pro His Ser Gln Ile
        115                 120                 125 aac tcg ctg gtc tac tgc tcc aaa caa acc acc aaa aag tac gac ttt    432
Asn Ser Leu Val Tyr Cys Ser Lys Gln Thr Thr Lys Lys Tyr Asp Phe
    130                 135                 140 tgc ccc acc atc aag gac tcg tac tca aac aat gcc ctg aac gtt ctc    480
Cys Pro Thr Ile Lys Asp Ser Tyr Ser Asn Asn Ala Leu Asn Val Leu
145                 150                 155                 160 ctg aaa tgc ggc aac cgc cag aaa caa ttc gtc caa tgc tgc caa ctt    528
```

```
Leu Lys Cys Gly Asn Arg Gln Lys Gln Phe Val Gln Cys Cys Gln Leu
            165                 170                 175 ctg att gaa aac ggg atc aac gta aac cag acc gat agc aac ggc gtg      576
Leu Ile Glu Asn Gly Ile Asn Val Asn Gln Thr Asp Ser Asn Gly Val
            180                 185                 190 tcc ccg tct gat tta atc tgg aaa atg gac aac agc gaa ctt aaa caa      624
Ser Pro Ser Asp Leu Ile Trp Lys Met Asp Asn Ser Glu Leu Lys Gln
            195                 200                 205 cta ctc aga gat aag aca agc ccg aaa atc gtt gat aac acc ttc ggg      672
Leu Leu Arg Asp Lys Thr Ser Pro Lys Ile Val Asp Asn Thr Phe Gly
            210                 215                 220 aac ata aaa ctg agc aaa atc cag cgc ttc ctc tcc ttg gac ttg tca      720
Asn Ile Lys Leu Ser Lys Ile Gln Arg Phe Leu Ser Leu Asp Leu Ser
225                 230                 235                 240 cac gaa gac gtg gac aga gta gac ggt gcc gat tgt cca act tcc agc      768
His Glu Asp Val Asp Arg Val Asp Gly Ala Asp Cys Pro Thr Ser Ser
            245                 250                 255 tgc aca atc ctg cag ttg tgc tgc gcc aaa gga ctg act tcg tgt gtc      816
Cys Thr Ile Leu Gln Leu Cys Cys Ala Lys Gly Leu Thr Ser Cys Val
            260                 265                 270 gtc cac ctt ttg gaa aaa ggc gca aac ccg aat aaa acc atc ccg aag      864
Val His Leu Leu Glu Lys Gly Ala Asn Pro Asn Lys Thr Ile Pro Lys
            275                 280                 285 aac ccc aac ttg ccg gtc atg atc gcc gtc aat tcc gac cac aag gaa      912
Asn Pro Asn Leu Pro Val Met Ile Ala Val Asn Ser Asp His Lys Glu
            290                 295                 300 atc gtc gaa ata ctc ctc cag aag aac gcg gat ttg ccc aac aat gtg      960
Ile Val Glu Ile Leu Leu Gln Lys Asn Ala Asp Leu Pro Asn Asn Val
305                 310                 315                 320 tta ctc cac ttg cag caa ttg cac cga gat gac gac act ctg gtc ctg     1008
Leu Leu His Leu Gln Gln Leu His Arg Asp Asp Asp Thr Leu Val Leu
            325                 330                 335 gct gat aga tac tta aaa ata att ttg aga cac ttg gct cgg ttt gaa     1056
Ala Asp Arg Tyr Leu Lys Ile Ile Leu Arg His Leu Ala Arg Phe Glu
            340                 345                 350 gcc aca act gtc cag aaa tat tta agt tgt aag gac gaa cag ggt cgg     1104
Ala Thr Thr Val Gln Lys Tyr Leu Ser Cys Lys Asp Glu Gln Gly Arg
            355                 360                 365 agt gct tta cac tac gcc att tcc tac gac tgt cgt gag aat att tta     1152
Ser Ala Leu His Tyr Ala Ile Ser Tyr Asp Cys Arg Glu Asn Ile Leu
            370                 375                 380 gcg ctc ctg gca ctt gga gcc tcc ttg gtg gag aaa gac gac ttc ggg     1200
Ala Leu Leu Ala Leu Gly Ala Ser Leu Val Glu Lys Asp Asp Phe Gly
385                 390                 395                 400 aac aaa tta ctt gag tca att gag ccc aaa act ttg gag act ttt ttc     1248
Asn Lys Leu Leu Glu Ser Ile Glu Pro Lys Thr Leu Glu Thr Phe Phe
            405                 410                 415 gag aat aat tgc aaa gta gcg caa agt cgc aca aat ggg gag agt aag     1296
Glu Asn Asn Cys Lys Val Ala Gln Ser Arg Thr Asn Gly Glu Ser Lys
            420                 425                 430 ttt aca gtg acc att gat tac aag tct ctg gtt gcg gaa aca agc cct     1344
Phe Thr Val Thr Ile Asp Tyr Lys Ser Leu Val Ala Glu Thr Ser Pro
            435                 440                 445 gat agt gat ttt ctc cac act atg acg aaa att ccc gag ttg aac tac     1392
Asp Ser Asp Phe Leu His Thr Met Thr Lys Ile Pro Glu Leu Asn Tyr
450                 455                 460 ttg acc aat cac ccc gtg gtg gcg ctt tat ttg gcc atg aaa tgg acc     1440
Leu Thr Asn His Pro Val Val Ala Leu Tyr Leu Ala Met Lys Trp Thr
465                 470                 475                 480 aaa tgt cag tgg ttt gtt tac ttc aac ttg ctg ctc tat ttc tgt gcc     1488
```

```
                Lys Cys Gln Trp Phe Val Tyr Phe Asn Leu Leu Tyr Phe Cys Ala
                                485                 490                 495 tat gtt tcg ttg ctg gtt tat ggt ttc acg ttc cgg gga att acc gaa         1536
Tyr Val Ser Leu Leu Val Tyr Gly Phe Thr Phe Arg Gly Ile Thr Glu
            500                 505                 510 agt tac agc tcg ttt ctc atg ttt gcc ttt ttt ctc cta ttg ttt gga         1584
Ser Tyr Ser Ser Phe Leu Met Phe Ala Phe Phe Leu Leu Leu Phe Gly
            515                 520                 525 gag gtg tta cag att gta acc ttc cga ttt tat tat ttc aga cgc ttg         1632
Glu Val Leu Gln Ile Val Thr Phe Arg Phe Tyr Tyr Phe Arg Arg Leu
            530                 535                 540 gat aat tac att gat tta ttc cta ctg tgt ggg ctc ttg tat att ata         1680
Asp Asn Tyr Ile Asp Leu Phe Leu Leu Cys Gly Leu Leu Tyr Ile Ile
545                 550                 555                 560 gcc tcc ggt tgg ttt aac act ttg aat aac agg aac tta tca gtg gcg         1728
Ala Ser Gly Trp Phe Asn Thr Leu Asn Asn Arg Asn Leu Ser Val Ala
                565                 570                 575 ttt tcc cta gtt ttc ctc act tcc acc ctt ggc att ttc atg cag ttg         1776
Phe Ser Leu Val Phe Leu Thr Ser Thr Leu Gly Ile Phe Met Gln Leu
                580                 585                 590 ggc aat ttc tcg ttt ttc aca gtc aag gtt atc att ttg caa gaa atc         1824
Gly Asn Phe Ser Phe Phe Thr Val Lys Val Ile Ile Leu Gln Glu Ile
            595                 600                 605 acg atc acg ttt ttc aaa tat ata gcg ttt tat agt ttt ccc ttg gtg         1872
Thr Ile Thr Phe Phe Lys Tyr Ile Ala Phe Tyr Ser Phe Pro Leu Val
            610                 615                 620 gcg ttt ttt ttc tgc ttt tac atg ctg aac gat gac aaa gac tat ttg         1920
Ala Phe Phe Phe Cys Phe Tyr Met Leu Asn Asp Asp Lys Asp Tyr Leu
625                 630                 635                 640 ttt ttc cca atg ctt tac gaa act gtg acc atg ttc act ggg gat ttt         1968
Phe Phe Pro Met Leu Tyr Glu Thr Val Thr Met Phe Thr Gly Asp Phe
                645                 650                 655 gac gcc gat tat cca atg cac ttc aaa cga aac cca att ttc ggg cac         2016
Asp Ala Asp Tyr Pro Met His Phe Lys Arg Asn Pro Ile Phe Gly His
                660                 665                 670 ttg att tac gtg gtt ttc gtc atc ttg att ggg att att ttg cac aac         2064
Leu Ile Tyr Val Val Phe Val Ile Leu Ile Gly Ile Ile Leu His Asn
            675                 680                 685 ttg ctg att ggt cta gcg gtc aat gat ttg caa gcg att tgt tac gaa         2112
Leu Leu Ile Gly Leu Ala Val Asn Asp Leu Gln Ala Ile Cys Tyr Glu
            690                 695                 700 gcg aag ttt atc gat aag agg gaa cgc tcg aaa tat ata aca aat gtt         2160
Ala Lys Phe Ile Asp Lys Arg Glu Arg Ser Lys Tyr Ile Thr Asn Val
705                 710                 715                 720 gaa aat gtt ctc ttt acc aag ttg caa aag tcc tat tat ttt aga ccg         2208
Glu Asn Val Leu Phe Thr Lys Leu Gln Lys Ser Tyr Tyr Phe Arg Pro
                725                 730                 735 atg ttt gaa aac gtg ctg aat ttt tgt cgc gtg ttc gat aat ttt gac         2256
Met Phe Glu Asn Val Leu Asn Phe Cys Arg Val Phe Asp Asn Phe Asp
                740                 745                 750 tac acc cta acg gtt tat tca gac tcg aag acg ttt tat ttg gag aaa         2304
Tyr Thr Leu Thr Val Tyr Ser Asp Ser Lys Thr Phe Tyr Leu Glu Lys
            755                 760                 765 atg ggg aaa aaa att gtg att cgt gat caa aat ata atc acg ttt ttg         2352
Met Gly Lys Lys Ile Val Ile Arg Asp Gln Asn Ile Ile Thr Phe Leu
770                 775                 780 caa aat ggg att aag gat ggc tct ctt aaa aat aaa agt act gaa gat         2400
Gln Asn Gly Ile Lys Asp Gly Ser Leu Lys Asn Lys Ser Thr Glu Asp
785                 790                 795                 800 tcg tac tcg ttg aag agc ttg cat aag aaa att gaa gac act tac tga        2448
```

Ser Tyr Ser Leu Lys Ser Leu His Lys Lys Ile Glu Asp Thr Tyr
            805                 810                 815

<210> SEQ ID NO 17
<211> LENGTH: 815
<212> TYPE: PRT
<213> ORGANISM: Tribolium castaneum

<400> SEQUENCE: 17

Met Thr Pro Lys Asn Ser Glu Thr Glu Phe Ser Lys Ile Glu Leu Glu
1               5                   10                  15

Glu Phe Asp Glu Pro Pro Asn Val Ser Lys Leu Ala Glu Asp Leu Leu
            20                  25                  30

Ile Ala Val Gln Lys Asn Ala Ile Pro Glu Ile Lys His Leu Val Ser
            35                  40                  45

Gln Asn Arg Ser Ile Leu Ser Tyr Glu Tyr Pro Phe Tyr Glu His Gln
        50                  55                  60

Thr Ile Leu Leu Leu Ala Cys Asn Asp Ser His Asn Met Cys Ser Val
65                  70                  75                  80

Thr Arg Glu Val Ile Glu Thr Leu Ile Glu Leu Gly Ala Asn Cys Asn
                85                  90                  95

Glu Pro Ser Arg Asn Asp His Trp Glu Pro Leu His Tyr Thr Ala Leu
            100                 105                 110

Asn Ala Asn Lys Thr Lys Met Gln Thr Ile Leu Pro His Ser Gln Ile
        115                 120                 125

Asn Ser Leu Val Tyr Cys Ser Lys Gln Thr Thr Lys Lys Tyr Asp Phe
130                 135                 140

Cys Pro Thr Ile Lys Asp Ser Tyr Ser Asn Asn Ala Leu Asn Val Leu
145                 150                 155                 160

Leu Lys Cys Gly Asn Arg Gln Lys Gln Phe Val Gln Cys Cys Gln Leu
                165                 170                 175

Leu Ile Glu Asn Gly Ile Asn Val Asn Gln Thr Asp Ser Asn Gly Val
            180                 185                 190

Ser Pro Ser Asp Leu Ile Trp Lys Met Asp Asn Ser Glu Leu Lys Gln
        195                 200                 205

Leu Leu Arg Asp Lys Thr Ser Pro Lys Ile Val Asp Asn Thr Phe Gly
210                 215                 220

Asn Ile Lys Leu Ser Lys Ile Gln Arg Phe Leu Ser Leu Asp Leu Ser
225                 230                 235                 240

His Glu Asp Val Asp Arg Val Asp Gly Ala Asp Cys Pro Thr Ser Ser
                245                 250                 255

Cys Thr Ile Leu Gln Leu Cys Cys Ala Lys Gly Leu Thr Ser Cys Val
            260                 265                 270

Val His Leu Leu Glu Lys Gly Ala Asn Pro Asn Lys Thr Ile Pro Lys
        275                 280                 285

Asn Pro Asn Leu Pro Val Met Ile Ala Val Asn Ser Asp His Lys Glu
290                 295                 300

Ile Val Glu Ile Leu Leu Gln Lys Asn Ala Asp Leu Pro Asn Asn Val
305                 310                 315                 320

Leu Leu His Leu Gln Gln Leu His Arg Asp Asp Thr Leu Val Leu
                325                 330                 335

Ala Asp Arg Tyr Leu Lys Ile Ile Leu Arg His Leu Ala Arg Phe Glu
            340                 345                 350

Ala Thr Thr Val Gln Lys Tyr Leu Ser Cys Lys Asp Glu Gln Gly Arg
        355                 360                 365

```
Ser Ala Leu His Tyr Ala Ile Ser Tyr Asp Cys Arg Glu Asn Ile Leu
    370                 375                 380

Ala Leu Leu Ala Leu Gly Ala Ser Leu Val Glu Lys Asp Asp Phe Gly
385                 390                 395                 400

Asn Lys Leu Leu Glu Ser Ile Glu Pro Lys Thr Leu Glu Thr Phe Phe
                405                 410                 415

Glu Asn Asn Cys Lys Val Ala Gln Ser Arg Thr Asn Gly Glu Ser Lys
                420                 425                 430

Phe Thr Val Thr Ile Asp Tyr Lys Ser Leu Val Ala Glu Thr Ser Pro
            435                 440                 445

Asp Ser Asp Phe Leu His Thr Met Thr Lys Ile Pro Glu Leu Asn Tyr
    450                 455                 460

Leu Thr Asn His Pro Val Val Ala Leu Tyr Leu Ala Met Lys Trp Thr
465                 470                 475                 480

Lys Cys Gln Trp Phe Val Tyr Phe Asn Leu Leu Leu Tyr Phe Cys Ala
                485                 490                 495

Tyr Val Ser Leu Leu Val Tyr Gly Phe Thr Phe Arg Gly Ile Thr Glu
            500                 505                 510

Ser Tyr Ser Ser Phe Leu Met Phe Ala Phe Leu Leu Leu Phe Gly
    515                 520                 525

Glu Val Leu Gln Ile Val Thr Phe Arg Phe Tyr Tyr Phe Arg Arg Leu
530                 535                 540

Asp Asn Tyr Ile Asp Leu Phe Leu Leu Cys Gly Leu Leu Tyr Ile Ile
545                 550                 555                 560

Ala Ser Gly Trp Phe Asn Thr Leu Asn Asn Arg Asn Leu Ser Val Ala
                565                 570                 575

Phe Ser Leu Val Phe Leu Thr Ser Thr Leu Gly Ile Phe Met Gln Leu
            580                 585                 590

Gly Asn Phe Ser Phe Phe Thr Val Lys Val Ile Ile Leu Gln Glu Ile
                595                 600                 605

Thr Ile Thr Phe Phe Lys Tyr Ile Ala Phe Tyr Ser Phe Pro Leu Val
        610                 615                 620

Ala Phe Phe Phe Cys Phe Tyr Met Leu Asn Asp Asp Lys Asp Tyr Leu
625                 630                 635                 640

Phe Phe Pro Met Leu Tyr Glu Thr Val Thr Met Phe Thr Gly Asp Phe
                645                 650                 655

Asp Ala Asp Tyr Pro Met His Phe Lys Arg Asn Pro Ile Phe Gly His
                660                 665                 670

Leu Ile Tyr Val Val Phe Val Ile Leu Ile Gly Ile Leu His Asn
        675                 680                 685

Leu Leu Ile Gly Leu Ala Val Asn Asp Leu Gln Ala Ile Cys Tyr Glu
690                 695                 700

Ala Lys Phe Ile Asp Lys Arg Glu Arg Ser Lys Tyr Ile Thr Asn Val
705                 710                 715                 720

Glu Asn Val Leu Phe Thr Lys Leu Gln Lys Ser Tyr Tyr Phe Arg Pro
                725                 730                 735

Met Phe Glu Asn Val Leu Asn Phe Cys Arg Val Phe Asp Asn Phe Asp
                740                 745                 750

Tyr Thr Leu Thr Val Tyr Ser Asp Ser Lys Thr Phe Tyr Leu Glu Lys
            755                 760                 765

Met Gly Lys Lys Ile Val Ile Arg Asp Gln Asn Ile Ile Thr Phe Leu
    770                 775                 780

Gln Asn Gly Ile Lys Asp Gly Ser Leu Lys Asn Lys Ser Thr Glu Asp
785                 790                 795                 800
```

```
Ser Tyr Ser Leu Lys Ser Leu His Lys Lys Ile Glu Asp Thr Tyr
            805                 810                 815

<210> SEQ ID NO 18
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 18
taaggagcca aacctgcgac                                                     20

<210> SEQ ID NO 19
<211> LENGTH: 22
<212> TYPE: DNA
<213> ORGANISM: Artificial Sequence
<220> FEATURE:
<223> OTHER INFORMATION: Artificially synthesized oligonucleotide primer

<400> SEQUENCE: 19
ttcgtggaac ttgaggagcg tg                                                  22

<210> SEQ ID NO 20
<211> LENGTH: 895
<212> TYPE: PRT
<213> ORGANISM: Drosophila melanogaster

<400> SEQUENCE: 20

Met Asp Phe Asn Asn Cys Gly Phe Ile Asp Pro Gln Ala Gln Leu Ala
1               5                   10                  15

Gly Lys Gln Asp Ile Arg Gln Phe Val Ala Ala Leu Asp Ser Gly Asp
            20                  25                  30

Leu Gln Asp Asp Arg His Thr Ser Ile Tyr Glu Lys Ala Leu Ser Thr
        35                  40                  45

Pro Gly Cys Arg Asp Phe Ile Glu Ala Cys Ile Asp His Gly Ser Gln
    50                  55                  60

Val Asn Tyr Ile Asn Lys Lys Leu Asp Lys Ala Ala Ile Ser Tyr Ala
65                  70                  75                  80

Ala Asp Ser Arg Asp Pro Gly Asn Leu Ala Ala Leu Leu Lys Tyr Arg
                85                  90                  95

Pro Gly Asn Lys Val Gln Val Asp Arg Lys Tyr Gly Gln Leu Thr Pro
            100                 105                 110

Leu Asn Ser Leu Ala Lys Asn Leu Thr Asp Glu Asn Ala Pro Asp Val
        115                 120                 125

Tyr Ser Cys Met Gln Leu Leu Leu Asp Tyr Gly Asn Ile Val Asp Gln
    130                 135                 140

Gly Glu Phe Thr Pro Leu His His Val Leu Arg Lys Ser Lys Val Lys
145                 150                 155                 160

Ala Gly Lys Lys Glu Leu Ile Gln Leu Phe Leu Asp His Pro Glu Leu
                165                 170                 175

Asp Ile Asp Ser Tyr Arg Asn Gly Glu Val Arg Arg Leu Leu Gln Ala
            180                 185                 190

Gln Phe Pro Glu Leu Lys Leu Pro Glu Glu Arg His Thr Gly Pro Glu
        195                 200                 205

Ile Asp Ile Gln Thr Leu Gln Arg Thr Leu Arg Asp Gly Asp Glu Thr
    210                 215                 220

Leu Phe Glu Gln Gln Phe Ala Glu Tyr Leu Gln Asn Leu Lys Gly Gly
225                 230                 235                 240
```

```
Ala Asp Asn Gln Leu Asn Ala His Gln Glu Glu Tyr Phe Gly Leu Leu
            245                 250                 255
Gln Glu Ser Ile Lys Arg Gly Arg Gln Arg Ala Phe Asp Val Ile Leu
            260                 265                 270
Ser Thr Gly Met Asp Ile Asn Ser Arg Pro Gly Arg Ala Asn Glu Ala
            275                 280                 285
Asn Leu Val Glu Thr Ala Val Ile Tyr Gly Asn Trp Gln Ala Leu Glu
            290                 295                 300
Arg Leu Leu Lys Glu Pro Asn Leu Arg Leu Thr Pro Asp Ser Lys Leu
305                 310                 315                 320
Leu Asn Ala Val Ile Gly Arg Leu Asp Glu Pro Pro Tyr Asp Gly Ser
                325                 330                 335
Ser His Gln Arg Cys Phe Glu Leu Leu Ile Asn Ser Asp Arg Val Asp
            340                 345                 350
Ile Asn Glu Ala Asp Ser Gly Arg Leu Val Pro Leu Phe Phe Ala Val
            355                 360                 365
Lys Tyr Arg Asn Thr Ser Ala Met Gln Lys Leu Leu Lys Asn Gly Ala
            370                 375                 380
Tyr Ile Gly Ser Lys Ser Ala Phe Gly Thr Leu Pro Ile Lys Asp Met
385                 390                 395                 400
Pro Pro Glu Val Leu Glu Glu His Phe Asp Ser Cys Ile Thr Thr Asn
            405                 410                 415
Gly Glu Arg Pro Gly Asp Gln Asn Phe Glu Ile Ile Asp Tyr Lys
            420                 425                 430
Asn Leu Met Arg Gln Glu Arg Asp Ser Gln Leu Gln Asp Glu Met Ala
            435                 440                 445
Pro Ile Ala Phe Ile Ala Glu Ser Lys Glu Met Arg His Leu Leu Gln
            450                 455                 460
His Pro Leu Ile Ser Ser Phe Leu Phe Leu Lys Trp His Arg Leu Ser
465                 470                 475                 480
Val Ile Phe Tyr Leu Asn Phe Leu Ile Tyr Ser Leu Phe Thr Ala Ser
            485                 490                 495
Ile Ile Thr Tyr Thr Leu Leu Lys Phe His Glu Ser Asp Gln Arg Ala
            500                 505                 510
Leu Thr Ala Phe Phe Gly Leu Leu Ser Trp Leu Gly Ile Ser Tyr Leu
            515                 520                 525
Ile Leu Arg Glu Cys Ile Gln Trp Ile Met Ser Pro Val Arg Tyr Phe
530                 535                 540
Trp Ser Ile Thr Asn Ile Met Glu Ile Thr Leu Ser Ile Phe Thr Cys
545                 550                 555                 560
Met Glu Ser Ser Phe Asp Lys Glu Thr Gln Arg Val Leu Ala Val Phe
            565                 570                 575
Thr Ile Leu Leu Val Ser Met Glu Phe Cys Leu Leu Val Gly Ser Leu
            580                 585                 590
Pro Val Leu Ser Ile Ser Thr His Met Leu Met Leu Arg Glu Val Ser
            595                 600                 605
Asn Ser Phe Leu Lys Ser Phe Thr Ile Phe Val Leu Thr Phe Ser Leu
            610                 615                 620
Cys Phe Tyr Ile Leu Phe Gly Lys Ser Val Glu Glu Asp Gln Ser Lys
625                 630                 635                 640
Ser Ala Thr Pro Cys Pro Pro Leu Gly Lys Lys Glu Gly Lys Asp Glu
            645                 650                 655
Glu Gln Gly Phe Asn Thr Phe Thr Lys Pro Ile Glu Ala Val Ile Lys
```

```
                  660                 665                 670
Thr Ile Val Met Leu Thr Gly Glu Phe Asp Ala Gly Ser Ile Gln Phe
            675                 680                 685

Thr Ser Ile Tyr Thr Tyr Leu Ile Phe Leu Leu Phe Val Ile Phe Met
        690                 695                 700

Thr Ile Val Leu Phe Asn Leu Leu Asn Gly Leu Ala Val Ser Asp Thr
705                 710                 715                 720

Gln Val Ile Lys Ala Gln Ala Glu Leu Asn Gly Ala Ile Cys Arg Thr
                725                 730                 735

Asn Val Leu Ser Arg Tyr Glu Gln Val Leu Thr Gly His Gly Arg Ala
            740                 745                 750

Gly Phe Leu Leu Gly Asn His Leu Phe Arg Ser Ile Cys Gln Arg Leu
        755                 760                 765

Met Asn Ile Tyr Pro Asn Tyr Leu Ser Leu Arg Gln Ile Ser Val Leu
    770                 775                 780

Pro Asn Asp Gly Asn Lys Val Leu Ile Pro Met Ser Asp Pro Phe Glu
785                 790                 795                 800

Met Arg Thr Leu Lys Lys Ala Ser Phe Gln Gln Leu Pro Leu Ser Ala
                805                 810                 815

Ala Val Pro Gln Lys Lys Leu Leu Asp Pro Pro Leu Arg Leu Leu Pro
            820                 825                 830

Cys Cys Cys Ser Leu Leu Thr Gly Lys Cys Ser Gln Met Ser Gly Arg
        835                 840                 845

Val Val Lys Arg Ala Leu Glu Val Ile Asp Gln Lys Asn Ala Ala Glu
    850                 855                 860

Gln Arg Arg Lys Gln Glu Gln Ile Asn Asp Ser Arg Leu Lys Leu Ile
865                 870                 875                 880

Glu Tyr Lys Leu Glu Gln Leu Ile Gln Leu Val Gln Asp Arg Lys
                885                 890                 895

<210> SEQ ID NO 21
<211> LENGTH: 18
<212> TYPE: DNA
<213> ORGANISM: Artificial Sequence
<220> FEATURE:
<223> OTHER INFORMATION: Artificially synthesized A. gambiae Sequencing
      Primers

<400> SEQUENCE: 21
acgacgattg gagaaagg                                                  18

<210> SEQ ID NO 22
<211> LENGTH: 18
<212> TYPE: DNA
<213> ORGANISM: Artificial Sequence
<220> FEATURE:
<223> OTHER INFORMATION: Artificially synthesized A. gambiae Sequencing
      Primers

<400> SEQUENCE: 22
acaagaacga ttacgccc                                                  18

<210> SEQ ID NO 23
<211> LENGTH: 19
<212> TYPE: DNA
<213> ORGANISM: Artificial Sequence
<220> FEATURE:
<223> OTHER INFORMATION: Artificially synthesized A. gambiae Sequencing
      Primers

<400> SEQUENCE: 23
```

```
atcgttgttg gtgacgcac                                              19
```

<210> SEQ ID NO 24
<211> LENGTH: 19
<212> TYPE: DNA
<213> ORGANISM: Artificial Sequence
<220> FEATURE:
<223> OTHER INFORMATION: Artificially synthesized A. gambiae Sequencing
      Primers

<400> SEQUENCE: 24

```
cagaactaca gcgtgaacg                                              19
```

<210> SEQ ID NO 25
<211> LENGTH: 18
<212> TYPE: DNA
<213> ORGANISM: Artificial Sequence
<220> FEATURE:
<223> OTHER INFORMATION: Artificially synthesized A. gambiae Sequencing
      Primers

<400> SEQUENCE: 25

```
agtttcttgc ggcttacg                                               18
```

<210> SEQ ID NO 26
<211> LENGTH: 20
<212> TYPE: DNA
<213> ORGANISM: Artificial Sequence
<220> FEATURE:
<223> OTHER INFORMATION: Artificially synthesized A. gambiae Sequencing
      Primers

<400> SEQUENCE: 26

```
acgaggacta cgaagtgagg                                             20
```

<210> SEQ ID NO 27
<211> LENGTH: 22
<212> TYPE: DNA
<213> ORGANISM: Artificial Sequence
<220> FEATURE:
<223> OTHER INFORMATION: Artificially synthesized A. gambiae Sequencing
      Primers

<400> SEQUENCE: 27

```
tagagtttac gctgctcgtc gg                                          22
```

<210> SEQ ID NO 28
<211> LENGTH: 19
<212> TYPE: DNA
<213> ORGANISM: Artificial Sequence
<220> FEATURE:
<223> OTHER INFORMATION: Artificially synthesized A. gambiae Sequencing
      Primers

<400> SEQUENCE: 28

```
caacctgatg aacggtctg                                              19
```

<210> SEQ ID NO 29
<211> LENGTH: 21
<212> TYPE: DNA
<213> ORGANISM: Artificial Sequence
<220> FEATURE:
<223> OTHER INFORMATION: Artificially synthesized A. gambiae Sequencing
      Primers

<400> SEQUENCE: 29

```
cctttctcca atcgtcgtat c                                           21
```

```
<210> SEQ ID NO 30
<211> LENGTH: 19
<212> TYPE: DNA
<213> ORGANISM: Artificial Sequence
<220> FEATURE:
<223> OTHER INFORMATION: Artificially synthesized A. gambiae Sequencing
      Primers

<400> SEQUENCE: 30
atcgttcagc aagatgccc                                                      19

<210> SEQ ID NO 31
<211> LENGTH: 18
<212> TYPE: DNA
<213> ORGANISM: Artificial Sequence
<220> FEATURE:
<223> OTHER INFORMATION: Artificially synthesized A. gambiae Sequencing
      Primers

<400> SEQUENCE: 31
gccgtagcaa aacacaac                                                       18

<210> SEQ ID NO 32
<211> LENGTH: 17
<212> TYPE: DNA
<213> ORGANISM: Artificial Sequence
<220> FEATURE:
<223> OTHER INFORMATION: Artificially synthesized A. gambiae Sequencing
      Primers

<400> SEQUENCE: 32
cgctgtttca tcaacgc                                                        17

<210> SEQ ID NO 33
<211> LENGTH: 18
<212> TYPE: DNA
<213> ORGANISM: Artificial Sequence
<220> FEATURE:
<223> OTHER INFORMATION: Artificially synthesized A. gambiae Sequencing
      Primers

<400> SEQUENCE: 33
atggtgatgc tgaagacg                                                       18

<210> SEQ ID NO 34
<211> LENGTH: 20
<212> TYPE: DNA
<213> ORGANISM: Artificial Sequence
<220> FEATURE:
<223> OTHER INFORMATION: Artificially synthesized A. gambiae Sequencing
      Primers

<400> SEQUENCE: 34
ggcgtagtcg ttctgtattg                                                     20
```

METHODS AND COMPOSITIONS FOR THE IDENTIFICATION OF INSECT REPELLENT COMPOUNDS

CROSS REFERENCE TO RELATED APPLICATION

The presently disclosed subject matter claims the benefit of U.S. Provisional Patent Application Ser. No. 60/993,816, filed Sep. 14, 2007, the disclosure of which is incorporated herein by reference in its entirety.

TECHNICAL FIELD

The presently disclosed subject matter generally relates to nucleic acid and amino acid sequences of insect transient receptor potential (TRP) channel gene products that function in nociceptors of insects. The presently disclosed subject matter also relates to methods and compositions for employing the disclosed nucleic acid and/or amino acid sequences in vitro or in vivo to identify agents that modulate a biological activity of a TRP channel gene product in a cell.

BACKGROUND

Each year there are hundreds of millions of cases involving diseases that are transmitted by insects and/or arachnids. These diseases result in millions of annual fatalities in addition to having a massive impact on health care resources throughout the world. For example, most orders of ticks include species of medical importance. While blood-sucking ticks can cause irritation and malaise in the host, the tick's role as carrier and transmitter of human disease organisms is of substantial medical concern. The disease organisms, which include but are not limited to viruses, rickettsiae, and spirochaeta bacteria, are transmitted through the tick's saliva during feeding. Tick-borne viruses can cause hemorrhagic fevers, encephalitis, and Lyme disease (LD), the latter of which is a multisystem inflammatory disease that can affect the skin and joints, nervous system, and other organic systems. Like a virus, *rickettsia* can develop only inside living cells. The main rickettsial infections observed in humans are the spotted fevers such as Rocky Mountain spotted fever, tick-bite fevers, and tick-typhus fevers. The condition known as Epizootic Bovine Abortion (EBA) has been associated with blood feeding by the soft tick *Ornithodoros coriaceus*, and causes in excess of $30 million in damage in the state of California alone, with losses in particularly bad years approaching $100 million. Another disease vector affecting cattle is a soft tick that serves as a vector for numerous arboviruses.

Larval mites of the family Trombiculidae, commonly called chiggers or red bugs, can cause a dermatitis (scrub-itch) that results from an allergic reaction to the chigger's saliva and can also transmit human disease organisms. The most common mites that infect humans are scabies or itch mites, which are also known to be severe irritants to cattle. Additional pests that have been shown to cause diseases or other conditions include house dust mites, which induce allergic reactions in the form of asthma and rhinitis in humans; food mites, which cause dermatitis in people handling infested food; and the crab louse, which causes discomfort to humans but can also act as a vector for exanthematous typhus, a disease caused by *Rickettsia prowazekii* that has caused millions of deaths Perhaps the most well known insect vectors for disease are the various types of mosquitoes. Mosquitoes are particularly adept at transmitting diseases caused by viruses, but can also carry disease-causing nematodes and protozoans. The mosquitos most closely associated with human disease are those of the genus *Aedes*. In terms of human health problems, the most important species of *Aedes* is *Aedes aegypti*, which is a vector for the virus that causes yellow fever in humans. Other viruses associated with the *Aedes* species include those that cause dengue fever, various forms of encephalitis, hemorrhagic fever, and yellow fever. Additionally, the common house mosquito, *Culex pipiens*, has been is implicated in the transmission of various forms of encephalitis and the filarial worms *Wuchereria banufti* or *Brugia malayi*, which is responsible for elephantiasis. Mosquitoes might also be a vector for Ebolavirus, a filovirus that causes a hemorrhagic fever that is frequently fatal. The mosquito genus *Anopheles* can also act as vectors for pathogenic organisms that circulate in the bloodstream such as members of the protozoan genus *Plasmodium*, which cause malaria in between 200 and 300 million people and which kill at least two million every year.

And finally, cockroaches can also transmit disease. Cockroaches of various species can be found in grocery stores, restaurants, hospitals, jails, hotels, apartments, homes, and in most any place where food is stored. The droppings and skin of cockroaches can cause hives or rashes, coughing, sneezing, and other contact and/or inhalant allergic reactions in humans. The prodigious ability of cockroaches to multiply, along with their close association with people and food and their tendency to hide in places that are difficult to access, make it difficult to successfully exterminate them.

As a result, tremendous efforts have been made to better understand the mechanisms that underlie host attraction, feeding, and other behaviors of insect species that can serve as vectors for diseases or other undesirable conditions in humans and other susceptible hosts. Such knowledge would allow for the design of strategies for intervening in the process by which pathogenic vectors spread disease.

What are needed, then, are new methods and compositions that can be employed in screening for agents that modulate insect and/or arachnid behavior, and in some cases, screening for agents that can act as repellents and even as pesticides for insects and/or arachnids.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In some embodiments, the presently disclosed subject matter provides methods for identifying a candidate repellent compound with an ability to modulate cation transport through a transient receptor potential (TRP) channel in a cell. In some embodiments, the methods comprise (a) providing a cell expressing a transient receptor potential (TRP) channel gene product; (b) contacting the cell with the candidate repellent compound; (c) comparing cation transport in the cell in the absence of the candidate repellent compound with cation transport in the cell in the presence of the candidate repellent compound; and (d) identifying a candidate repellent compound through comparing step (c) that modulates cation transport in the cell through the transient receptor potential (TRP) channel. In some embodiments, the cell is an insect cell or an arachnid cell. In some embodiments, the transient receptor potential (TRP) channel gene product is encoded by a recombinant nucleic acid sequence. In some embodiments, the recombinant nucleic acid sequence is operably linked to a promoter that is functional in the cell and comprises a cDNA sequence or a splicable DNA sequence that must be spliced in the cell for the cell to express the transient receptor potential (TRP) channel gene product. In some embodiments, the candidate repellent compound is provided as a member of a pool of candidate repellent compounds, and the identifying step comprises identifying at least one member in the pool of candidate repellent compounds that modulates cation transport through the transient receptor potential (TRP) channel in the cell. In some embodiments, the candidate repellent compounds are peptides or small molecules. In some embodiments, the pool of candidate repellent compounds comprises a phage display library. In some embodiments, the candidate repellent compounds are immobilized on a substrate or a plurality of substrates.

The presently disclosed subject matter also provides isolated nucleic acid molecules comprising a nucleotide sequence having at least 85% identity to a subsequence of at least 100 contiguous nucleotides of SEQ ID NO: 7. In some embodiments, the nucleotide sequence has at least 85% identity to nucleotides 236-2368 of SEQ ID NO: 7 over the entire 2133 nucleotide subsequence of SEQ ID NO: 7. In some embodiments, the isolated nucleic acid molecule encodes a polypeptide with at least 85% amino acid sequence identity to SEQ ID NO: 8.

The presently disclosed subject matter also provides isolated polypeptides encoded by the disclosed isolated nucleic acid molecules. In some embodiments, the isolated polypeptide comprises an amino acid sequence as set forth in SEQ ID NO: 8.

The presently disclosed subject matter also provides isolated variants of the disclosed polypeptides. In some embodiments, an isolated variant is a variant of a protein comprising the amino acid sequence shown in SEQ ID NO: 8. In some embodiments, the variant comprises an amino acid sequence that is at least 85%, 90%, 95%, 97%, or 99% identical to SEQ ID NO: 8.

The presently disclosed subject matter also provides isolated and purified antibodies capable of specifically binding to the isolated polypeptides disclosed herein. In some embodiments, the isolated and purified antibody is a monoclonal antibody, a fragment thereof that comprises at least one antigen-binding domain, or a humanized derivative thereof.

The presently disclosed subject matter also provides hybridoma cell lines which produce the disclosed monoclonal antibodies.

The presently disclosed subject matter also provides host cells modified to express the disclosed nucleic acid molecules. In some embodiments, the host cells express a recombinant nucleotide sequence encoding a polypeptide comprising an amino acid sequence at least 85%, 90%, 95%, 97%, or 99% identical to any of SEQ ID NOs: 5, 8, 10, 12, 15, and 17. In some embodiments, the recombinant nucleic acid molecule encodes a polypeptide comprising an amino acid sequence as set forth in SEQ ID NO: 8.

It is thus an object of the presently disclosed subject matter to provide methods for identifying candidate compounds that modulate cation transport through a transient receptor potential (TRP) channel in a cell.

An object of the presently disclosed subject matter having been stated hereinabove, and which is achieved in whole or in part by the presently disclosed subject matter, other objects will become evident as the description proceeds when taken in connection with the accompanying drawings as best described hereinbelow.

BRIEF DESCRIPTION OF THE FIGURES

The file of this patent contains at least one drawing executed in color. Copies of this patent with color drawing(s) will be provided by the Patent and Trademark Office upon request and payment of the necessary fee.

FIG. 6A shows the avoidance behavior of wild type flies to different concentrations of DEET. NA: no third antennal segment. A: intact third antennal segment.

FIG. 6B is a bar graph summarizing the results of the experiments depicted in FIG. 6A.

FIGS. 8A-8C show the results of calcium imaging in S2R+ cells transfected with an expression construct encoding a Drosophila painless transcription unit with 2.0 kb of upstream genomic DNA (see Tracey et al., 2003). FIG. 8A depicts confocal imaging of S2R+ cells loaded with FLUO-4 AM (green) and FURA-RED AM (red) at time 0 before the addition of 0.5% DEET. FIGS. 8B and 8C are graphs showing detection of strong calcium increases in both Channel 1 (FLUO-4) and Channel 2 (FURA-RED AM), respectively, in response to 0.5% DEET treatment in each of the six regions of interest (ROI) shown in FIG. 8A.

FIGS. 8D-8F show the results of calcium imaging in non transfected S2R+ cells. These Ca++ signals might result from endogenous painless is expressed in these cells (see FIG. 9). FIG. 8D depicts confocal imaging of S2R+ cells loaded with FLUO-4 AM (green) and FURA-RED AM (red) at time 0 before the addition of 0.5% DEET. FIGS. 8E and 8F are graphs showing detection of strong calcium increases in both Channel 1 (FLUO-4) and Channel 2 (FURA-RED AM), respectively, in response to 0.5% DEET treatment in each of the seven regions of interest (ROI) shown in FIG. 8D.

BRIEF DESCRIPTION OF THE SEQUENCE LISTING

Figure 1:
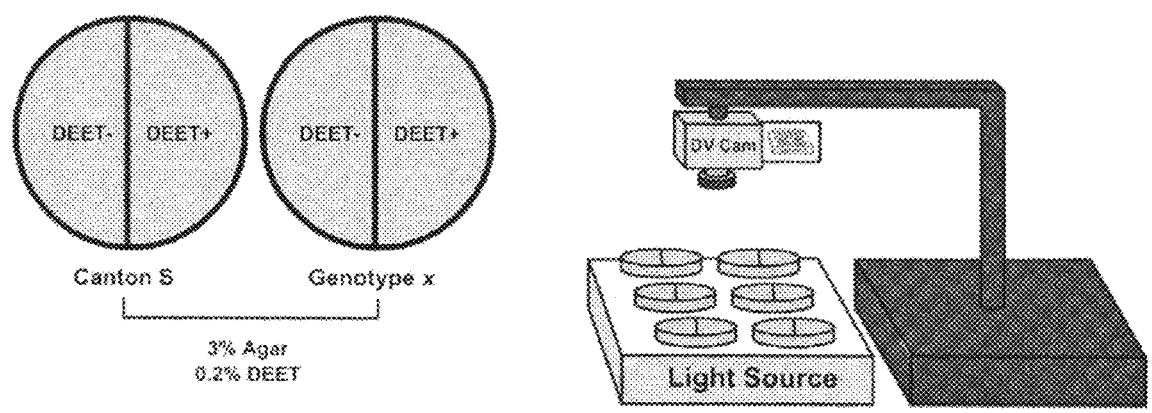
FIG. 1 is a schematic depicting a setup for Avoidance Evaluation Chamber assays in which *Drosophila* are placed onto agar plates, optionally wherein a region of the plate contains a potential stimulus that attracts or repels the flies. The attraction/avoidance activity of the flies is viewed over 60 minutes using a digital video camera, and analyzed over specific time frames.

SEQ ID NO: 1 is a nucleotide sequence of expression vector UAS-Painless, which contains a Drosophila painless genomic DNA sequence in a UAS expression p-element transformation vector. The UAS sites included in the expression vector are binding sites for the yeast transcription factor GAL4. This construct allows painless to be expressed when GAL4 is supplied in trans.

SEQ ID NO: 2 is a nucleotide sequence of an expression vector that includes a Drosophila painless genomic DNA sequence (nucleotides 2775-5718) under the control of a Drosophila actin 5C gene promoter.

SEQ ID NO: 3 is a nucleotide sequence of an expression vector that includes a Drosophila painless genomic DNA sequence under the control of a Drosophila actin 5C gene promoter.

SEQ ID NOs: 4 and 5 are nucleotide and amino acid sequences, respectively, of a painless gene product from Aedes aegypti.

SEQ ID NO: 6 is a genomic sequence from Anopheles gambiae that includes painless coding sequences for a painless gene product.

SEQ ID NOs: 7 and 8 are nucleotide and amino acid sequences, respectively, of a painless gene product from Anopheles gambiae.

SEQ ID NOs: 9 and 10 are nucleotide and amino acid sequences, respectively, of a gene product from the Third Chromosome of Anopheles gambiae that is similar to the painless gene product of SEQ ID NOs: 7 and 8.

SEQ ID NOs: 11 and 12 are nucleotide and amino acid sequences, respectively, of a predicted painless orthologous gene product from Apis mellifera.

SEQ ID NO: 13 is a nucleotide sequence of expression vector pTFM-AgPain, which encodes the Anopheles gambiae painless protein under control of the Drosophila actin-5c promoter. The vector also encodes both FLAG and MYC epitope tags at the N-terminus of the painless protein.

SEQ ID NOs: 14 and 15 are nucleotide and amino acid sequences, respectively, of a painless gene product from Culex quinquefasciatus.

SEQ ID NOs: 16 and 17 are nucleotide and amino acid sequences, respectively, of a painless gene product from Tribolium castaneum.

SEQ ID NOs: 18 and 19 are the nucleotide sequences of oligonucleotide primers that can be employed to amplify a subsequence of a Drosophila painless gene product.

SEQ ID NO: 20 is an amino acid sequence of a painless gene product from Drosophila.

SEQ ID NOs: 21-34 are nucleotide sequences of oligonucleotide primers that were employed for sequencing the Anopheles gambiae painless gene product disclosed in SEQ ID NO: 7.

DETAILED DESCRIPTION

I. General Considerations

The painless gene encodes an ion channel gene in the fruitfly Drosophila melanogaster. To elaborate the Drosophila painless gene encodes a member of the Transient Receptor Potential Channel (TRP) superfamily, many of which are non-selective cation channels. The painless channel was found to play a role in the function of nociceptive neurons in Drosophila larvae. In adult flies, the painless channel was found to be expressed in gustatory receptor neurons.

Insects have several different types of gustatory neurons, some of which mediate appetitive behaviors while others of which mediate repulsive gustatory behaviors. Disclosed herein is the determination that the painless channel is expressed specifically in gustatory neurons that trigger repulsion and not in neurons that mediate appetitive feeding behaviors. For example, flies that are mutant for the painless gene are defective in their ability to avoid isothiocyanate compounds, which comprise the irritant component of mustard oils. However, painless mutant flies are not defective in their ability to taste sugars, salts, or a variety of bitter compounds.

Given that the painless channel is expressed in neurons that mediate repulsion, it was hypothesized that agents that activate the painless channel might be repellent to insects. To that end, disclosed herein is the discovery that the painless gene product is required for avoidance of the insect repellent compound N,N-diethyl-meta-toluamide (DEET). Adult *Drosophila* that are mutant for painless fail to avoid DEET, demonstrating that painless is a molecular component of a genetic pathway that is required for repellency of this compound.

In addition, disclosed herein are assays, including but not limited to cell-based assays, which can be used to identify agents (i.e., small molecules) that modulate (e.g., enhance or inhibit) a biological activity of a painless gene product. Such agents represent candidates for compositions that are predicted to inhibit feeding of insects by activation of the repulsive chemosensory neurons which express painless in adult flies.

In some embodiments, the presently disclosed cell-based assays utilize the *Drosophila* S2R+ cell line. These cells can be grown on cover slips and can be transfected with plasmids that comprise painless genomic DNA sequences operably linked to a promoter that is functional in the S2R+ cell line (*e.g., the actin 5c promoter). The cells can be loaded with calcium indicator dyes such as Fura-red and FLUO-4 in order to image channel activity and transferred to an imaging device such as a microscope or a high throughput fluorimeter. Calcium responses can then be measured and compared to that seen in control cells that do not express (or in some embodiments overexpress) a painless protein.

The disclosed assays can be used to identify agents that produce a calcium signal in the painless-expressing cells but not in the control cells. These agents would in some embodiments represent candidate insect repellents. Identification of new insect repellent agents is desirable since repellents such as DEET are not ideal. Many people do not wish to apply DEET to themselves or others due to the foul odor it has and/or its perceived potential to cause cancer in animal models. Additionally, DEET is not recommended for application to infants. And finally, DEET can damage or stain certain fabrics when applied to them.

Thus, whether N,N-diethyl-meta-toluamide (DEET) activates calcium transport in cells expressing painless has been tested. Observed data indicated that DEET activates a robust calcium signal in insect cells. Consistent with this, it has also been determined that *Drosophila* flies that are mutant for painless are defective in behavioral avoidance of DEET.

Also disclosed herein are nucleic acid and predicted amino acid sequences of painless orthologs from other species such as the mosquito *Anopheles gambae* and *Aedes egypti*. These genes can be placed into the disclosed expression systems and compounds that modulate biological activities of these orthologs can also be identified.

However, it should be noted that the subject matter disclosed herein is not limited to identification of agents that inhibit insects that feed on or otherwise infect humans. Agriculturally important pests can also be targeted through identification of compounds that target their painless orthologs and homologs in these pests using the techniques disclosed herein.

II. Definitions

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in this application, including the claims. Thus, for example, reference to "a cell" (e.g., "an insect cell") includes a plurality of such cells (e.g., a plurality of insect cells in culture, in a tissue, in an organ), and so forth.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

The term "biological sample" as used herein refers to a sample that comprises a biomolecule and/or is derived from a subject. Representative biomolecules include, but are not limited to total DNA, RNA, mRNA, and polypeptides. As such, a biological sample can comprise a cell, a group of cells, fragments of cells, or cell products. Also encompassed within the phrase "biological sample" are biomolecules that are derived from a cell or group of cells that permit gene expression and/or biological activity levels to be determined, including but not limited to nucleic acids and polypeptides.

The term "coding sequence" and "open reading frame" (ORF) are used interchangeably and refer to a nucleic acid sequence that is transcribed into RNA such as mRNA, rRNA, tRNA, snRNA, sense RNA, or antisense RNA. In some embodiments, the RNA is then translated in vivo or in vitro to produce a polypeptide.

The term "complementary" refers to two nucleotide sequences that comprise antiparallel nucleotide sequences capable of pairing with one another upon formation of hydrogen bonds between the complementary base residues in the antiparallel nucleotide sequences. As is known in the art, the nucleic acid sequences of two complementary strands are the reverse complement of each other when each is viewed in the 5' to 3' direction. As is also known in the art, two sequences that hybridize to each other under a given set of conditions do not necessarily have to be 100% fully complementary. The terms "fully complementary" and "100% complementary" refer to sequences for which the complementary regions are 100% in Watson-Crick base-pairing, i.e., that no mismatches occur within the complementary regions. However, as is often the case with recombinant molecules (for example, cDNAs) that are cloned into cloning vectors, certain of these molecules can have non-complementary overhangs on either the 5' or 3' ends that result from the cloning event. In such a situation, it is understood that the region of 100% or full complementarity excludes any sequences that are added to the recombinant molecule (typically at the ends) solely as a result of, or to facilitate, the cloning event. Such sequences are, for example, polylinker sequences, linkers with restriction enzyme recognition sites, etc.

The term "expression cassette" refers to a nucleic acid molecule capable of directing expression of a particular nucleotide sequence in an appropriate host cell, comprising a promoter operatively linked to the nucleotide sequence of interest which is operatively linked to termination signals. It also typically comprises sequences required for proper translation of the nucleotide sequence. The coding region usually encodes a polypeptide of interest but can also encode a functional RNA of interest, for example antisense RNA or a non-translated RNA, in the sense or antisense direction. The expression cassette comprising the nucleotide sequence of interest can be chimeric, meaning that at least one of its components is heterologous with respect to at least one of its other components. The expression cassette can also be one that is naturally occurring but has been obtained in a recombinant form useful for heterologous expression. Typically, however, the expression cassette is heterologous with respect to the host; i.e., the particular DNA sequence of the expression cassette does not occur naturally in the host cell and was introduced into the host cell or an ancestor of the host cell by a transformation event. The expression of the nucleotide sequence in the expression cassette can be under the control of a constitutive promoter or of an inducible promoter that initiates transcription only when the host cell is exposed to some particular external stimulus. In the case of a multicellular organism such as a plant, the promoter can also be specific to a particular tissue, organ, or stage of development.

The term "fragment" refers to a sequence that comprises a subsequence of another sequence. When used in the context of a nucleic acid or amino acid sequence, the terms "fragment" and "subsequence" are used interchangeably. A fragment of a nucleic acid sequence can be any number of nucleotides that is less than that found in another nucleic acid sequence, and thus includes, but is not limited to, the sequences of an exon or intron, a promoter, an enhancer, an origin of replication, a 5' or 3' untranslated region, a coding region, and a polypeptide binding domain. It is understood that a fragment or subsequence can also comprise less than the entirety of a nucleic acid sequence, for example, a portion of an exon or intron, promoter, enhancer, etc. Similarly, a fragment or subsequence of an amino acid sequence can be any number of residues that is less than that found in a naturally occurring polypeptide, and thus includes, but is not limited to, domains, features, repeats, etc. Also similarly, it is understood that a fragment or subsequence of an amino acid sequence need not comprise the entirety of the amino acid sequence of the domain, feature, repeat, etc.

A fragment can also be a "functional fragment", in which the fragment retains a specific biological function of the nucleic acid sequence or amino acid sequence of interest. For example, a functional fragment of a transcription factor can include, but is not limited to, a DNA binding domain, a transactivating domain, or both. Similarly, a functional fragment of a receptor tyrosine kinase includes, but is not limited to a ligand binding domain, a kinase domain, an ATP binding domain, and combinations thereof.

The term "gene" is used broadly to refer to any segment of DNA associated with a biological function. Thus, genes include, but are not limited to, coding sequences and/or the regulatory sequences required for their expression. Genes can also include non-expressed DNA segments that, for example, form recognition sequences for a polypeptide. Genes can be obtained from a variety of sources, including cloning from a source of interest or synthesizing from known or predicted sequence information, and can include sequences designed to have desired parameters.

The term "isolated", when applied to a nucleic acid or polypeptide, denotes that the nucleic acid or polypeptide is essentially free of other cellular components with which it is associated in the natural state. It can be in a homogeneous state although it can be in either a dry or aqueous solution. Homogeneity and whether a molecule is isolated can be determined using analytical chemistry techniques such as polyacrylamide gel electrophoresis or high performance liquid chromatography. A polypeptide that is the predominant species present in a preparation is substantially isolated. The term "isolated" denotes that a nucleic acid or polypeptide gives rise to essentially one band in an electrophoretic gel. Particularly, it means that the nucleic acid or polypeptide is in some embodiments at least about 50% pure, in some embodiments at least about 85% pure, and in some embodiments at least about 99% pure.

The terms "label" and "labeled" refer to the attachment of a moiety, capable of detection by spectroscopic, radiologic, or other methods, to a molecule. Thus, the terms "label" or "labeled" refer to incorporation or attachment, optionally covalently or non-covalently, of a detectable marker into a molecule, such as a biomolecule. Various methods of labeling biomolecules are known in the art and can be used. Examples of labels for biomolecules include, but are not limited to, the following: radioisotopes, fluorescent labels, heavy atoms, enzymatic labels or reporter genes, chemiluminescent groups, and biotinyl groups. In some embodiments, labels are attached by spacer arms of various lengths to reduce potential steric hindrance. Fluorescent probe that can be utilized include, but are not limited to fluorescein isothiocyanate; fluorescein dichlorotriazine and fluorinated analogs of fluorescein; naphthofluorescein carboxylic acid and its succinimidyl ester; carboxyrhodamine 6G; pyridyloxazole derivatives; Cy2, 3, 3.5, 5, 5.5, and 7; phycoerythrin; phycoerythrin-Cy conjugates; fluorescent species of succinimidyl esters, carboxylic acids, isothiocyanates, sulfonyl chlorides, and dansyl chlorides, including propionic acid succinimidyl esters, and pentanoic acid succinimidyl esters; succinimidyl esters of carboxytetramethylrhodamine; rhodamine Red-X succinimidyl ester; Texas Red sulfonyl chloride; Texas Red-X succinimidyl ester; Texas Red-X sodium tetrafluorophenol ester; Red-X; Texas Red dyes; tetramethylrhodamine; lissamine rhodamine B; tetramethylrhodamine; tetramethylrhodamine isothiocyanate; naphthofluoresceins; coumarin derivatives (e.g., hydroxycoumarin, aminocoumarin, and methoxycoumarin); pyrenes; pyridyloxazole derivatives; dapoxyl dyes; Cascade Blue and Yellow dyes; benzofuran isothiocyanates; sodium tetrafluorophenols; 4,4-difluoro-4-bora-3a,4a-diaza-s-indacene; Alexa fluors (e.g., 350, 430, 488, 532, 546, 555, 568, 594, 633, 647, 660, 680, 700, and 750); green fluorescent protein; and yellow fluorescent protein. The peak excitation and emission wavelengths will vary for these compounds and selection of a particular fluorescent probe for a particular application can be made in part based on excitation and/or emission wavelengths.

The terms "modified nucleotide sequence", "modified nucleic acid sequence", "modified amino acid sequence", "modified polypeptide", and "modified polypeptide sequence" refer to a nucleic acid or amino acid sequence (or a polypeptide comprising that amino acid sequence) that is different from a second nucleic acid or amino acid sequence (or a polypeptide that has such an amino acid sequence) that results from an intentional manipulation of the amino acid sequence or the nucleic acid sequence encoding the amino acid sequence. For example, a nucleic acid or polypeptide sequence that is substantially similar (e.g., at least about 95%, 96%, 97%, 98%, 99%, or 100% identical to) another nucleic acid or polypeptide sequence can be a modified nucleic acid or polypeptide sequence if there is at least one difference in the nucleic acid or amino acid sequence between the two sequences. It should be noted that due to the degeneracy of the genetic code, a modified nucleic acid sequence need not encode a modified amino acid sequence, and a modified amino acid sequence need not necessarily have any assayable difference in activity as compared to the corresponding unmodified amino acid sequence. For example, it is known in the art that certain amino acid changes (e.g., conservative amino acid changes) can result in a change in a polypeptides primary structure (i.e., its amino acid sequence) with little or no difference in its secondary, tertiary, or quaternary structure and/or biological activity.

The term "conservatively substituted" refers to a peptide or polypeptide comprising an amino acid sequence in which one or more residues have been conservatively substituted with a functionally similar residue and which displays the targeting activity as described herein. Examples of conservative substitutions include the substitution of one non-polar (hydrophobic) residue such as isoleucine, valine, leucine or methionine for another; the substitution of one polar (hydrophilic) residue for another such as between arginine and lysine, between glutamine and asparagine, between glycine and serine; the substitution of one basic residue such as lysine, arginine or histidine for another; or the substitution of one acidic residue, such as aspartic acid or glutamic acid for another.

The term "modulate" refers to an increase, decrease, or other alteration of any, or all, chemical and/or biological activities and/or properties of a biomolecule, such as a nucleic acid or polypeptide of the presently disclosed subject matter.

The term "modulation" as used herein thus refers to both upregulation (i.e., activation or stimulation) and downregulation (i.e., inhibition or suppression) of such an activity or property. As would be understood by one of ordinary skill in the art, a modulation of a chemical and/or biological activity and/or property of a biomolecule, such as a nucleic acid or polypeptide of the presently disclosed subject matter, can result from an increase or decrease in the expression of the biomolecule in a cell. Accordingly, the terms "modulate" and grammatical variants thereof are intended to encompass both direct modulation (e.g., inhibition of a chemical and/or biological activity and/or property of a polypeptide via binding of an inhibitor to the polypeptide) as well as indirect modulation (e.g., upregulation or downregulation of expression of a gene product or inhibition or stimulation of a biomolecule that acts together with a biomolecule of the presently disclosed subject matter to produce a biological effect).

The term "native" refers to a gene that is naturally present in the genome of an untransformed cell. Similarly, when used in the context of a polypeptide, a "native polypeptide" is a polypeptide that is encoded by a native gene of an untransformed cell's genome.

The term "naturally occurring" refers to an entity (e.g., a cell, biomolecule, etc) that is found in nature as distinct from being artificially produced by man. For example, a polypeptide or nucleotide sequence that is present in an organism in its natural state, which has not been intentionally modified or isolated by man in the laboratory, is naturally occurring. As such, a polypeptide or nucleotide sequence is considered "non-naturally occurring" if it is encoded by or present within a recombinant molecule, even if the amino acid or nucleic acid sequence is identical to an amino acid or nucleic acid sequence found in nature.

The term "nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al., 1991; Ohtsuka et al., 1985; Rossolini et al., 1994). The terms "nucleic acid" or "nucleic acid sequence" can also be used interchangeably with gene, open reading frame (ORF), cDNA, and mRNA encoded by a gene.

The term "operably linked" refers to two nucleic acid sequences that are related physically or functionally. For example, a promoter or regulatory DNA sequence is said to be "operably linked to" a DNA sequence that encodes an RNA or a polypeptide if the two sequences are situated such that the regulatory DNA sequence will affect the expression level of the coding or structural DNA sequence. A promoter is also said to be operably linked to a nucleotide sequence if when an RNA polymerase binds to the promoter under conditions sufficient for transcription, the nucleotide sequence is transcribed.

As used herein, the phrases "percent identical" and "percent identity", in the context of two nucleic acid or polypeptide sequences, refers to two or more sequences or subsequences that have in some embodiments 60% (e.g., 60, 61, 62, 63, 64, 65, 66, 67, 68, or 69%), in some embodiments 70% (e.g., 70, 71, 72, 73, 74, 75, 76, 77, 78, or 79%), in some embodiments 80% (e.g., 80, 81, 82, 83, 84, 85, 86, 87, 88, or 89%), in some embodiments 90% (e.g., 90, 91, 92, 93, 94, 95, 96, 97, 98, or more), and in some embodiments at least 99% nucleotide or amino acid residue identity, respectively, when compared and aligned for maximum correspondence, as measured using one of the following sequence comparison algorithms or by visual inspection. The percent identity exists in some embodiments over a region of the sequences that is at least about 50 nucleotides/residues in length, in some embodiments over a region of at least about 100 nucleotides/residues in length, and in some embodiments, the percent identity exists over at least about 150 nucleotides/residues in length. In some embodiments, the percent identity exists over the entire length of the sequences.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, for example, by the local homology algorithm disclosed in Smith & Waterman, 1981, by the homology alignment algorithm disclosed in Needleman & Wunsch, 1970, by the search for similarity method disclosed in Pearson & Lipman, 1988, by computerized implementations of these algorithms (GAP, BESTFIT, FASTA, and TFASTA in the GCG® WISCONSIN PACKAGE®, available from Accelrys, Inc., San Diego, Calif., United States of America), or by visual inspection. See generally, Ausubel et al., 2002; Ausubel et al., 2003.

One example of an algorithm that is suitable for determining percent sequence identity and sequence similarity is the BLAST algorithm, which is described in Altschul et al., 1990. Software for performing BLAST analysis is publicly available through the website of the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. See generally, Altschul et al., 1990. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See Henikoff & Henikoff, 1992.

In addition to calculating percent sequence identity, the BLAST algorithm also performs a statistical analysis of the similarity between two sequences (see e.g., Karlin & Altschul, 1993). One measure of similarity provided by the BLAST algorithm is the smallest sum probability (P(N)), which provides an indication of the probability by which a match between two nucleotide or amino acid sequences would occur by chance. For example, a test nucleotide sequence is considered similar to a reference sequence if the smallest sum probability in a comparison of the test nucleotide sequence to the reference nucleotide sequence is in some embodiments less than about 0.1, in some embodiments less than about 0.01, and in some embodiments less than about 0.001.

The terms "polypeptide", "protein", and "peptide", which are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide" and "peptide" are used interchangeably herein when referring to a gene product. Thus, exemplary polypeptides include gene products, naturally occurring proteins, homologs, orthologs, paralogs, fragments and other equivalents, variants, and analogs of the foregoing.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both. Fragments typically are at least 5, 6, 8 or 10 amino acids long, at least 14 amino acids long, at least 20, 30, 40 or 50 amino acids long, at least 75 amino acids long, or at least 100, 150, 200, 300, 500 or more amino acids long. A fragment can retain one or more of the biological activities of the reference polypeptide. In some embodiments, a fragment can comprise a domain or feature, and optionally additional amino acids on one or both sides of the domain or feature, which additional amino acids can number from 5, 10, 15, 20, 30, 40, 50, or up to 100 or more residues. Further, fragments can include a sub-fragment of a specific region, which sub-fragment retains a function of the region from which it is derived.

The terms "significance" or "significant" relates to a statistical analysis of the probability that there is a non-random association between two or more entities. To determine whether or not a relationship is "significant" or has "significance", statistical manipulations of the data can be performed to calculate a probability, expressed as a "p-value". Those p-values that fall below a user-defined cutoff point are regarded as significant. A p-value in some embodiments less than or equal to 0.1, in some embodiments less than or equal to 0.05, in some embodiments less than 0.01, in some embodiments less than 0.005, and in some embodiments less than 0.001, are regarded as significant.

As used herein, the phrase "splicable DNA sequence" refers to a DNA sequence that must be spliced in the cell for the cell to express a polypeptide of interest. Stated another way, a "splicable DNA sequence" is a DNA sequence that encodes an RNA molecule that is spliced to produce an mRNA molecule that encodes a polypeptide of interest (e.g., a transient receptor potential (TRP) channel polypeptide). In some embodiments, a splicable DNA sequence is a sequence that comprises one or more introns, which can be introns that are naturally found in the splicable DNA sequence, introns that are artificially placed into the splicable DNA sequence, or a combination thereof. In some embodiments, a splicable DNA sequence is a genomic DNA sequence.

The term "subsequence" refers to a sequence of nucleic acids or amino acids that comprises a part of a longer sequence of nucleic acids or amino acids (e.g., polypeptide), respectively.

The term "transformation" refers to a process for introducing heterologous DNA into a cell. Transformed cells are understood to encompass not only the end product of a transformation process, but also transgenic progeny thereof.

The terms "transformed" and "transgenic" refer to a cell of a host organism such as an insect, an arachnid, a mammal, or any other organism, into which a heterologous nucleic acid molecule has been introduced. The nucleic acid molecule can be stably integrated into the genome of the cell or the nucleic acid molecule can also be present as an extrachromosomal molecule. Such an extrachromosomal molecule can be auto-replicating. Transformed cells, tissues, or subjects are understood to encompass not only the end product of a transformation process, but also transgenic progeny thereof. Similarly, the terms "transformed" and "transgenic" can also refer to a cell, tissue, organ, or a whole organism in which at least one cell is transformed or transgenic. A "non-transformed", "non-transgenic", or "non-recombinant" host refers to a wild type organism, e.g., a mammal or a cell therefrom, which does not contain the heterologous nucleic acid molecule.

III. Methods for Identifying Candidate Compounds that Modulate TRP Channels

In some embodiments, the presently disclosed subject matter provides methods for identifying a candidate compound with an ability to modulate cation transport through a transient receptor potential (TRP) channel in a cell. In some embodiments, the methods comprise (a) providing a cell expressing a recombinant nucleic acid sequence encoding an transient receptor potential (TRP) channel gene product or a functional fragment or derivative thereof, wherein the functional fragment or derivative comprises an amino acid sequence is at least 95% identical at the amino acid sequence of the transient receptor potential (TRP) channel gene product; (b) contacting the cell with the candidate compound; (c) comparing cation transport in the cell in the absence of the candidate compound with cation transport in the cell in the presence of the candidate compound; and (d) identifying a candidate compound through comparing step (c) that modulates cation transport in the cell through the transient receptor potential (TRP) channel.

As used herein, the phrase "transient receptor potential (TRP) channel" refers to a gene product that mediates cation transport in a cell, in some embodiments cation transport in a cell in response to nociception. Representative TRP channels include the painless gene products disclosed herein including, but not limited to painless gene products that correspond to SEQ ID NOs: 4-8 and 11-17.

In some embodiments, a cell expressing a recombinant nucleic acid sequence encoding a TRP channel gene product is a cell that has been transformed with an expression vector comprising a nucleotide sequence encoding a TRP channel gene product such as, but not limited to the TRP gene products discloses herein. Methods for transforming cells that would be known to one of ordinary skill in the art include, but are not limited to, infection using viral vectors, lipofection, electroporation, particle bombardment, and transfection. Detailed procedures for representative methods can be found in Sambrook & Russell, 2001, and references cited therein. Useful expression vectors and methods of introducing such vectors into cells or expression of the encoded polypeptide are also known to one of ordinary skill in the art. For example, a plasmid expression vector can be introduced into a cell by calcium-phosphate mediated transfection, DEAE-Dextran-mediated transfection, lipofection, polybrene- or polylysine-mediated transfection, electroporation, or by conjugation to an antibody, gramacidin S, artificial viral envelopes, or other intracellular carriers. A viral expression vector can be introduced into a cell in an expressible form by infection or transduction, for example, or by encapsulation in a liposome.

When a cell expressing a recombinant nucleic acid sequence encoding a TRP channel gene product has been produced, these cells can then be employed in testing candidate compounds for an ability to modulate cation transport in the cell through the transient receptor potential (TRP) channel. An exemplary method for testing cation transport in the cells is presented in the section of the Experimental Procedures Employed in the EXAMPLES entitled "Calcium Imaging for S2R+ cells". Other applicable methods would be known to those of skill in the art upon consideration of this disclosure.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently disclosed subject matter.

Experimental Procedures Employed in the Examples

*Drosophila* Stocks. All fly stocks were maintained on conventional cornmeal-agar-molasses medium under a 12 hour light/12 hour dark cycle at 22° C. Fly strains used were the wild-type Canton-S, the painless mutant pain1 (EP(2)2451), the dTRPA1 mutant (dTRPA1$^{23-5939}$/Df(3L)ED4415), the painless– dTRPA1 double mutant pain1; dTRPA1$^{23-5939}$, the Or83b mutant W;ΔOr83b (provided by Dr. Hubert Amrein, Duke University, Durham, N.C., United States of America), and the Or83b-painless double mutant pain1; W;ΔOr83b.

Evaluation of Toxin Avoidance.

Avoidance Evaluation Chambers: 3% agar (Fisher Scientific, Pittsburgh, Pa., United States of America) and 3% sucrose (Fisher Scientific) was dissolved in distilled $H_2O$. 0.2% (1:500, or 20 mM) N,N-diethyl-3-methylbenzamide (DEET) or 0.01% (1:10000, or 1 mM) allyl-isothiocyanate (AITC) was added and mixed into the agar/sucrose solution immediately before 22 milliliters of solution was poured into each 60 diameter×15 mm HBD Falcon Standard Tissue Culture Dish. The agar was allowed for harden for approximately 1 hour. Using a template below each dish, the agar was then split along the midline with a clean razor blade and half of each plate was excised and placed onto a clean absorbent towel. In order to assess preference, the empty half of each plate was then replaced with solidified 3% agar and 3% sucrose without the addition of DEET or AITC. Care was taken to not contaminate surfaces of toxin and toxin-free agar during this switch.

Olfactory Desensitization: To prevent most odorant detection, the third antennal segment of each antennae was removed from flies under $CO_2$ anesthesia 24 hours before avoidance trials. Removal of both aristae, but not any part of the antennae, was used as a sham to control for non-specific effects that may have resulted from the surgical procedure.

Trial Recording: Testing areas (e.g., plates), each containing toxin-containing and toxin-free halves, were placed on a fluorescent-bulb containing light box and arranged so that all fit within the viewfinder of a digital video camera (SONY Handycam; see FIG. 1). Multiple flies to be used on each plate of the trial were sorted under $CO_2$ anesthesia 24 hours before the experiment into glass vials containing fly food. During the experiment, the flies were transferred onto the agar plates by gentle tapping after vials were cooled horizontally on ice. The lids were replaced on the agar plates after fly transfer and animals were allowed a 5-minute acclimation time prior to the start of each trial. The video camera began recording after this acclimation time and ran for 60 minutes. External noise and odors were avoided throughout the trial.

Data Analysis—Avoidance Behavior: Video was downloaded from the digital video camera to a computer using Image Video Mixer (Sony Electronics Inc.) and saved as an MPEG2 file. The movie was then converted to and saved as an image stack at the rate of 1-3 images/second through Image Video Machine (DanDans Digital Media, Boston, Mass., United States of America). Image stacks for each trial were then analyzed at 10 or 15-minute intervals. Each interval was imported and converted to grayscale into ImageJ (Rasband, ImageJ, U.S. National Institutes of Health, Bethesda, Md., United States of America) as a stack and thresholded (Image→Threshold) so that only flies were visible. Care was taken to make sure only flies were visible in each slice since fluorescence in the light box may be of different brightness in each image. The Z-stack Standard Deviation function of ImageJ (Image→Stack→Z-stack→Standard Deviation) was used to visualize the position of all flies throughout each time interval. This inverts and stacks pixels (flies) from each stack image so that the most occupied areas are standardized to be the brightest, and the least occupied areas remain dark. To quantify this amount of time each space was occupied, the "mean gray value" for each side was calculated using the Analyze Measurements menu of ImageJ. Visualization of results and statistical significance tests were conducted in Microsoft Excel.

Alternatively, the threshold intensity of a single frame in NIH ImageJ was determined automatically; this function highlighted only the flies against an otherwise white background. A frame-by-frame, overlaid reconstruction of the thresholded frames was created using the "Z Stacks" function that produced a single image that represented all the activity within the arenas over 15 minutes (900 frames). The mean pixel intensity (i.e., activity of the flies) on a given half of the plate was measured in NIH Image J and converted into a percentage with the following formula:

$$\frac{\text{Mean Pixel Intensity } DEET(-) \text{ side}}{\text{Sum [Mean Pixel Intensity of } DEET(-) \text{ and } DEET(+) \text{ sides]}}$$

Evaluation of Activity Level—Speed of Flies: Video of trials were downloaded and converted to image stacks and thresholded as described above. The ImageJ plug-in "Multitracker" was used to analyze the paths taken by each fly. The total distance traveled by all flies on each plate was calculated using the Multitracker plug-in, and this distance was divided by the time interval (in minutes) to gauge the average speed of flies on each plate in path lengths/minute.

Calcium Phosphate Transfection of Drosophila S2R+ Cells: Drosophila S2R+ cells were maintained at room temperature, in ambient atmosphere, in Schneider's Drosophila medium modified with L-glutamine plus 10% heat-inactivated fetal bovine serum. On the day before DNA transfection, cells were plated at a density of $1.2 \times 10^5$ cells per $cm^2$ growth area. DNA to be transfected was added to 250 mM $CaCl_2$ (a volume equal to 1/20th of the volume of the medium in the dish of cells to be transfected) then this mixture was added dropwise to the same volume of 280 mM NaCl/1.5 mM/$Na_2HPO_4$/50 mM HEPES, pH 7.08 (2×HEPES buffered saline) while bubbling air gently through the liquid to mix. Precipitate was allowed to form at room temperature for 40 minutes. Immediately before introducing the precipitate, all growth medium was removed form the cells and fresh growth medium was added. Precipitate was added dropwise to the cells, and the dish was gently swirled. 18-24 hour later all liquid on the dish was withdrawn and was replaced with fresh growth medium. Expression was examined on the third day.

For the DEET experiments, 2 ml of culture medium containing $5.75 \times 10^5$ cells/ml was placed onto #1.5 25 mm diameter round glass cover slips placed in 6-well multiwell dishes. Cells were transfected with 0.5 µg pApainless, co-transfected with 0.075 µg pTpainless with introns/stop and 0.75 µg ubiquitin Gal4, with 0.75 µg ubiquitin Gal4 alone (control), or with no added DNA (control).

Calcium Imaging for S2R+ cells: the following protocol was followed:

Dye loading:
Cell medium was removed.
100 µl of the following Fluo4+Fura-Red solution was added per well:
1 µl FLUO-4 stock
1 µl FURA-Red stock
1 µl Pluronic stock
200 µl Stop solution
Loaded for 45 min at RT
Added 200 µl of fly saline.
If in Ca++ free condition, the cells were washed with Ca++ free fly saline supplemented with 5 mM EGTA 3 times. Then 200 µl of Ca++ free, 5 mM EGTA fly saline was added.
The ligand solution was added (with or without Ca++ fly saline).
Solutions used:
Fly saline: standard fly saline
HBS: Hank's Solution with 10 mM HEPES and 5 mM glucose (1 ml of 45% sol for 500 ml)
Stop Solution: HBS (or MEM with HEPES) with 0.1 mg/ml BSA
FLUO-4 AM or FURA-Red AM stock in DMSO (12.5 µl for 50 µg)
20% Pluronic F-127 in DMSO (Invitrogen Corp., Carlsbad, Calif., United States of America)
Microscope setting:
FLUO-4: Ex 488, Em 500-560
FURA-Red: Ex 488, Em 605-700

Example 1

AITC and DEET are Both Repellents, not Just Behavioral Inhibitors

Using avoidance evaluation chambers (see FIG. 1), the behavior of Drosophila in the presence of DEET and wasabi (i.e., a source of AITC) was observed over the period of 60 minutes. As predicted by prior food-ingestion assays (Al-Anzi et al., 2006), wild-type Canton S flies of both genders avoided wasabi at concentrations as low as 1:50,000 but avoided best at 1:10,000. Wild-type Canton S flies consistently avoided agar containing as low as 0.2% DEET with and without the presence of sugar, indicating that DEET not only prevents the initiation of feeding behaviors, but also repels them from the target as well.

Example 2

Canton S Avoids AITC and DEET Without the Third Antennal Segment

Wild type Canton S flies were able to avoid both AITC and DEET without the third antennal segment, indicating that both noxious chemicals can be mediated through either olfactory neurons in the maxillary palps or mediated through a gustatory pathway. Testing olfactory and gustatory mutants would thus be helpful in distinguishing the mechanism of DEET.

Example 3

Painless$^{-/-}$ Mutants are Deficient in Both AITC and DEET Detection

Figure 2:
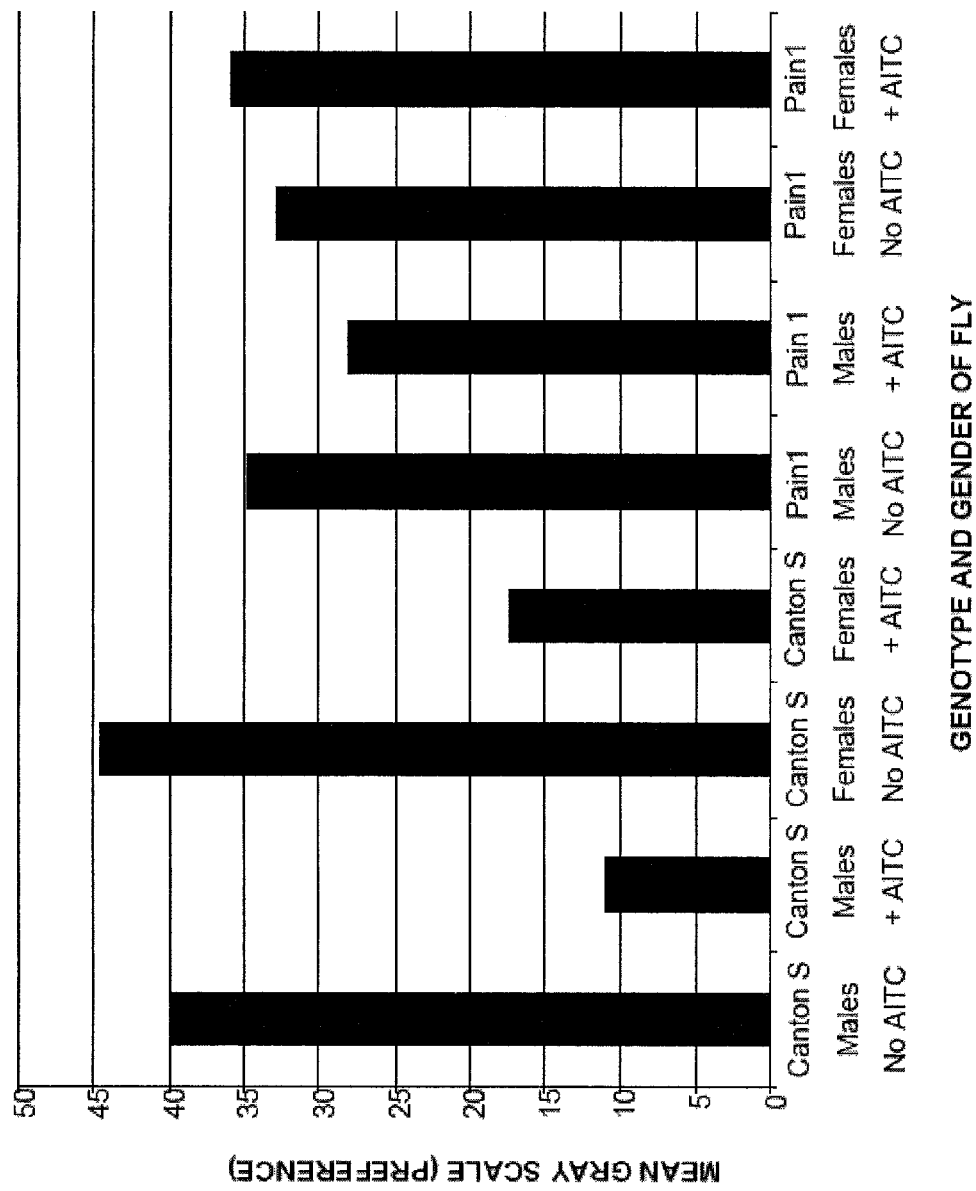
FIG. 2 is a bar graph showing the avoidance behavior of male and female wild type Canton S or painless mutant flies (expressed as Mean Gray Scale (Preference)) to a 1:10000 dilution of allyl-isothiocyanate (AITC) placed on the right half of each Chamber in Avoidance Evaluation Chamber assays.

Painless$^{-/-}$ mutant Drosophila appeared to be deficient in AITC detection at 1:10,000 dilution using the avoidance assays disclosed herein as compared to wild type Canton S flies (see FIG. 2). However, though painless$^{-/-}$ males did show slight preference for the non-AITC side of the AITC avoidance test, they did not appear to avoid AITC as robustly as Canton S flies.

Figure 3A:
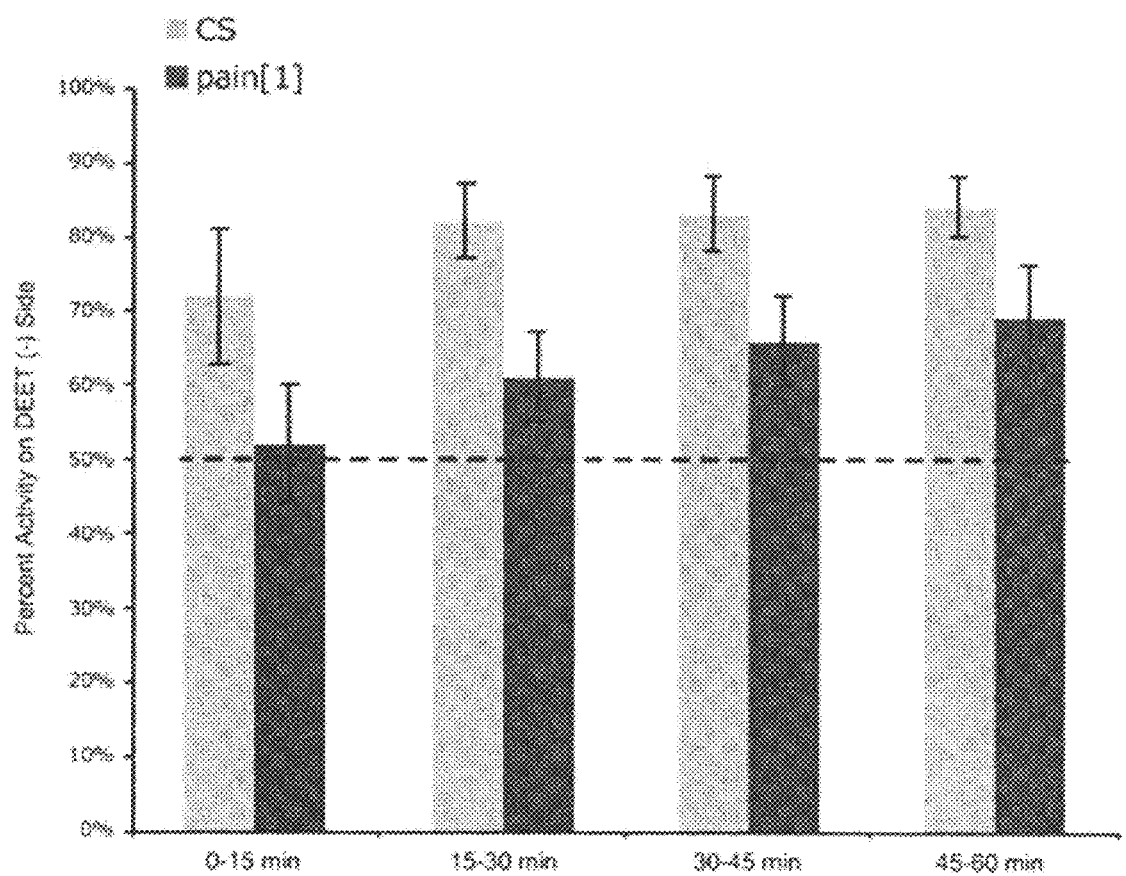
FIGS. 3A and 3B are bar graphs of Avoidance Evaluation Chamber assays of pain[1] females (FIG. 3A) and males (FIG. 3B) showing the both males and females failed to avoid DEET for the first fifteen minutes after exposure, whereas wild type Canton-S flies clearly avoided DEET during the same interval. As the trials progressed, the painless mutants gradually increased their avoidance of DEET. pain1 females N=13 trials, males: N=11 trials.
Figure 3B:
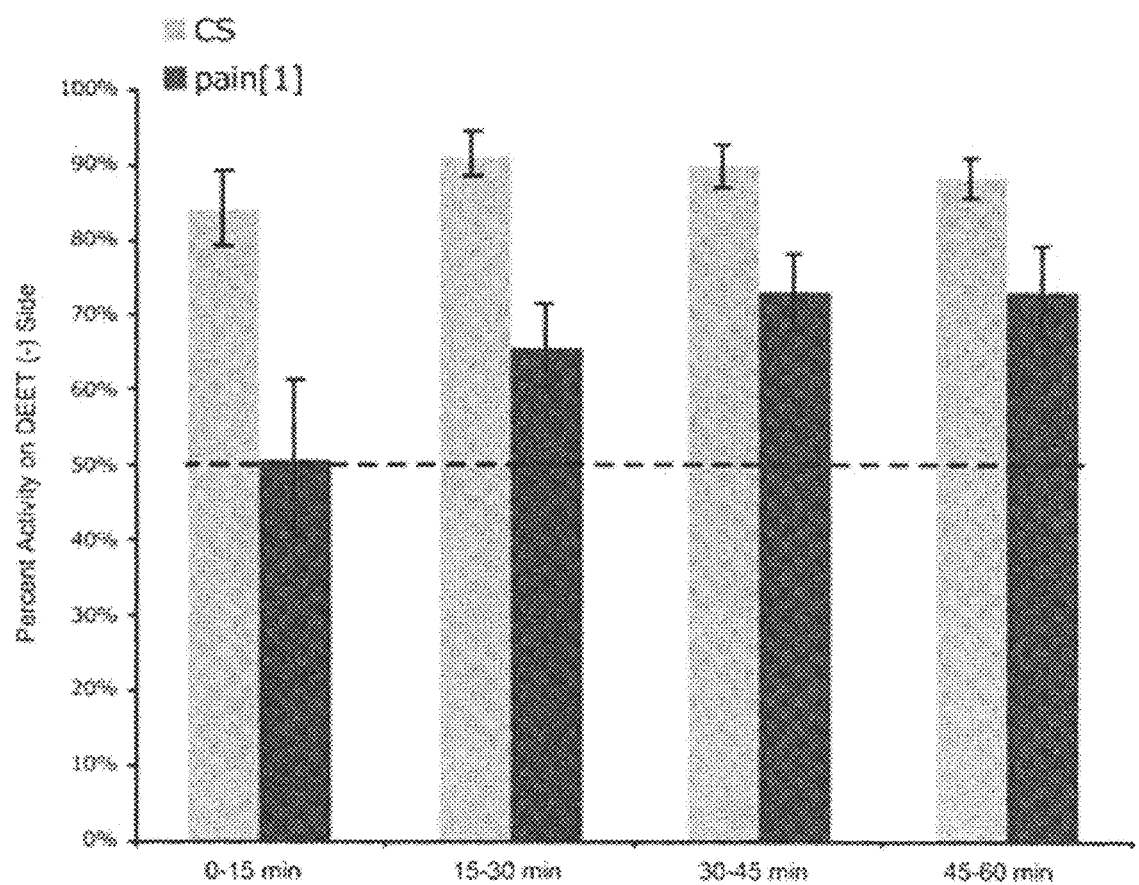
Figure 4A:
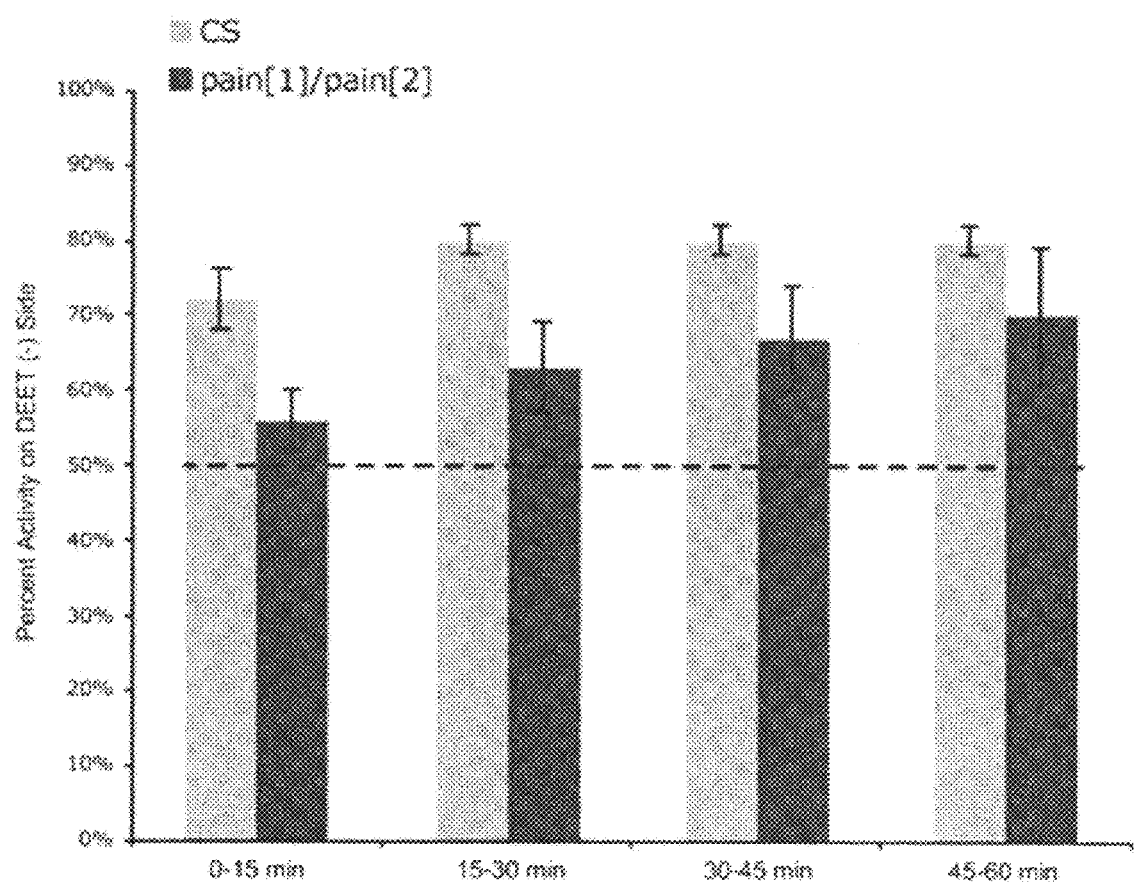
FIGS. 4A and 4B are bar graphs of Avoidance Evaluation Chamber assays of pain1/pain2 females (FIG. 4A) and males (FIG. 4B) showing that both males and females failed to avoid DEET for the first fifteen minutes after exposure, whereas wild type Canton-S flies avoided DEET during the same interval. As the trials progressed, the painless mutants gradually increased avoidance of DEET. Females: N=10 trials; males: N=10 trials.
Figure 4B:
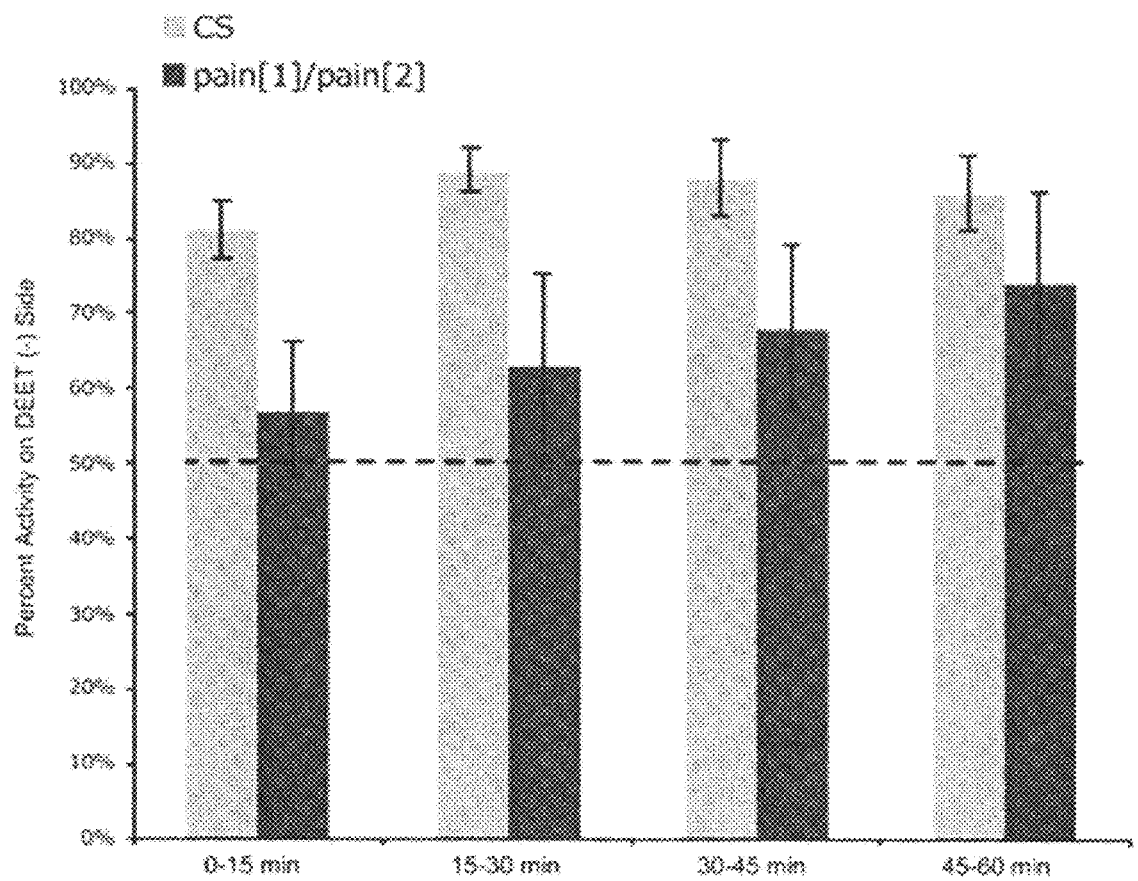

Avoidance Evaluation Chamber assays were also employed to test whether Painless$^{-/-}$ mutant *Drosophila* avoided DEET. As shown in FIG. 3, pain1 females (FIG. 3A) and males (FIG. 3B) both failed to avoid DEET for the first fifteen minutes after exposure, whereas wild type Canton-S flies clearly avoided DEET during the same interval. As the trials progressed, the painless mutants gradually increased their avoidance of DEET. A similar result was seen when pain1/pain2 females (FIG. 4A) and males (FIG. 4B) were tested. Again, as the trials progressed, the painless mutants gradually increased avoidance of DEET.

Figure 5A:
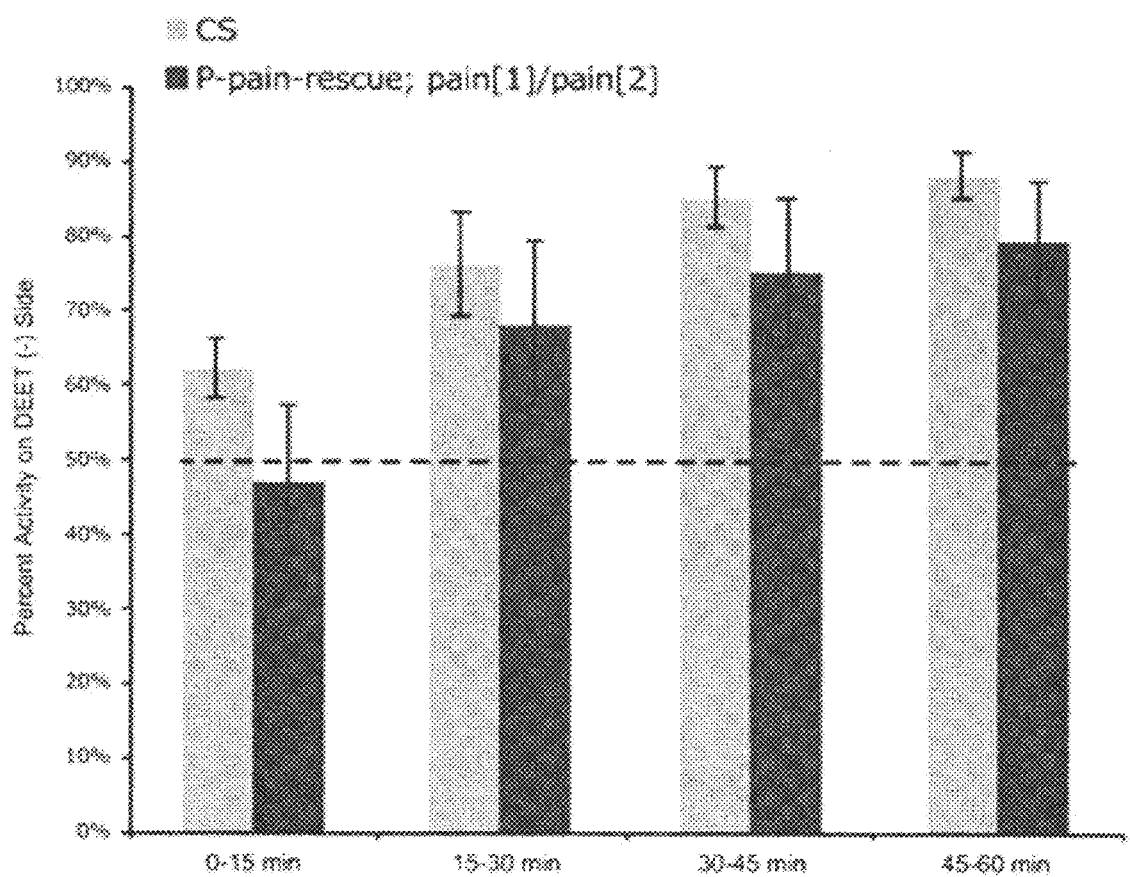
FIGS. 5A and 5B are bar graphs of Avoidance Evaluation Chamber assays of transgenic flies having a genomic painless rescue construct in a pain1 background (P-pain-rescue; pain1). As shown in the Figures, the genomic painless rescue construct partially rescued the DEET insensitivity defect in both females (FIG. 5A) and males (FIG. 5B). The flies showed some avoidance of DEET in the first 15 minutes. In addition, the avoidance of DEET at the later time points was similar to wild type. In contrast, the avoidance seen in the pain1 mutant in the absence of the rescue construct never reaches the level of Canton-S even after one hour. This result showed that the mutant phenotypes depicted in FIGS. 3 and 4 were due to the mutant painless gene. The rescue transgene was more effective in females than in males. Females N=13 trials; males N=10 trials.
Figure 5B:
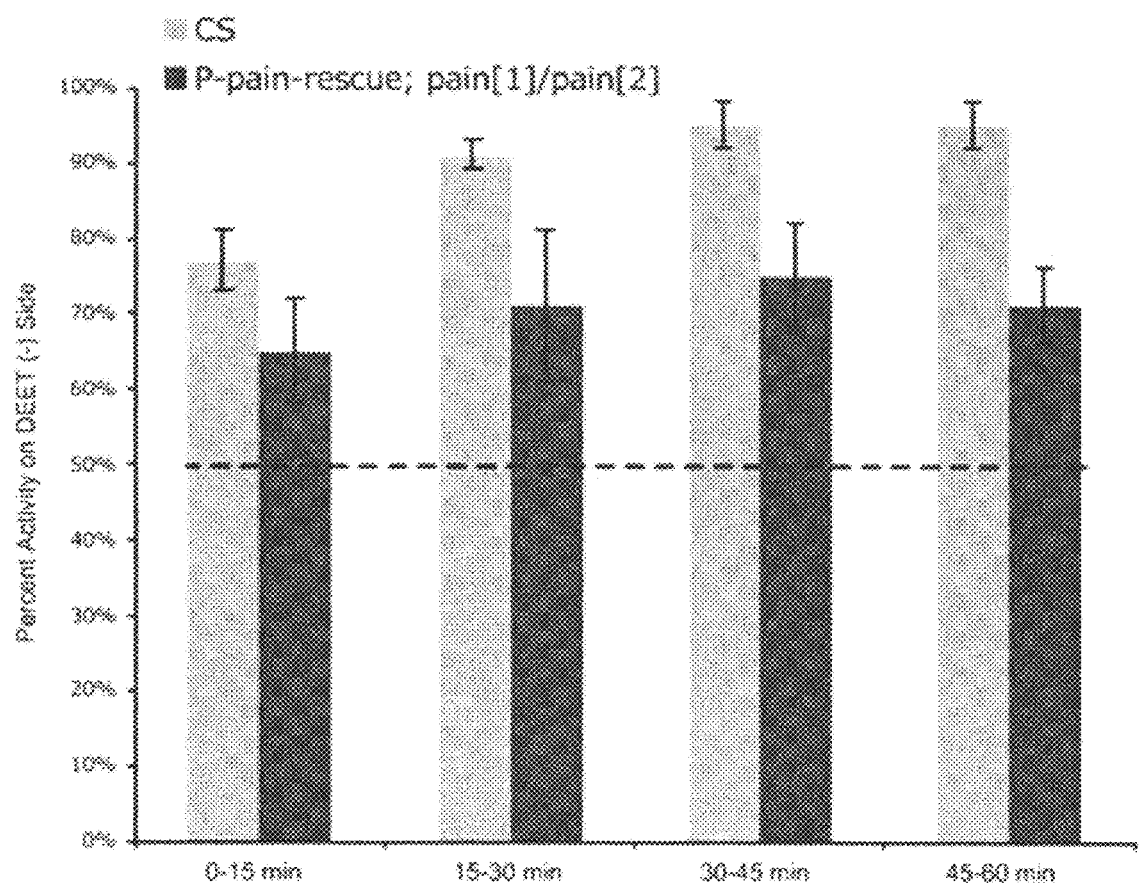

And finally, whether or not the delayed avoidance activity was a direct result of the painless mutation was tested by generating transgenic flies having a genomic painless rescue construct in a pain1 background (P-pain-rescue; pain1; see Tracey et al., 2003). As shown in FIGS. 5A and 5B, the genomic painless rescue construct partially rescued the DEET insensitivity defect in both females (FIG. 5A) and males (FIG. 5B). The flies showed some avoidance of DEET in the first 15 minutes that was greater than the avoidance seen in the pain 1 mutant itself over the same time period. This result showed that the mutant phenotypes depicted in FIGS. 3A and 3B and FIGS. 4A and 4B were due to the mutant painless gene. The rescue transgene was more effective in females than in males.

Figure 6A:
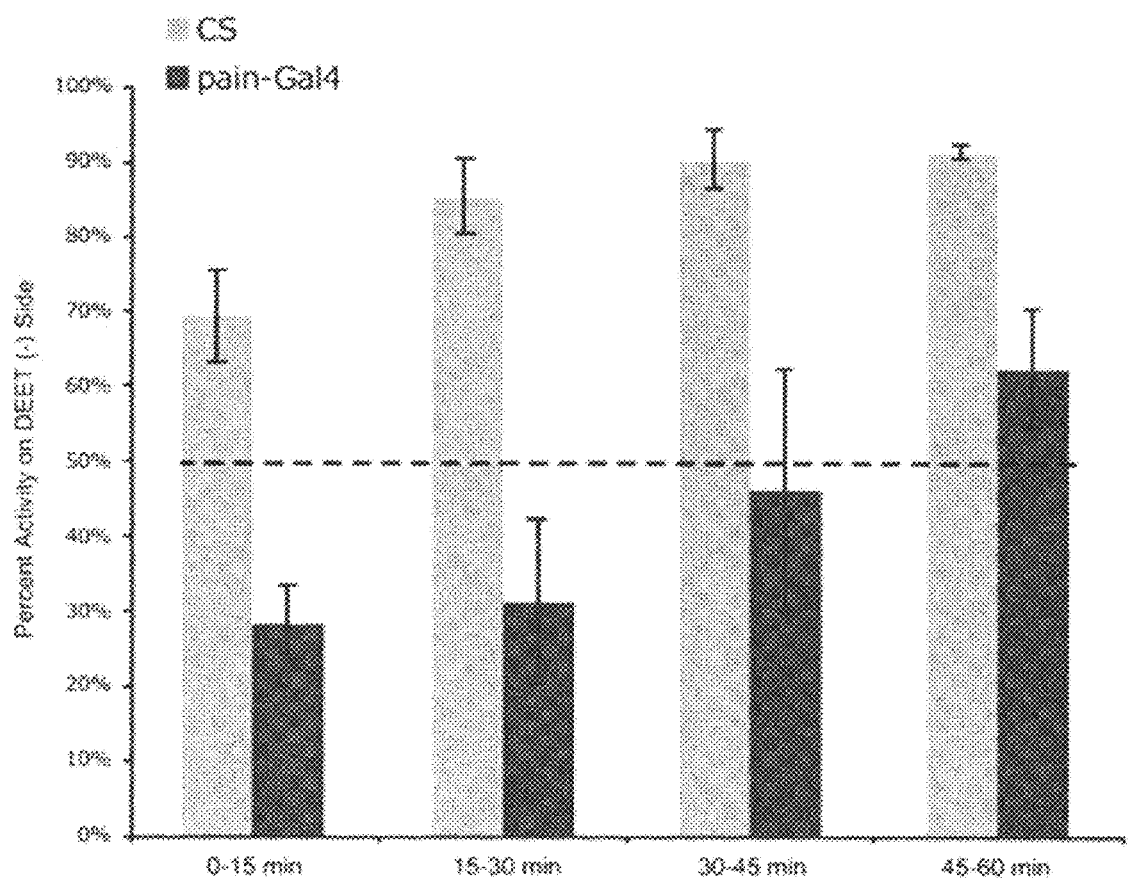
FIGS. 6A and 6B are bar graphs of Avoidance Evaluation Chamber assays showing that painless-Gal4 females (FIG. 6A) and males (FIG. 6B) failed to avoid DEET for the first fifteen minutes of the trial—indeed, the animals were actually attracted to it—whereas wild type Canton-S flies clearly avoid DEET in the same interval. As the trial progresses the painless-Gal4 mutants gradually increased avoidance of DEET at the later time points. Females: N=13 trials; Males: N=13 trials.
Figure 6B:
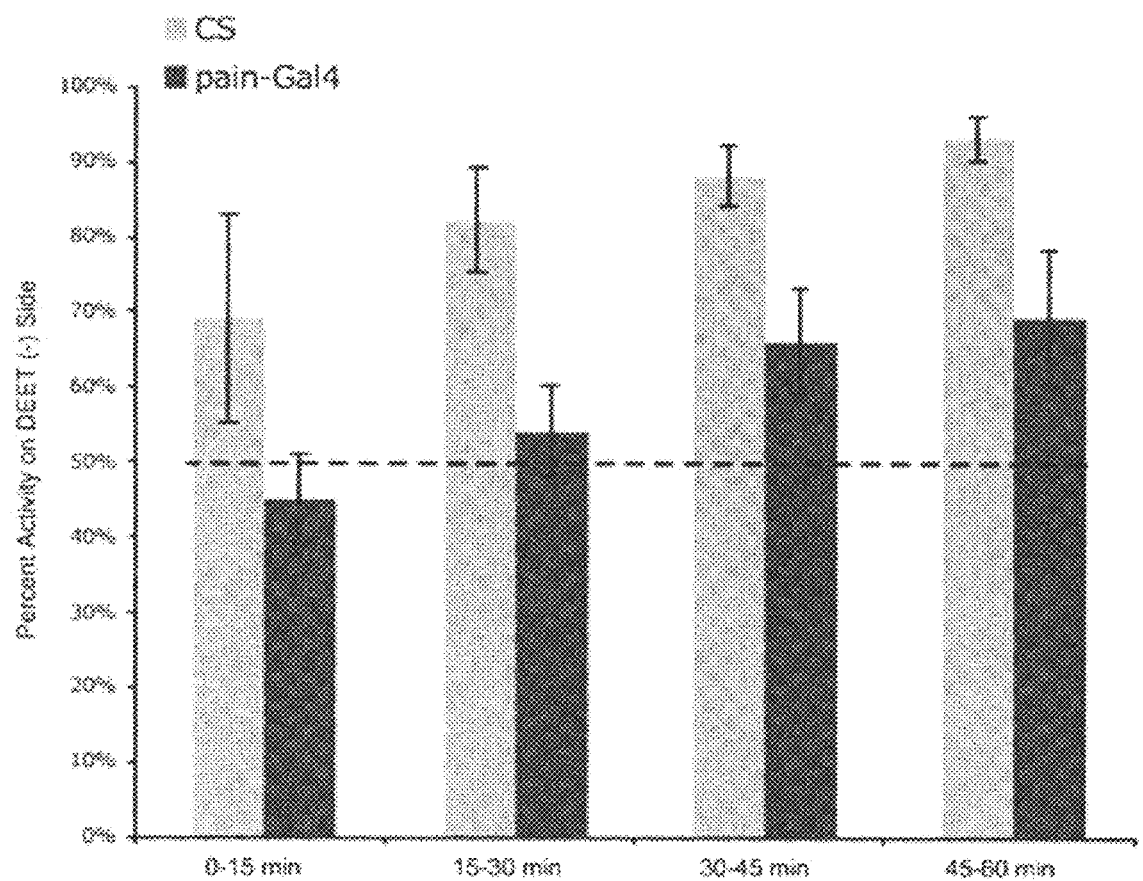
Figure 7:
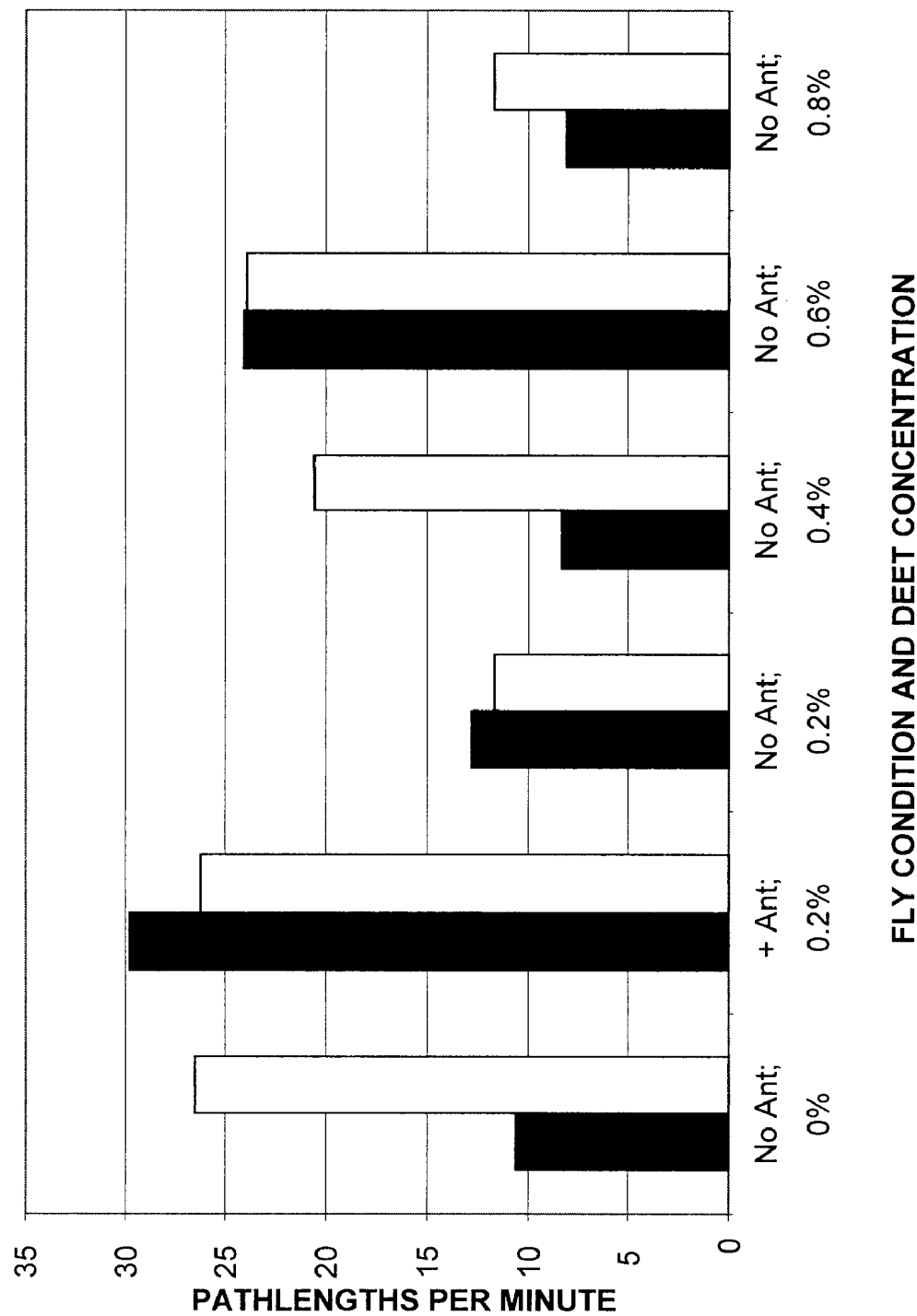
FIG. 7 is a bar graph showing the avoidance behavior of wild type flies to different concentrations of DEET in Avoidance Evaluation Chamber assays. NA: no third antennal segment. A: intact third antennal segment.

FIGS. 6A and 6B show that painless-Gal4 females (FIG. 6A) and males (FIG. 6B) failed to avoid DEET for the first fifteen minutes of the trial—indeed, the animals were actually attracted to it—whereas wild type Canton-S flies clearly avoid DEET in the same interval. As the trial progresses the painless-Gal4 mutants gradually increased avoidance of DEET at the later time points.

For FIGS. 3A-6B, if the percent activity is equal to 50% the flies were randomly distributed with respect to DEET. If the percent activity on DEET- is less than 50%, the flies showed a preference for DEET. The observation that flies with the allele of painless assayed in FIGS. 5A and 5B preferred DEET suggested that painless mutant flies had the ability to detect DEET, but in the absence of painless the compound was no longer aversive.

Similarly, painless$^{-/-}$ males also appeared to favor the non-DEET side of DEET-avoidance test, they took longer to begin avoiding DEET, taking about 30 minutes whereas Canton S flies without antennae were able to avoid DEET almost immediately. Further, painless$^{-/-}$ females appeared to show an even more delayed response to DEET detection compared to painless males, barely avoiding at the last 65 min time point.

This suggested that perhaps a sexual difference in painless expression exists in *Drosophila*. In addition, both painless$^{-/-}$ males and females with surgically removed third antennal segments showed no avoidance of DEET. In fact, these olfaction-deficient flies appeared more attracted to the DEET side initially.

Since painless is expressed in the gustatory receptor neurons of the labial palpus, tarsus, and wing anterior margin, painless$^{-/-}$ flies are most likely deficient in gustatory nociception. This might still allow them to detect DEET through the olfactory pathway. However, removing the third antennal segment of painless$^{-/-}$ files ablated both the putative olfactory and gustatory pathways of DEET detection, preventing DEET avoidance behavior. Wild-type Canton S flies without the third antennal segment might still detect and avoid DEET through the gustatory pathway which painless$^{-/-}$ files lacks.

Example 4

Or83b Avoids DEET but not AITC

Like antennaeless wild-type Canton S flies, olfaction-deficient Or83b mutants were able to avoid DEET by exhibiting increased activity until they are on agar that does not contain the repellent (see FIG. 10). However, their avoidance was not as strong. They also exhibited grouping behavior by choosing to cluster around the edges of the plates on the non-DEET side.

Alone, these data suggested that DEET detection was either conducted through olfactory neurons that are not dependent on the Or83b receptor or that it was mediated through a gustatory circuit. Along with the finding that antennaeless Canton S flies also avoided DEET, however, this indicated that both the OSNs in the maxillary palps and the OSNs in the third antennal segment were not necessary for DEET detection and that there might be redundancy in the chemicals detected by these organs.

In contrast, Or83b mutants did not show the same avoidance of AITC, instead choosing to cluster around the edge of both sides of the plate. This indicated that olfaction might be necessary to AITC avoidance in this paradigm.

Example 5 dTRPA1 Mutant Avoids DEET but Adapts to AITC

Flies expressing mutant dTRPA1, the closest homologue to the mammalian "wasabi receptor", were able to avoid DEET consistently after less than 15 minutes of exposure to the 0.2% concentration (see FIGS. 10A-10D). When exposed to 1:10,000 AITC, the flies avoided the toxin for the first 30 minutes, but afterwards showed no preference for either side of the plate (see FIGS. 10A-10D). Since painless was shown to be necessary for AITC perception herein (see also Al-Anzi et al., 2006), dTRPA1's role did not appear to be redundant for AITC perception in *Drosophila*; however, it is still possible that dTRPA1 and painless are redundant for DEET detection.

Example 6

Changes in Activity in Response to AITC and DEET

Wild type Canton S flies with intact third-antennal segments also increased their activity level (measured in path lengths/min) significantly if in the presence of DEET and that flies without the third antennal segment, however, were significantly less active, suggesting a role of olfaction in mediating activity in response to noxious stimuli. Similarly, Or83b flies are much less active in the presence of DEET compared to their Canton S, TrpA1, and painless mutant counterparts. This could be also be visualized by the fact that they resembled bright spots in the mean gray scale analysis because they were superimposed while in the same position over time. It is possible that this high-activity "escape" response was mediated through olfaction while the avoidance behavior is avoided through a gustatory pathway.

Example 7

Cell Culture and Transfection of S2R+ Cells

S2R+ cells were plated onto 25 mm diameter coverslips in the wells of a 6-well plate ($1.15 \times 10^6$ cells per 35 mm well).

Cells were transfected with p-Act5C painless (SEQ ID NO: 2) at a concentration of 0.5 µg/well on the day after plating (see Echalier, 1997). Transfection was a DNA-Calcium Phosphate Co-precipitation Transfection method: DNA was put into 250 mM Calcium Chloride solution, and then added dropwise to HEPES-buffered saline with aeration to mix. The precipitate (which stays in suspension) was allowed to form for 40 minutes and then was added drop wise to the cells. After 18-24 hours the medium was changed. Cells were examined by Calcium imaging on the third day after the DNA is introduced to the cells.

Control cells were S2R+ cells mock-transfected (no DNA was introduced in the co-precipitation buffers).

Transfected cells were fixed for 15 minutes in 4% PFA in PBS pH 7.4, washed with PBS and then permeabilized for 15 minutes with 1% Triton X-100 in PBS. Cells were blocked with 1% Normal Goat Serum (NGS) in PBS for 30 minutes before incubating with an anti-myc tag primary antibody at a concentration of 1:200 in blocking buffer for one hour. Cells were washed and then incubated in an ALEXA FLUOR® 568-conjugated secondary antibody (Invitrogen Corp., Carlsbad, Calif., United States of America) at concentration of 1:1000 in blocking buffer for one hour. After washing, the 25 mm round cover slips were mounted on 24×55 mm cover slips with mounting medium. Immunostained cells as depicted in FIG. 10 were imaged using a confocal microscope.

Example 8

Ca Imaging of S2R+ Cells Expressing Painless

After removal of the cell medium from the transfected cells of EXAMPLE 8, 100 µl of FLUO-4+ FURA-Red solution was added to well. This solution included 0.5 µl FLUO-4 stock, 0.5 µl FURA-Red stock, 0.5 µl Pluronic stock and 100 µl Stop solution. The cells were incubate in this solution at room temperature for 45 minutes. The saline was removed and 200 µl of fly saline was added. In Ca++ free conditions, the cells were washed with Ca++ free fly saline supplemented with 5 mM EGTA three times, and then 200 µl of Ca++ free, 5 mM EGTA fly saline was added. The ligand solution was then added with or without Ca++ fly saline.

The loaded cells were imaged by confocal microscopy using 488 nm excitation and Long Pass 650 nm and Band Pass 500-525 nm filters. Regions of interest were selected based upon the location of cells that showed uniform cytoplasmic loading of both the green and red dyes. Cells that showed intense punctuate fluorescence typical of intracellular organelles were not examined.

Solutions used:
Fly saline: standard fly saline
HBS: Hank's Solution with 10 mM HEPES and 5 mM glucose (1 ml of 45% sol for 500 ml)
Stop Solution: HBS (or MEM with HEPES) with 0.1 mg/ml BSA
FLUO-4 AM or FURA-Red AM stock in DMSO (12.5 µl for 50 µg)
20% Pluronic F-127 in DMSO (Invitrogen Corp.)

Figure 8A:
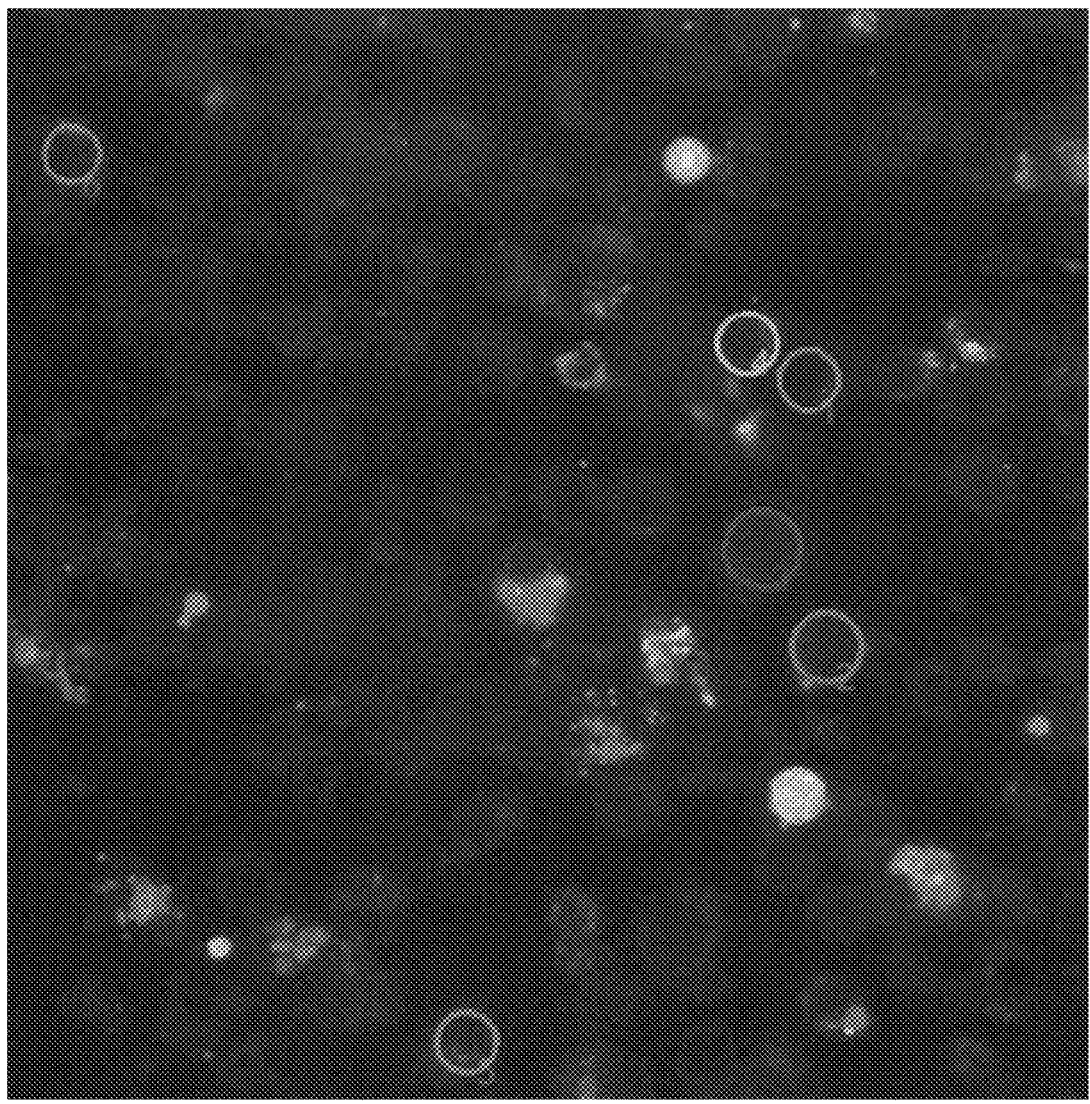
FIGS. 8A-8F depict calcium imaging of S2R+ cells transfected with a painless coding sequence in response to various DEET treatments.
Figure 8B:
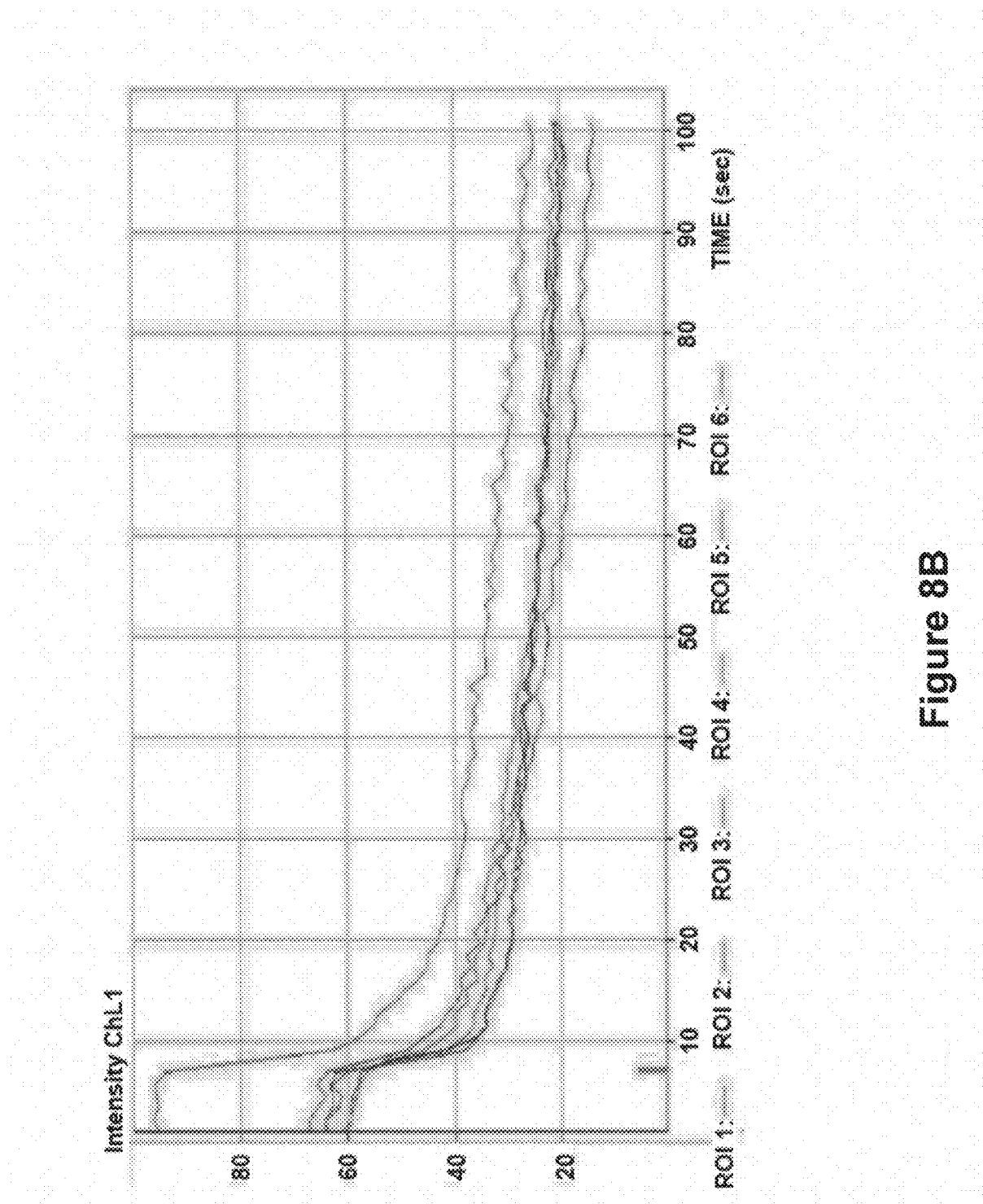
Figure 8C:
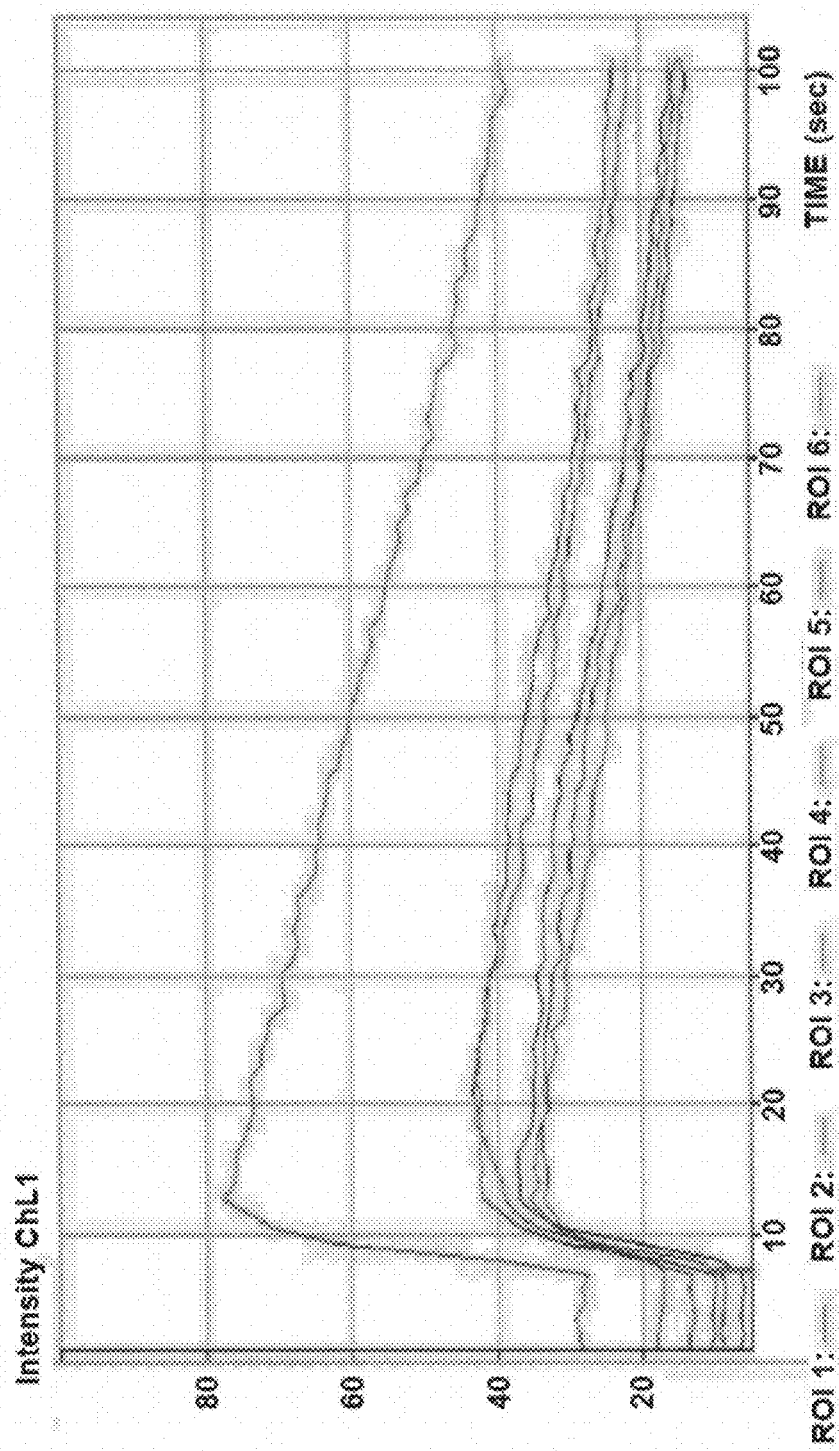
Figure 8D:
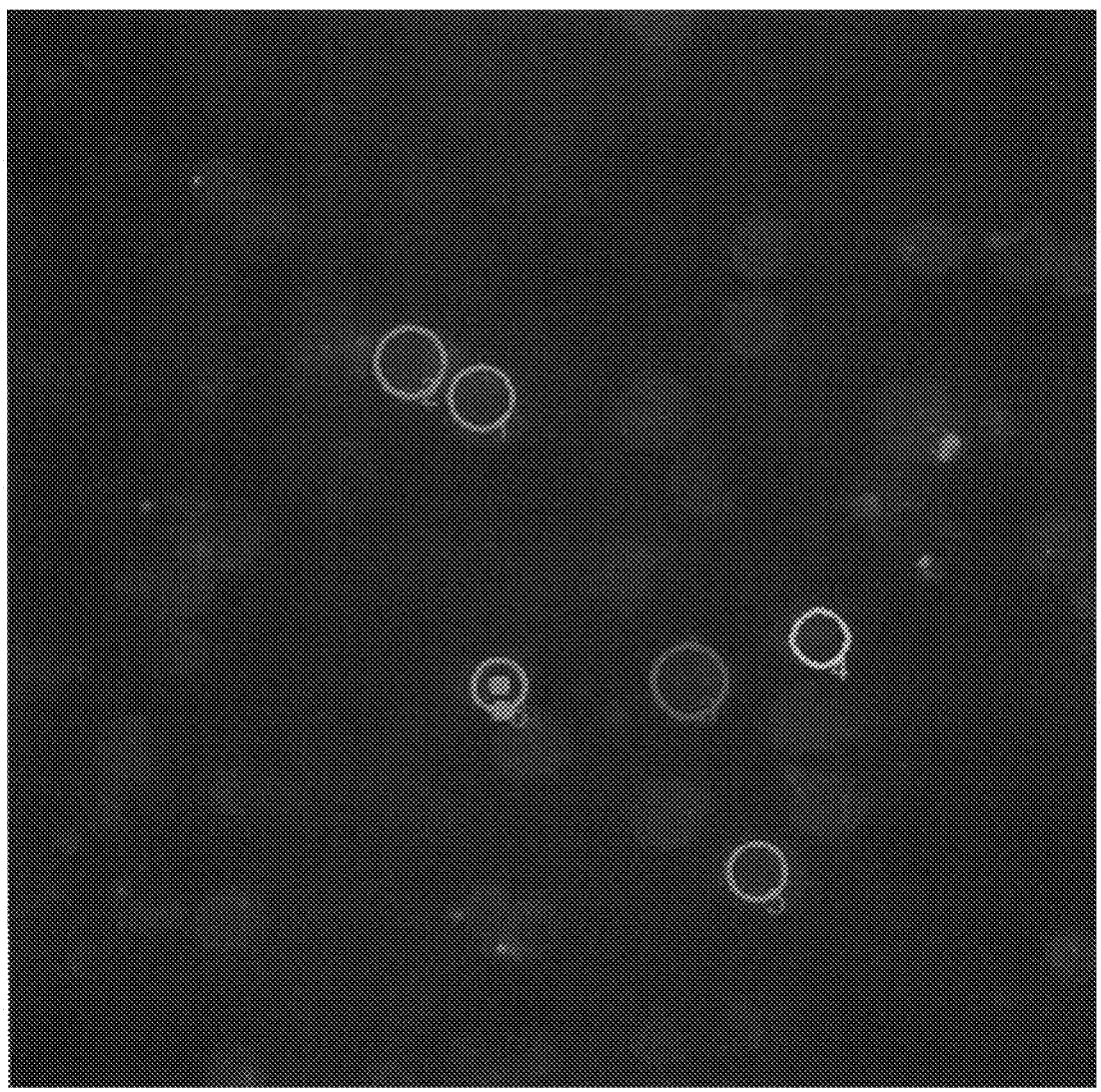
Figure 8E:
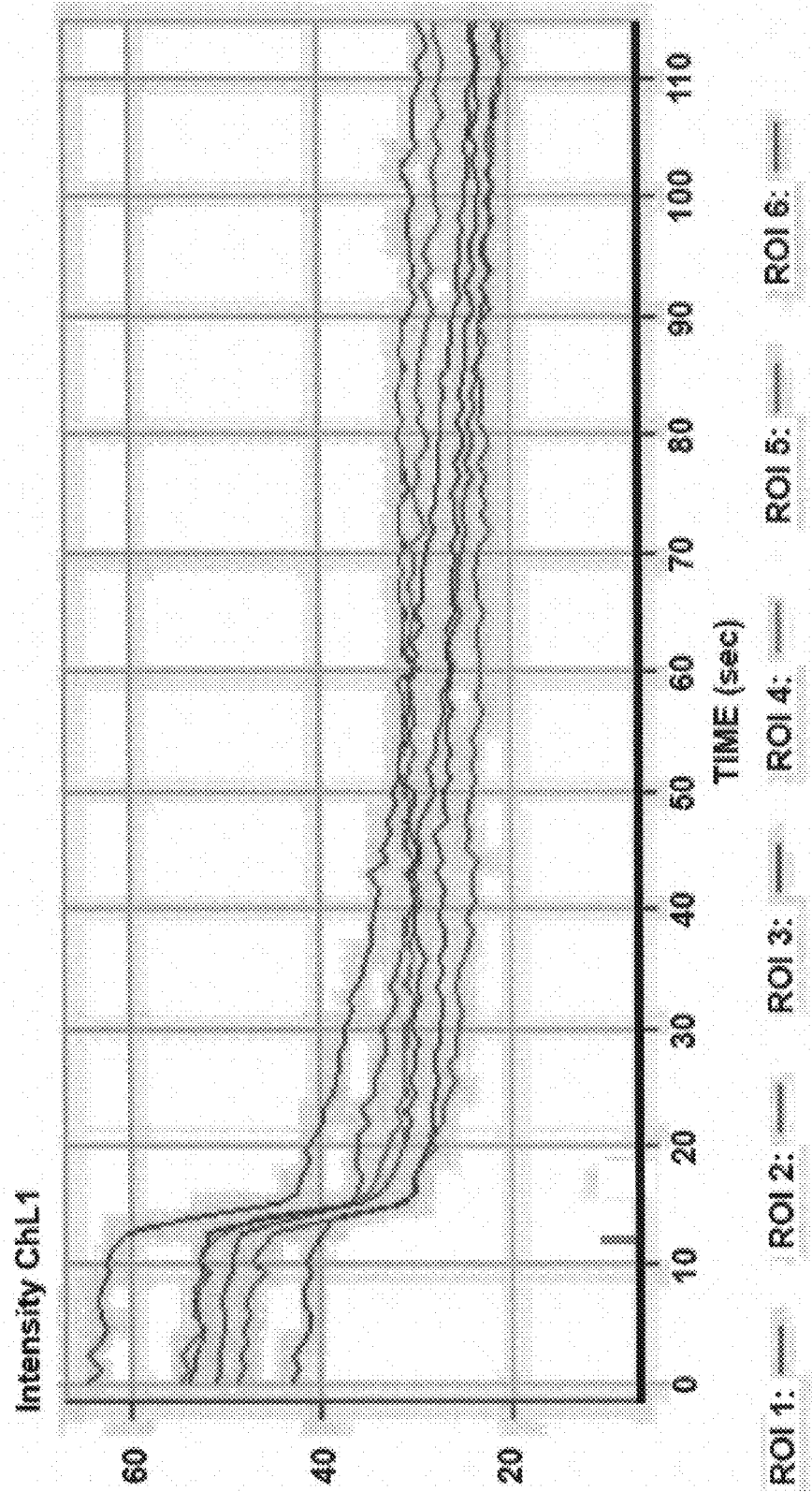
Figure 8F:
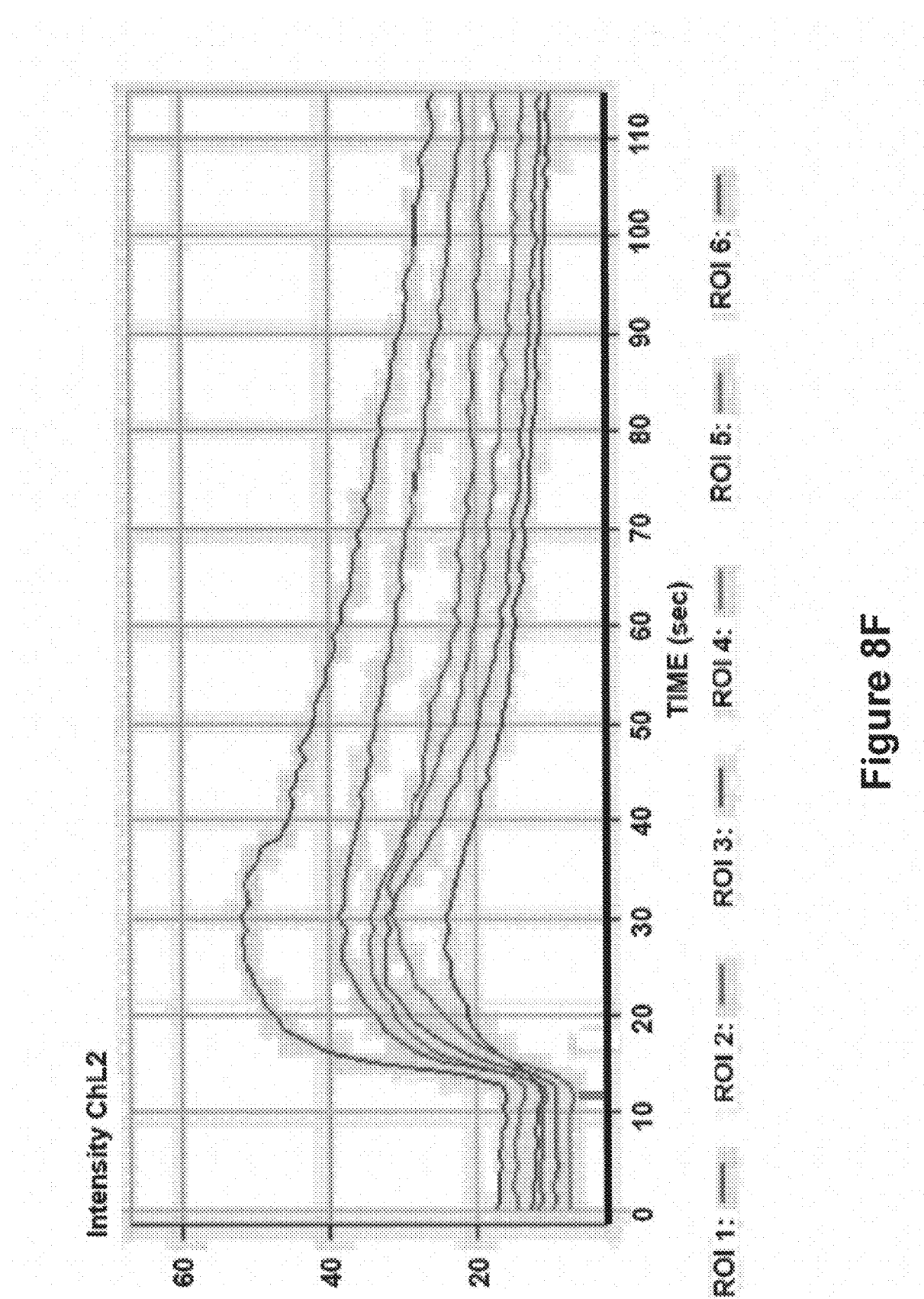

FIGS. 8A-8F show the results of the calcium imaging. FIG. 8A depicts confocal imaging of S2R+ cells loaded with FLUO-4 AM (green) and FURA-RED AM (red) at time 0 before the addition of 0.5% DEET. FIGS. 8B and 8C are graphs showing detection of strong calcium increases in both Channel 1 (FLUO-4) and Channel 2 (FURA-RED AM), respectively, in response to 0.5% DEET treatment in each of the six regions of interest (ROI) shown in FIG. 8A. FIGS. 8D-8F show the results of calcium imaging in non-transfected S2R+ cells. FIG. 8D depicts confocal imaging of S2R+ cells loaded with FLUO-4 AM (green) and FURA-RED AM (red) at time 0 before the addition of 0.5% DEET. FIGS. 8E and 8F are graphs showing detection of strong calcium increases in both Channel 1 (FLUO-4) and Channel 2 (FURA-RED AM), respectively, in response to 0.5% DEET treatment in each of the seven regions of interest (ROI) shown in FIG. 8D. The Ca++ signals observed in the non-transfected cells might result from endogenous painless expressed in these cells.

Example 9

RT-PCR Detection of Painless in S2R+ Cells

In order to test for the presence of painless expression in non-transfected S2R+ cells, total RNA was isolated from and purified from S2R+ cells. 1 µg of RNA was employed in a first strand cDNA synthesis reaction (oligo-dT primed), and one-tenth of the reverse-transcribed product was used in each PCR reaction. The PCR primers used for the PCR were as follows:

```
                                              (SEQ ID NO: 18
forward primer:      TAAGGAGCCAAACCTGCGAC;
and
                                              (SEQ ID NO: 19)
reverse primer:      TTCGTGGAACTTGAGGAGCGTG 3'.
```

The PCR conditions were as follows (per reaction):
5 µl 10×PCR buffer with MgCl2
2 µl first strand cDNA reaction (represents amount made from 0.1 µg RNA)
1 µl dNTPs
39.5 µl water
1 µl each primer (10 µM)
0.5 µl TAQ polymerase The thermocycling program was as follows:
1. 94° C. for 10 minutes;
2. 34 cycles of 94° C. for 15 seconds/57.4° C. for 30 seconds/68° C. for 45 seconds;
3. 72° C. for 10 minutes; and
4. 4° C. hold.

A control PCR reaction was employed that included first strand "cDNA" that was prepared without the addition of reverse transcriptase.

Figure 9:
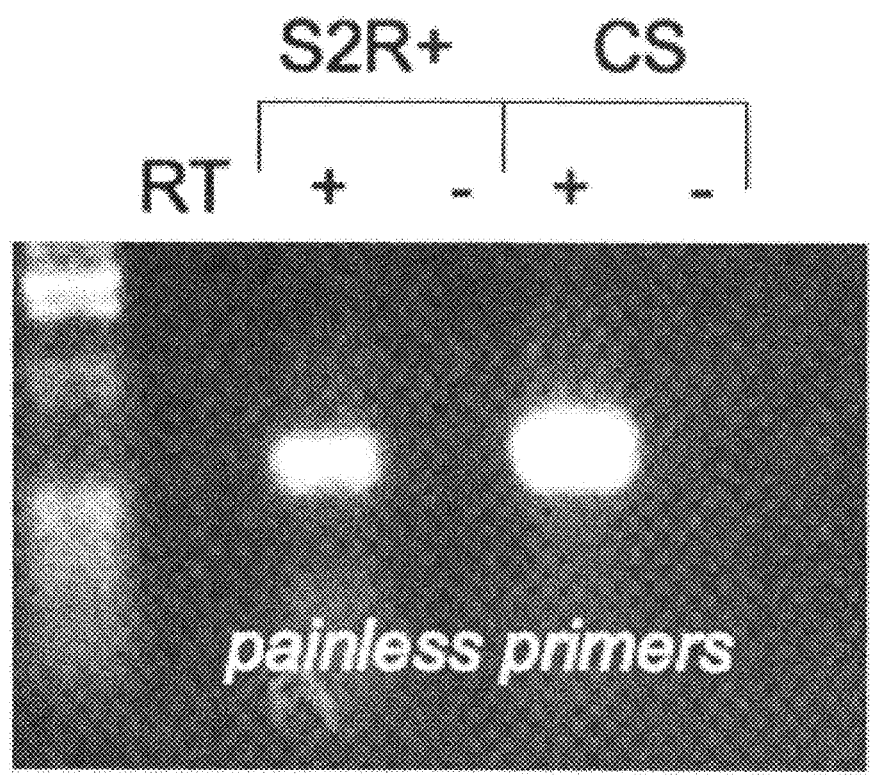
FIG. 9 is a digital image depicting RT-PCR analysis of non-transfected S2R+ cells showing endogenous painless expression.
Figure 10A:
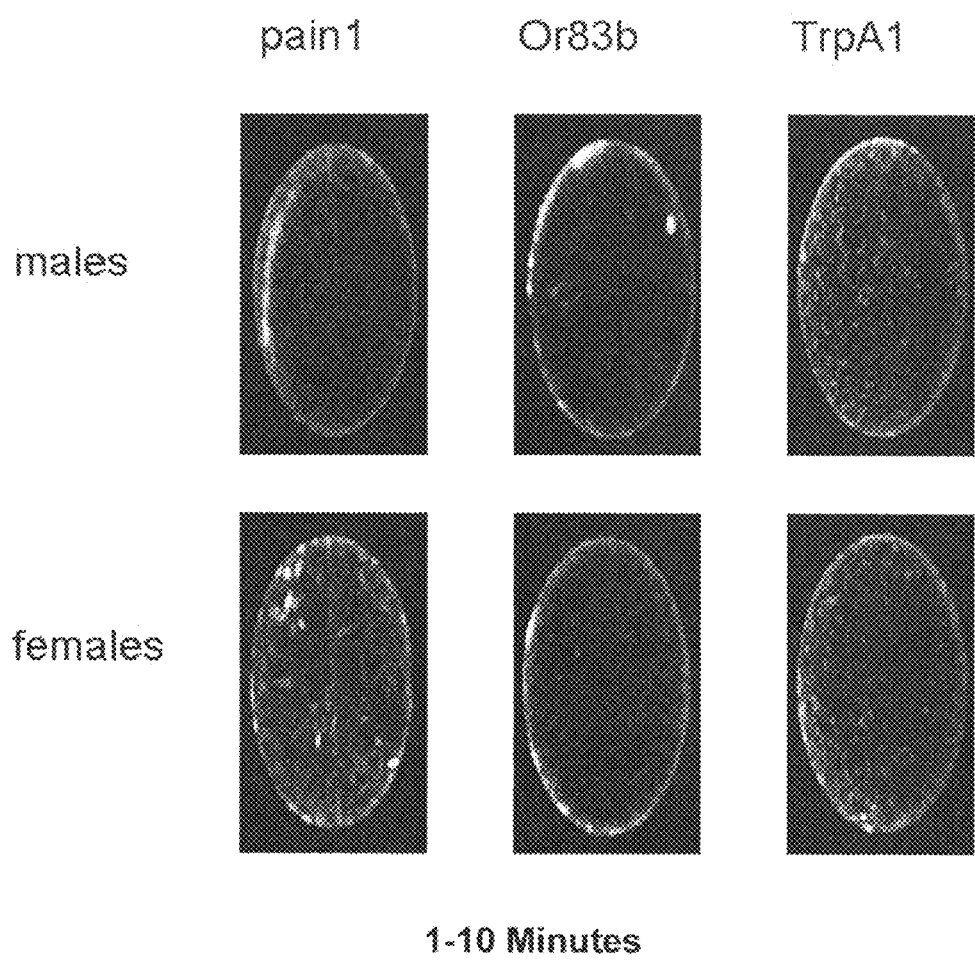
FIGS. 10A-10D are panels of photographs of Avoidance Evaluation Chamber assays of male and female Drosophila with different genetic backgrounds at 1-10 minutes after acclimatization (FIG. 10A), at 10-20 minutes after acclimatization (FIG. 10B), at 20-30 minutes after acclimatization (FIG. 10C), and at 30-40 minutes after acclimatization (FIG. 10D) of flies to AITC (1:10000 dilution of wasabi) placed on the right half of each Chamber. In each of the individual four Figures, the three chambers on top are male flies, and the three chambers on the bottom are female flies. Additionally, in each of the individual four Figures, the left two chambers depict avoidance behavior of painless mutants, the middle two chambers depict avoidance behavior of Or83b mutants, and the right two chambers depict avoidance behavior of dTRPA1 mutants.
Figure 10B:
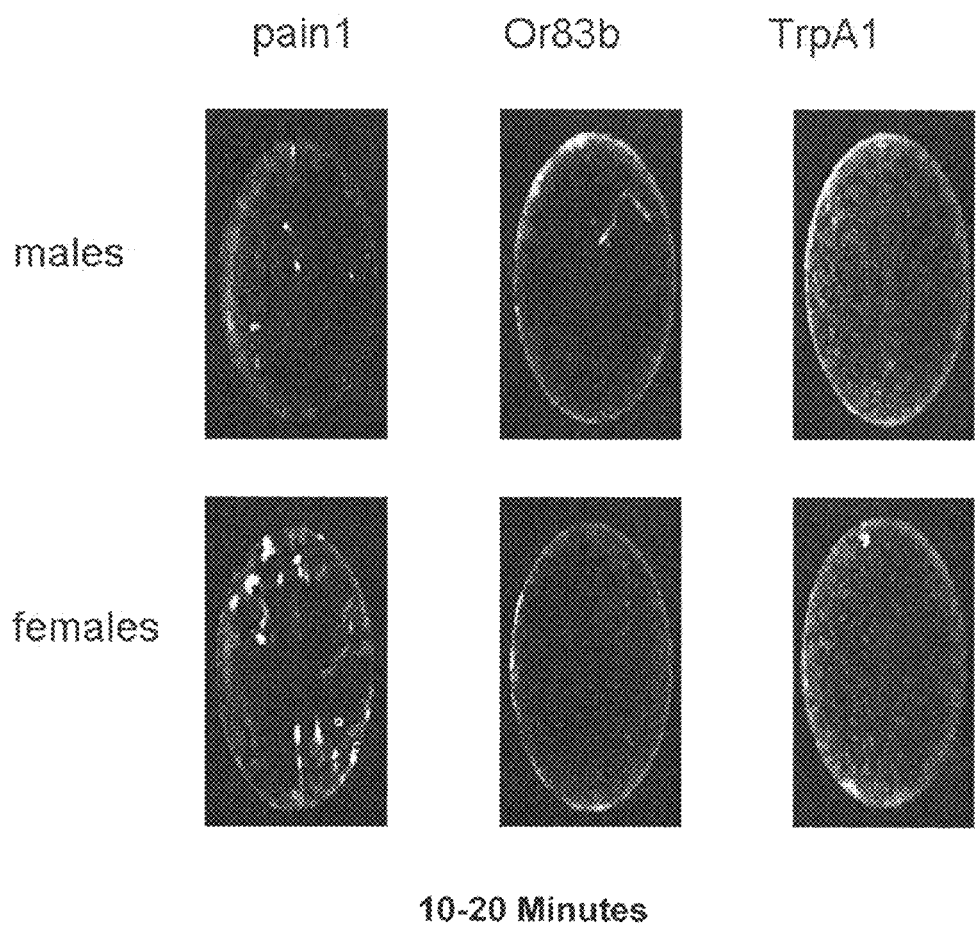
Figure 10C:
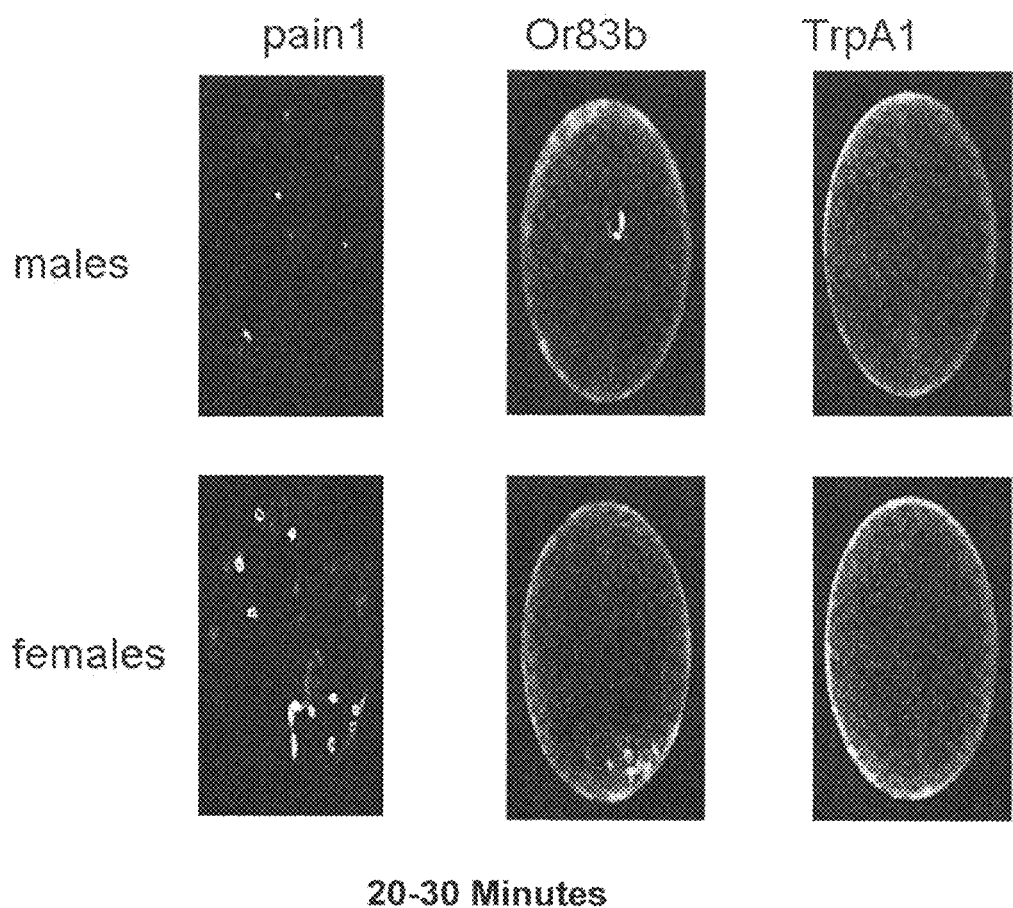
Figure 10D:
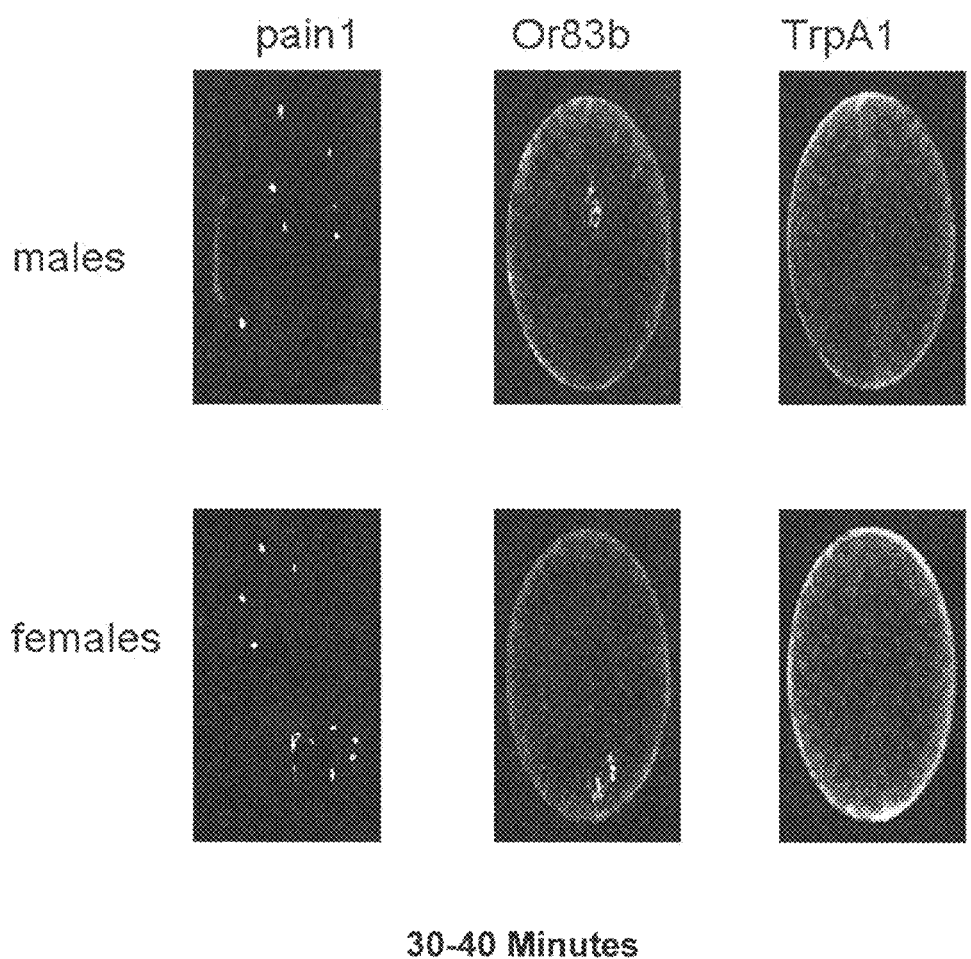
Figure 11:
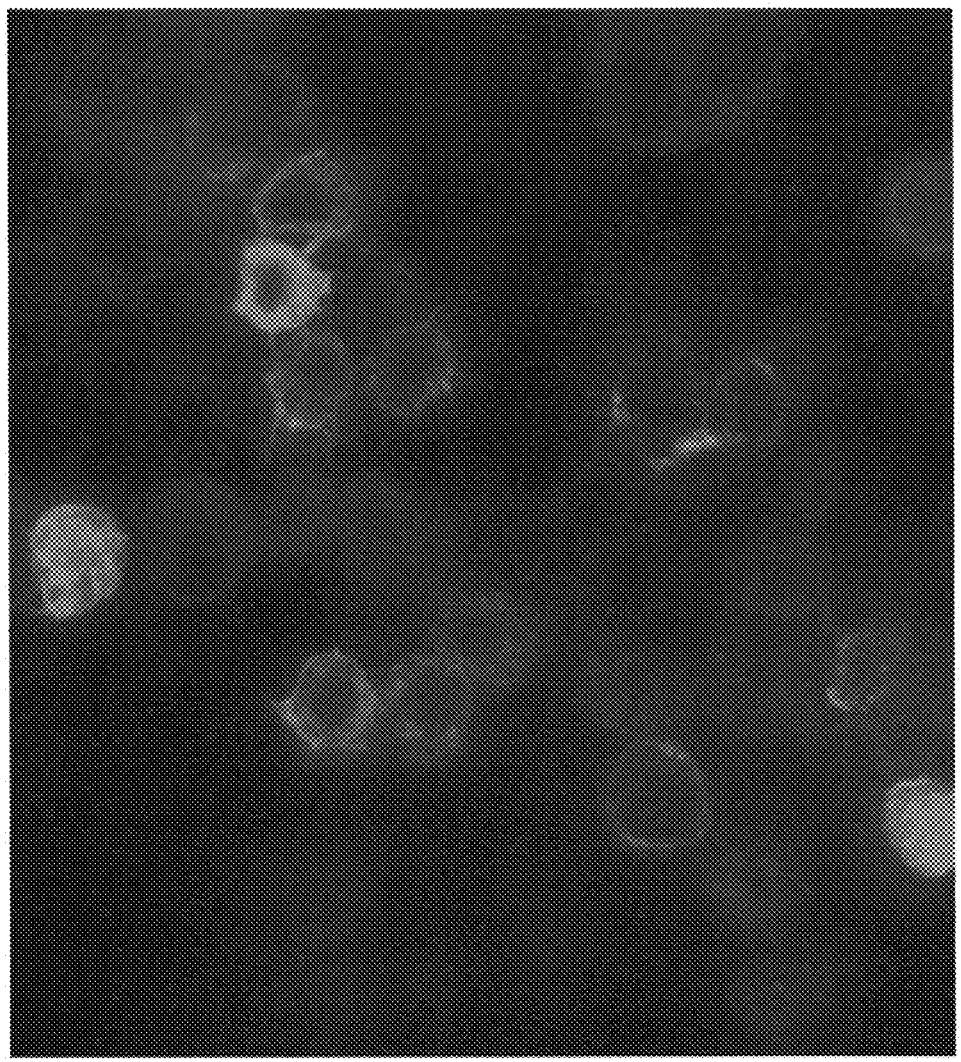
FIG. 11 is a fluorescence micrograph of heterologous expression of Anopheles gambiae painless protein in Drosophila S2R+ cells.

After the PCR reaction ended, a fraction of the PCR reaction of separated on an agarose gel and visualized. The results are shown in FIG. 9.

Example 10

Cloning and Sequencing of an *Anopheles gambiae* Painless Gene Product

A plasmid containing an expressed sequence tag (EST) corresponding to a painless coding sequence from *Anopheles gambiae* was obtained from the Malaria Research and Reference Reagent Resource Center (MR4; managed by the American Type Culture Collection, Manassas, Va., United States of America; catalogue number MRA-468-77; clone 19600449713864) and sequenced. The sequences of the sequencing primers employed are set forth in SEQ ID NOs: 21-34. Sequencing of the EST generated that sequence set forth in SEQ ID NO: 7.

Example 11

Isolation of Candidate Mosquito Repellents

Heterologous expression of *Anopheles gambiae* painless protein in *Drosophila* S2R+ cells is employed as an assay for isolation of agonists and potential mosquito repellents. To identify novel antagonists of mosquito painless, these transfected cells are exposed to candidate molecules and observed with calcium imaging using standard techniques. Agonists that do not activate calcium signals in non-transfected cells but do activate the *Anopheles gambiae* painless transfected cells represent candidate painless agonists and thus are candidates for inclusion in mosquito repellent compositions.

Example 12

Comparisons of Amino Acid Sequences of Painless Polypeptides

The amino acid sequences of painless gene products from *Anopheles gambiae, Aedes aegypti, Drosophila, Culex quinquefasciatus*, and *Tribolium castaneum* (corresponding to SEQ ID NOs: 8, 5, 20, 15, and 17, respectively) were compared using the ClustalX program (Thompson et al., 1997). The result of the comparison is presented in FIG. 12.

Figure 12:
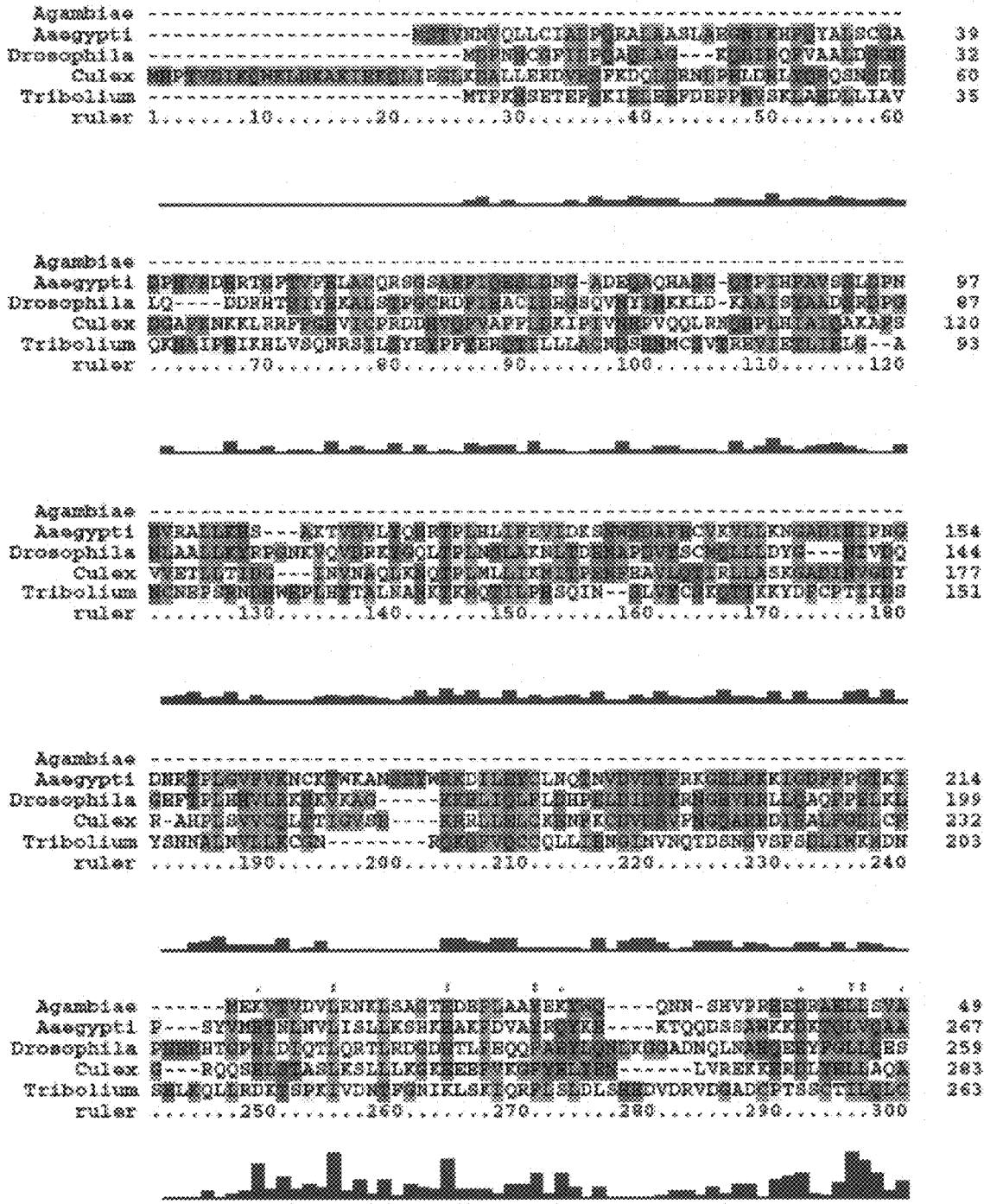
FIG. 12 is a comparison of painless sequences from different organisms.
Figure 12:
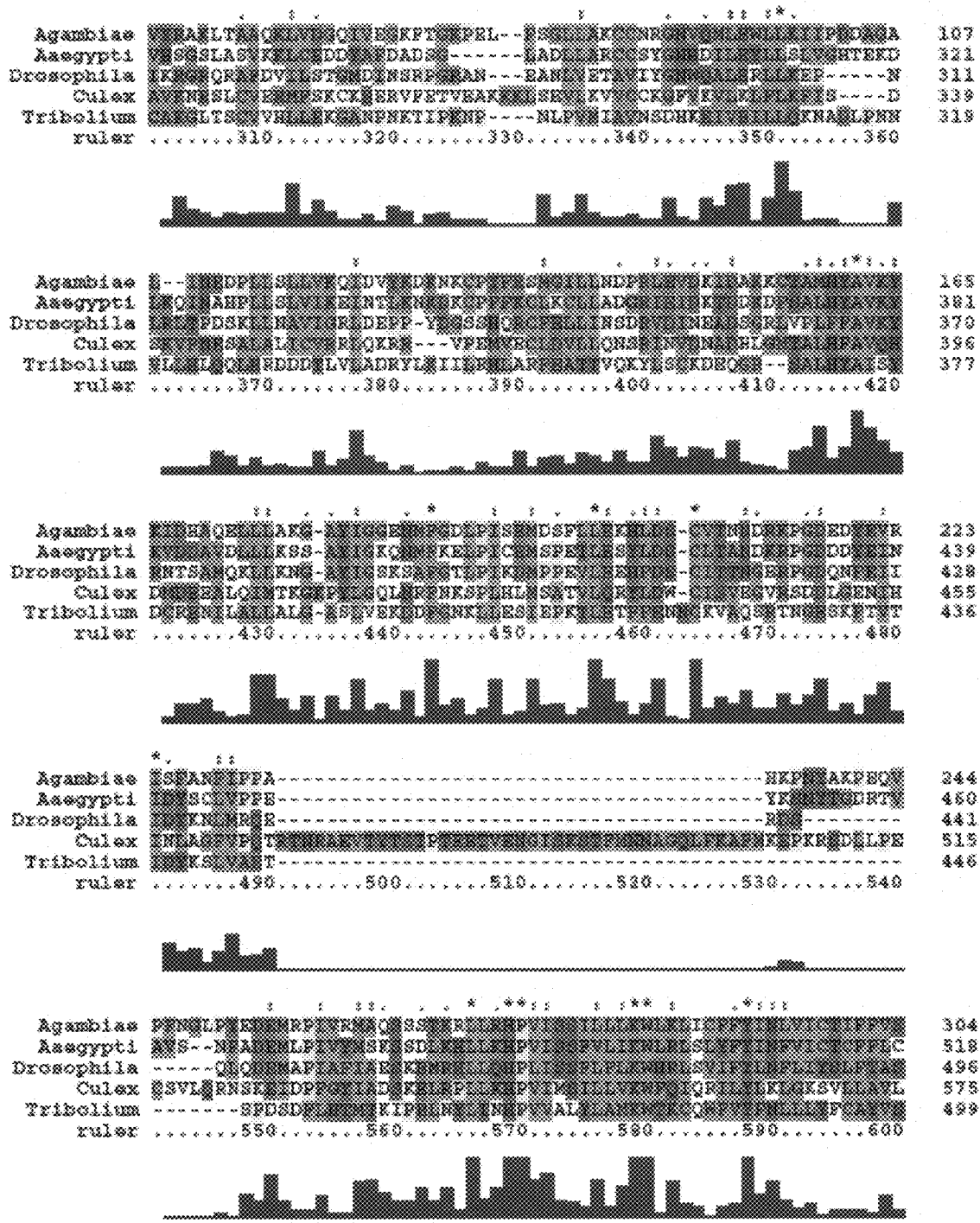
Figure 12:
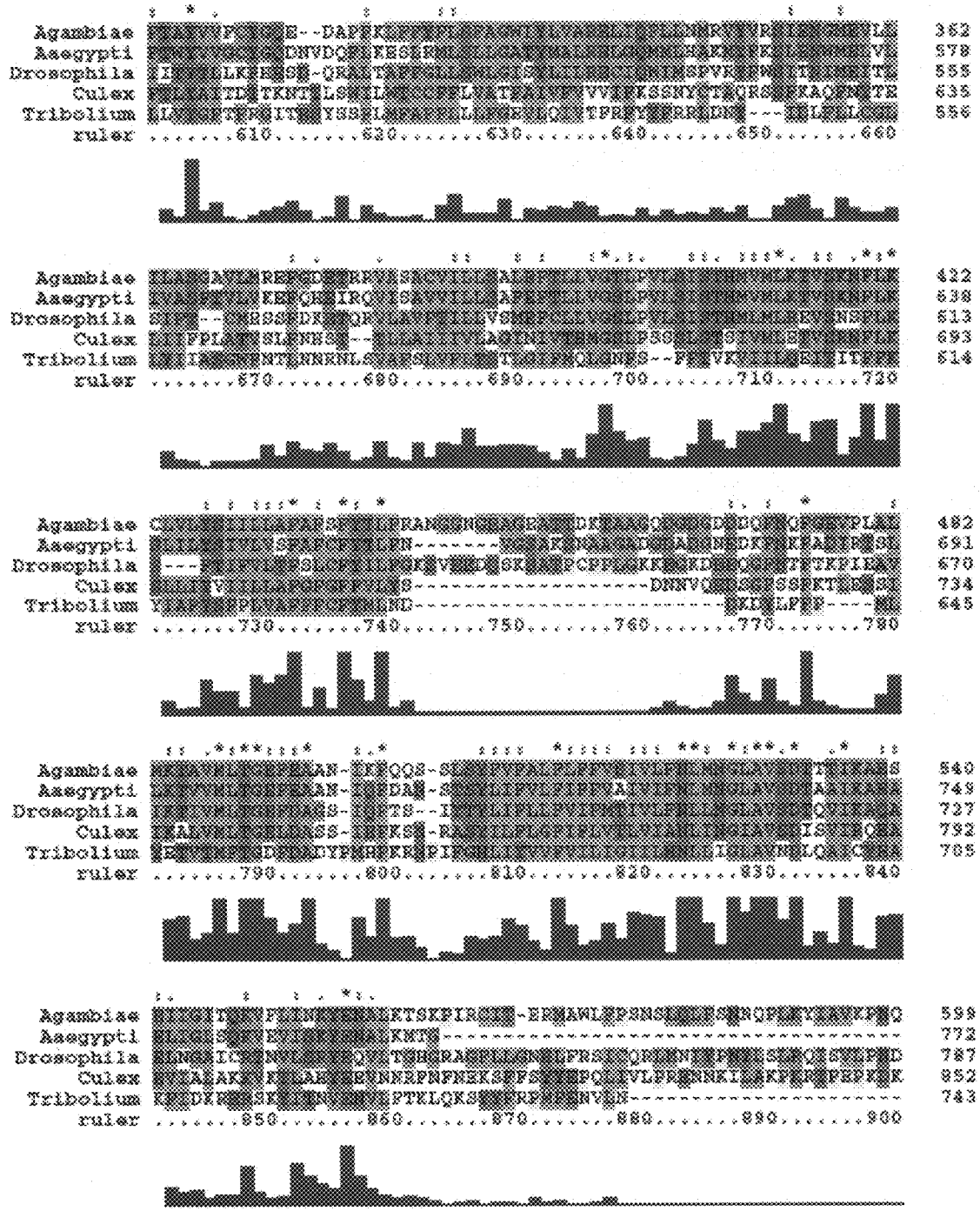

As seen in FIG. 12, certain regions of the painless gene products show considerable homology even among these diverse species. The comparison was truncated at amino acid 1032 of SEQ ID NO: 15 due to the extended C terminus of the *Culex* ortholog.

Discussion of the Examples

Using the avoidance evaluation test disclosed herein, it was possible to measure the behavior of wild-type and olfactory/gustatory mutant flies in the presence of noxious stimuli. As expected, the avoidance of wild-type flies towards DEET and wasabi indicated that both of these chemicals acted as repellents of *Drosophila melanogaster* and not simply as behavioral inhibitors of proboscis extension. In contrast to previous data, however, disclosed herein is evidence that DEET detection occurred, at least in part, through a gustatory circuit. First, Canton S flies were able to avoid DEET after the removal of their third-antennal segment, which eliminated >90% of their olfactory sensory neurons. Though DEET might be detected through OSNs in the maxillary palps to account for this result, Or83b mutants that had no olfactory sensation in their maxillary palps were also able to avoid DEET. This could indicate that there are redundant DEET detection receptors in the maxillary palps and the 20-30% of OSNs not co-expressing Or83b, or it might suggest that Or83b and antennaeless Canton S flies were able to detect DEET through a gustatory mechanism.

Particularly interesting was the response of painless mutants to the DEET avoidance test. First, it was determined that painless males were able to avoid DEET successfully, though it took a more prolonged period of exposure compared to Canton S flies with and without antennae. However, painless females appeared to be much more deficient in their avoidance of DEET, taking twice as long as their male counterparts.

This might indicate a sexual variance in the expression of painless or a sexual difference in the gustatory role of painless. Since female mosquitoes are the key carriers of the malaria parasite and the feeder of human blood meals, this difference in effect of DEET towards females could partially account for the success of DEET as a repellent and in the prevention of malaria transmission.

Also interesting was the finding that painless mutants without antennae did not choose to avoid DEET in both genders, and that, if anything, painless females without antennae were more attracted to DEET. This suggested that in addition to the gustatory detection of DEET through painless, there might be an alternate, antennae-mediated olfactory mechanism of DEET detection. Nevertheless screening against painless as disclosed herein can identify candidate repellents and insecticides.

Another possibility is that dTRPA1, the closest homologue to the mammalian "wasabi receptor", might be redundant for the action of painless. However, this did not appear to be the case since painless mutants were not able to effectively avoid DEET without antennae.

Even in the presence of DEET and AITC, fly activity was lower in the partially anosmic Or83b and antennaeless flies. This was demonstrated by looking at the average path lengths/min traveled by these flies compared to that of intact flies. Though there was still avoidance of DEET and AITC in trials containing antennaeless wild-type and intact Or83b flies, these flies did not appear as anxious to escape the plate and actually remained in one coordinate for extended periods of time, as shown by bright spots in the stacked gray-scale figures. This might suggest that olfaction is important for anxious and escape-seeking behavior while gustation is important for the avoidance of noxious stimuli.

Thus, the data presented herein suggested that painless, a nociceptive gustation mutant, was necessary for the detection of DEET in *Drosophila melanogaster*. This suggested that DEET operated by having a noxious "bitter" or "spicy" taste to insects. In addition, alternate olfactory pathways might be redundant for the gustatory detection of DEET. Finally, olfaction can play a role in escape-seeking behavior while gustation is important for avoidance.

As disclosed herein, a heterologous expression system that allows for expression of the painless protein in the S2R+ cell line is described. These cells can be used to identify compounds that activate the painless channels.

In some methods for expressing the painless protein, the *Drosophila* S2R+ cell line was co-transfected with two DNA constructs. The first construct contained the genomic DNA of painless downstream of binding sites for the yeast transcription factor GAL4 (UAS-PAIN; see SEQ ID NO: 1). The painless protein can also be epitope tagged, or expressed as a fusion protein with fluorescent proteins as shown in other sequences. The construct that was co-transfected with the UAS-Pain clones contained a cDNA for the yeast transcription factor GAL4. A ubiquitin promoter has been successfully employed to drive GAL4, but other promoters can also be used (e.g., actin 5c or the GAL4 promoter itself).

Also disclosed herein is an expression vector wherein the painless genomic sequence was directly fused downstream of the Actin-5c promoter (see SEQ ID NO: 2). This construct was directly transfected into S2R+ cells for expression of painless bypassing the need for co-transfection.

Once the cells were transfected, they were loaded with calcium indicator dyes. Chemical compounds can then be applied to the cells. Compounds that result in a calcium signal that is stronger in cells expressing painless than in the non-transfected cells represent candidate chemicals that can be used as insect repellents.

As an example of this, disclosed herein is the discovery that DEET (N,N-diethyl-m-toluamide) activates painless-expressing S2R+ cells. However, in non-transfected cells there is also a calcium response. This could be due to endogenous painless expression in these cells or alternatively a distinct molecular pathway for DEET is present in these cells. The former possibility is supported by RT-PCR experiments of S2R+ cells that demonstrated endogenous expression of painless in these cells (see FIG. 9).

Genome wide RNAi knockout is possible in Drosophila. When combined with the assay disclosed herein, any additional molecular mechanisms of DEET action can be identified including, but not limited to those that do not depend exclusively on the painless protein. RNAi of genes can be used in this system to unravel molecular mechanisms of DEET signaling.

The methods disclosed herein can also be extended to other species. Disclosed herein are nucleotide and protein sequences of painless orthologs from species other than Drosophila. These sequences can also be used in the expression system described above. Compounds that activate painless proteins from important pest species such as mosquitoes can be identified, for example by employing cell culture systems that express the one or more of the painless orthologs disclosed herein.

REFERENCES

All publications, patent applications, patents, and other references mentioned herein are incorporated by reference in their entirety. Some of the polynucleotide and polypeptide sequences disclosed herein are cross-referenced to GEN-BANK® accession numbers. The sequences cross-referenced in the GENBANK® database are expressly incorporated by reference as are equivalent and related sequences present in GENBANK® or other public databases. Also expressly incorporated herein by reference are all annotations present in the GENBANK® database associated with the sequences disclosed herein. In case of conflict, the present specification, including definitions, will control.

Acree et al. (1968) *Science* 161:1346-1347.
Al-Anzi (2006) *Current Biology* 16:1034-1040.
Altschul et al. (1990) *J Mol Biol* 215:403-410.
Amrein & Thorne (2005) *Current Biology* 15:R673-R684.
Ausubel et al. (2002) *Short Protocols in Molecular Biology*, Fifth ed. Wiley, New York, N.Y., United States of America.
Ausubel et al. (2003) *Current Protocols in Molecular Biology*, John Wylie & Sons, Inc., New York, N.Y., United States of America.
Batzer et al. (1991) *Nucleic Acid Res* 19:5081.
Bessou & Perl (1969) *Journal of Neurophysiology* 32:1025-1043.
Caterina et al. (1997) *Nature* 389:816-824.
Davis (1985) *Journal of Medical Entomology* 22:237-243.
Davis & Sokolove (1976) *Journal of Comparative Physiology* 105:43-54.
Dobritsa et al. (2003) *Neuron* 37:827-841.
Dogan et al. (1999) *Medical and Veterinary Entomology* 13:97-100.
Echalier (1997) *Drosophila Cells in Culture*. Chapter 9, Gene Transfer into Cultured *Drosophila* Cells. pp. 439-511, Academic Press, New York, N.Y., United States of America.
Elmore et al. (2003) *Journal of Neuroscience* 23:9906-9912.
Hallem et al. (2004) *Cell* 117:965-979.
Henikoff & Henikoff (1992) *Proc Natl Acad Sci U.S.A.* 89:10915-10919.
Karlin & Altschul (1993) *Proc Natl Acad Sci U.S.A.* 90:5873-5877.
Keene et al. (2004) *Neuron* 44(3):521-533.
Khan & Maibach (1972) *Journal of Economic Entomology* 65:1318-1321.
Klowden (1996) In *The Biology of Disease Vectors*, Beaty & Marquardt (eds) pp. 34-50, University Press of Colorado, Boulder, Colo., United States of America.
Larsson et al. (2004) *Neuron* 43:703-714.
Marella et al. (2006) *Neuron* 49:285-295.
Needleman & Wunsch (1970) *J Mol Biol* 48:443-453.
Ohtsuka et al. (1985) *J Biol Chem* 260:2605-2608.
Pearson & Lipman (1988) *Proc Natl Acad Sci U.S.A.* 85:2444 2448.
Reeder et al. (2001) *Journal of Economic Entomology* 94:1584-1588.
Roayaie et al. (1998) *Neuron* 20:55-67.
Robbins & Chemiack (1986) *Journal of Toxicology and Environmental Health* 18:503-525.
Rossolini et al. (1994) *Mol Cell Probes* 8:91-98.
Skinner et al. (1968) *Experentia* 24:679-680.
Smith & Waterman (1981) *Adv Appl Math* 2:482-489.
Smith et al. (1970) *Annals of Entomological Society of America* 63:760-770.
Stocker (1994) *Cell Tissue Research* 275:3-26.
Thorne et al. (2004) *Current Biology* 14:1065-1079.
Tracey et al. (2003) *Cell* 113:261-273.
Vosshall et al. (1999) *Cell* 96:725-736.
Wang & Woolf (2005) *Neuron* 46:9-12.

It will be understood that various details of the presently disclosed subject matter may be changed without departing from the scope of the presently disclosed subject matter. Furthermore, the foregoing description is for the purpose of illustration only, and not for the purpose of limitation.

---

What is claimed is:

1. A method for identifying a candidate repellent compound with an ability to modulate cation transport through a transient receptor potential (TRP) channel in a cell, the method comprising:
   (a) providing a cell expressing a transient receptor potential (TRP) channel gene product wherein the TRP channel comprises the amino acid sequence of SEQ ID NO: 8;
   (b) contacting the cell with the candidate repellent compound;
   (c) comparing cation transport in the cell in the absence of the candidate repellent compound with cation transport in the cell in the presence of the candidate repellent compound; and
   (d) identifying a candidate repellent compound through comparing step (c) that modulates cation transport in the cell through the transient receptor potential (TRP) channel.

2. The method of claim 1, wherein the cell is an insect cell or an arachnid cell.

3. The method of claim 1, wherein the transient receptor potential (TRP) channel gene product is encoded by a recombinant nucleic acid sequence.

4. The method of claim 3, wherein the recombinant nucleic acid sequence is operably linked to a promoter that is functional in the cell and comprises a cDNA sequence or a splicable DNA sequence that must be spliced in the cell for the cell to express the transient receptor potential (TRP) channel gene product.

5. The method of claim 1, wherein the candidate repellent compound is provided as a member of a pool of candidate repellent compounds, and the identifying step comprises identifying at least one member in the pool of candidate repellent compounds that modulates cation transport through the transient receptor potential (TRP) channel in the cell.

6. The method of claim 5, wherein the candidate repellent compounds are peptides or small molecules.

7. The method of claim 5, wherein the pool of candidate repellent compounds comprises a phage display library.

8. The method of claim 5, in which the candidate repellent compounds are immobilized on a substrate or a plurality of substrates.

* * * * *